United States Patent
Lu et al.

(10) Patent No.: US 12,234,223 B2
(45) Date of Patent: *Feb. 25, 2025

(54) PHTHALAZINONE COMPOUND, AND PREPARATION METHOD THEREFOR AND MEDICAL USE THEREOF

(71) Applicants: SHANGHAI JEMINCARE PHARMACEUTICALS CO., LTD, Shanghai (CN); JIANGXI JEMINCARE GROUP CO., LTD, Jiangxi (CN)

(72) Inventors: Hongfu Lu, Shanghai (CN); Weiqiang Xing, Shanghai (CN); Yongcong Lv, Shanghai (CN); Baojian Qi, Shanghai (CN); Jianbiao Peng, Shanghai (CN); Haibing Guo, Shanghai (CN)

(73) Assignees: SHANGHAI JEMINCARE PHARMACEUTICALS CO., LTD., Shanghai (CN); JIANGXI JEMINCARE GROUP CO., LTD, Jiangxi (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/804,443

(22) Filed: Aug. 14, 2024

(65) Prior Publication Data

US 2024/0400540 A1   Dec. 5, 2024

Related U.S. Application Data

(63) Continuation of application No. 18/079,778, filed on Dec. 12, 2022, which is a continuation of application No. PCT/CN2021/099654, filed on Jun. 11, 2021.

(30) Foreign Application Priority Data

| Jun. 12, 2020 | (CN) | 202010536221.6 |
| Oct. 23, 2020 | (CN) | 202011147078.8 |
| Nov. 12, 2020 | (CN) | 202011261665.X |
| Apr. 30, 2021 | (CN) | 202110485680.0 |
| Jun. 2, 2021 | (CN) | 202110614030.1 |

(51) Int. Cl.
| C07D 401/14 | (2006.01) |
| A61K 31/502 | (2006.01) |
| A61K 31/506 | (2006.01) |
| A61K 31/55 | (2006.01) |
| A61P 5/26 | (2006.01) |
| A61P 13/08 | (2006.01) |
| A61P 15/14 | (2006.01) |
| A61P 21/00 | (2006.01) |
| A61P 35/00 | (2006.01) |
| A61P 35/04 | (2006.01) |

(Continued)

(52) U.S. Cl.
CPC ............ C07D 401/14 (2013.01); A61P 35/00 (2018.01); C07D 487/08 (2013.01); *C07B 2200/07* (2013.01)

(58) Field of Classification Search
CPC .. C07D 401/14; C07D 487/08; C07D 471/04; A61P 35/00; A61P 5/26; A61P 13/08; A61P 15/14; A61P 21/00; A61P 35/04; C07B 2200/07; Y02P 20/55; A61K 31/502; A61K 31/506; A61K 31/55

See application file for complete search history.

(56) References Cited

U.S. PATENT DOCUMENTS

| 11,767,312 B2 | 9/2023 | Lu et al. |
| 2003/0203902 A1 | 10/2003 | Lehmann et al. |
| 2015/0291562 A1 | 10/2015 | Crew et al. |

(Continued)

FOREIGN PATENT DOCUMENTS

| CN | 110194762 A | 3/2019 |
| CN | 112390852 A | 2/2021 |

(Continued)

OTHER PUBLICATIONS

Liu, J., "PROTACs: a novel strategy for cancer therapy." Seminars in Cancer Biology. vol. 67. Academic Press, 2020.*

(Continued)

*Primary Examiner* — John M Mauro
(74) *Attorney, Agent, or Firm* — Mintz, Levin, Cohn, Ferris, Glovsky and Popeo, P.C.

(57) ABSTRACT

Disclosed are a phthalazinone compound, and a preparation method therefor and the medical use thereof. In particular, disclosed are a compound as represented by formula (I), and a pharmacodynamically acceptable salt, and the use of the compound as an androgen receptor (AR) for degradation.

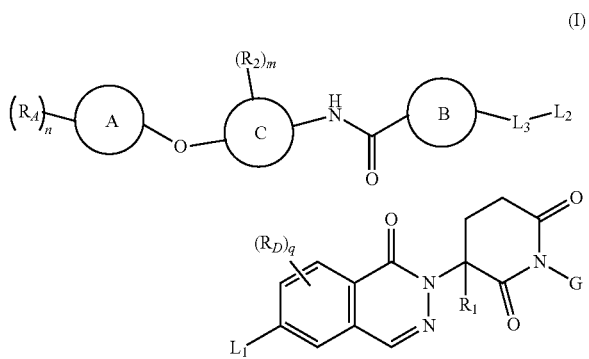

30 Claims, No Drawings

(51) Int. Cl.
  *C07D 471/04* (2006.01)
  *C07D 487/08* (2006.01)

(56) References Cited

U.S. PATENT DOCUMENTS

| | | |
|---|---|---|
| 2016/0058872 A1 | 3/2016 | Crew et al. |
| 2016/0214972 A1 | 7/2016 | Jin et al. |
| 2018/0099940 A1 | 4/2018 | Crew et al. |
| 2018/0134684 A1 | 5/2018 | Bradner et al. |
| 2018/0215731 A1 | 8/2018 | Crew et al. |
| 2018/0228907 A1 | 8/2018 | Crew et al. |
| 2019/0262458 A1 | 8/2019 | Gray et al. |
| 2019/0263823 A1 | 8/2019 | Bradner et al. |

FOREIGN PATENT DOCUMENTS

| | | |
|---|---|---|
| CN | 112457366 A | 3/2021 |
| CN | 112457367 A | 3/2021 |
| CN | 112574278 A | 3/2021 |
| CN | 113582974 A | 11/2021 |
| WO | WO-2016/197032 A1 | 12/2013 |
| WO | WO-2021/129653 A1 | 1/2021 |

OTHER PUBLICATIONS

Helin-Tanninen, M. "Oral solids." Practical Pharmaceutics: An International Guideline for the Preparation, Care and Use of Medicinal Products (2015): 51-75.*

Lto, N., "A medium-term rat liver bioassay for rapid in vivo detection of carcinogenic potential of chemicals." Cancer science 94.1 (2003): 3-8.*

Guo et al, Design of oxobenzimidazoles and oxindoles as novel androgen receptor antagonists, Bioorganic & Medicinal Chemistry Letters, vol. 22, pp. 2572-2578 (2012).

Xin Han et al., Discovery of ARD-69 as a Highly Potent Proteolysis Targeting Chimera (PROTAC) Degrader of Androgen Receptor (AR) for the Treatment of Prostate Cancer, J. Med. Chem., 62:941-964, (Jan. 10, 2019).

Jiantao Hu et al., Discovery of ERD-308 as a Highly Potent Proteolysis Targeting Chimera (PROTAC) Degrader of Estrogen Receptor (ER), J. Med. Chem., 62:1420-1442, (Jan. 18, 2019).

Mette Ishoey et al, The translation termination factor GSPT1 is a phenotypically relevant off-target of heterobifunctional phthalimide degraders, ACS Chem. Biol., 13(3):553-560 (2018).

Wei Li et al, Patent Overview of Phthalazinone-Type PARP Inhibitors Structural Modification Based on Patented Technologies in China, Guangzhou Chemical Industry, 47(9):34-40 (May 2019) Machine Translation in English.

Shyam Panga et al, Design, Synthesis, Characterization, and In Vitro Evaluation of Isatin-Pomalidomide Hybrids for Cytotoxicity against Multiple Myeloma Cell Lines, J. Heterocyclic Chem., 55(12):2919-2928 (2018).

Ran et al, Recent Developments in Androgen Receptor Antagonists, Arch. Pharm. Chem. Life Sci., 348:757-775 (2015).

Haiban Wei et al, The Application and Progress of Chimeric Molecules (DHT-PROTAC) in Prostate Cancer, Progress in Modern Biomedicine, 14(3):590-592 (2014). Machine Translation in English.

International Search Report and International Preliminary Report on Patentability for PCT/CN2021/099654 (Sep. 15, 2021)(6 pages).

Li Wei et al, Patent Overview of Phtalazinone-type PARP Inhibitors Structural Modification Based on Patented Technologies in China, Guangzhou Chemical Industry, 47(9):34-40 (May 2019).

* cited by examiner

PHTHALAZINONE COMPOUND, AND PREPARATION METHOD THEREFOR AND MEDICAL USE THEREOF

CROSS-REFERENCE TO RELATED APPLICATIONS

This application is a continuation of U.S. application Ser. No. 18/079,778 filed Dec. 12, 2022, which is a continuation of International Application No. PCT/CN2021/099654 filed Jun. 11, 2021, which claims priority to Chinese Application No. 202010536221.6 filed Jun. 12, 2020, Chinese Application No. 202011147078.8 filed Oct. 23, 2020, Chinese Application No. 202011261665.X filed Nov. 12, 2020, Chinese Application No. 202110485680.0 filed Apr. 30, 2021, and Chinese Application No. 202110614030.1 filed Jun. 2, 2021. The above-mentioned Chinese patent applications are incorporated herein by reference in its entirety. This application is related to U.S. application Ser. No. 18/131,309 filed Apr. 5, 2023, issued as U.S. Pat. No. 11,767,312.

BACKGROUND

Prostate cancer (PCa), which is one of the most common cancers worldwide, is the second major cancer killer leading to death in adult males in the world. The prostate cancer has no significant symptoms and grows relatively slowly at early stage, and may have symptoms such as frequent urination, dysuria, hematuria and odynuria at late stage and probably metastasize to other parts. Therefore, a patient concerned is generally found to have an advanced cancer. In the US, the prostate cancer with an incidence exceeding that of lung cancer, has ranked first in the dangers to health of males. The number of new patients with prostate cancer in China in 2016 was 120,000, which is estimated to reach 237,000 by 2030, with a compound annual growth rate of 5% for the number of new patients. It also means that in the next 10 years, the incidence of prostate cancer in China will enter a peak period, and such cancer will become the first cancer killer in men. Due to a low early diagnosis rate, the mortality rate of prostate cancer patients in China is much higher than that in developed countries. In the US, the survival rate of patients with the disease for 5 years is more than 98%, while the survival rate of the same patients in China is only 50%.

The prostate cancer is an androgen-dependent tumor, and androgens can stimulate prostate cancer cell growth and result in disease progression. Endocrine therapy is one of the conventional treatment means. For example, the treatment standard for advanced PCa is androgen deprivation therapy (ADT), such as surgical castration (bilateral orchiectomy)/drug castration (such as injection of Zoladex). The ADT therapy has a significant effect in the initial period of treatment, but as the disease progresses, the androgen receptor (AR) is subjected to mutation, and the mutated AR becomes more sensitive to a low level of androgens, driving the disease to progress to a castration-resistant prostate cancer (CRPC). Almost all patients with an advanced prostate cancer will eventually progress to the CRPC after receiving the endocrine therapy. Furthermore, up to 30% of the prostate cancer patients will develop to have a metastatic castration-resistant prostate cancer (mCRPC) within 10 years of initial treatment. At present, clinically, the patients diagnosed with an early focal prostate cancer are usually curable, but the patients diagnosed with asymptomatic or mildly-symptomatic metastatic castration-resistant prostate cancer (mCRPC) have no clinically curative options.

Oral drugs currently approved for treating the metastatic castration-resistant prostate cancer mainly comprise abiraterone and enzalutamide. Therein, abiraterone is a novel androgen biosynthesis inhibitor, which can block synthesis of androgen in the environment within testis, adrenal gland or tumor cells. However, enzalutamide is an androgen receptor inhibitor that can competitively inhibit the binding of androgen to a receptor. After binding to AR, the enzalutamide can further inhibit the nuclear transport of AR, thereby blocking the interaction between AR and DNA.

Despite being castration-refractory, CRPC still relies on an AR signaling axis for continuous growth. The mutation of AR reduces the small molecule antagonistic activity of a targeted AR, and even converts it into an AR agonist, which is clinically manifested as drug resistance. Therefore, a selective androgen receptor degrader (SARD) can not only inhibit the androgen receptor and block the process of androgen receptor signaling, but also degrade the receptor itself, thus bringing more benefits.

The present invention mainly relies on the proteolysis targeting chimeras (PROTAC) technology to afford a type of selective AR degraders (SARDs). The PROTAC technology mainly relies on an intracellular ubiquitin-proteasome system. The system is an intracellular "cleaner", and a main role of a ubiquitination system is to ubiquitinate the denatured, mutated or harmful proteins in the cells. The ubiquitinated proteins are degraded by the proteasome system inside the cells. The design idea of the PROTAC lies in that: one end of a molecule is an AR interaction fragment, and the other end is a ubiquitin-proteasome interaction fragment, and the two ends are linked to form a chimeric molecule by means of intermediate junction. PROTAC interacts with a target protein (AR) and the proteasome system at the same time, so that the proteasome and AR proteins are spatially close to each other, and thus the AR is degraded by ubiquitination.

The small molecule PROTAC technology was reported in 2008. Currently, only a small molecule drug ARV-110 (currently unknown in structure) based on AR degradation from Arvinas is in the Phase I clinical development. PROTAC technology belongs to the frontier field. In recent years, as shown in a large number of literature reports, PROTAC works by binding a degradation target and the ubiquitination system simultaneously. The action mechanism thereof is much more complicated than that of a traditional small molecule drug: the action mode of such molecules involves three-body binding kinetics, and is affected by PROTAC's own catalyst characteristics (and potential hook effect issues). Therefore, the molecular design idea of PROTAC is completely different from a small molecule design idea, and there is no obvious regularity at all. Common drug-chemical strategies, such as equivalent replacement of effective fragments, are not necessarily applicable in the design of such molecules.

At present, there is still a need to develop PROTAC molecules with a novel structure and used for AR degradation.

BRIEF SUMMARY

In an aspect of the present invention, the present invention proposes a compound as represented by formula (I), an optical isomer thereof and a pharmacodynamically acceptable salt thereof,

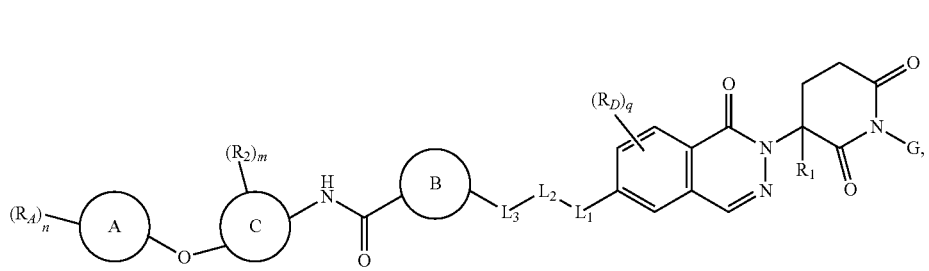

(I)

wherein R₁ is selected from H, F, Cl, Br, I and $C_{1-6}$ alkyl, and the $C_{1-6}$ alkyl is optionally substituted with 1, 2 or 3 R; G is selected from H, F, Cl, Br, I and $C_{1-6}$ alkyl, and the $C_{1-6}$ alkyl is optionally substituted with 1, 2 or 3 R; ring B is selected from phenyl and 5- to 6-membered heteroaryl, and the phenyl or 5- to 6-membered heteroaryl is optionally substituted with 1, 2 or 3 R; ring C is selected from $C_{4-6}$ cycloalkyl; $R_2$ is selected from H and $C_{1-6}$ alkyl, and the $C_{1-6}$ alkyl is optionally substituted with 1, 2 or 3 R; ring A is selected from 6- to 12-membered aryl and 5- to 12-membered heteroaryl; $R_A$ is selected from H, $NO_2$, halogen, $NH_2$, CN, $C_{1-6}$ alkyl and $C_{1-6}$ alkoxy, and the $C_{1-6}$ alkyl or $C_{1-6}$ alkoxy is optionally substituted with 1, 2 or 3 R; $R_D$ is selected from H, CN, halogen, $C_{1-6}$ alkyl, $C_{1-6}$ alkoxy, $C_{3-6}$ cycloalkyl and 3- to 6-membered heterocycloalkyl, and the $C_{1-6}$ alkyl, $C_{1-6}$ alkoxy, $C_{3-6}$ cycloalkyl or 3- to 6-membered heterocycloalkyl is optionally substituted with 1, 2 or 3 R; R is independently selected from H, F, Cl, Br, I, OH, $NH_2$ and $C_{1-6}$ alkyl respectively, and the $C_{1-6}$ alkyl is optionally substituted with 1, 2 or 3 R'; each $L_1$, $L_2$ and $L_3$ is independently selected from a single bond, O, S, NH, C(=O), S(=O), S(=O)₂, $C_{1-6}$ alkyl, —$C_{1-6}$ alkyl-O—, $C_{2-3}$ alkenyl, $C_{2-3}$ alkynyl, $C_{3-10}$ cycloalkyl, 3- to 10-membered heterocycloalkyl, phenyl and 5- to 9-membered heteroaryl respectively, and the $C_{1-6}$ alkyl, —$C_{1-6}$ alkyl-O—, $C_{2-3}$ alkenyl, $C_{2-3}$ alkynyl, $C_{3-10}$ cycloalkyl, 3- to 10-membered heterocycloalkyl, phenyl or 5- to 9-membered heteroaryl is optionally substituted with 1, 2 or 3 $R_L$; $R_L$ is independently selected from H, halogen, OH, $NH_2$, CN,

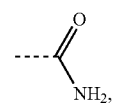

$C_{1-6}$ alkyl, $C_{3-6}$ cycloalkyl, $C_{1-6}$ alkyl-C(=O)—, $C_{1-6}$ alkoxy, $C_{1-6}$ alkylthio and $C_{1-6}$ alkylamino respectively, and the $C_{1-6}$ alkyl, $C_{3-6}$ cycloalkyl, $C_{1-6}$ alkyl-C(=O)—, $C_{1-6}$ alkoxy, $C_{1-6}$ alkylthio or $C_{1-6}$ alkylamino is optionally substituted with 1, 2 or 3 R'; R' is independently selected from H, halogen, $C_{1-6}$ alkyl, OH, $NH_2$,

$CH_3$, $CH_2F$, $CHF_2$ and $CF_3$ respectively; n is 0, 1, 2, 3 or 4; m is 0, 1, 2, 3 or 4; q is 1, 2, 3 or 4; the 3- to 10-membered heterocycloalkyl, 3- to 6-membered heterocycloalkyl, 5- to 12-membered heteroaryl, 5- to 6-membered heteroaryl or 5- to 9-membered heteroaryl comprises 1, 2 or 3 heteroatoms or heteroatom groups independently selected from O, NH, S, C(=O), C(=O)O, S(=O), S(=O)₂ and N.

In another aspect of the present invention, the present invention further proposes a compound as represented by formula (I-X-1) or formula (I-X-2), an optical isomer thereof and a pharmacodynamically acceptable salt thereof,

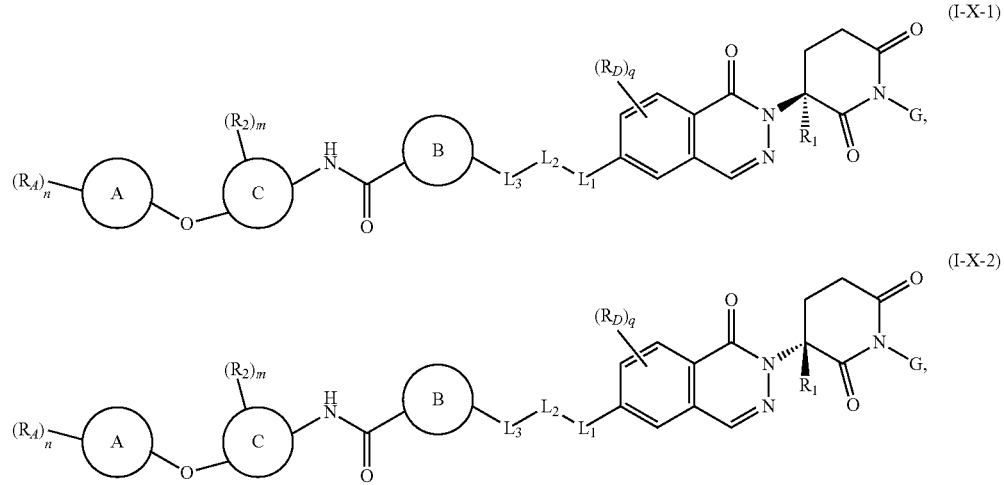

wherein ring A, ring B, ring C, R₁, R₂, R₄, R_D, G, L₁, L₂, L₃, m, n and q are as defined in the present invention.

In another aspect of the present invention, the present invention further proposes a compound as represented by formula (II), an optical isomer thereof and a pharmacodynamically acceptable salt thereof,

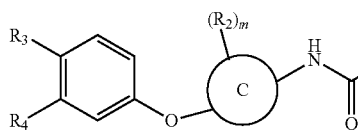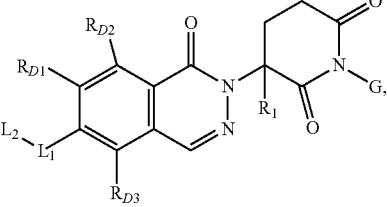

wherein R₁ is selected from H, F, Cl, Br, I and C₁₋₆ alkyl, and the C₁₋₆ alkyl is optionally substituted with 1, 2 or 3 R; G is selected from H, F, Cl, Br, I and C₁₋₆ alkyl, and the C₁₋₆ alkyl is optionally substituted with 1, 2 or 3 R; ring B is selected from phenyl and 5- to 6-membered heteroaryl, and the phenyl or 5- to 6-membered heteroaryl is optionally substituted with 1, 2 or 3 R; ring C is selected from C₄₋₆ cycloalkyl; R₂ is selected from H and C₁₋₆ alkyl, and the C₁₋₆ alkyl is optionally substituted with 1, 2 or 3 R; each R₃ and R₄ is independently selected from H, NO₂, halogen, NH₂, CN, C₁₋₆ alkyl and C₁₋₆ alkoxy respectively, and the C₁₋₆ alkyl or C₁₋₆ alkoxy is optionally substituted with 1, 2 or 3 R; each R_D1, R_D2 and R_D3 is independently selected from H, CN, halogen, C₁₋₆ alkyl and C₁₋₆ alkoxy respectively, and the C₁₋₆ alkyl or C₁₋₆ alkoxy is optionally substituted with 1, 2 or 3 R; R is independently selected from H, F, Cl, Br, I, OH, NH₂ and C₁₋₆ alkyl respectively, and the C₁₋₆ alkyl is optionally substituted with 1, 2 or 3 R'; each L₁, L₂ and L₃ is independently selected from a single bond, O, S, NH, C(=O), S(=O), S(=O)₂, C₁₋₆ alkyl, —C₁₋₆ alkyl-O—, C₂₋₃ alkenyl, C₂₋₃ alkynyl, C₃₋₁₀ cycloalkyl, 3- to 10-membered heterocycloalkyl, phenyl and 5-to 9-membered heteroaryl respectively, and the C₁₋₆ alkyl, —C₁₋₆ alkyl-O—, C₂₋₃ alkenyl, C₂₋₃ alkynyl, C₃₋₁₀ cycloalkyl, 3- to 10-membered heterocycloalkyl, phenyl or 5- to 9-membered heteroaryl is optionally substituted with 1, 2 or 3 R_L; R_L is independently selected from H, halogen, OH, NH₂, CN,

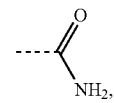

C₁₋₆ alkyl, C₃₋₆ cycloalkyl, C₁₋₆ alkyl-C(=O)—, C₁₋₆ alkoxy, C₁₋₆ alkylthio and C₁₋₆ alkylamino respectively, and the C₁₋₆ alkyl, C₃₋₆ cycloalkyl, C₁₋₆ alkyl-C(=O)—, C₁₋₆ alkoxy, C₁₋₆ alkylthio or C₁₋₆ alkylamino is optionally substituted with 1, 2 or 3 R'; R' is independently selected from H, halogen, C₁₋₆ alkyl, OH, NH₂, CH₃, CH₂F, CHF₂ and CF₃ respectively; m is 0, 1, 2, 3 or 4; the above-mentioned 3- to 10-membered heterocycloalkyl, 5- to 6-membered heteroaryl or 5- to 9-membered heteroaryl comprises 1, 2 or 3 heteroatoms or heteroatom groups independently selected from O, NH, S, C(=O), C(=O)O, S(=O), S(=O)₂ and N.

In another aspect of the present invention, the present invention further proposes a compound as represented by formula (II-A-1) or formula (II-A-2), an optical isomer thereof and a pharmacodynamically acceptable salt thereof,

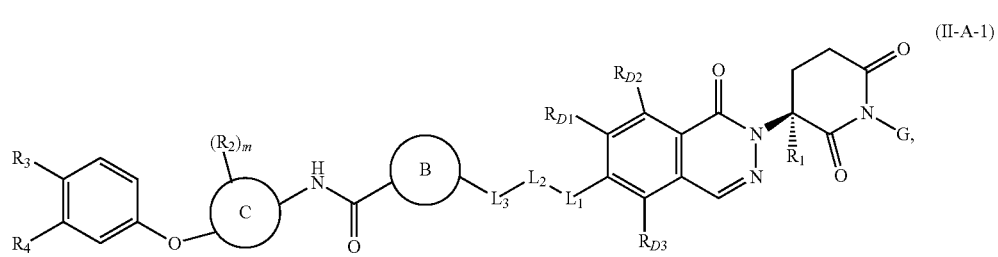

-continued

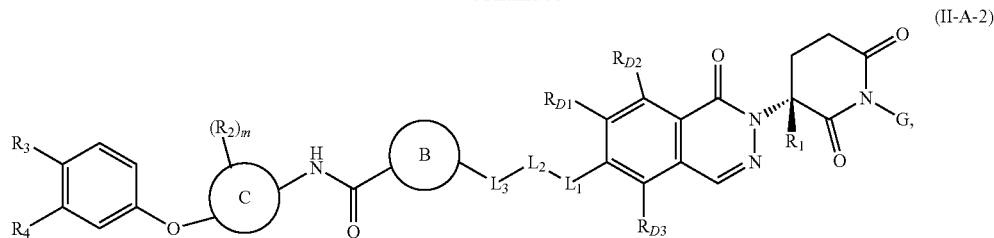
(II-A-2)

wherein ring B, ring C, $R_1$, $R_2$, $R_3$, $R_4$, $R_{D1}$, $R_{D2}$, $R_{D3}$, G, $L_1$, $L_2$, $L_3$ and m are as defined in the present invention.

In another aspect of the present invention, the present invention further proposes a compound as represented by formula (III), an optical isomer thereof and a pharmacodynamically acceptable salt thereof,

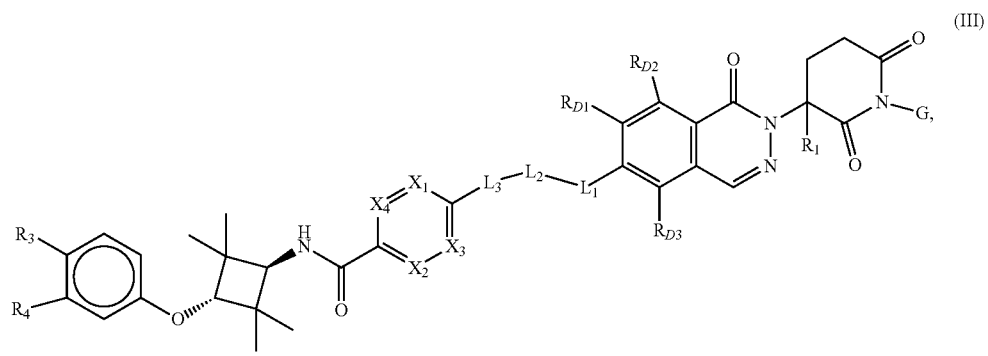
(III)

wherein $R_1$ is selected from H, F, Cl, Br, I and $C_{1-6}$ alkyl, and the $C_{1-6}$ alkyl is optionally substituted with 1, 2 or 3 R; G is selected from H, F, Cl, Br, I and $C_{1-6}$ alkyl, and the $C_{1-6}$ alkyl is optionally substituted with 1, 2 or 3 R; each $R_3$ and $R_4$ is independently selected from H, $NO_2$, halogen, $NH_2$, CN, $C_{1-6}$ alkyl and $C_{1-6}$ alkoxy respectively, and the $C_{1-6}$ alkyl or $C_{1-6}$ alkoxy is optionally substituted with 1, 2 or 3 R; each $X_1$, $X_2$, $X_3$ and $X_4$ is independently selected from C(R) and N respectively; each $R_{D1}$, $R_{D2}$ and $R_{D3}$ is independently selected from H, CN, halogen, $C_{1-6}$ alkyl and $C_{1-6}$ alkoxy respectively, and the $C_{1-6}$ alkyl or $C_{1-6}$ alkoxy is optionally substituted with 1, 2 or 3 R; R is independently selected from H, F, Cl, Br, I, OH, $NH_2$ and $C_{1-6}$ alkyl respectively, and the $C_{1-6}$ alkyl is optionally substituted with 1, 2 or 3 R'; each $L_1$, $L_2$ and $L_3$ is independently selected from a single bond, O, S, NH, C(=O), S(=O), S(=O)$_2$, $C_{1-6}$ alkyl, —$C_{1-6}$ alkyl-O—, $C_{2-3}$ alkenyl, $C_{2-3}$ alkynyl, $C_{3-10}$ cycloalkyl, 3- to 10-membered heterocycloalkyl, phenyl and 5- to 9-membered heteroaryl respectively, and the $C_{1-6}$ alkyl, —$C_{1-6}$ alkyl-O—, $C_{2-3}$ alkenyl, $C_{2-3}$ alkynyl, $C_{3-10}$ cycloalkyl, 3- to 10-membered heterocycloalkyl, phenyl or 5- to 9-membered heteroaryl is optionally substituted with 1, 2 or 3 $R_L$; $R_L$ is independently selected from H, halogen, OH, $NH_2$, CN,

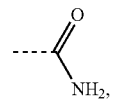

$C_{1-6}$ alkyl, $C_{3-6}$ cycloalkyl, $C_{1-6}$ alkyl-C(=O)—, $C_{1-6}$ alkoxy, $C_{1-6}$ alkylthio and $C_{1-6}$ alkylamino respectively, and the $C_{1-6}$ alkyl, $C_{3-6}$ cycloalkyl, $C_{1-6}$ alkyl-C(=O)—, $C_{1-6}$ alkoxy, $C_{1-6}$ alkylthio or $C_{1-6}$ alkylamino is optionally substituted with 1, 2 or 3 R'; R' is independently selected from H, halogen, $C_{1-6}$ alkyl, OH, $NH_2$,

$CH_3$, $CH_2F$, $CHF_2$ and $CF_3$ respectively; the above-mentioned 3- to 10-membered heterocycloalkyl, 5- to 6-membered heteroaryl or 5- to 9-membered heteroaryl comprises 1, 2 or 3 heteroatoms or heteroatom groups independently selected from O, NH, S, C(=O), C(=O)O, S(=O), S(=O)$_2$ and N.

In yet another aspect of the present invention, the present invention further proposes a compound as represented by formula (III-A-1) or formula (III-A-2), an optical isomer thereof and a pharmacodynamically acceptable salt thereof,

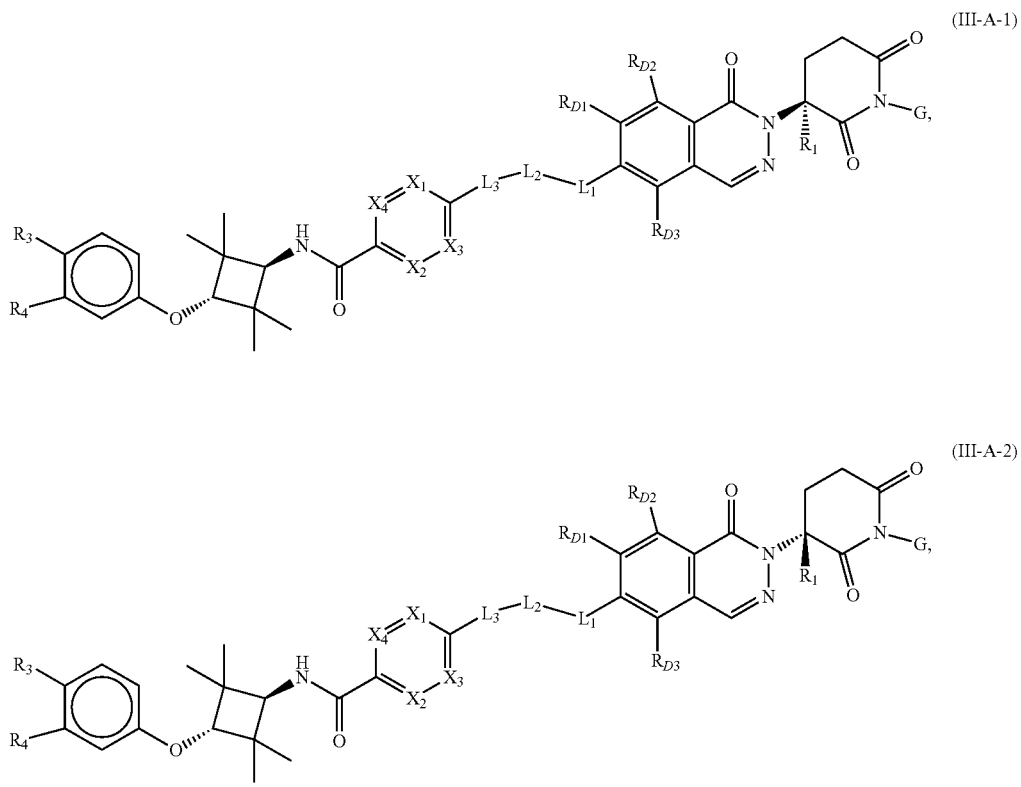

(III-A-1)

(III-A-2)

wherein $R_1$, $R_3$, $R_4$, $R_{D1}$, $R_{D2}$, $R_{D3}$, G, $L_1$, $L_2$, $L_3$, $X_1$, $X_2$, $X_3$ and $X_4$ are as defined in the present invention.

In yet another aspect of the present invention, the present invention further proposes a compound as represented by formula (I-A), an optical isomer thereof and a pharmacodynamically acceptable salt thereof,

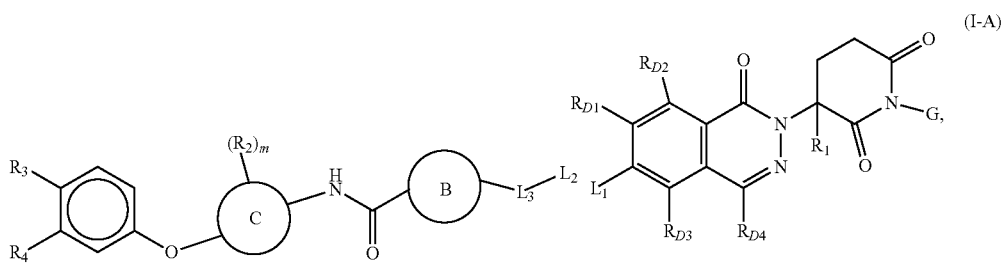

(I-A)

wherein $R_1$ is selected from H, F, Cl, Br, I and $C_{1-6}$ alkyl, and the $C_{1-6}$ alkyl is optionally substituted with 1, 2 or 3 R; G is selected from H, F, Cl, Br, I and $C_{1-6}$ alkyl, and the $C_{1-6}$ alkyl is optionally substituted with 1, 2 or 3 R; ring B is selected from phenyl and 5- to 6-membered heteroaryl, and the phenyl or 5- to 6-membered heteroaryl is optionally substituted with 1, 2 or 3 R; ring C is selected from $C_{4-6}$ cycloalkyl; $R_2$ is selected from H and $C_{1-6}$ alkyl, and the $C_{1-6}$ alkyl is optionally substituted with 1, 2 or 3 R; each $R_3$ and $R_4$ is independently selected from H, $NO_2$, halogen, $NH_2$, CN, $C_{1-6}$ alkyl and $C_{1-6}$ alkoxy respectively, and the $C_{1-6}$ alkyl or $C_{1-6}$ alkoxy is optionally substituted with 1, 2 or 3 R; each $R_{D1}$, $R_{D2}$ and $R_{D3}$ is independently selected from H, CN, halogen, $C_{1-6}$ alkyl and $C_{1-6}$ alkoxy respectively, and the $C_{1-6}$ alkyl or $C_{1-6}$ alkoxy is optionally substituted with 1, 2 or 3 R; $R_{D4}$ is independently selected from H, CN, halogen, $C_{1-6}$ alkyl, $C_{1-6}$ alkoxy, $C_{3-6}$ cycloalkyl and 3- to 6-membered heterocycloalkyl respectively, and the $C_{1-6}$ alkyl, $C_{3-6}$ cycloalkyl or 3- to 6-membered heterocycloalkyl is optionally substituted with 1, 2 or 3 R; R is independently selected from H, F, Cl, Br, I, OH, $NH_2$ and $C_{1-6}$ alkyl respectively, and the $C_{1-6}$ alkyl is optionally substituted with 1, 2 or 3 R'; each $L_1$, $L_2$ and $L_3$ is independently selected from a single bond, O, S, NH, C(=O), S(=O), S(=O)$_2$, $C_{1-6}$ alkyl, —$C_{1-6}$ alkyl-O—, $C_{2-3}$ alkenyl, $C_{2-3}$ alkynyl, $C_{3-10}$ cycloalkyl, 3-to 10-membered heterocycloalkyl, phenyl and 5- to 9-membered heteroaryl respectively, and the $C_{1-6}$ alkyl, —$C_{1-6}$ alkyl-O—, $C_{2-3}$ alkenyl, $C_{2-3}$ alkynyl, $C_{3-10}$ cycloalkyl, 3- to 10-membered heterocycloalkyl, phenyl or 5- to 9-membered heteroaryl is optionally substituted with 1, 2 or 3 $R_L$; $R_L$ is independently selected from H, halogen, OH, $NH_2$, CN,

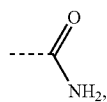

$C_{1-6}$ alkyl, $C_{3-6}$ cycloalkyl, $C_{1-6}$ alkyl-C(=O)—, $C_{1-6}$ alkoxy, $C_{1-6}$ alkylthio and $C_{1-6}$ alkylamino respectively, and the $C_{1-6}$ alkyl, $C_{3-6}$ cycloalkyl, $C_{1-6}$ alkyl-C(=O)—, $C_{1-6}$ alkoxy, $C_{1-6}$ alkylthio or $C_{1-6}$ alkylamino is optionally substituted with 1, 2 or 3 R'; R' is independently selected from H, halogen, $C_{1-6}$ alkyl, OH, $NH_2$, $CH_3$, $CH_2F$, $CHF_2$ and $CF_3$ respectively; m is 0, 1, 2, 3 or 4; the 3- to 10-membered heterocycloalkyl, 3- to 6-membered heterocycloalkyl, 5- to 6-membered heteroaryl or 5- to 9-membered heteroaryl comprises 1, 2 or 3 heteroatoms or heteroatom groups independently selected from O, NH, S, C(=O), C(=O)O, S(=O), S(=O)$_2$ and N.

In yet another aspect of the present invention, the present invention further provides a compound represented by formula (I-A-1) or formula (I-A-2), an optical isomer thereof and a pharmacodynamically acceptable salt thereof,

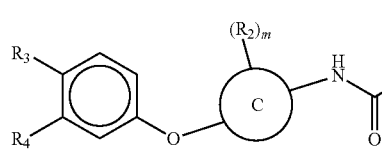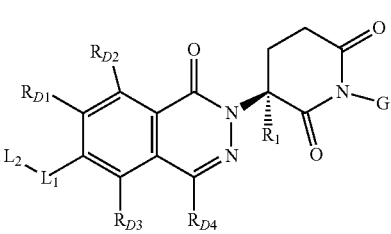

(I-A-1)

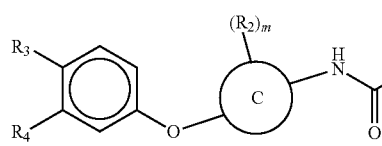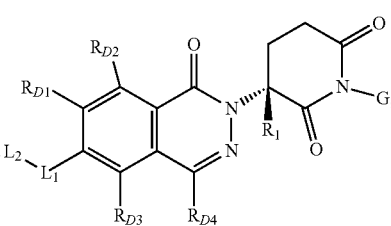

(I-A-2)

wherein ring B, ring C, $R_1$, $R_2$, $R_3$, $R_4$, $R_{D1}$, $R_{D2}$, $R_{D3}$, $R_{D4}$, G, $L_1$, $L_2$, $L_3$ and m are as defined in the present invention.

In yet another aspect of the present invention, the present invention further proposes a compound as represented by formula (I-B), an optical isomer thereof and a pharmacodynamically acceptable salt thereof,

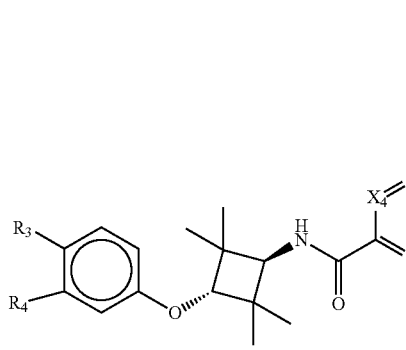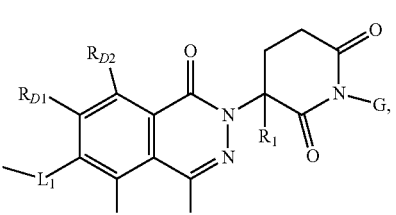

(I-B)

wherein $R_1$ is selected from H, F, Cl, Br, I and $C_{1-6}$ alkyl, and the $C_{1-6}$ alkyl is optionally substituted with 1, 2 or 3 R; G is selected from H, F, Cl, Br, I and $C_{1-6}$ alkyl, and the $C_{1-6}$ alkyl is optionally substituted with 1, 2 or 3 R; each $R_3$ and $R_4$ is independently selected from H, $NO_2$, halogen, $NH_2$, CN, $C_{1-6}$ alkyl and $C_{1-6}$ alkoxy respectively, and the $C_{1-6}$ alkyl or $C_{1-6}$ alkoxy is optionally substituted with 1, 2 or 3 R; each $X_1$, $X_2$, $X_3$ and $X_4$ is independently selected from C(R) and N respectively; each $R_{D1}$, $R_{D2}$ and $R_{D3}$ is independently selected from H, CN, halogen, $C_{1-6}$ alkyl and $C_{1-6}$ alkoxy respectively, and the $C_{1-6}$ alkyl or $C_{1-6}$ alkoxy is optionally substituted with 1, 2 or 3 R; $R_{D4}$ is independently selected from H, CN, halogen, $C_{1-6}$ alkyl, $C_{1-6}$ alkoxy, $C_{3-6}$ cycloalkyl and 3- to 6-membered heterocycloalkyl respectively, and the $C_{1-6}$ alkyl, $C_{3-6}$ cycloalkyl or 3- to 6-membered heterocycloalkyl is optionally substituted with 1, 2 or 3 R; R is independently selected from H, F, Cl, Br, I, OH, $NH_2$ and $C_{1-6}$ alkyl respectively, and the $C_{1-6}$ alkyl is optionally substituted with 1, 2 or 3 R';

$C_{1-6}$ alkyl, $C_{3-6}$ cycloalkyl, $C_{1-6}$ alkyl-C(=O)—, $C_{1-6}$ alkoxy, $C_{1-6}$ alkylthio and $C_{1-6}$ alkylamino respectively, and the $C_{1-6}$ alkyl, $C_{3-6}$ cycloalkyl, $C_{1-6}$ alkyl-C(=O)—, $C_{1-6}$ alkoxy, $C_{1-6}$ alkylthio or $C_{1-6}$ alkylamino is optionally substituted with 1, 2 or 3 R'; R' is independently selected from H, halogen, $C_{1-6}$ alkyl, OH, $NH_2$,

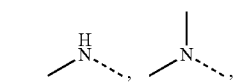

$CH_3$, $CH_2F$, $CHF_2$ and $CF_3$ respectively; the 3- to 10-membered heterocycloalkyl, 3- to 6-membered heterocycloalkyl or 5- to 9-membered heteroaryl comprises 1, 2 or 3 heteroatoms or heteroatom groups independently selected from O, NH, S, C(=O), C(=O)O, S(=O), $S(=O)_2$ and N.

In yet another aspect of the present invention, the present invention further provides a compound as represented by formula (I-B-1) or formula (I-B-2), an optical isomer thereof and a pharmacodynamically acceptable salt thereof,

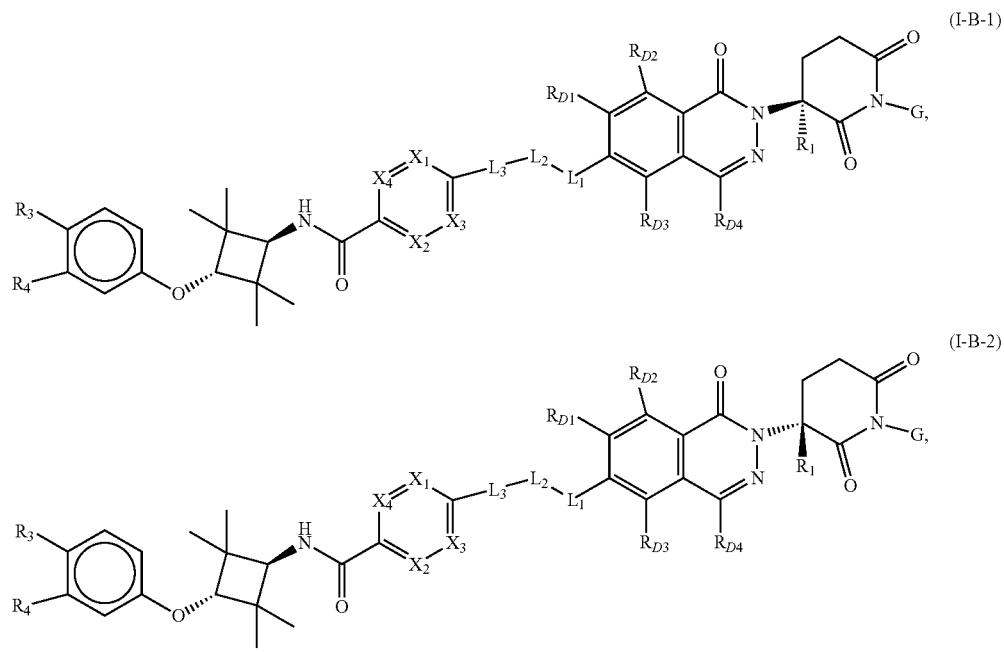

each $L_1$, $L_2$ and $L_3$ is independently selected from a single bond, O, S, NH, C(=O), S(=O), $S(=O)_2$, $C_{1-6}$ alkyl, —$C_{1-6}$ alkyl-O—, $C_{2-3}$ alkenyl, $C_{2-3}$ alkynyl, $C_{3-10}$ cycloalkyl, 3- to 10-membered heterocycloalkyl, phenyl and 5- to 9-membered heteroaryl respectively, and the $C_{1-6}$ alkyl, —$C_{1-6}$ alkyl-O—, $C_{2-3}$ alkenyl, $C_{2-3}$ alkynyl, $C_{3-10}$ cycloalkyl, 3- to 10-membered heterocycloalkyl, phenyl or 5- to 9-membered heteroaryl is optionally substituted with 1, 2 or 3 $R_L$; $R_L$ is independently selected from H, halogen, OH, $NH_2$, CN,

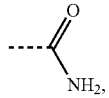

wherein $R_1$, $R_3$, $R_4$, $R_{D1}$, $R_{D2}$, $R_{D3}$, $R_{D4}$, $L_1$, $L_2$, $L_3$, $X_1$, $X_2$, $X_3$, $X_4$ and G are as defined previously.

In some schemes of the present invention, the above-mentioned ring A is selected from phenyl, and other variables are as defined in the present invention.

In some schemes of the present invention, the above-mentioned each $R_3$ and $R_4$ is independently selected from H, $NO_2$, F, Cl, Br, I, $NH_2$, CN, $CF_3$, methyl, ethyl, n-propyl, isopropyl, methoxy and ethoxy respectively, and other variables are as defined in the present invention.

In some schemes of the present invention, the above-mentioned $R_2$ is selected from H, methyl and ethyl, and other variables are as defined in the present invention.

In some schemes of the present invention, the above-mentioned ring C is selected from cyclobutyl and cyclohexanyl, and other variables are as defined in the present invention.

In some schemes of the present invention, the above-mentioned building block

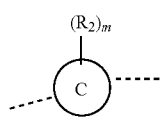

is selected from

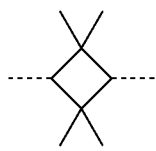

and

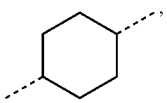

and other variables are as defined in the present invention.

In some schemes of the present invention, the above-mentioned ring B is selected from phenyl, pyridyl, pyridazinyl, pyrimidinyl and pyrazinyl, and the phenyl, pyridyl, pyridazinyl, pyrimidinyl or pyrazinyl is optionally substituted with 1, 2 or 3 R, and other variables are as defined in the present invention.

In some schemes of the present invention, the above-mentioned building block

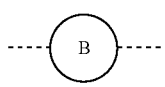

is selected from

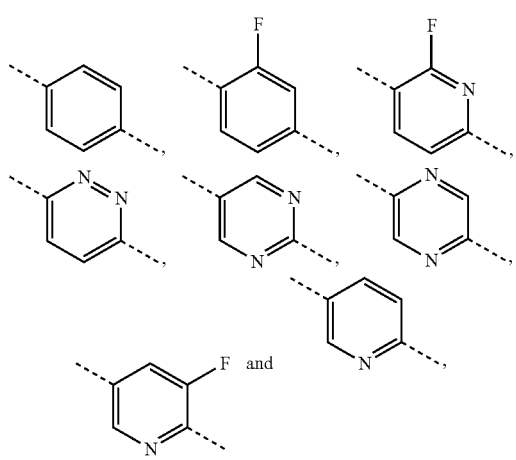

and other variables are as defined in the present invention.

In some schemes of the present invention, the above-mentioned each $L_1$, $L_2$ and $L_3$ are independently a single bond, O, S, NH, C(=O), S(=O), S(=O)$_2$, $C_{1-3}$ alkyl, —$C_{1-3}$ alkyl-O—, $C_{2-3}$ alkenyl, $C_{2-3}$ alkynyl, $C_{3-6}$ cycloalkyl, 4- to 8-membered heterocycloalkyl, phenyl and 5- to 6-membered heteroaryl respectively, and the $C_{1-3}$ alkyl, —$C_{1-3}$ alkyl-O—, $C_{2-3}$ alkenyl, $C_{2-3}$ alkynyl, $C_{3-6}$ cycloalkyl, 4- to 8-membered heterocycloalkyl, phenyl or 5- to 6-membered heteroaryl is optionally substituted with 1, 2 or 3 $R_L$; other variables are as defined in the present invention.

In some schemes of the present invention, the above-mentioned $R_L$ is independently selected from H, halogen, OH, NH$_2$, CN,

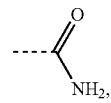

$C_{1-3}$ alkyl, $C_{3-6}$ cycloalkyl, $C_{1-3}$ alkyl-C(=O)—, $C_{1-3}$ alkoxy, $C_{1-3}$ alkylthio and $C_{1-3}$ alkylamino respectively, and the $C_{1-3}$ alkyl, $C_{3-6}$ cycloalkyl, $C_{1-3}$ alkyl-C(=O)—, $C_{1-3}$ alkoxy, $C_{1-3}$ alkylthio or $C_{1-3}$ alkylamino is optionally substituted with 1, 2 or 3 R'; other variables are as defined in the present invention.

In some schemes of the present invention, the above-mentioned each $L_1$, $L_2$ and $L_3$ are independently a single bond, O, S, NH, C(=O), S(=O), S(=O)$_2$, CH$_2$,

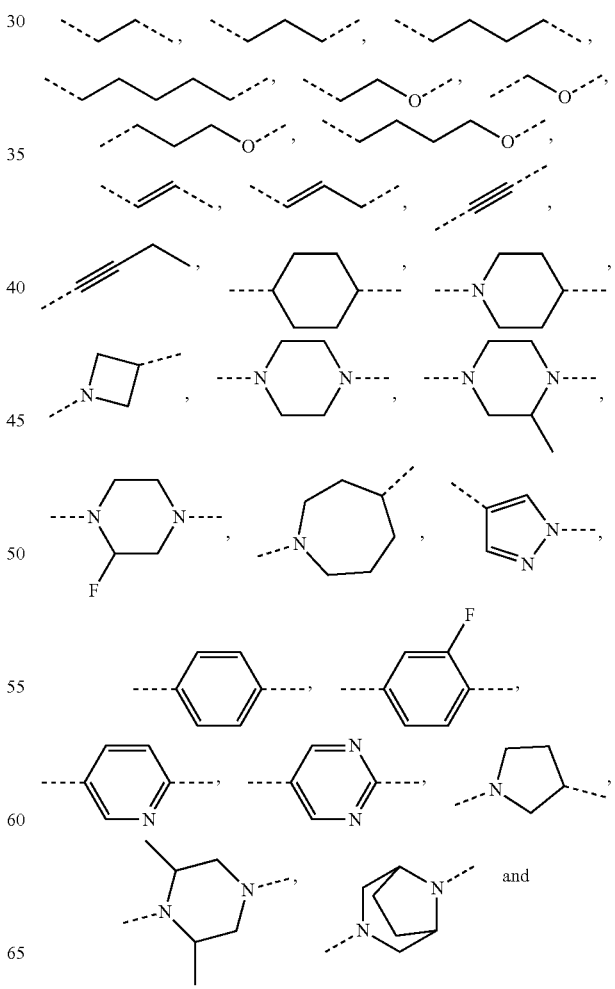

-continued
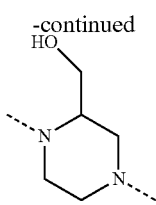
respectively, and other variables are as defined in the present invention.
In some schemes of the present invention, the above-mentioned building block
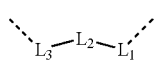
is selected from
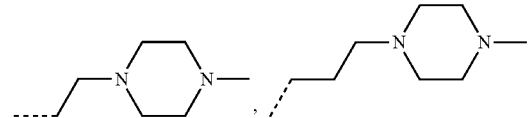
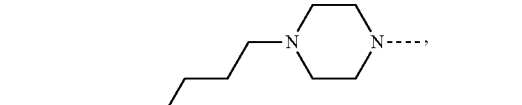
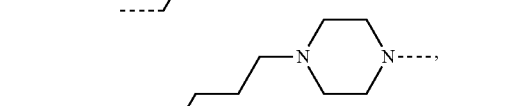
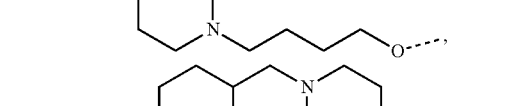
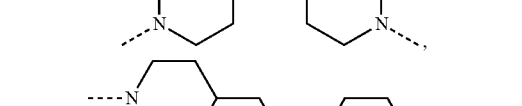
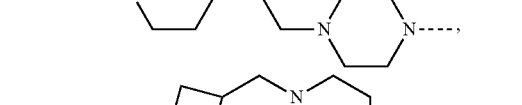
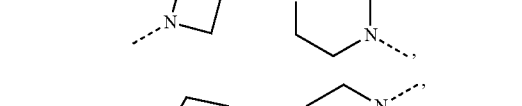
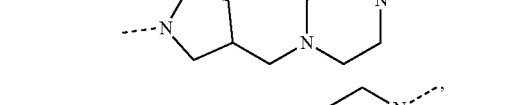
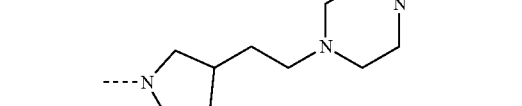
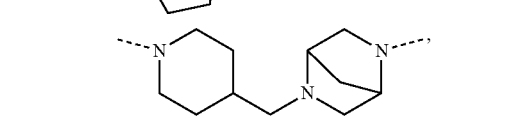
-continued
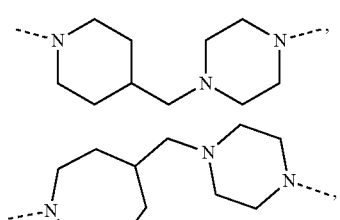
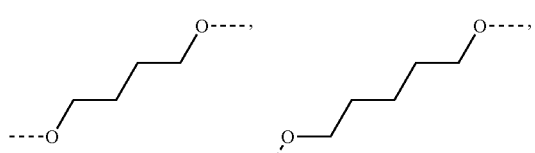
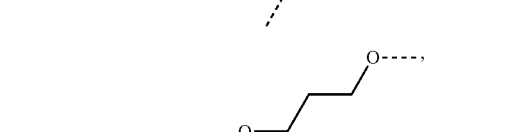
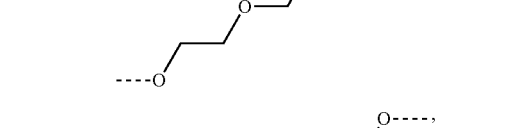
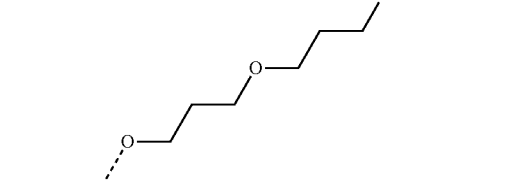
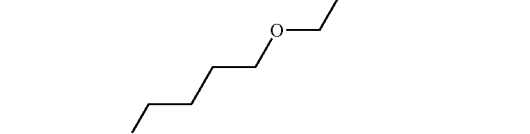
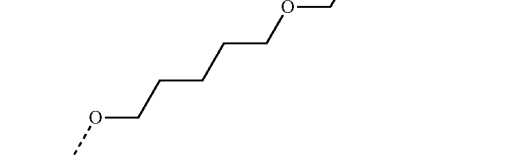
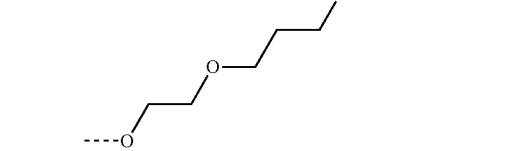
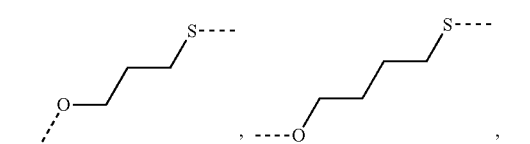

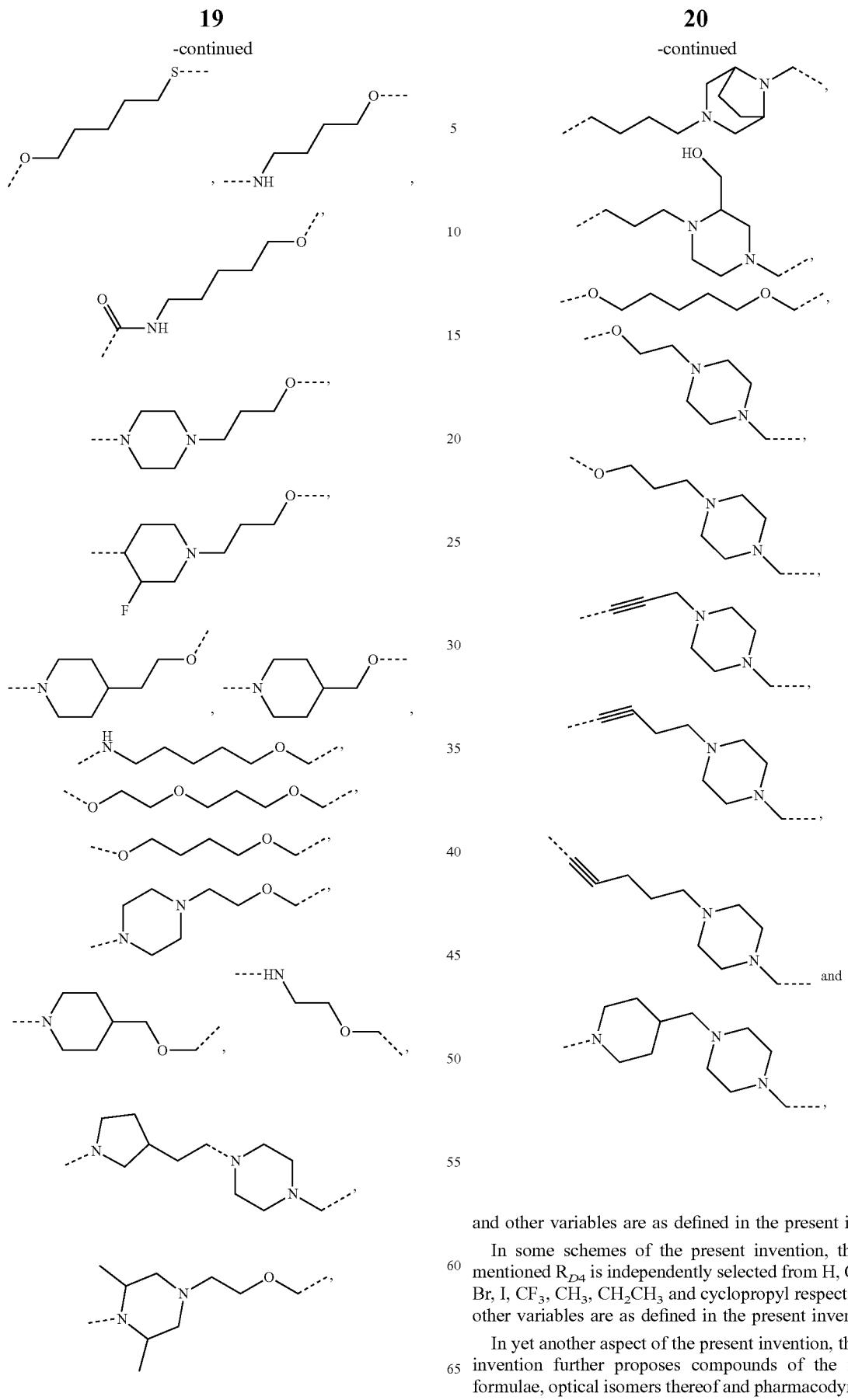

and other variables are as defined in the present invention.

In some schemes of the present invention, the above-mentioned $R_{D4}$ is independently selected from H, CN, F, Cl, Br, I, $CF_3$, $CH_3$, $CH_2CH_3$ and cyclopropyl respectively, and other variables are as defined in the present invention.

In yet another aspect of the present invention, the present invention further proposes compounds of the following formulae, optical isomers thereof and pharmacodynamically acceptable salts thereof, which are selected from 21 22
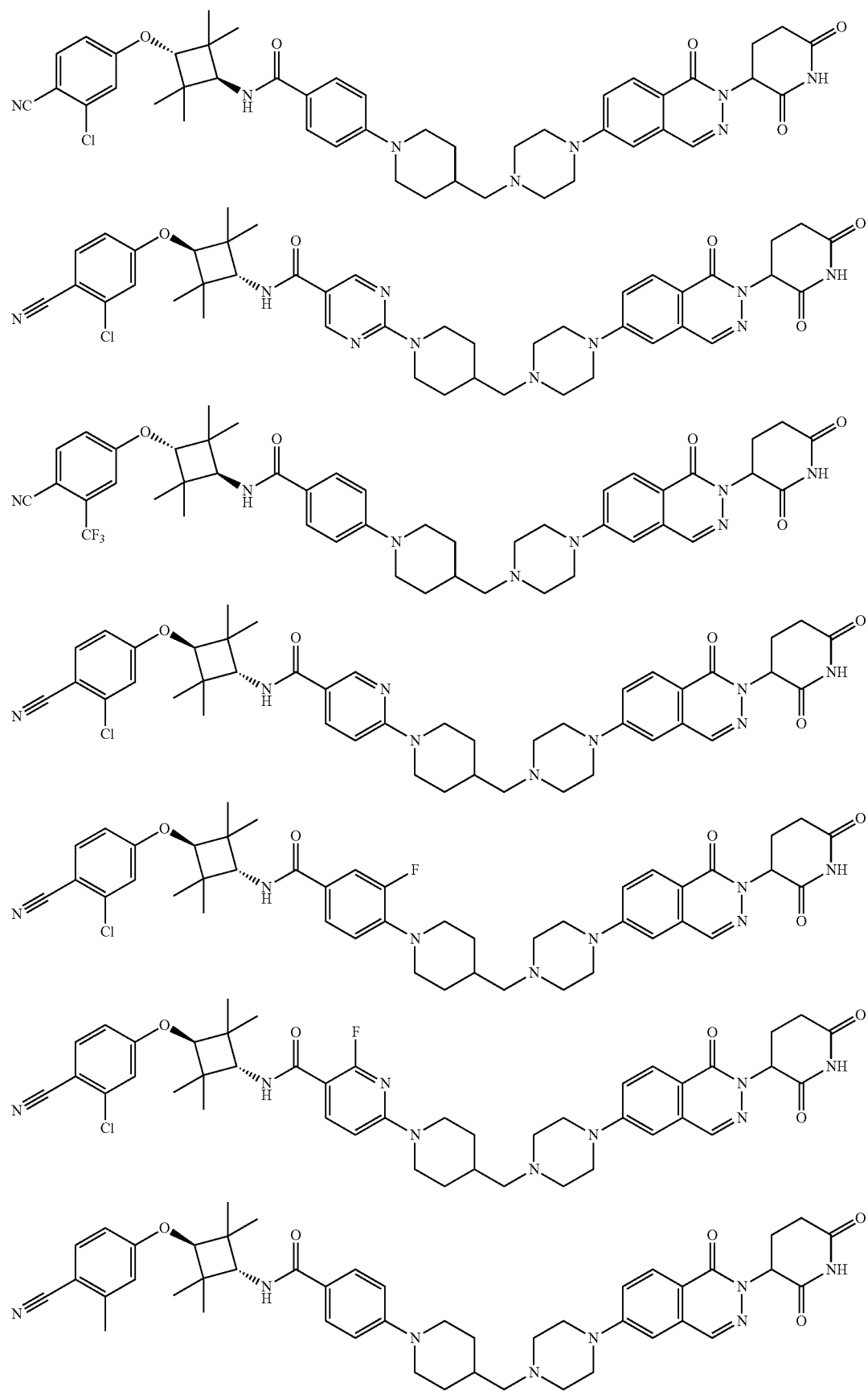

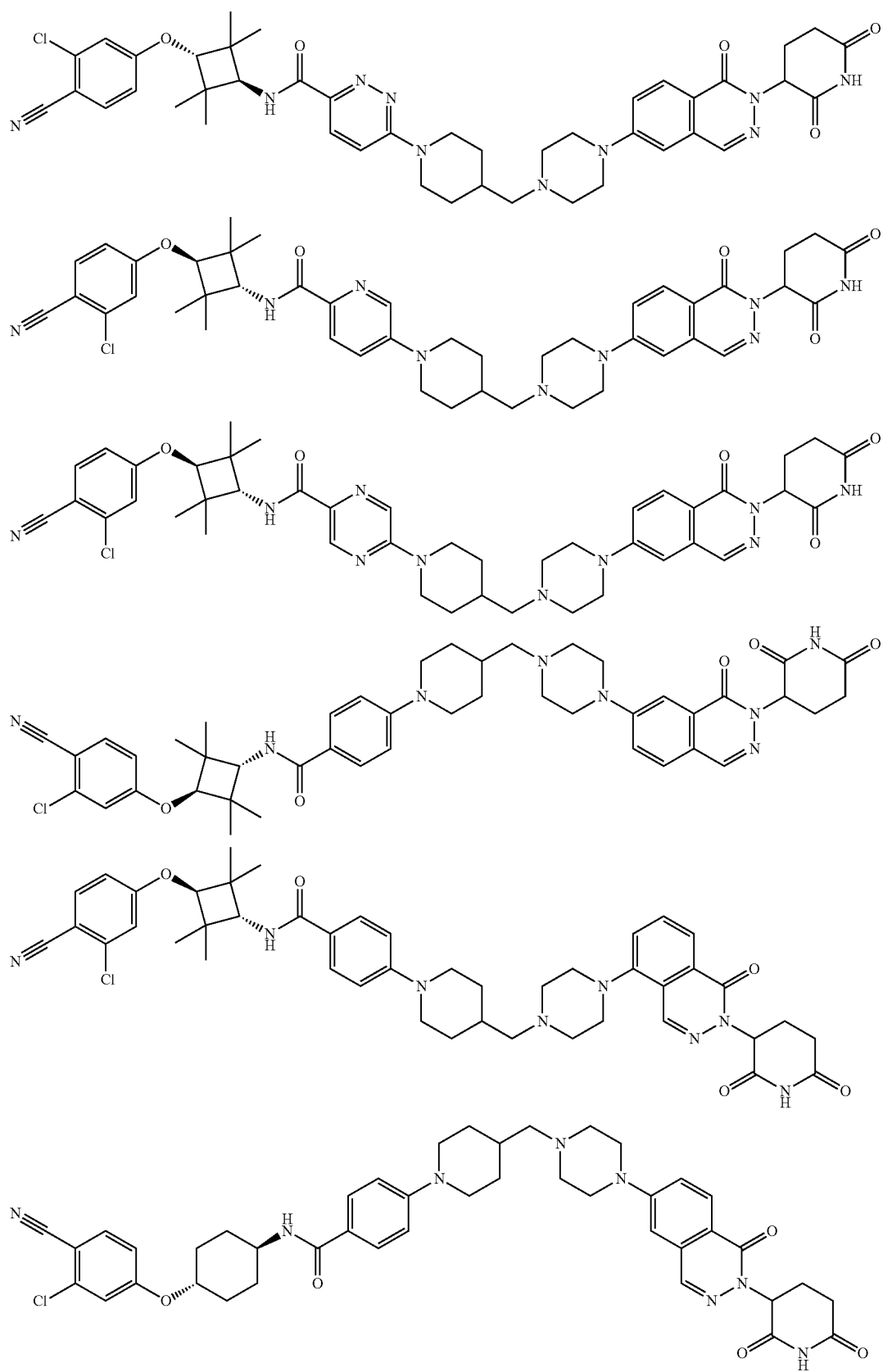

-continued
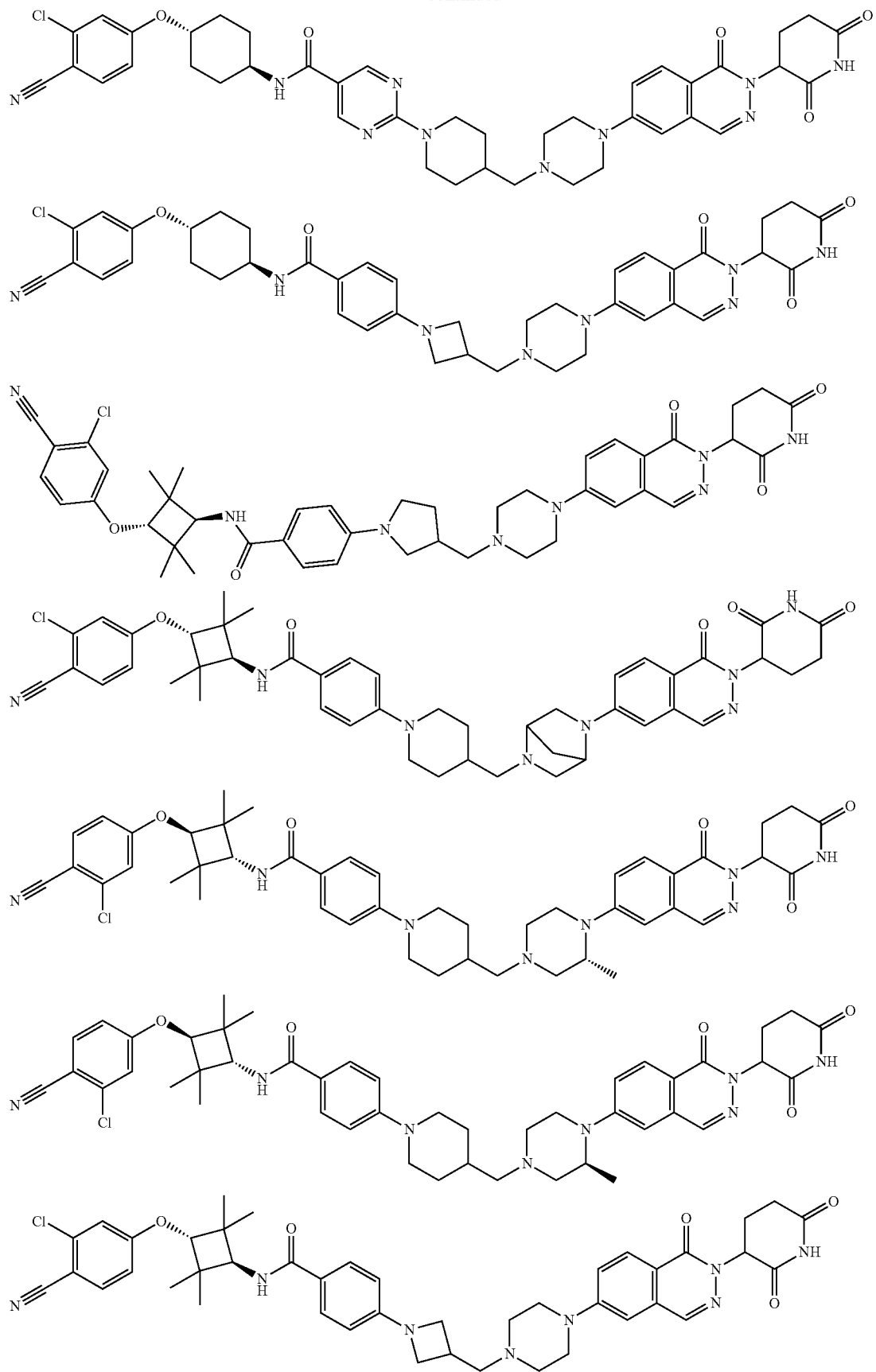

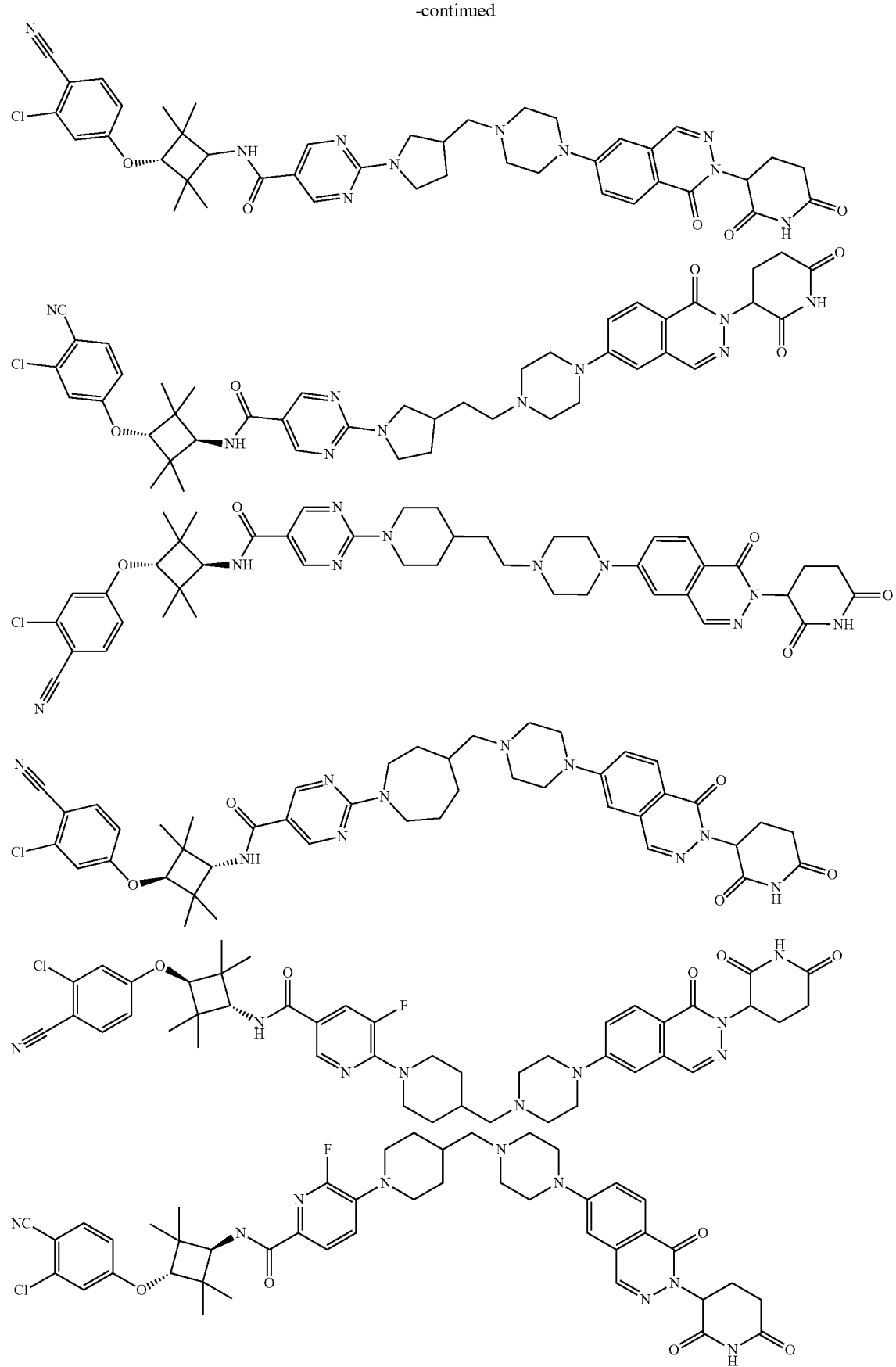

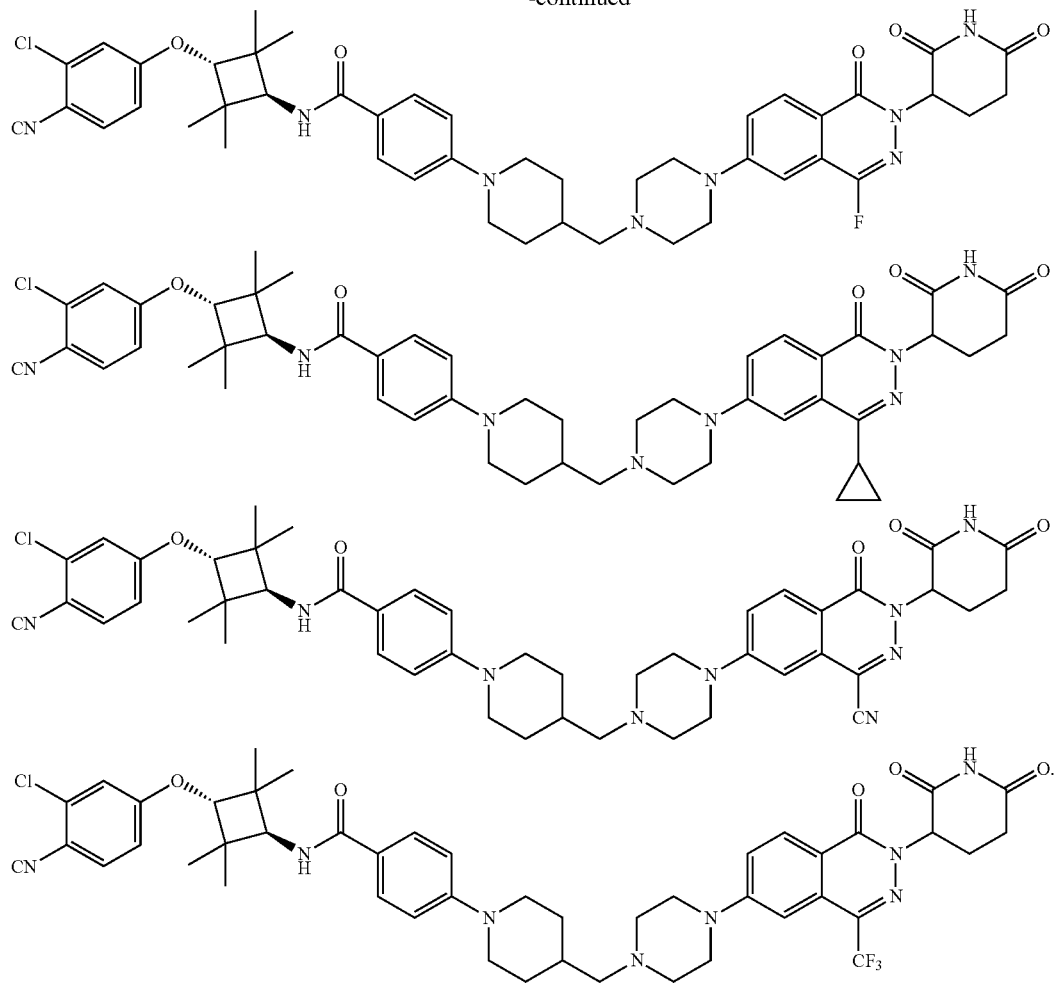
In yet another aspect of the present invention, the present invention further proposes compounds of the following formulae, optical isomers thereof and pharmacodynamically acceptable salts thereof, which are selected from
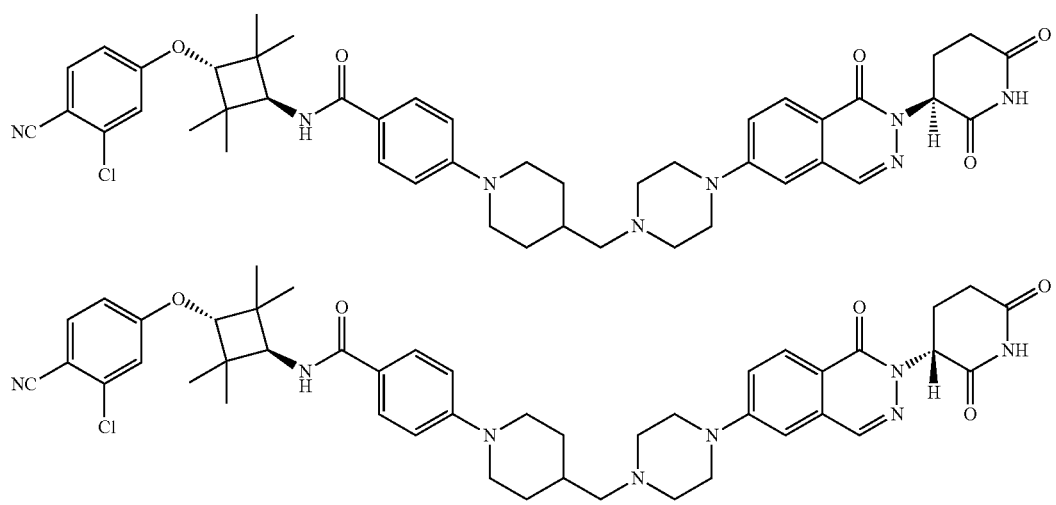

-continued
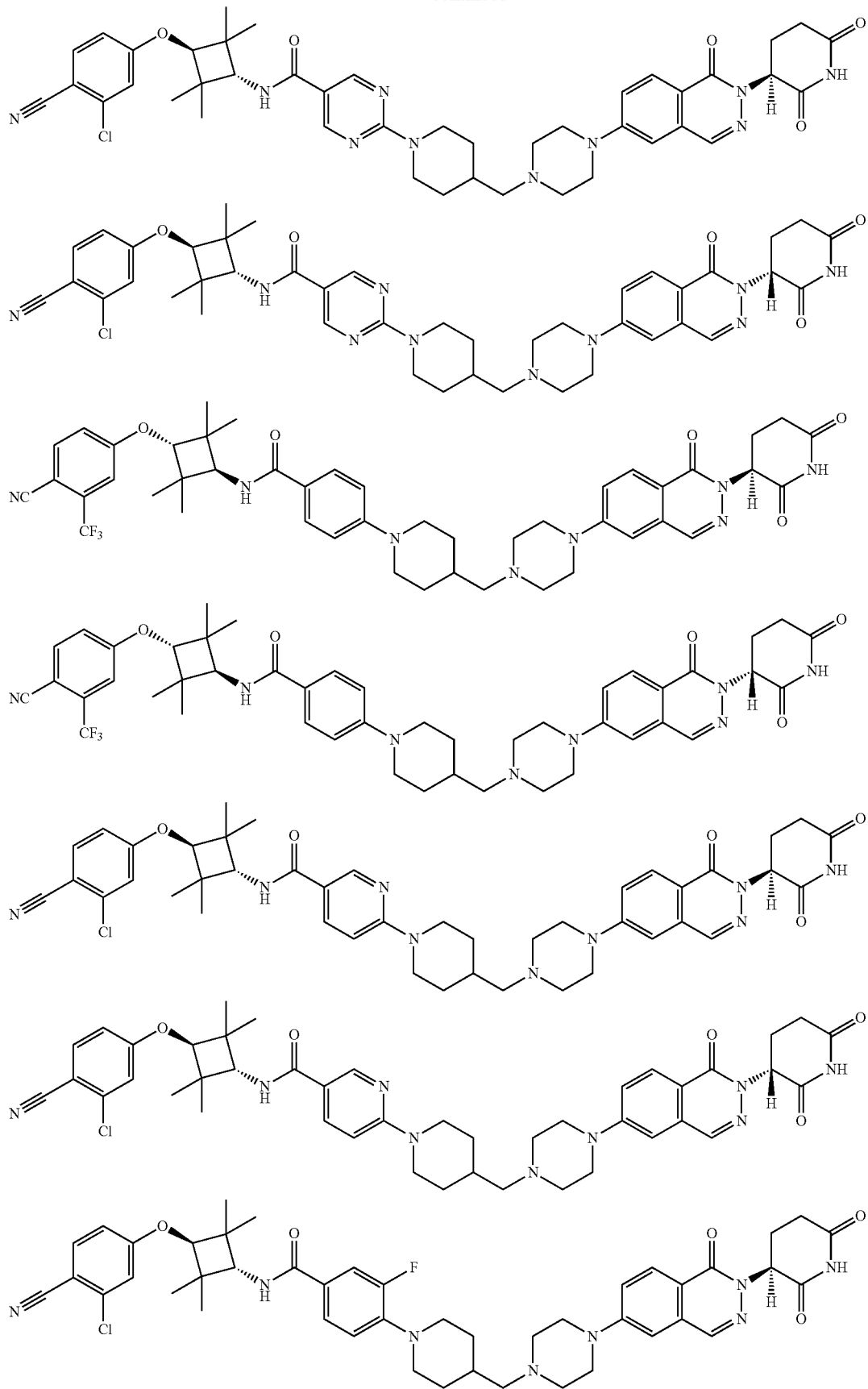

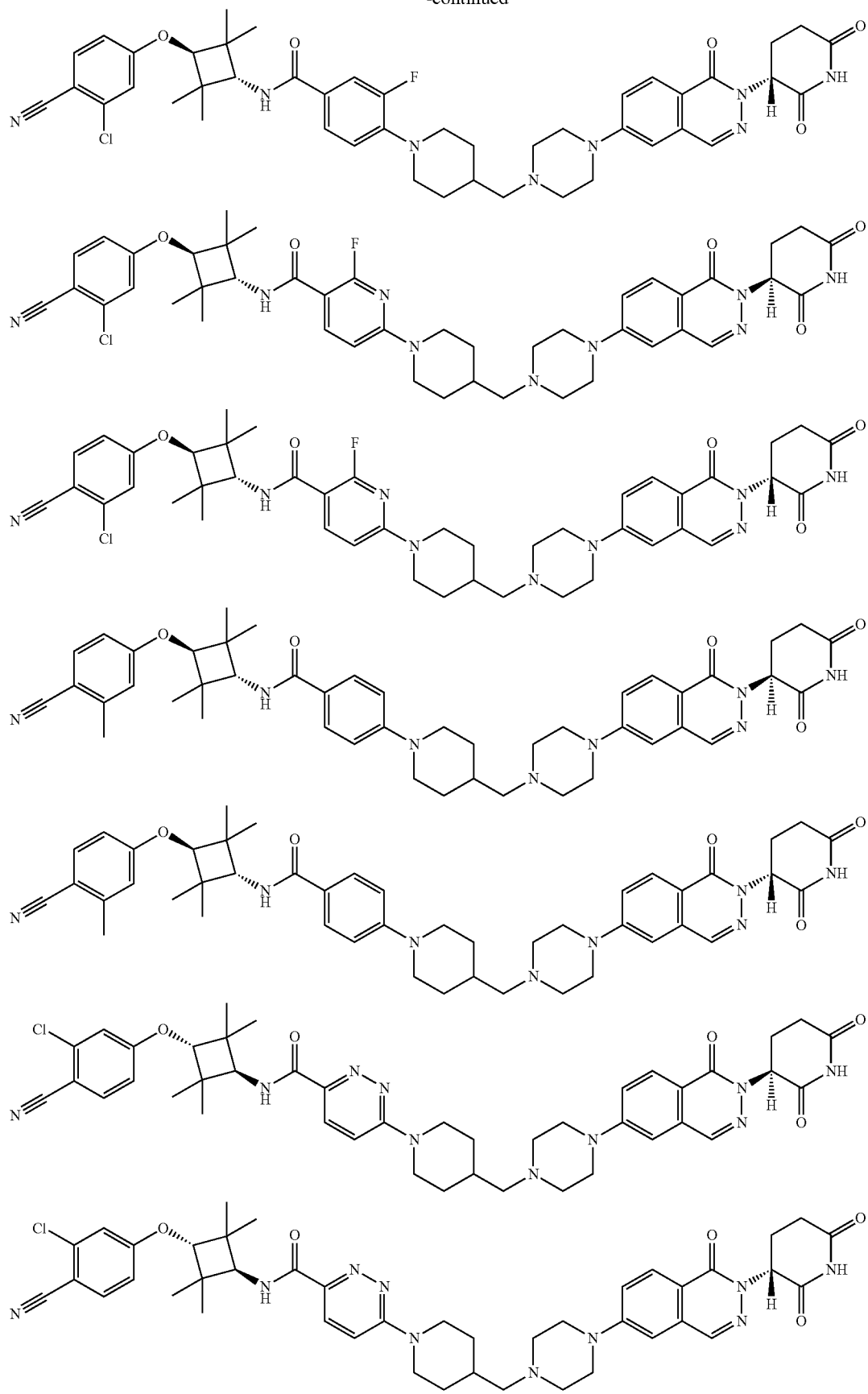

-continued
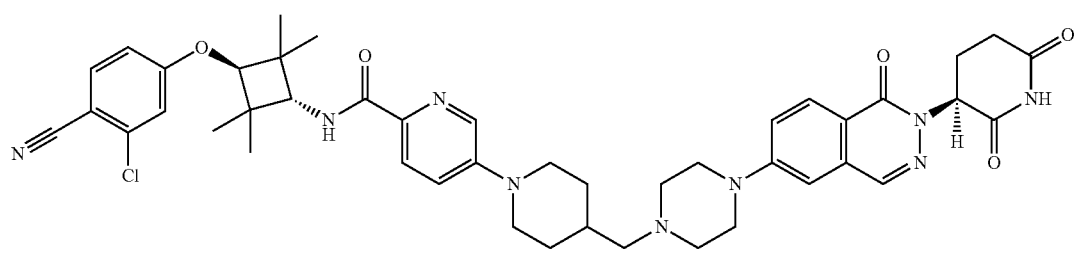
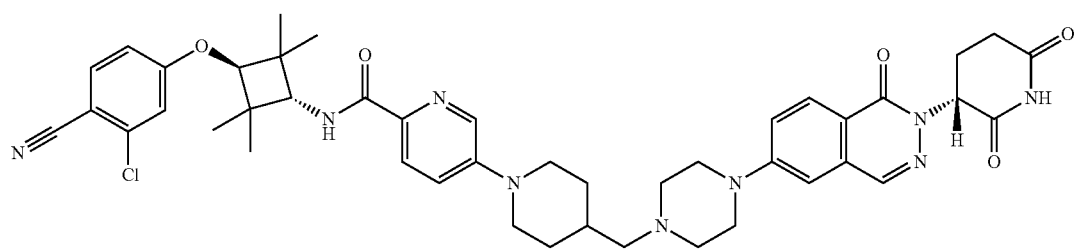
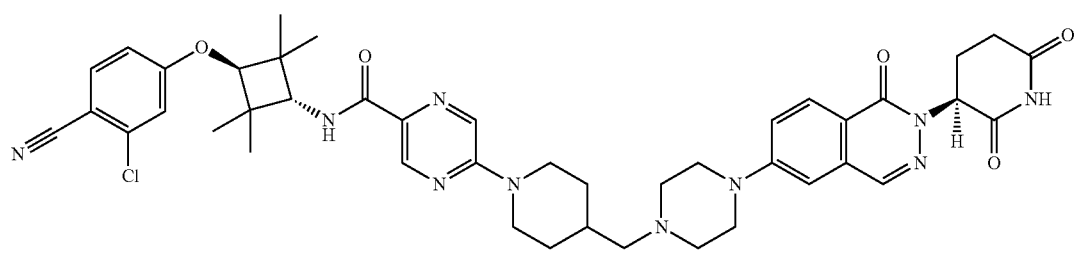
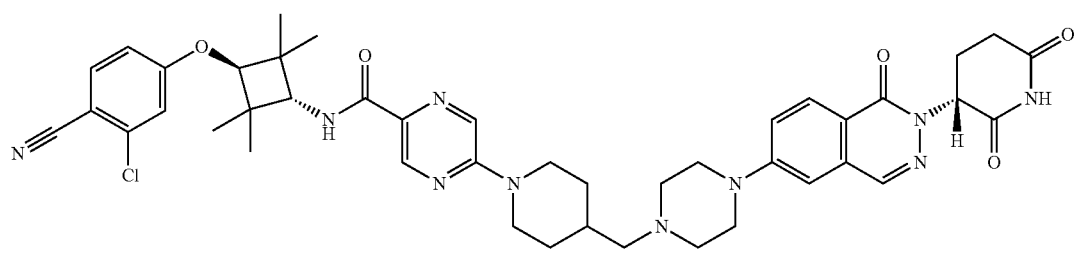
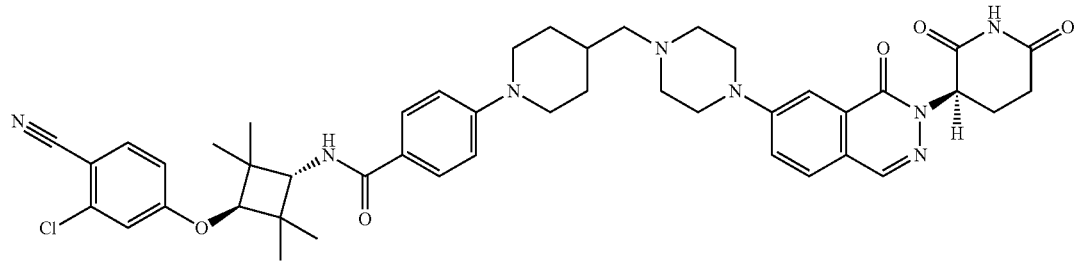
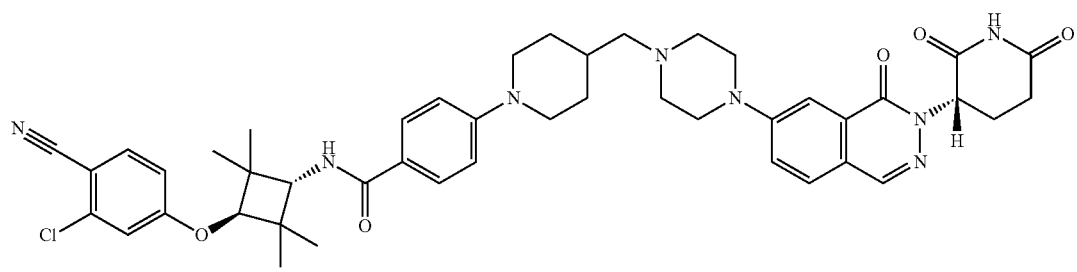

-continued
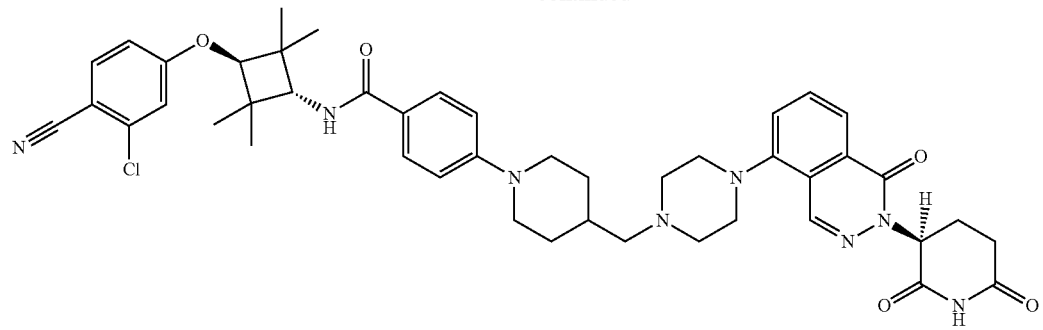
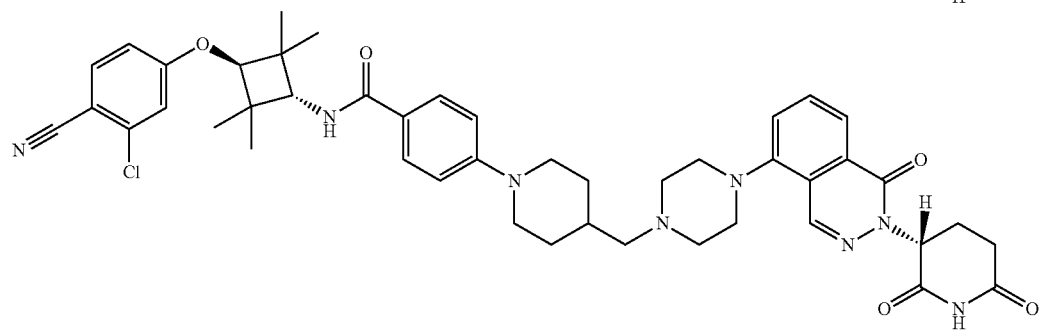
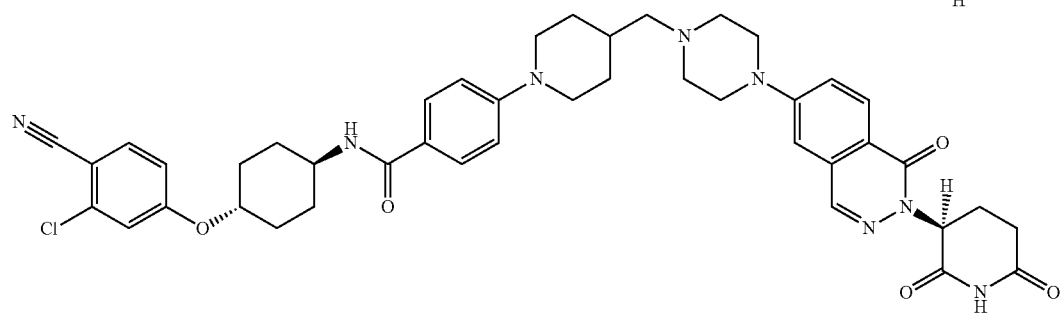
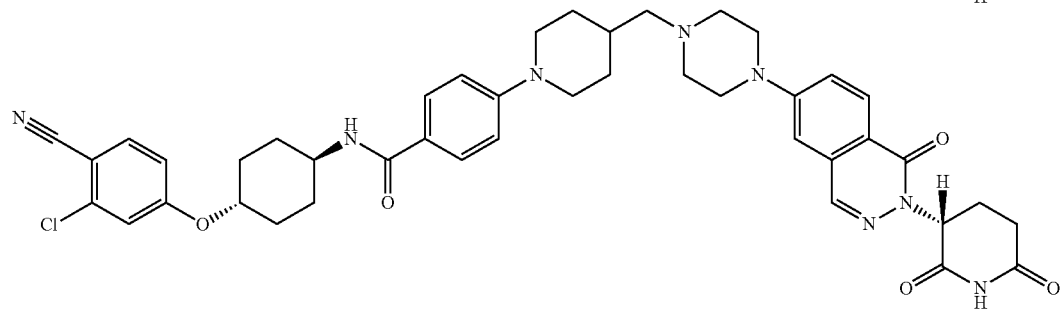
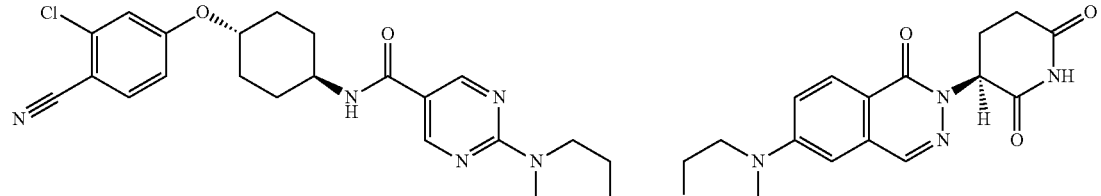
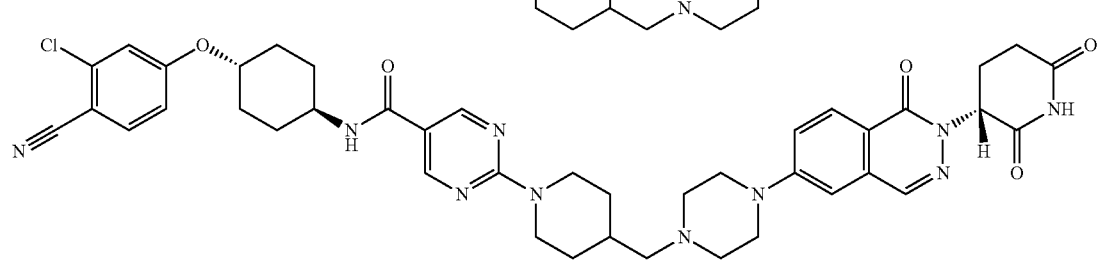

-continued
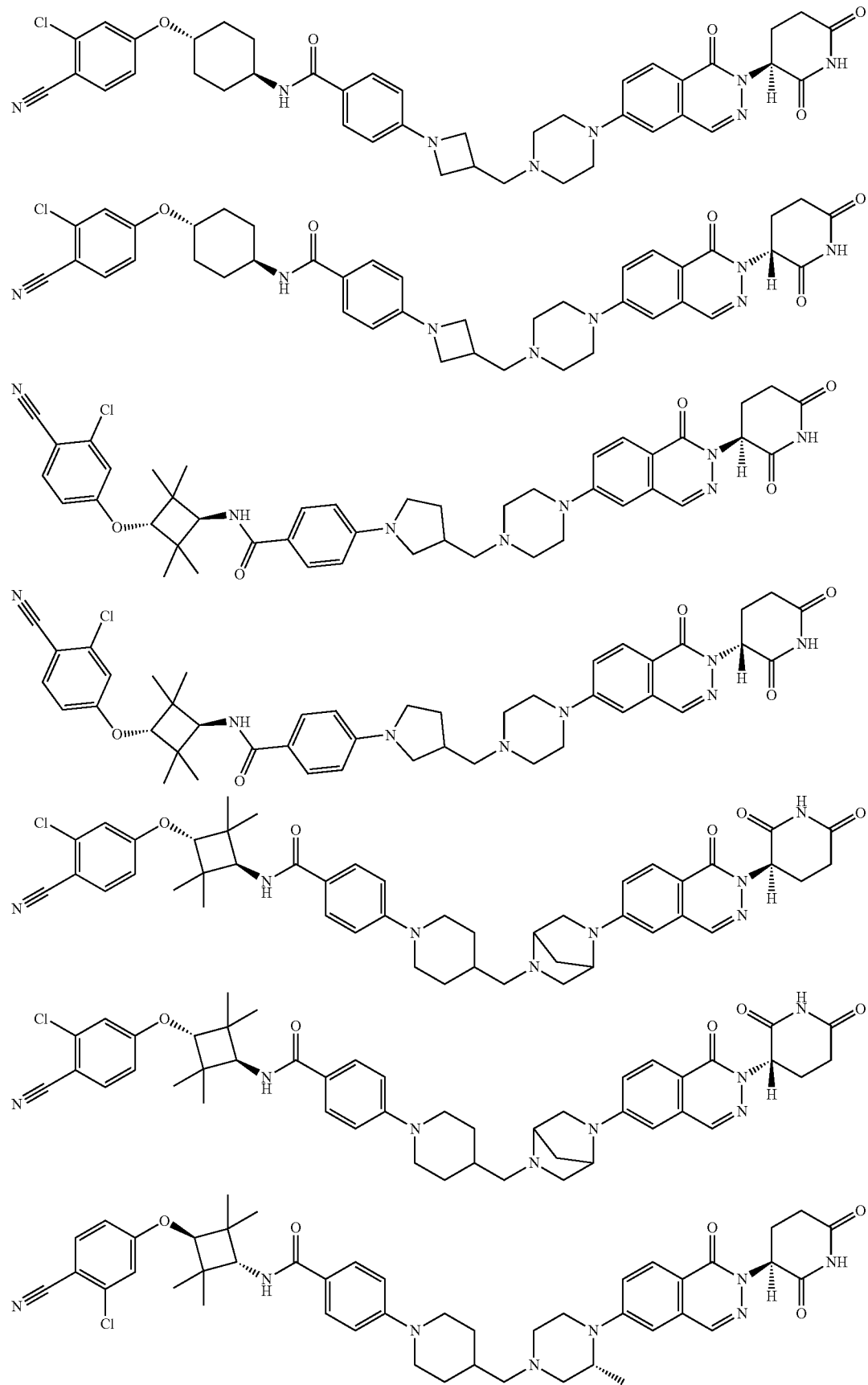

-continued
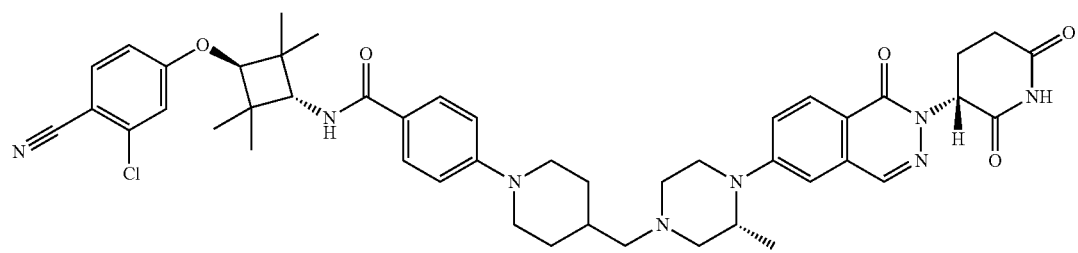
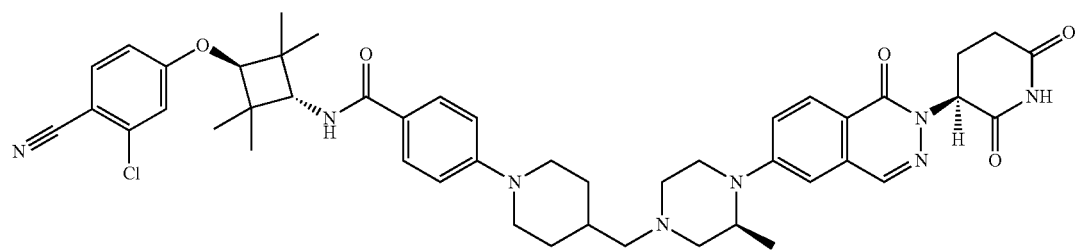
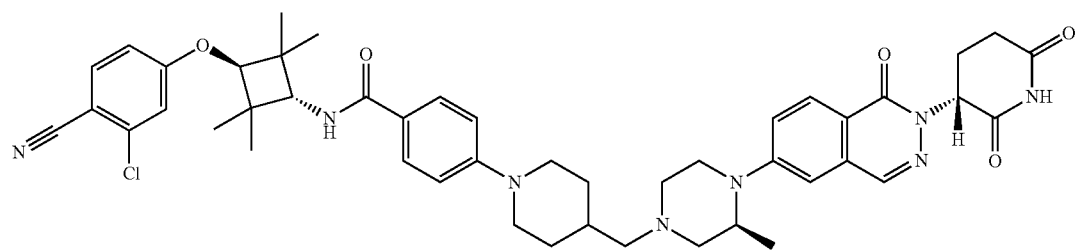
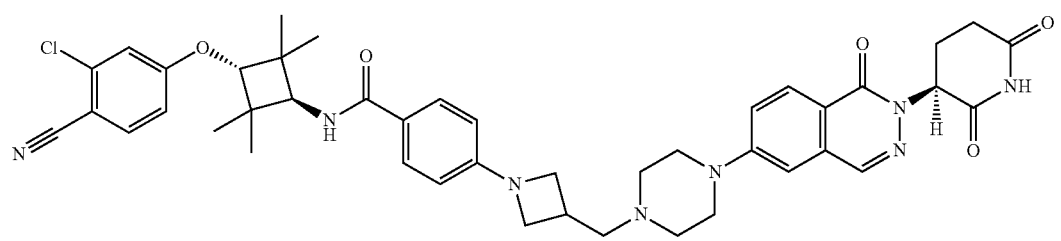
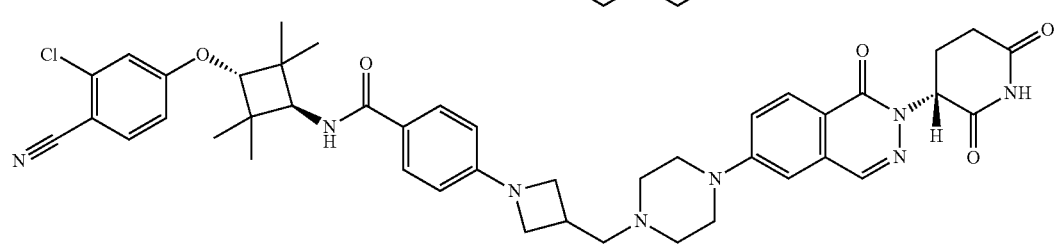
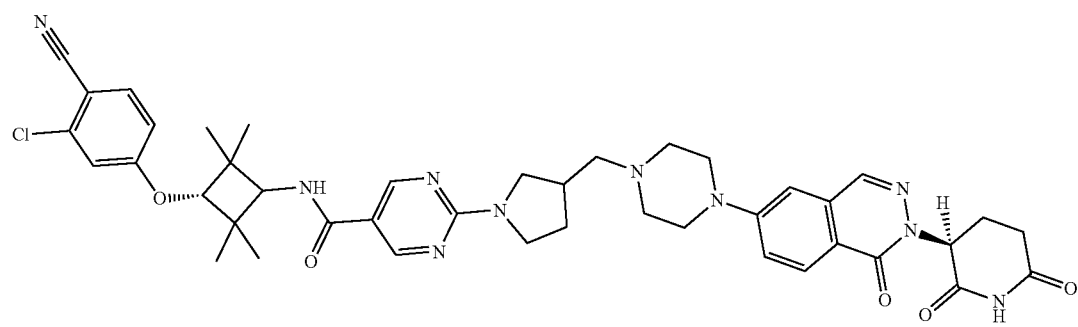

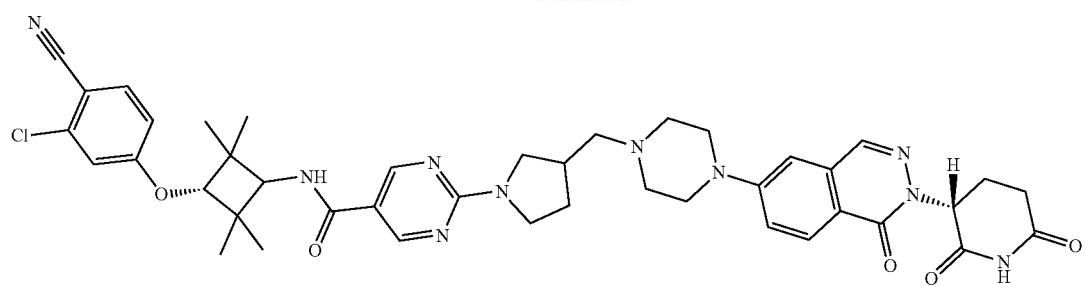
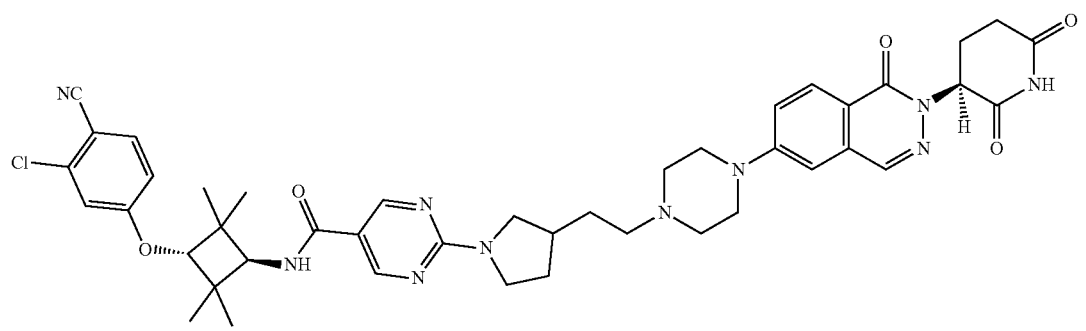
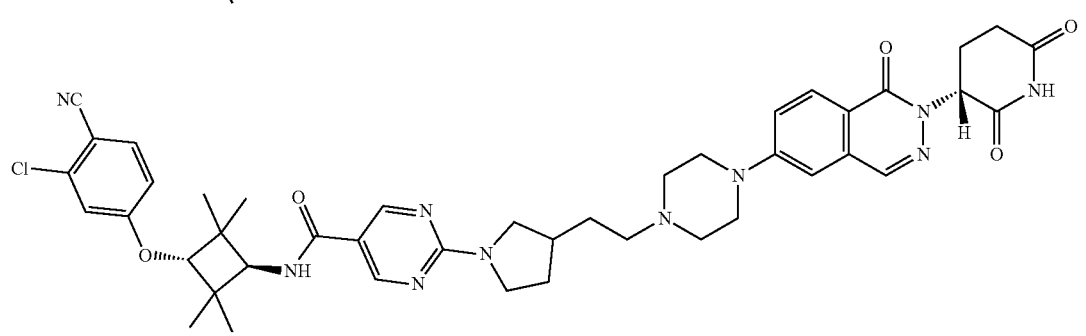
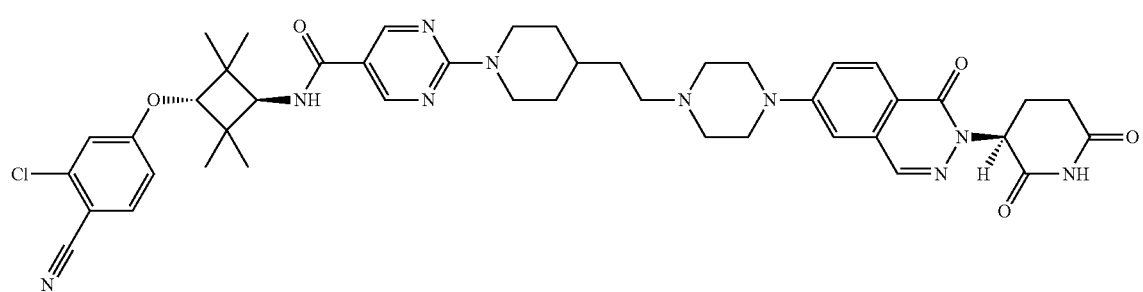
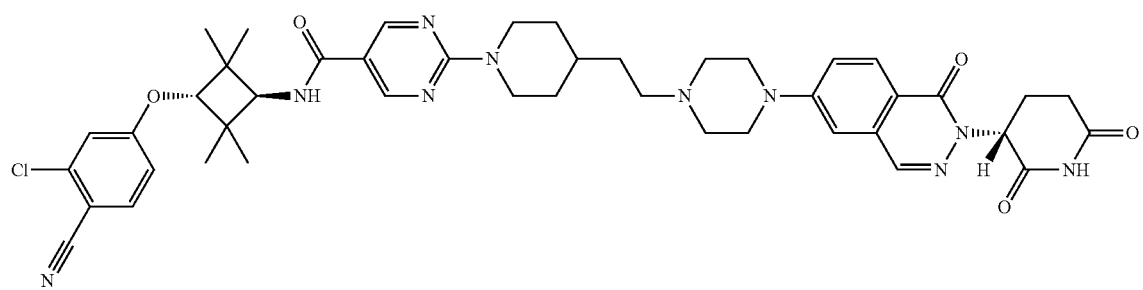

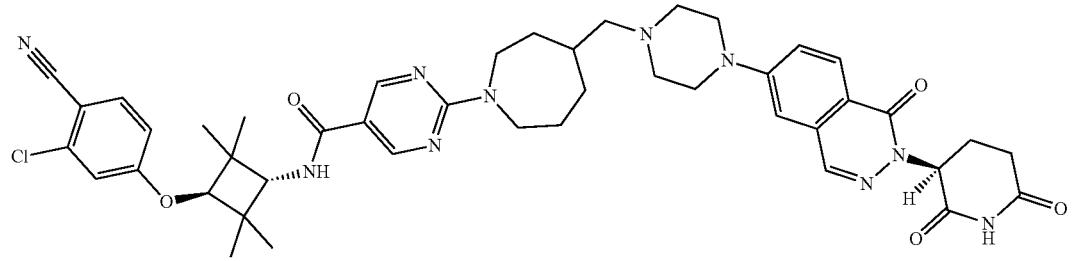
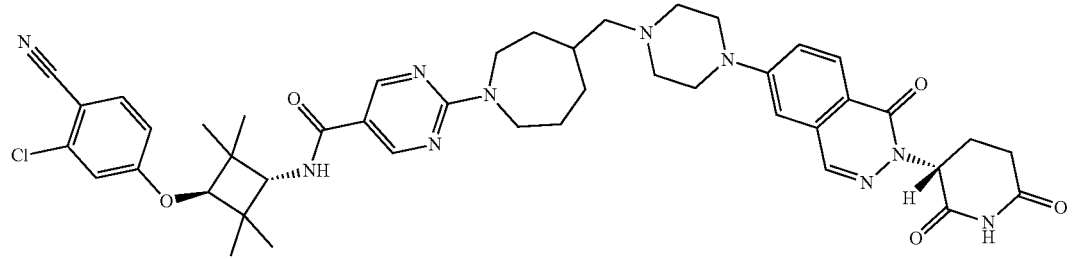
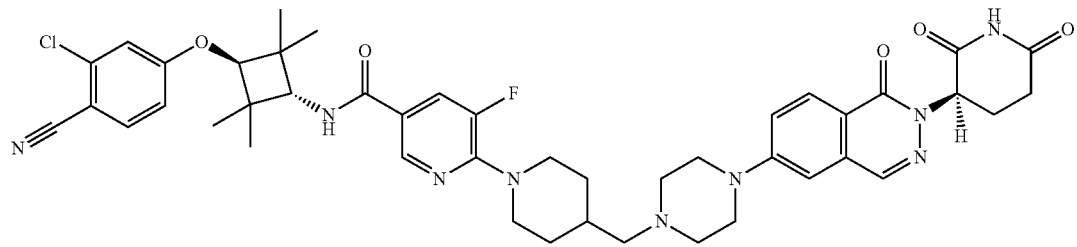
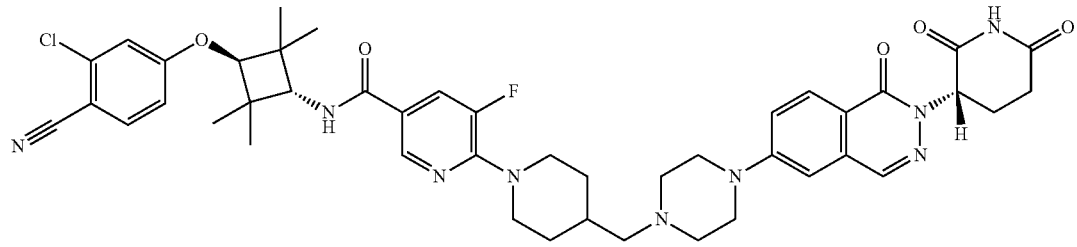
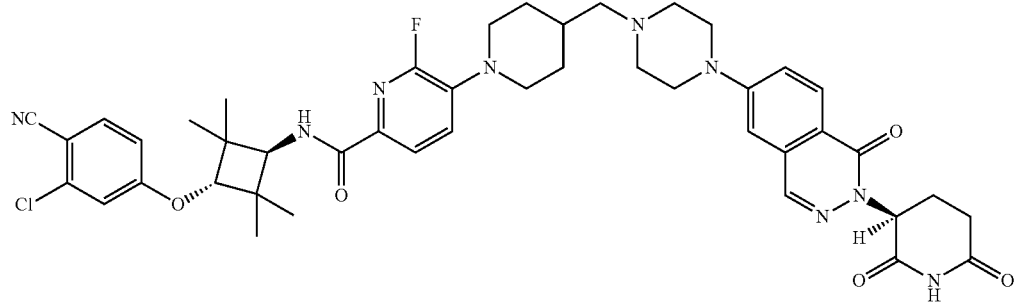
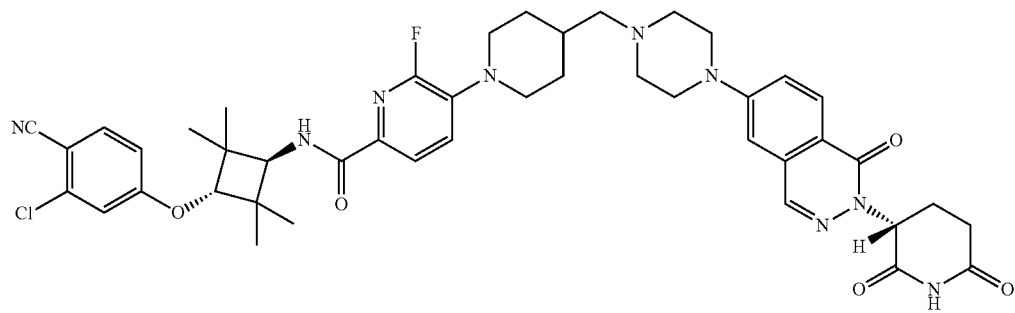

-continued
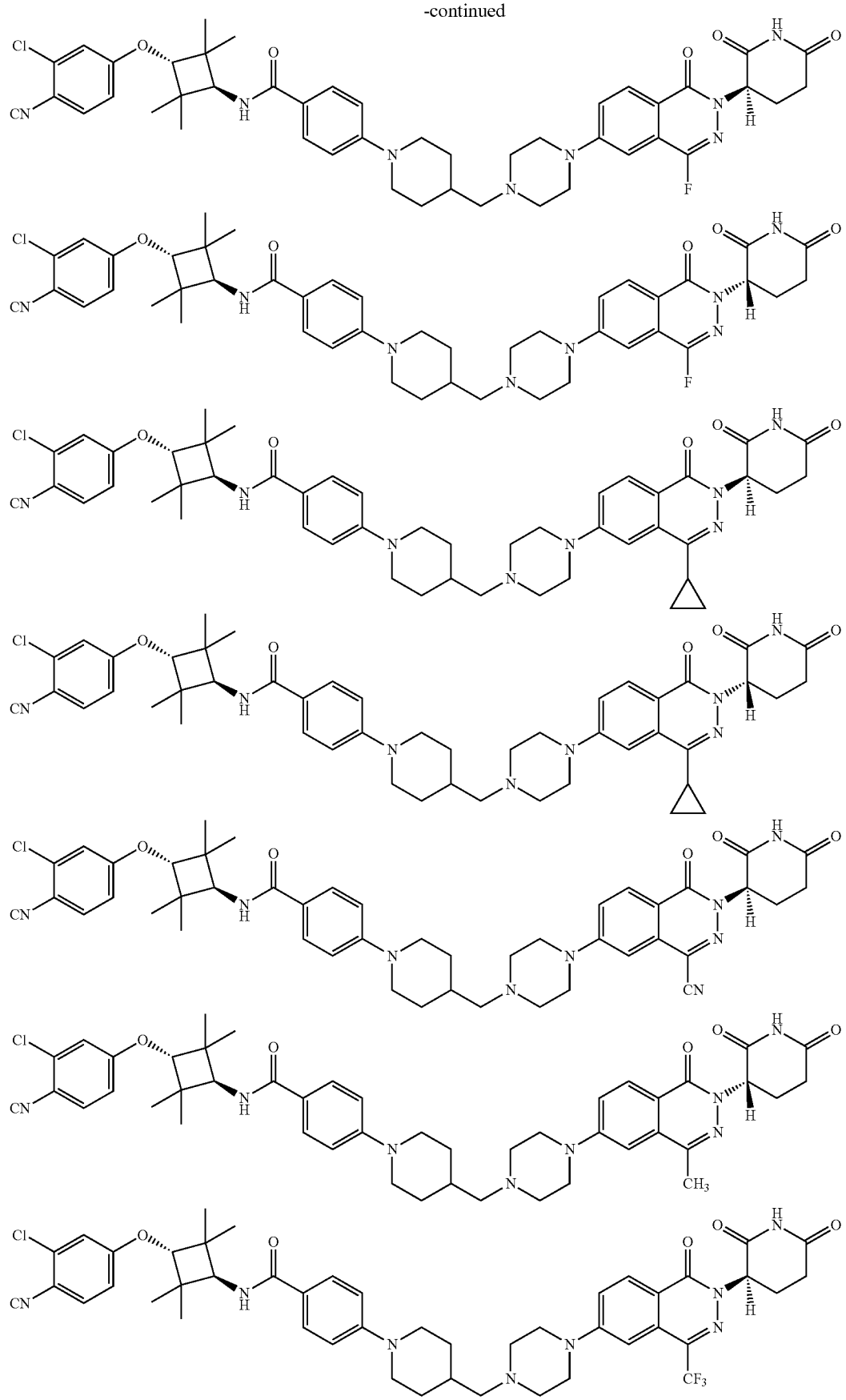

-continued

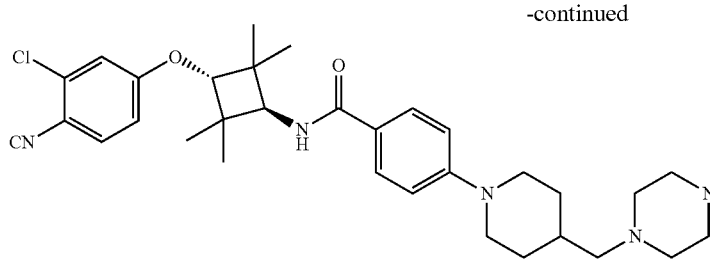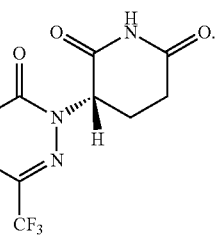

In yet another aspect of the present invention, the present invention further proposes use of the aforementioned compounds, optical isomers thereof and pharmacodynamically acceptable salts thereof in the preparation of a medicament for preventing and/or treating a cancer or Kennedy's disease.

In some schemes of the present invention, the above-mentioned cancer is an AR-related cancer, such as prostate cancer, breast cancer, and the like.

In yet another aspect of the present invention, the present invention further proposes a method for treating a cancer (e.g., the prostate cancer, the breast cancer, etc.) or Kennedy's disease.

The method comprises administering the aforementioned compound, an optical isomer thereof and a pharmacodynamically acceptable salt thereof to a patient.

DETAILED DESCRIPTION

Unless otherwise specified, the following terms and phrases used herein are intended to have the following meanings. A specific term or phrase should not be considered to be indeterminate or unclear without specific definitions, but should be understood in its ordinary meaning. When a trade name appears herein, it is intended to refer to a corresponding commercial product or an active ingredient thereof.

As used in the present invention, it should be appreciated that the phrase "at least one", when referring to a list of one or more elements, is intended to mean at least one element selected from any one or more elements in the list of elements, but does not necessarily include at least one of each element specifically listed in the list of elements, and does not exclude any combination of the elements in the list of elements. This definition further allows that elements, other than those specifically determined within the list of elements to which the phrase "at least one" refers, may be optionally present, no matter whether they are related or unrelated to those specifically determined elements.

The term "pharmacodynamically acceptable" as used herein is directed at those compounds, materials, compositions and/or dosage forms that, within the scope of reliable medical judgement, are suitable for use in contact with human and animal tissues, without excessive toxic, irritative and allergic reactions or other problems or complications, and it is commensurate with a reasonable benefit/risk ratio.

The term "pharmacodynamically acceptable salt" refers to a salt of a compound of the present invention, which is prepared from the compound with a specific substituent discovered by the present invention and a relatively non-toxic acid or base. When the compound of the present invention contains a relatively acidic functional group, a base addition salt can be obtained by contacting a neutral form of such compound with a sufficient amount of base in a pure solution or in a suitable inert solvent. The pharmacodynamically acceptable base addition salt includes sodium, potassium, calcium, ammonium, organic amine or magnesium salts or similar salts. When the compound of the present invention contains a relatively basic functional group, an acid addition salt can be obtained by contacting a neutral form of such compound with a sufficient amount of acid in a solution or in a suitable inert solvent. Examples of the pharmacodynamically acceptable acid addition salt include inorganic acid salts, the inorganic acids including, for example, hydrochloric acid, hydrobromic acid, nitric acid, carbonic acid, bicarbonate radical, phosphoric acid, monohydrogenphosphate radical, dihydrogenphosphate radical, sulfuric acid, hydrosulfate radical, hydroiodic acid, phosphorous acid, etc.; and organic acid salts, the organic acids including, for example, acetic acid, propionic acid, isobutyric acid, trifluoroacetic acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; and these examples also include salts of amino acids (such as arginine), and salts of organic acids such as glucuronic acid. Certain specific compounds of the present invention contain both basic and acidic functional groups and thus can be converted into either base or acid addition salts.

The pharmacodynamically acceptable salt of the present invention can be synthesized from a parent compound containing an acid racial or a basic group by a conventional chemical method.

Generally, a preparation method of such salts is as follows: reacting these compounds in a form of a free acid or base with a stoichiometric amount of an appropriate base or acid in water or an organic solvent or a mixture thereof.

The compound of the present invention may exist in a specific geometric or stereoisomeric form. All such compounds contemplated in the present invention comprise cis and trans isomers, (−)- and (+)-enantiomers, (R)- and (S)-enantiomers, diastereoisomers, (D)-isomers, (L)-isomers, and racemic mixtures and other mixtures thereof, for example, enantiomerically or diastereomerically enriched mixtures, and all these mixtures shall fall within the scope of the present invention.

Additional asymmetric carbon atoms may be present in substituents such as alkyl. All these isomers and the mixtures thereof are incorporated into the scope claimed in the present invention.

Unless otherwise stated, a wedged solid bond and a wedged dotted bond

are used to represent an absolute configuration of a stereocenter.

The compound of the present invention may exist in a specific form. Unless otherwise specified, the term "tautomers" or "tautomeric forms" means that isomers of different functional groups are in a dynamic equilibrium and can be rapidly interconverted at room temperature. A chemical equilibrium of tautomers can be achieved if tautomers are possible (such as in a solution). For example, a proton tautomer (also referred to as a prototropic tautomer) comprises an interconversion via migration of a proton, such as keto-enol and imine-enamine isomerizations. A valence tautomer includes interconversions by recombination of some bonding electrons. Therein, a specific example of the keto-enol tautomerization is an interconversion between two tautomers, pentane-2,4-dione and 4-hydroxypent-3-en-2-one, or, for example,

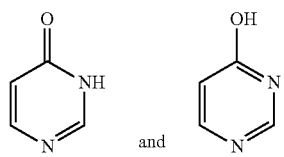 [SMILES: O=c1ccnc[nH]1 ; Oc1ccncn1]

are tautomers.

Optically active (R)- and (S)-isomers as well as D and L isomers can be prepared by chiral synthesis or a chiral reagent or other conventional techniques. If one enantiomer of a certain compound of the present invention is desired, it can be prepared by asymmetric synthesis or derivatization with a chiral auxiliary, wherein the resulting mixture of diastereomers is separated and an auxiliary group is cleaved to provide a pure desired enantiomer. Or, when the molecule contains an alkaline functional group (such as an amino group) or an acidic functional group (such as a carboxyl group), a diastereoisomer salt is formed with an appropriate optically-active acid or alkali, a diastereoisomer is subsequently resolved by a conventional method known in the art, and a pure enantiomer is subsequently recovered and obtained. In addition, the enantiomer and the diastereomer are usually separated by chromatography in which a chiral stationary phase is used optionally in combination with chemical derivatization (for example, carbamate is generated from amines). The compound of the present invention may contain an unnatural proportion of atomic isotopes at one or more atoms that constitute the compound. For example, compounds can be labeled with radioisotopes, such as tritium ($^3$H), iodine-125 ($^{125}$I) or C-14 ($^{14}$C). For another example, a deuterated drug can be formed by replacing hydrogen with deuterium, and the bond formed by deuterium and carbon is stronger than that formed by ordinary hydrogen and carbon. Compared with a non-deuterated drug, the deuterated drug has the advantages of reducing toxic and side effects, increasing drug stability, improving therapeutic effect, prolonging the biological half-life of a drug, etc. Transformations of all isotopic compositions of the compounds of the present invention, regardless of radioactivity, are included within the scope of the present invention. "Optional" or "optionally" means that the subsequently described event or circumstance may or may not occur, which includes instances where the event or circumstance occurs or does not occur.

The compound of the present invention may contain an unnatural proportion of atomic isotopes at one or more atoms that constitute the compound. For example, compounds can be labeled with radioisotopes, such as tritium ($^3$H), iodine-125 ($^{125}$I) or C-14 ($^{14}$C). For another example, a deuterated drug can be formed by replacing hydrogen with deuterium, and the bond formed by deuterium and carbon is stronger than that formed by ordinary hydrogen and carbon. Compared with a non-deuterated drug, the deuterated drug has the advantages of reducing toxic and side effects, increasing drug stability, improving therapeutic effect, prolonging the biological half-life of a drug, etc. Transformations of all isotopic compositions of the compounds of the present invention, regardless of radioactivity, are included within the scope of the present invention. "Optional" or "optionally" means that the subsequently described event or circumstance may or may not occur, which includes instances where the event or circumstance occurs or does not occur.

When a valence bond of a group has a dotted line

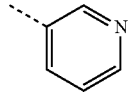

for example, in

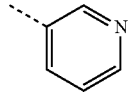

the dotted line represents a point of attachment of the group to the remainder of a molecule. When a single bond has

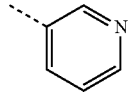

for example, in

the dotted line represents a single bond or inexistence, and also means that

represents a single bond

or a double bond

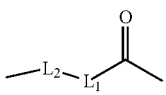

The term "substituted" or "substituted with . . ." means that any one or more hydrogen atoms on a specified atom are substituted with a substituent which may include deuterium and a hydrogen variant, as long as the valence of the specified atom is normal and the substituted compound is stable. The term "optionally substituted" or "optionally substituted with . . ." means that it may or may not be substituted; unless otherwise specified, the type and number of substituents may be optional on a chemically achievable basis.

When any variable (e.g., R) appears more than once in the composition or structure of a compound, the definition thereof in each case is independent. Thus, for example, if a group is substituted with 1, 2 or 3 R', the group may be optionally substituted with 1 or 2 or 3 R', with independent alternatives for R' in each case. Furthermore, combinations of substituents and/or variants thereof are permissible only if such combinations produce stable compounds.

When one of the variables is selected from a single bond, it represents that two groups attached thereto are directly attached, for example, when $L_1$ in

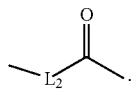

represents the single bond, it means that the structure is actually

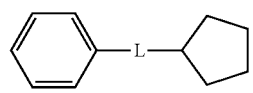

When the enumerated substituent does not indicate through which atom it is attached to a substituted group, such substituent may be bonded through any atoms thereof, for example, pyridyl as a substituent may be attached to the substituted group through any one of the carbon atoms on a pyridine ring.

When the enumerated linking group does not indicate a linking direction thereof, the linking direction thereof is optional, for example, the linking group L in

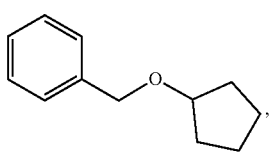 [SMILES: c1ccc(COC2CCCC2)cc1]

is —CH$_2$O—, then —CH$_2$O— can be attached to phenyl and cyclopentyl in a direction the same as a reading sequence from left to right to form and can also be attached to phenyl and cyclopentyl in a direction opposite to the reading sequence from left to right to form

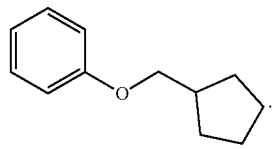 [SMILES: c1ccc(OCC2CCCC2)cc1]

Combinations of the linking groups, substituents and/or variants thereof are permissible only if such combinations produce stable compounds.

Unless otherwise specified, the number of atoms on a ring is generally defined as the number of ring members, for example, "a 3- to 6-membered ring" refers to a "ring" having 3 to 6 atoms arranged around.

Unless otherwise specified, the term "$C_{1-6}$ alkyl" is used to represent a linear or branched-chain saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl, etc.; they can be monovalent (e.g., $CH_3$), bivalent (—$CH_2$—) or multivalent (e.g., hypo

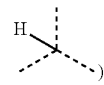

Examples of $C_{1-6}$ alkyl include, but are not limited to, $CH_3$,

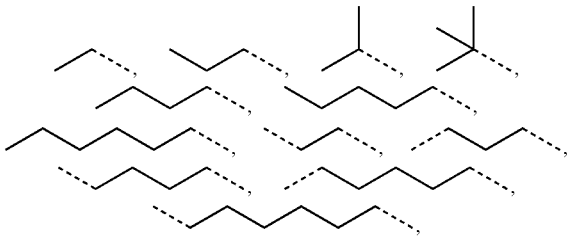

etc.

Unless otherwise specified, the term "$C_{1-4}$ alkyl" is used to represent a linear or branched-chain saturated hydrocarbon group consisting of 1 to 4 carbon atoms. The $C_{1-4}$ alkyl includes $C_{1-2}$, $C_{1-3}$, $C_{3-4}$ and $C_{2-3}$ alkyl, etc.; they can be monovalent (e.g., $CH_3$), bivalent (e.g., —$CH_2$—) or multivalent (e.g., sec

Examples of the $C_{1-4}$ alkyl include, but are not limited to, $CH_3$,

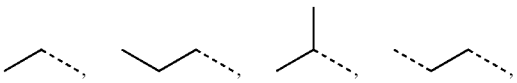

-continued

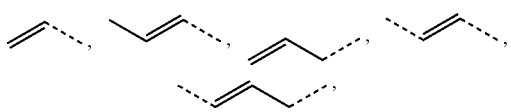

Unless otherwise specified, "$C_{2-3}$ alkenyl" is used to represent a linear or branched-chain hydrocarbon group including at least one carbon-carbon double bond and consisting of 2 to 3 carbon atoms, and the carbon-carbon double bond can be located at any position of the group. The $C_{2-3}$ alkenyl includes $C_3$ and $C_2$ alkenyl; the $C_{2-3}$ alkenyl can be monovalent bivalent or multivalent. Examples of $C_{2-3}$ alkenyl include, but are not limited to,

etc.

Unless otherwise specified, "$C_{2-3}$ alkynyl" is used to represent a linear or branched-chain hydrocarbon group including at least one carbon-carbon triple bond and consisting of 2 to 3 carbon atoms, and the triple bond can be located at any position of the group. It can be monovalent, bivalent or multivalent. The $C_{2-3}$ alkynyl includes $C_3$ and $C_2$ alkynyl. Examples of the $C_{2-3}$ alkynyl include, but are not limited to, etc.

Unless otherwise specified, the term "$C_{1-6}$ alkoxy" represents an alkyl group containing 1 to 6 carbon atoms and attached to the remainder of the molecule through one oxygen atom. The $C_{1-6}$ alkoxy includes $C_{1-4}$, $C_{1-3}$, $C_{1-2}$, $C_{2-6}$, $C_{2-4}$, $C_6$, $C_5$, $C_4$ and $C_3$ alkoxy, etc. Examples of the $C_{1-6}$ alkoxy include, but are not limited to, methoxy, ethoxy, propoxy (including n-propoxy and isopropoxy), butoxy (including n-butoxy, isobutoxy, s-butoxy and t-butoxy), pentyloxy (including n-pentyloxy, isopentyloxy and neopentyloxy), hexyloxy, etc.

Unless otherwise specified, the term "$C_{1-3}$ alkoxy" represents those alkyl groups containing 1 to 3 carbon atoms and attached to the remainder of the molecule through one oxygen atom. The $C_{1-3}$ alkoxy includes $C_{1-3}$, $C_{1-2}$, $C_{2-3}$, $C_1$, $C_2$ and $C_3$ alkoxy, etc. Examples of the $C_{1-3}$ alkoxy include, but are not limited to, methoxy, ethoxy, propoxy (including n-propoxy and isopropoxy), etc.

Unless otherwise specified, the term "$C_{1-6}$ alkylamino" represents an alkyl group containing 1 to 6 carbon atoms and attached to the remainder of the molecule through amino. The $C_{1-6}$ alkylamino includes $C_{1-4}$, $C_{1-3}$, $C_{1-2}$, $C_{2-6}$, $C_{2-4}$, $C_6$, $C_5$, $C_4$, $C_3$ and $C_2$ alkylamino, etc. Examples of $C_{1-6}$ alkylamino include, but are not limited to, —NHCH$_3$, —N(CH$_3$)$_2$, —NHCH$_2$CH$_3$, —N(CH$_3$)CH$_2$CH$_3$, —N(CH$_2$CH$_3$)(CH$_2$CH$_3$), —NHCH$_2$CH$_2$CH$_3$, —NHCH$_2$(CH$_3$)$_2$, —NHCH$_2$CH$_2$CH$_2$CH$_3$, etc.

Unless otherwise specified, the term "$C_{1-3}$alkylamino" represents those alkyl groups containing 1 to 3 carbon atoms and attached to the remainder of the molecule through amino. The $C_{1-3}$ alkylamino includes $C_{1-3}$, $C_{1-2}$, $C_{2-3}$, $C_1$, $C_2$ and $C_3$ alkylamino, etc. Examples of $C_{1-3}$alkylamino include, but are not limited to, —NHCH$_3$, —N(CH$_3$)$_2$, —NHCH$_2$CH$_3$, —N(CH$_3$)CH$_2$CH$_3$, —NHCH$_2$CH$_2$CH$_3$, and —NHCH$_2$(CH$_3$)$_2$.

Unless otherwise specified, the term "$C_{1-6}$ alkylthio" represents an alkyl group containing 1 to 6 carbon atoms and attached to the remainder of the molecule through a sulfur atom. The $C_{1-6}$ alkylthio includes $C_{1-4}$, $C_{1-3}$, $C_{1-2}$, $C_{2-6}$, $C_{2-4}$, $C_6$, $C_5$, $C_4$, $C_3$ and $C_2$ alkylthio, etc. Examples of the $C_{1-6}$ alkylthio include, but are not limited to, —SCH$_3$, —SCH$_2$CH$_3$, —SCH$_2$CH$_2$CH$_3$, —SCH$_2$(CH$_3$)$_2$, etc.

Unless otherwise specified, the term "$C_{1-3}$ alkylthio" represents an alkyl group containing 1 to 3 carbon atoms and attached to the remainder of the molecule through a sulfur atom. The $C_{1-3}$ alkylthio includes $C_{1-3}$, $C_{1-2}$, $C_{2-3}$, $C_1$, $C_2$ and $C_3$ alkylthio, etc. Examples of the $C_{1-3}$ alkylthio include, but are not limited to, —SCH$_3$, —SCH$_2$CH$_3$, —SCH$_2$CH$_2$CH$_3$, —SCH$_2$(CH$_3$)$_2$, etc.

Unless otherwise specified, "$C_{3-9}$ cycloalkyl" represents a saturated cyclic hydrocarbon group consisting of 3 to 9 carbon atoms, which is monocyclic and bicyclic systems, and the $C_{3-9}$ cycloalkyl includes $C_{3-8}$, $C_{3-7}$, $C_{3-6}$, $C_{3-5}$ and $C_{5-6}$ cycloalkyl; it can be monovalent, divalent or multivalent. Examples of the $C_{3-9}$ cycloalkyl include, but are not limited to, cyclopropyl, cyclobutyl, cyclopentyl, cyclohexyl, cycloheptyl, etc.

Unless otherwise specified, "$C_{3-6}$cycloalkyl" represents a saturated cyclic hydrocarbon group consisting of 3 to 6 carbon atoms, which is monocyclic and bicyclic systems, and the $C_{3-6}$cycloalkyl includes $C_{3-5}$, $C_{4-5}$ and $C_{5-6}$cycloalkyl; it can be monovalent, divalent or multivalent. Examples of $C_{3-6}$cycloalkyl include, but are not limited to, cyclopropyl, cyclobutyl, cyclopentyl, cyclohexyl, etc.

Unless otherwise specified, "$C_{4-6}$cycloalkyl" represents a saturated cyclic hydrocarbon group consisting of 4 to 6 carbon atoms, which is monocyclic and bicyclic systems, and the $C_{4-6}$cycloalkyl includes $C_{4-5}$, $C_{4-6}$ and $C_{5-6}$cycloalkyl; it can be monovalent, divalent or multivalent. Examples of $C_{4-6}$cycloalkyl include, but are not limited to, cyclobutyl, cyclopentyl, cyclohexyl, etc.

Unless otherwise specified, the term "3- to 10-membered heterocycloalkyl" by itself or in combination with other terms respectively represents a saturated cyclic group consisting of 3 to 10 ring atoms, and 1, 2, 3 or 4 ring atoms thereof are heteroatoms independently selected from O, S and N, and the remainder are carbon atoms, wherein the nitrogen atom is optionally quaternized, and the nitrogen and sulfur heteroatoms can be optionally oxidized (i.e., NO and $S(O)_p$, where p is 1 or 2). It includes monocyclic, bicyclic and tricyclic systems, wherein the bicyclic and tricyclic systems include spiro rings, fused rings and bridged rings. Furthermore, with respect to the "3- to 10-membered heterocycloalkyl", a heteroatom may occupy an attachment position of the heterocycloalkyl and the remainder of the molecule. The 3- to 10-membered heterocycloalkyl includes 3- to 9-membered, 3- to 8-membered, 3- to 6-membered, 3- to 5-membered, 4- to 6-membered, 5- to 6-membered, 4-membered, 5-membered and 6-membered heterocycloalkyl, etc. Examples of the 3- to 10-membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl and tetrahydrothiophen-3-yl, etc.), tetrahydrofuranyl (including tetrahydrofuran-2-yl, etc.), tetrahydropyranyl, piperidyl (including 1-piperidyl, 2-piperidyl and 3-piperidyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidyl, dioxepanyl or

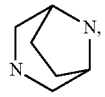

etc.

Unless otherwise specified, the term "4- to 8-membered heterocycloalkyl" by itself or in combination with other terms respectively represents a saturated cyclic group consisting of 4 to 8 ring atoms, and 1, 2, 3 or 4 ring atoms thereof are heteroatoms independently selected from O, S and N, and the remainder are carbon atoms, wherein the nitrogen atom is optionally quaternized, and the nitrogen and sulfur heteroatoms can be optionally oxidized (i.e., NO and $S(O)_p$, where p is 1 or 2). It includes monocyclic and bicyclic systems, wherein the bicyclic system includes spiro rings, fused rings and bridged rings. Furthermore, with respect to the "4- to 8-membered heterocycloalkyl", a heteroatom may occupy an attachment position of the heterocycloalkyl and the remainder of the molecule. The 4- to 8-membered heterocycloalkyl includes 4- to 6-membered, 5-to 6-membered, 4-membered, 5-membered, 6-membered, 7-membered and 8-membered heterocycloalkyl, etc. Examples of the 4- to 8-membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl and tetrahydrothiophen-3-yl, etc.), tetrahydrofuranyl (including tetrahydrofuran-2-yl, etc.), tetrahydropyranyl, piperidyl (including 1-piperidyl, 2-piperidyl and 3-piperidyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidyl or

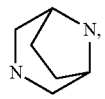

etc.

Unless otherwise specified, the term "3- to 6-membered heterocycloalkyl" by itself or in combination with other terms respectively represents a saturated cyclic group consisting of 3 to 6 ring atoms, and 1, 2, 3 or 4 ring atoms thereof are heteroatoms independently selected from O, S and N, and the remainder are carbon atoms, wherein the nitrogen atom is optionally quaternized, and the nitrogen and sulfur heteroatoms can be optionally oxidized (i.e., NO and $S(O)_p$, where p is 1 or 2). It includes monocyclic and bicyclic systems, wherein the bicyclic system includes spiro rings, fused rings and bridged rings. Furthermore, with respect to the "3- to 6-membered heterocycloalkyl", a heteroatom may occupy an attachment position of the heterocycloalkyl and the remainder of the molecule. The 3- to 6-membered heterocycloalkyl includes 4- to 6-membered, 5-to 6-membered, 4-membered, 5-membered and 6-membered heterocycloalkyl, etc. Examples of the 3- to 6-membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl and tetrahydrothiophen-3-yl, etc.), tetrahydrofuranyl (including tetrahydrofuran-2-yl, etc.), tetrahydropyranyl, piperidyl (including 1-piperidyl, 2-piperidyl and 3-piperidyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl or homopiperidyl, etc.

Unless otherwise specified, the terms "$C_{6-10}$ aryl ring" and "$C_{6-10}$ aryl" can be used interchangeably in the present invention, and the term "$C_{6-10}$ aryl ring" or "$C_{6-10}$ aryl" represents a cyclic hydrocarbon group consisting of 6 to 10 carbon atoms and having a conjugated R-electron system, which can be a monocyclic, fused-bicyclic or fused-tricyclic system, wherein each ring is aromatic. It can be monovalent, divalent or polyvalent, and the $C_{6-10}$ aryl includes $C_{6-9}$, $C_9$, $C_{10}$ and $C_6$ aryl, etc. Examples of the $C_{6-10}$ aryl include, but are not limited to, phenyl and naphthyl (including 1-naphthyl and 2-naphthyl, etc.).

Unless otherwise specified, the terms "5- to 12-membered heteroaromatic ring" and "5- to 12-membered heteroaryl" can be used interchangeably in the present invention; the term "5- to 12-membered heteroaryl" represents a cyclic group consisting of 5 to 12 ring atoms and having a conjugated π-electron system, 1, 2, 3 or 4 ring atoms thereof are heteroatoms independently selected from O, S and N, and the remainder are carbon atoms. It can be a monocyclic, fused-bicyclic or fused-tricyclic system, wherein each ring is aromatic. Therein, the nitrogen atom is optionally quaternized, and the nitrogen and sulfur heteroatoms can be optionally oxidized (i.e., NO and $S(O)_p$, where p is 1 or 2). 5- to 12-membered heteroaryl can be attached to the remainder of the molecule through a heteroatom or a carbon atom. The 5- to 12-membered heteroaryl includes 5- to 10-membered, 5- to 9-membered, 5- to 8-membered, 5- to 7-membered, 5- to 6-membered, 5-membered and 6-membered heteroaryl, etc. Examples of the 5- to 12-membered heteroaryl include, but are not limited to, pyrrolyl (including N-pyrrolyl, 2-pyrrolyl and 3-pyrrolyl, etc.), pyrazolyl (including 2-pyrazolyl and 3-pyrrolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furyl (including 2-furyl and 3-furyl, etc.), thienyl (including 2-thienyl and 3-thienyl, etc.), pyridyl (including 2-pyridyl, 3-pyridyl and 4-pyridyl, etc.), pyrazinyl, pyrimidinyl (including 2-pyrimidinyl and 4-pyrimidinyl, etc.), benzothiazolyl (including 5-benzothiazolyl, etc.), purinyl, benzimidazolyl (including 2-benzimidazolyl, etc.), benzoxazolyl, indolyl (including 5-indolyl, etc.), isoquinolinyl (including 1-isoquinolinyl and 5-isoquinolinyl, etc.), quinoxalinyl (including 2-quinoxalinyl and 5-quinoxalinyl, etc.) or quinolinyl (including 3-quinolinyl and 6-quinolinyl, etc.).

Unless otherwise specified, the terms "5- to 6-membered heteroaromatic ring" and "5- to 6-membered heteroaryl" can be used interchangeably in the present invention; the term "5- to 6-membered heteroaryl" represents a monocyclic group consisting of 5 to 6 ring atoms and having a conjugated π-electron system, 1, 2, 3 or 4 ring atoms thereof are heteroatoms independently selected from O, S and N, and the remainder are carbon atoms. Therein, the nitrogen atom is optionally quaternized, and the nitrogen and sulfur heteroatoms can be optionally oxidized (i.e., NO and $S(O)_p$, where p is 1 or 2). 5- to 6-membered heteroaryl can be attached to the remainder of the molecule through a heteroatom or a carbon atom. The 5- to 6-membered heteroaryl includes 5-membered and 6-membered heteroaryl. Examples of the 5- to 6-membered heteroaryl include, but are not limited to, pyrrolyl (including N-pyrrolyl, 2-pyrrolyl and 3-pyrrolyl, etc.), pyrazolyl (including 2-pyrazolyl and 3-pyrrolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furyl (including 2-furyl and 3-furyl, etc.), thienyl (including 2-thienyl and 3-thienyl, etc.), pyridyl (including 2-pyridyl, 3-pyridyl and 4-pyridyl, etc.), pyrazinyl or pyrimidinyl (including 2-pyrimidinyl and 4-pyrimidinyl, etc.).

Unless otherwise specified, the terms "5- to 10-membered heteroaromatic ring" and "5- to 10-membered heteroaryl" can be used interchangeably in the present invention; the term "5- to 10-membered heteroaryl" represents a monocyclic group consisting of 5 to 10 ring atoms and having a conjugated π-electron system, 1, 2, 3 or 4 ring atoms thereof are heteroatoms independently selected from O, S and N, and the remainder are carbon atoms. Therein, the nitrogen atom is optionally quaternized, and the nitrogen and sulfur heteroatoms can be optionally oxidized (i.e., NO and $S(O)_p$, where p is 1 or 2). 5- to 10-membered heteroaryl can be attached to the remainder of the molecule through a heteroatom or a carbon atom. The 5- to 10-membered heteroaryl includes 5-membered, 6-membered, 7-membered, 8-membered, 9-membered and 10-membered heteroaryl. Examples of the 5- to 10-membered heteroaryl include, but are not limited to, pyrrolyl (including N-pyrrolyl, 2-pyrrolyl and 3-pyrrolyl, etc.), pyrazolyl (including 2-pyrazolyl and 3-pyrrolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furyl (including 2-furyl and 3-furyl, etc.), thienyl (including 2-thienyl and 3-thienyl, etc.), pyridyl (including 2-pyridyl, 3-pyridyl and 4-pyridyl, etc.), pyrazinyl or pyrimidinyl (including 2-pyrimidinyl and 4-pyrimidinyl, etc.).

Unless otherwise specified, $C_{n-n+m}$ or $C_n$-$C_{n+m}$ includes any specific instance of n to n+m carbons, for example, $C_{1-12}$ includes $C_1, C_2, C_3, C_4, C_5, C_6, C_7, C_8, C_9, C_{10}, C_{11}$ and $C_{12}$, and also includes any range from n to n+m, for example, $C_{1-12}$ includes $C_{1-3}, C_{1-6}, C_{1-9}, C_{3-6}, C_{3-9}, C_{3-12}, C_{6-9}, C_{6-12}$ and $C_{9-12}$, etc.; similarly, n- to n+m-membered represents that the number of atoms on a ring is n to n+m, for example, a 3- to 12-membered ring includes a 3-membered ring, a 4-membered ring, a 5-membered ring, a 6-membered ring, a 7-membered ring, a 8-membered ring, a 9-membered ring, a 10-membered ring, a 11-membered ring and a 12-membered ring, and also includes any range from n to n+m, for example, a 3- to 12-membered ring includes a 3- to 6-membered ring, a 3- to 9-membered ring, a 5- to 6-membered ring, a 5- to 7-membered ring, a 5- to 10-membered ring, a 6-to 7-membered ring, a 6- to 8-membered ring and a 6- to 10-membered ring, etc.

The term "leaving group" refers to a functional group or atom that can be substituted with another functional group or atom through a substitution reaction (for example, a nucleophilic substitution reaction). For example, representative leaving groups include: triflate; chloro, bromo, iodo; sulfonate radicals, such as mesylate, tosylate, p-bromobenzenesulfonate, p-toluenesulfonate, etc.; acyloxy, such as acetoxy, trifluoroacetoxy, etc.

The term "protecting group" includes, but is not limited to, "an amino protecting group", "a hydroxy protecting group" or "a thiol protecting group". The term "amino protecting group" refers to a protecting group suitable for preventing side reactions at an amino nitrogen position. Representative amino protecting groups include, but are not limited to: formyl; acyl, for example, alkanoyl (such as acetyl, trichloroacetyl, or trifluoroacetyl); alkoxycarbonyl, such as tert-butoxycarbonyl (Boc); arylmethoxycarbonyl, such as benzyloxycarbonyl (Cbz) and 9-fluorenylmethoxycarbonyl (Fmoc); arylmethyl, such as benzyl (Bn), trityl (Tr), 1,1-di-(4'-methoxyphenyl)methyl; methylsilyl, such as trimethylsilyl (TMS) and tert-butyldimethylsilyl (TBS), etc. The term "hydroxy protecting group" refers to a protecting group suitable for preventing hydroxy side reactions. Representative hydroxy protecting groups include, but are not limited to: alkyl, such as methyl, ethyl and tert-butyl; acyl, for example, alkanoyl (such as acetyl); arylmethyl, such as benzyl (Bn), p-methoxybenzyl (PMB), 9-fluorenylmethyl (Fm) and diphenylmethyl (DPM); methylsilyl, such as trimethylsilyl (TMS) and tert-butyldimethylsilyl (TBS), etc.

The compounds of the present invention can be prepared by a variety of synthetic methods well known to those skilled in the art, including the specific embodiments enumerated below, embodiments formed in combination with other chemical synthetic methods, and the equivalent alternatives well known to those skilled in the art; the preferred embodiments include, but are not limited to, the embodiments of the present invention.

The solvents used in the present invention are commercially available.

Compounds were named according to conventional nomenclature in the art or by using ChemDraw® software, and commercially available compounds were named in supplier catalogs.

The present application will be described in detail below with reference to embodiments, but it does not mean that there is any unfavorable limitation to the present application. The present application has been described in detail herein, and the specific embodiments thereof are also disclosed. For those skilled in the art, it would be obvious to make various changes and improvements to the specific embodiments of the present application without departing from the spirit and scope of the present application.

EXAMPLES

Preparation of Intermediates

Reference Example 1: Preparation of Intermediate I-1

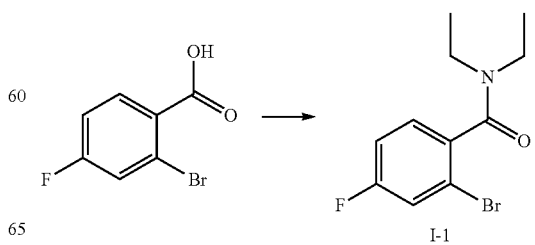

2-bromo-4-fluorobenzoic acid (7.00 g, 31.9 mmol) was dissolved in thionyl chloride (30.0 mL), and N,N-dimethylformamide (0.25 mL) was added. A reaction solution was stirred at 80° C. for 2 hours under nitrogen protection. The reaction solution was cooled to room temperature, thionyl chloride was removed under reduced pressure, and a residue was dissolved in dichloromethane (100 mL). Diethylamine (11.7 g, 159.8 mmol) was added, and the reaction solution was stirred at room temperature overnight. The reaction solution was washed with a saturated aqueous sodium bicarbonate solution (30.0 mL), water (30.0 mL) and saturated saline, dried over anhydrous sodium sulfate, and filtered. A filtrate was concentrated under reduced pressure to afford a crude product of intermediate I-1, and the crude product was directly used in the next reaction without purification. LC-MS (ESI) [M+H]$^+$ 274.0. $^1$H NMR (400 MHz, Chloroform-d) δ 7.30 (dd, J=8.3, 2.5 Hz, 1H), 7.22 (dd, J=8.5, 5.8 Hz, 1H), 7.05 (td, J=8.3, 2.5 Hz, 1H), 3.78 (dt, J=14.5, 7.1 Hz, 1H), 3.42-3.21 (m, 1H), 3.12 (ddt, J=17.6, 10.5, 7.2 Hz, 2H), 1.24 (t, J=7.1 Hz, 3H), 1.04 (t, J=7.1 Hz, 3H).

Reference Example 2: Preparation of Intermediate I-2

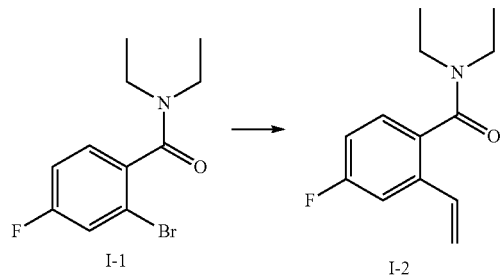

Intermediate I-1 (8.50 g), potassium vinylfluoroborate (4.98 g, 37.2 mmol) and potassium carbonate (10.7 g, 77.5 mmol) were dissolved in a mixed solution of dioxane (80.0 mL)/water (20.0 mL), and bistriphenylphosphine palladium dichloride (1.09 g, 1.55 mmol) was added. A reaction solution was stirred at 90° C. overnight under nitrogen protection. The reaction solution was cooled to room temperature and filtered, and a filtrate was concentrated under reduced pressure to afford a residue. The residue was dissolved in ethyl acetate (100.0 mL), washed successively with water (30.0 mL) and saturated saline, dried over anhydrous sodium sulfate, and filtered. A filtrate was concentrated under reduced pressure to afford a crude product of intermediate I-2, and the crude product was directly used in the next reaction without purification. LC-MS (ESI) [M+H]$^+$ 222.2. $^1$H NMR (400 MHz, Chloroform-d) δ 7.24 (d, J=2.6 Hz, 1H), 7.17 (dd, J=8.4, 5.7 Hz, 1H), 6.97 (td, J=8.3, 2.5 Hz, 1H), 6.67 (ddd, J=17.4, 11.0, 1.7 Hz, 1H), 5.75 (d, J=17.4 Hz, 1H), 5.36 (d, J=11.0 Hz, 1H), 3.55 (brs, 2H), 3.10-3.01 (m, 2H), 1.25 (t, J=7.1 Hz, 3H), 1.00 (t, J=7.1 Hz, 3H).

Reference Example 3: Preparation of Intermediate I-3

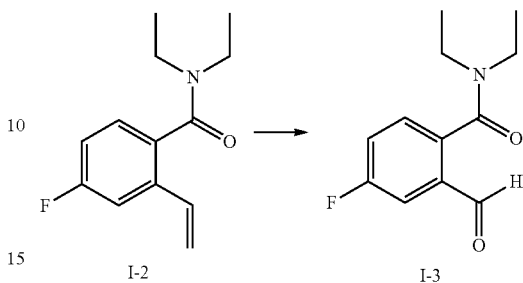

Intermediate I-2 (7.00 g) was dissolved in a mixed solvent of dioxane (70.0 mL)/water (30.0 mL), followed by addition of potassium osmate dihydrate (466.0 mg, 1.27 mmol) and sodium periodate (13.5 g, 63.2 mmol). A reaction solution was stirred at room temperature for 2 hours. The reaction solution was filtered, and a filtrate was concentrated to afford a residue. The residue was dissolved in ethyl acetate (100.0 mL), washed successively with water (30.0 mL) and saturated saline, dried over anhydrous sodium sulfate, and filtered. A filtrate was concentrated to afford a residue, and the residue was separated and purified by silica gel chromatography to afford intermediate I-3. $^1$H NMR (400 MHz, Chloroform-d) δ 9.99 (d, J=2.3 Hz, 1H), 7.63-7.57 (m, 1H), 7.38-7.28 (m, 2H), 3.59 (q, J=7.1 Hz, 2H), 3.11 (q, J=7.1 Hz, 2H), 1.27 (t, J=7.1 Hz, 3H), 1.02 (t, J=7.1 Hz, 3H).

Reference Example 4: Preparation of Intermediate I-4

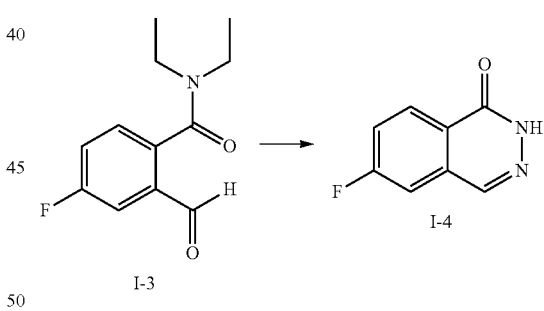

Intermediate I-3 (3.00 g, 13.4 mmol) was dissolved in acetic acid (10.0 mL), and hydrazine hydrate (1.03 g, 17.4 mmol, mass fraction 85.0%) was added. A reaction solution was stirred at 145° C. for 1 hour under microwave irradiation. The reaction solution was cooled to room temperature and filtered, a filter cake was dried to afford a crude product of intermediate I-4, and the crude product was directly used in the next reaction without purification. LC-MS (ESI) [M+H]$^+$ 165.0. $^1$H NMR (400 MHz, DMSO-d6) δ 12.69 (brs, 1H), 8.34 (s, 1H), 8.28 (dd, J=8.8, 5.5 Hz, 1H), 7.79 (dd, J=9.0, 2.6 Hz, 1H), 7.70 (td, J=8.9, 2.6 Hz, 1H).

Reference Example 5: Preparation of Intermediate I-5

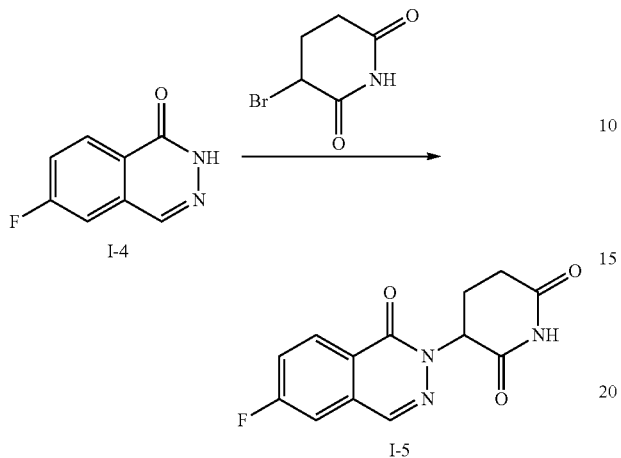

Intermediate I-4 (200.0 mg) was dissolved in N,N-dimethylformamide (5.00 mL), and sodium hydride (58.0 mg, 1.46 mmol, mass fraction 60.0%) was added. A reaction solution was stirred at room temperature for half an hour under nitrogen protection, and 3-bromopiperidine-2,6-dione (280.0 mg, 1.46 mmol) was added and stirred at room temperature overnight. The reaction solution was diluted with ethyl acetate (100.0 mL); organic phases were washed with water (30.0 mL) and saturated saline, dried over anhydrous sodium sulfate, filtered, and concentrated to afford a crude product of intermediate I-5; the crude product was directly used in the next reaction without purification. LC-MS (ESI) [M+H]⁺ 276.2.

Reference Example 6: Preparation of Intermediate I-6

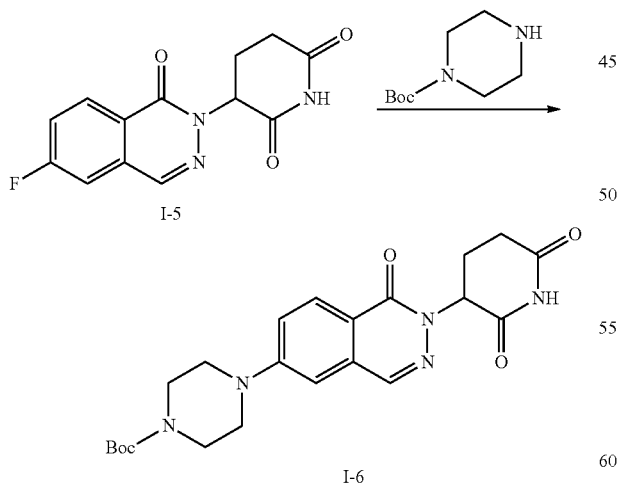

Intermediate I-5 (200.0 mg), 1-Boc-piperazine (176.0 mg, 0.94 mmol) and N,N-diisopropylethylamine (200.0 μL) were dissolved in dimethylsulfoxide (3.00 mL), and a reaction solution was stirred at 130° C. overnight under nitrogen protection. A reaction solution was cooled to room temperature, diluted with ethyl acetate (100.0 mL), washed with water (30.0 mL) and saturated saline, dried over anhydrous sodium sulfate, and filtered. A filtrate was concentrated under reduced pressure to afford a residue, and the residue was separated and purified by chromatography to afford intermediate I-6. LC-MS (ESI) [M+H]⁺ 442.3.

Reference Example 7: Preparation of Intermediate I-7

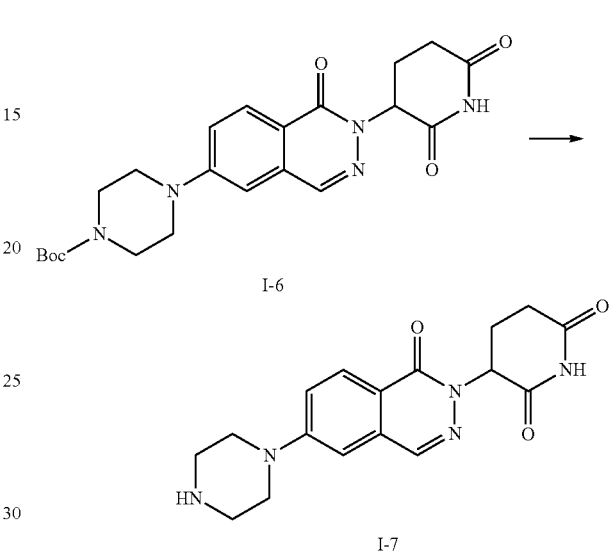

Intermediate I-6 (20.0 mg, 0.045 mmol) was dissolved in dichloromethane (2.00 mL), and trifluoroacetic acid (2.00 mL) was added. A reaction solution was stirred at room temperature for 2 hours under nitrogen protection. The reaction solution was concentrated under reduced pressure to afford a crude product of intermediate I-7, and the crude product was directly used in the next reaction without purification. LC-MS (ESI) [M+H]⁺ 342.2.

Reference Example 8: Preparation of Intermediate I-8

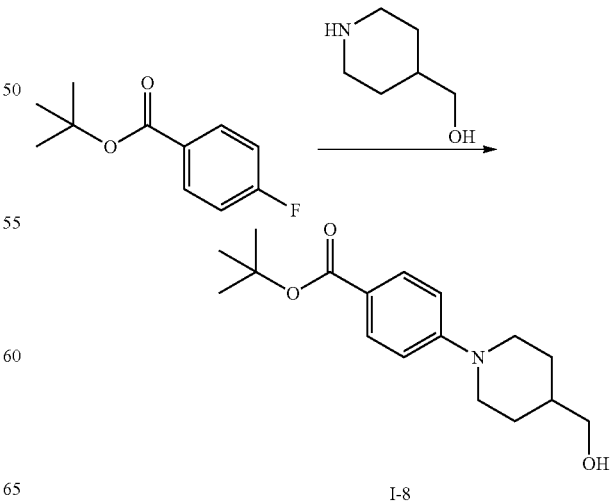

Tert-butyl 4-fluorobenzoate (3.00 g, 15.3 mmol), 4-hydroxymethylpiperidine (2.10 g, 18.2 mmol) were dissolved in N,N-dimethylformamide (20.0 mL), and potassium carbonate (2.64 g, 19.1 mmol) was added. A reaction solution was stirred at 80° C. overnight under nitrogen protection. The reaction solution was cooled to room temperature, and diluted with ethyl acetate (100.0 mL); organic phases were washed with water (30.0 mL) and saturated saline, dried over anhydrous sodium sulphate and then filtered. A filtrate was concentrated under reduced pressure to afford a residue, and the residue was separated and purified by silica gel chromatography to afford intermediate I-8. LC-MS (ESI) [M+H]$^+$ 292.2.

Reference Example 9: Preparation of Intermediate I-9

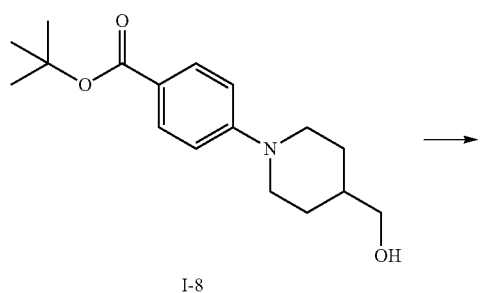

I-8

→

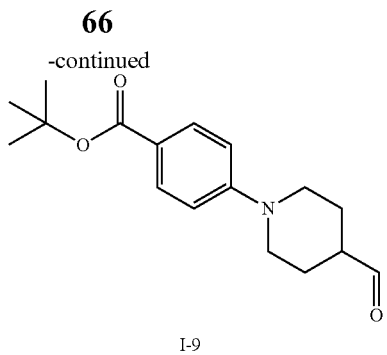

I-9

To a solution of intermediate I-8 (400.0 mg, 1.37 mmol) in dichloromethane (20.0 mL) was added Dess-Martin periodinane (864.0 mg, 2.03 mmol), and a reaction solution was stirred at room temperature overnight under nitrogen protection. A reaction solution was filtered, and a filtrate was concentrated under reduced pressure to afford a residue; the residue was separated and purified by silica gel chromatography to afford intermediate I-9. LC-MS (ESI) [M+H]$^+$ 290.2.

Reference Example 10: Preparation of Intermediate I-10

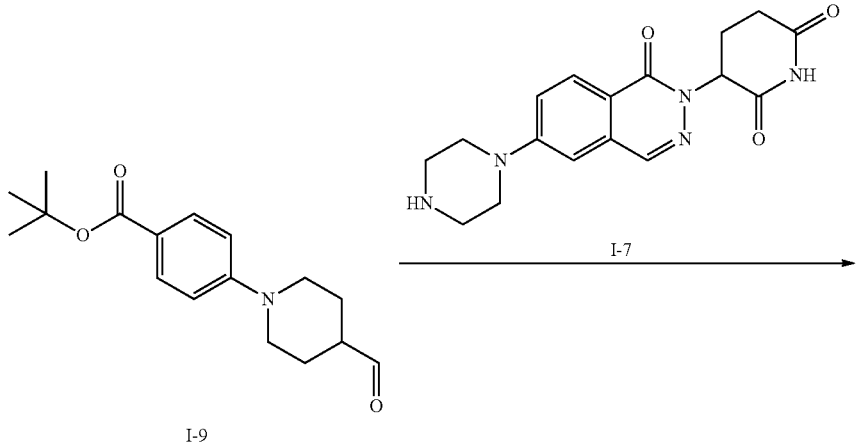

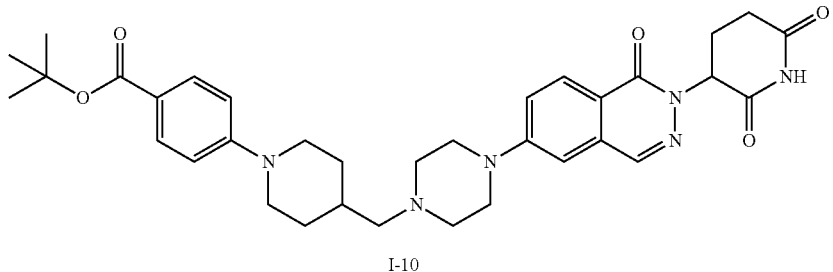

I-10

Intermediates I-7 (15.0 mg) and I-9 (19.0 mg, 0.066 mmol) were dissolved in 1,2-dichloroethane (3.00 mL), followed by addition of potassium acetate (3.60 mg, 0.044 mmol) and sodium triacetoxyborohydride (18.0 mg, 0.085 mmol). A reaction solution was stirred at room temperature overnight under nitrogen protection. The reaction solution was concentrated under reduced pressure to afford a residue. The residue was separated and purified by silica gel chromatography to afford intermediate I-10. LC-MS (ESI) [M+H−56]$^+$ 559.3.

Reference Example 11: Preparation of Intermediate I-11

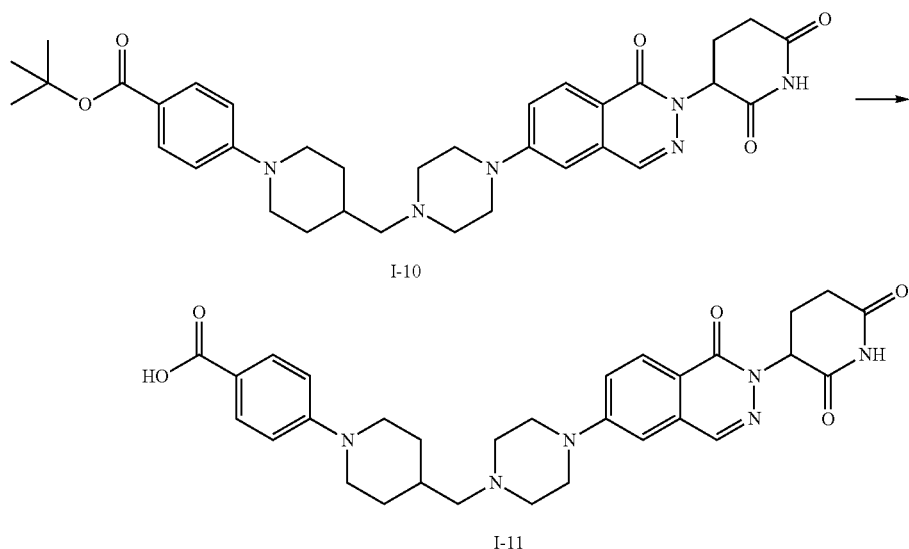

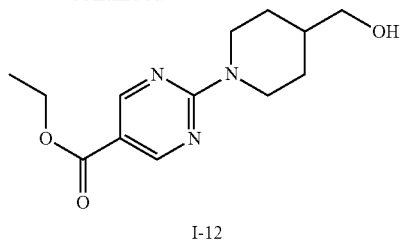

Intermediate I-10 (21.0 mg, 0.034 mmol) was dissolved in dichloromethane (3.00 mL), and trifluoroacetic acid (1.00 mL) was added. A reaction solution was stirred at room temperature overnight under nitrogen protection. The reaction solution was concentrated under reduced pressure to afford a crude product of intermediate I-11, and the crude product was directly used in the next reaction without purification.

Reference Example 12: Preparation of Intermediate I-12

Ethyl 2-chloropyrimidine-5-carboxylate (500 mg, 2.68 mmol), 4-hydroxymethylpiperidine (309 mg, 2.68 mmol) and potassium carbonate (370 mg, 2.68 mmol) were mixed and dissolved in N,N-dimethylformamide (20 mL). A reaction mixture was stirred and reacted at 50° C. overnight. The mixture was cooled to room temperature, poured into water (100 mL), and extracted with ethyl acetate (50 mL×3). Organic phases were combined, washed with saturated saline (30 mL), dried over anhydrous sodium sulfate, and filtered. A filtrate was concentrated under reduced pressure to afford a residue. The residue was separated and purified by silica gel chromatography to afford intermediate I-12. LC-MS (ESI) [M+H]$^+$ 266.1.

Reference Example 13: Preparation of Intermediate I-13

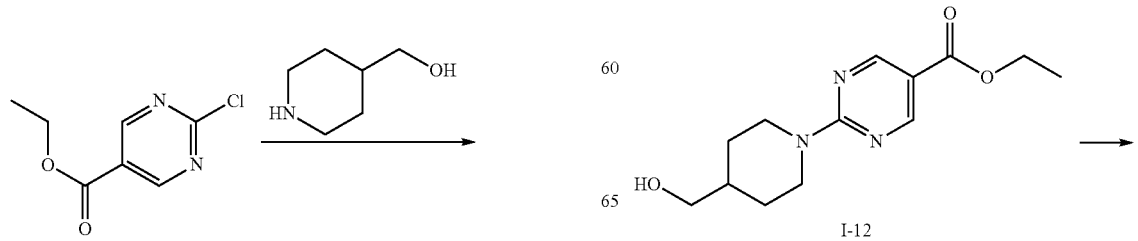

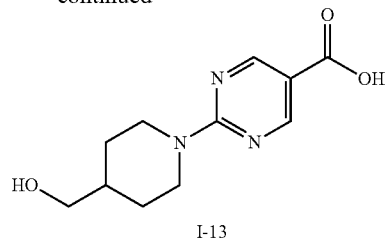

I-13

At room temperature, intermediate I-12 (19.0 g, 71.6 mmol) was dissolved in tetrahydrofuran (200 mL); then, a solution of lithium hydroxide monohydrate (6.01 g, 143 mmol) in water (50 mL) was added dropwise into the above-mentioned solution. After addition was completed, a reaction mixture was stirred at room temperature overnight. A reaction solution was concentrated under reduced pressure to remove an organic solvent, and a residue was adjusted to have pH=3 with a 2 N aqueous hydrochloric acid solution; a white solid was precipitated and filtered to afford a crude product of intermediate I-13, and the crude product was directly used in the next step without purification. LC-MS (ESI) [M+H]$^+$ 238.2.

Reference Example 14: Preparation of Intermediate I-14

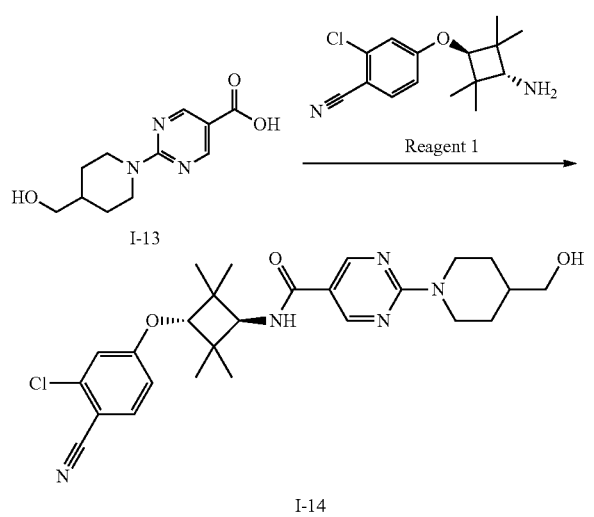

At room temperature, intermediate I-13 (2.50 g, 10.5 mmol), reagent 1 (3.31 g) and diisopropylethylamine (5.22 mL, 31.6 mmol) were dissolved in N,N-dimethylformamide (150 mL). Under the conditions of argon replacement and stirring, 0-(7-azabenzotriazol-1-yl)-N,N,N,N-tetramethyluronium hexafluorophosphate (6.01 g, 15.8 mmol) was added to a reaction solution. A reaction mixture was stirred at room temperature for 3 hours. A reaction solution was diluted with water (100 mL) and extracted with ethylacetate (50 mL×3); organic phases were dried over anhydrous sodium sulfate and filtered. A filtrate was concentrated under reduced pressure to remove an organic solvent, and a residue was separated and purified by silica gel chromatography to afford intermediate I-14. LC-MS (ESI) [M+H]$^+$ 498.2.

Reference Example 15: Preparation of Intermediate I-15

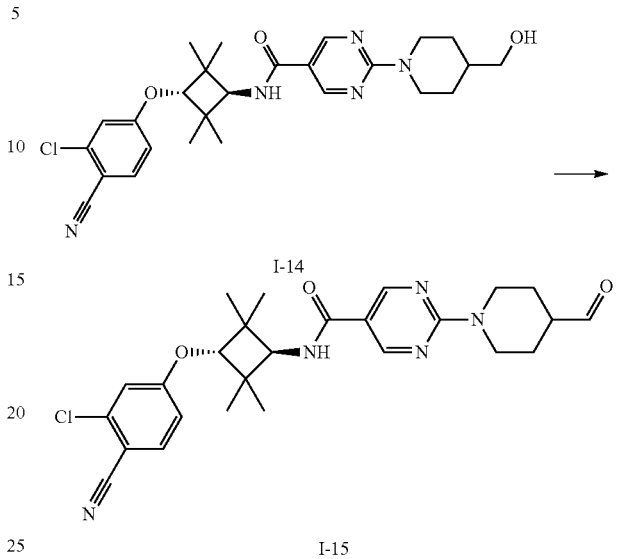

At room temperature, intermediate I-14 (400 mg, 0.803 mmol) and Dess-Martin periodinane (681 mg, 1.606 mmol) were dissolved in dichloromethane (10 mL). After addition was completed, a reaction solution was stirred at room temperature for 2 hours. The reaction solution was added with a saturated aqueous sodium thiosulfate solution (10 mL) and a saturated aqueous sodium bicarbonate solution (10 mL), and then extracted with dichloromethane (20 mL×3). Organic phases were combined, dried over anhydrous sodium sulfate, and filtered. A filtrate was concentrated under reduced pressure to afford intermediate I-15. The intermediate was directly used in the next reaction without purification.

Reference Example 16: Preparation of Intermediate I-16

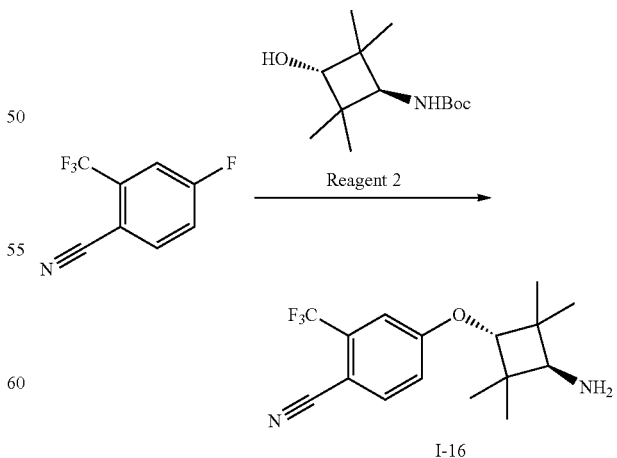

At room temperature, reagent 2 (777 mg, 4.11 mmol) was dissolved in N,N-dimethylformamide (15 mL); sodium hydride (296 mg, 60% content, 7.40 mg) was added at 0° C.

under nitrogen protection, followed by stirring for 30 minutes; 4-fluoro-2-(trifluoromethyl)benzonitrile (1.00 g, 4.11 mmol) was added, and a mixture was stirred and reacted at 40° C. for 3 hours; a reaction solution was added with water (50 mL) and extracted with acetic acid (50 mL×3); organic phases were combined, dried over anhydrous sodium sulfate, filtered and concentrated; after a crude product was purified by normal-phase column chromatography, a solution of hydrogen chloride in dioxane (15 mL, 3 M) was added, a reaction was conducted at room temperature for 1 hour, and the reaction solution was directly spin-dried and concentrated to afford intermediate I-16. The intermediate was directly used in the next reaction without purification.

Reference Example 18: Preparation of Intermediate I-18

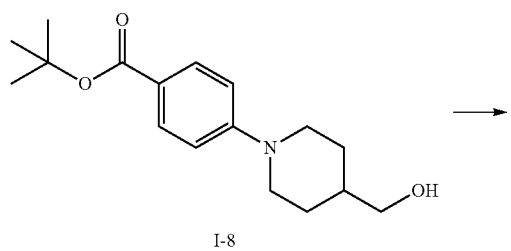

I-8

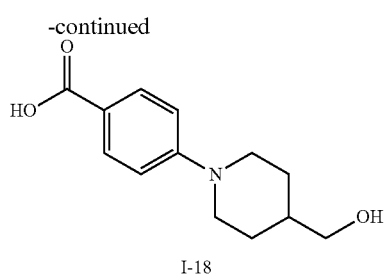

I-18

Intermediate I-8 (54.0 g, 185 mmol) was dissolved in anhydrous dioxane (500 mL), and a solution of hydrogen chloride in dioxane (1500 mL, 3 M) was added; a reaction system was protected with argon, warmed up to 75° C., and stirred and reacted for 16 hours. A mixture was concentrated under reduced pressure to remove an organic solvent to afford a crude product, and the crude product was purified by beating with ethyl acetate (500 mL); suction filtration was performed, and a filter cake was purified by beating with anhydrous acetonitrile (500 mL); the suction filtration was performed, and a filter cake was dried to afford intermediate I-18.

Reference Example 19: Preparation of Intermediate I-19

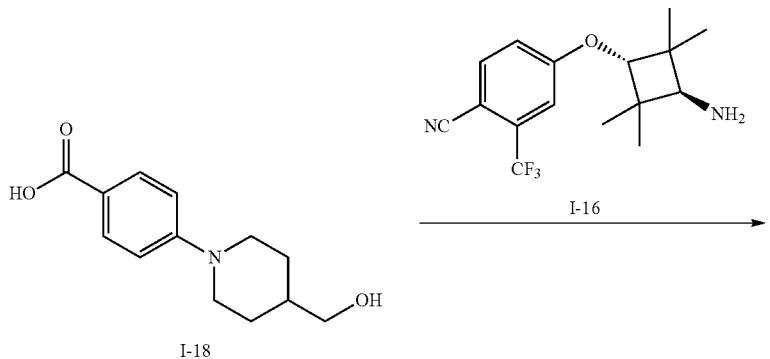

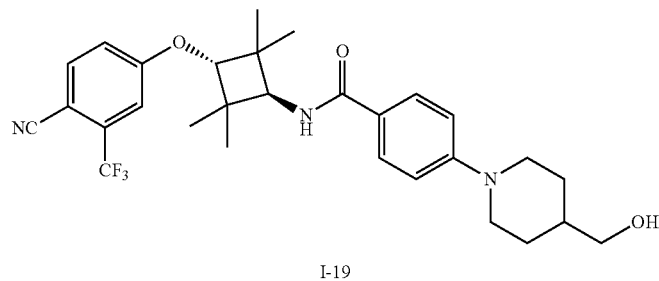

I-19

Intermediate I-18 (200 mg) was dissolved in N,N-dimethylformamide (30 mL), followed by successive addition of 1-hydroxybenzotriazole (230 mg, 1.702 mmol), 1-(3-dimethylaminopropyl)-3-ethylcarbodiimide hydrochloride (327 mg, 1.702 mmol), N,N-diisopropylethylamine (0.42 mL, 2.55 mmol) and intermediate I-16 (385 mg). A reaction mixture was stirred and reacted at room temperature for 16 hours. Water (50 mL) was added for dilution, and dichloromethane (50 mL×3) was used for extraction. Organic phases were combined, washed with saturated saline (30 mL), and dried over anhydrous sodium sulfate. Filtration was performed, and a filtrate was concentrated under reduced pressure to remove an organic solvent to afford a crude product. The crude product was separated and purified by silica gel chromatography to afford intermediate I-19.

Reference Example 20: Preparation of Intermediate I-20

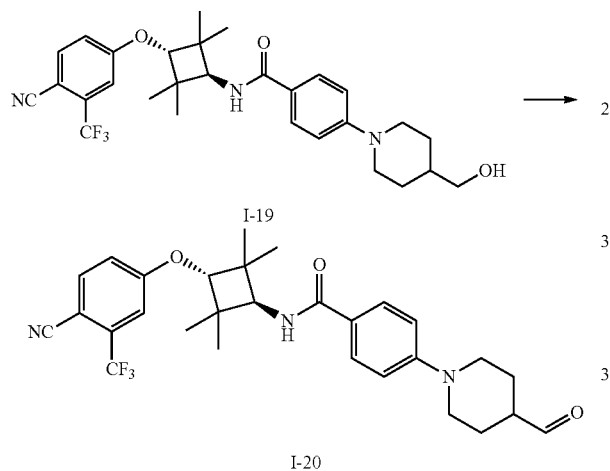

Intermediate I-19 (120 mg, 0.226 mmol) was dissolved in anhydrous dichloromethane (20 mL), and a system was cooled to 0° C. and added with Dess-Martin periodinane (192 mg, 0.452 mmol). A reaction system was protected with argon, and stirred and reacted at room temperature for 2 hours. Filtration was performed, and a filtrate was quenched with a saturated aqueous sodium bicarbonate solution (200 mL) and extracted with dichloromethane (200 mL×3). Organic phases were combined, washed with saturated saline (200 mL), and dried over anhydrous sodium sulfate. Filtration was performed, and a filtrate was concentrated under reduced pressure to remove an organic solvent to afford a crude product. The crude product was separated and purified by silica gel chromatography to afford intermediate I-20.

Reference Example 21: Preparation of Intermediate I-21

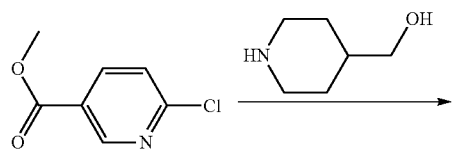

-continued

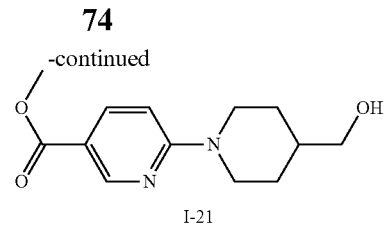

At room temperature, methyl 6-chloronicotinate (500 mg, 2.91 mmol) was dissolved in a N,N-dimethylformamide (5 mL) solution, followed by successive addition of 4-piperidinemethanol (402 mg, 3.50 mmol) and N,N-diisopropylethylamine (1.13 g, 8.73 mmol); after addition was completed, a reaction mixture was stirred and reacted at 80° C. for 3 hours. After a reaction was completed, water (10 mL) was added for dilution, and ethyl acetate (10 mL×3) was used for extraction; organic phases were combined, washed with water (10 mL×3), dried over anhydrous sodium sulfate and filtered; a filtrate was concentrated under reduced pressure, and a residue was separated and purified by silica gel chromatography to afford intermediate I-21.

Reference Example 22: Preparation of Intermediate I-22

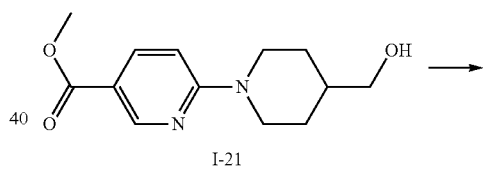

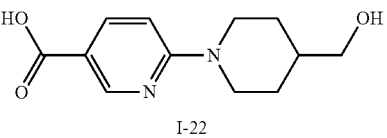

At room temperature, intermediate I-21 (250 mg, 1.00 mmol) was dissolved in tetrahydrofuran (3 mL), and a solution of lithium hydroxide monohydrate (420 mg, 10.0 mmol) in water (2 mL) was added; after addition was completed, a reaction mixture was stirred at room temperature overnight. After a reaction was completed, a reaction solution was acidified with a 1 N hydrochloric acid solution to pH=6 and concentrated under reduced pressure, and a residue was separated and purified by reverse-phase silica gel chromatography to afford intermediate I-22.

Reference Example 23: Preparation of Intermediate I-23

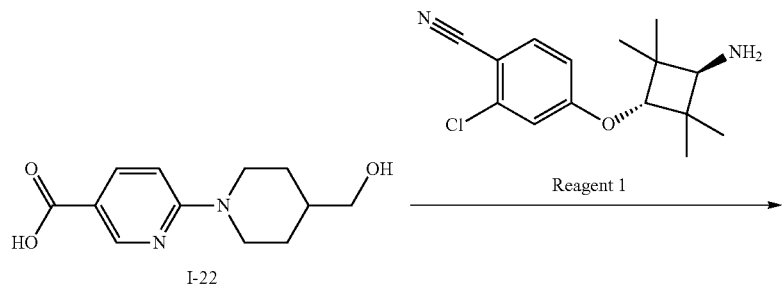

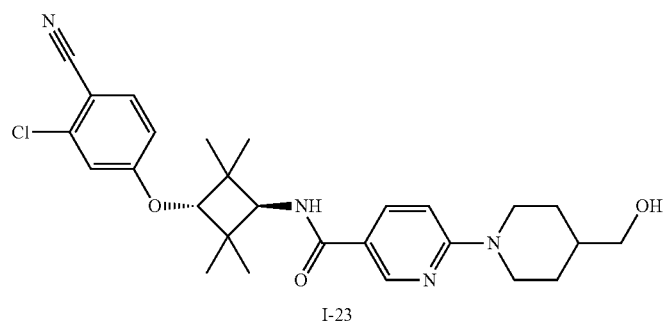

At room temperature, intermediate I-22 (100 mg, 0.42 mmol) was dissolved in a N,N-dimethylformamide (5 mL) solution, followed by successive addition of reagent 1 (117 mg), 1-hydroxybenzotriazole (113 mg, 0.84 mmol), 1-(3-dimethylaminopropyl)-3-ethylcarbodiimide hydrochloride (161 mg, 0.84 mmol) and N,N-diisopropylethylamine (163 mg, 1.26 mmol); after addition was completed, a reaction mixture was stirred at room temperature overnight. After a reaction was completed, water (10 mL) was added for dilution, and ethyl acetate (10 mL×3) was used for extraction; organic phases were combined, washed with water (10 mL×3), dried over anhydrous sodium sulfate and filtered; a filtrate was concentrated under reduced pressure, and a residue was purified by normal-phase silica gel chromatography to afford intermediate I-23.

Reference Example 24: Preparation of Intermediate I-24

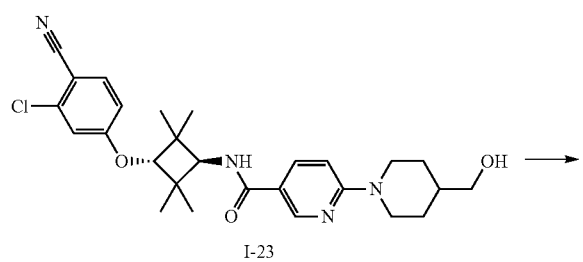

-continued

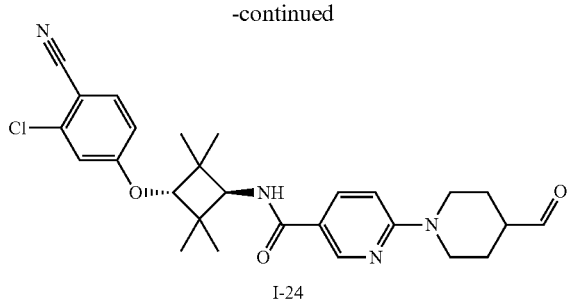

In an ice-water bath, intermediate I-23 (100 mg, 0.20 mmol) was dissolved in dichloromethane (10 mL), and Dess-Martin periodinane (170 mg, 0.40 mmol) was added; after addition was completed, a reaction mixture was stirred and reacted at room temperature for 2 hours. A saturated sodium sulfite solution (10 mL) was added for dilution, standing for layering was performed, and an aqueous phase was extracted with dichloromethane (10 mL×2); organic phases were combined, and washed successively with a saturated sodium sulfite solution (10 mL), a saturated sodium bicarbonate solution (10 mL) and water (10 mL), dried over anhydrous sodium sulfate and filtered; a filtrate was concentrated under reduced pressure to afford intermediate I-24. The intermediate was directly used in the next reaction without further purification.

Reference Example 25: Preparation of Intermediate I-25

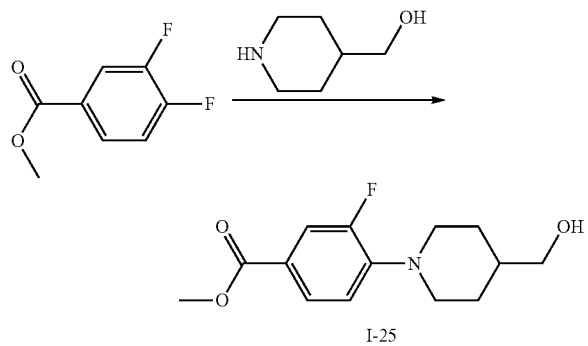

At room temperature, methyl 3,4-difluorobenzoate (200 mg, 1.16 mmol) was dissolved in a N,N-dimethylformamide (10 mL) solution, followed by successive addition of 4-piperidinemethanol (133 mg, 1.16 mmol) and potassium carbonate (480 g, 3.48 mmol); after addition was completed, a reaction mixture was stirred and reacted at 100° C. for 2 hours. Water (20 mL) was added for dilution, and ethyl acetate (20 mL×3) was used for extraction; organic phases were combined, washed with water (20 mL×3), dried over anhydrous sodium sulfate and filtered; a filtrate was concentrated under reduced pressure, and a residue was purified by silica gel chromatography to afford intermediate I-25. LC-MS (ESI) [M+H]$^+$ 268.1.

Reference Example 26: Preparation of Intermediate I-26

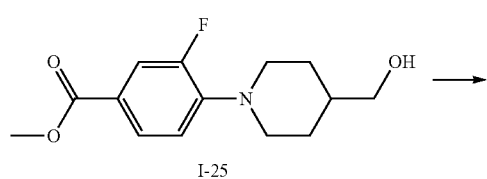

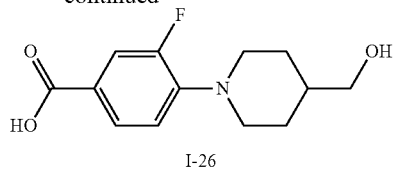

At room temperature, intermediate I-25 (160 mg, 0.60 mmol) was dissolved in tetrahydrofuran (5 mL), and a solution of lithium hydroxide monohydrate (252 mg, 6.0 mmol) in water (2 mL) was added; after addition was completed, a reaction mixture was stirred and reacted at room temperature overnight. A reaction solution was adjusted to have pH=4-5 with a 1 N aqueous hydrochloric acid solution; filtration was performed, and a filter cake was dried to afford intermediate I-26. LC-MS (ESI) [M+H]$^+$ 254.1.

Reference Example 27: Preparation of Intermediate I-27

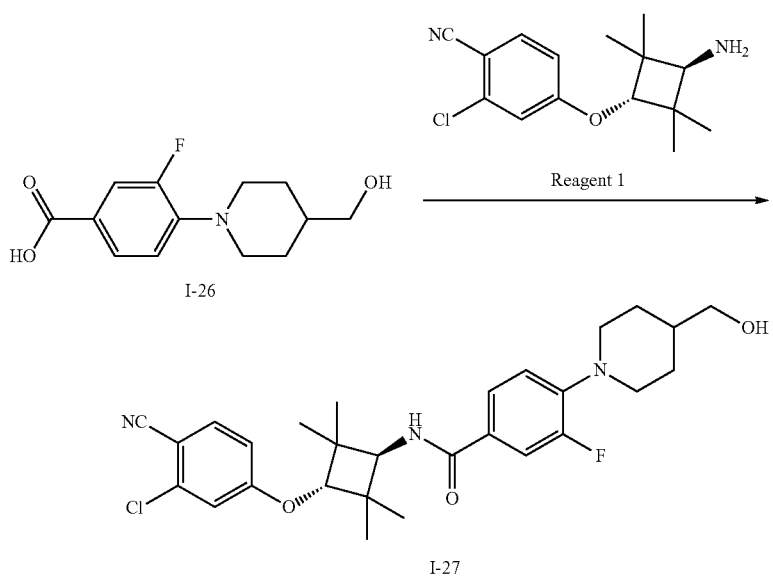

At room temperature, intermediate I-26 (120 mg, 0.47 mmol) was dissolved in a N,N-dimethylformamide (5 mL) solution, followed by successive addition of reagent 1 (131 mg), 1-hydroxybenzotriazole (127 mg, 0.94 mmol), 1-(3-dimethylaminopropyl)-3-ethylcarbodiimide hydrochloride (180 mg, 0.94 mmol) and N,N-diisopropylethylamine (182 mg, 1.41 mmol); after addition was completed, a reaction mixture was stirred and reacted at room temperature for 3 hours. Water (20 mL) was added for dilution, and ethyl acetate (20 mL×3) was used for extraction; organic phases were combined, washed with water (20 mL×3), dried over anhydrous sodium sulfate and filtered; a filtrate was concentrated under reduced pressure, and a residue was purified by silica gel chromatography to afford intermediate I-27. LC-MS (ESI) [M+H]$^+$ 514.1.

Reference Example 28: Preparation of Intermediate I-28

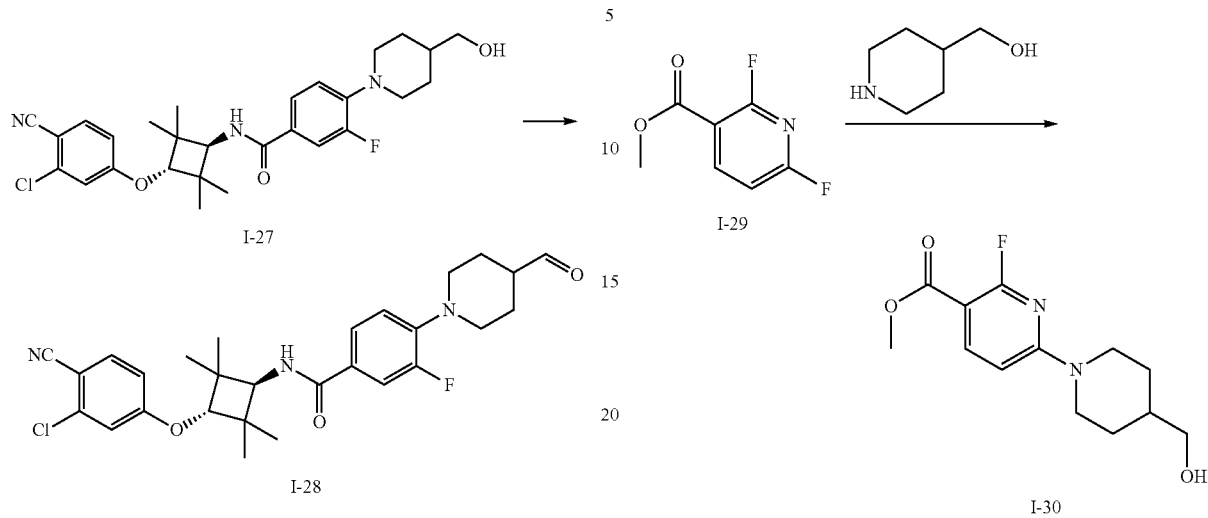

At 0° C., intermediate I-27 (122 mg, 0.24 mmol) was dissolved in dichloromethane (10 mL), and Dess-Martin periodinane (204 mg, 0.48 mmol) was added; after addition was completed, a reaction mixture was stirred and reacted at room temperature for 2 hours. A saturated sodium sulfite solution (20 mL) was added for dilution, standing for layering was performed, and an aqueous phase was extracted with dichloromethane (20 mL×2); organic phases were combined, and washed successively with a saturated sodium sulfite solution (20 mL×2), a saturated sodium bicarbonate solution (20 mL×3) and water (20 mL×3), dried over anhydrous sodium sulfate and filtered; a filtrate was concentrated under reduced pressure to afford intermediate I-28. The intermediate was directly used in the next reaction without further purification.

Reference Example 29: Preparation of Intermediate I-29

2,6-difluoronicotinic acid (1.0 g, 0.322 mmol) was dissolved in ethanol (20 mL), and concentrated sulfuric acid (61.7 mg, 0.629 mmol) was added; a system was protected with nitrogen, and a mixture was stirred and reacted at 100° C. for 16 hours. The mixture was added to water (20 mL) and extracted with ethyl acetate (20 mL×3), and organic phases were combined, washed with saturated saline (10 mL), dried over anhydrous sodium sulfate, filtered, and concentrated to afford intermediate I-29. The intermediate was directly used in the next reaction without further purification.

Reference Example 30: Preparation of Intermediate I-30

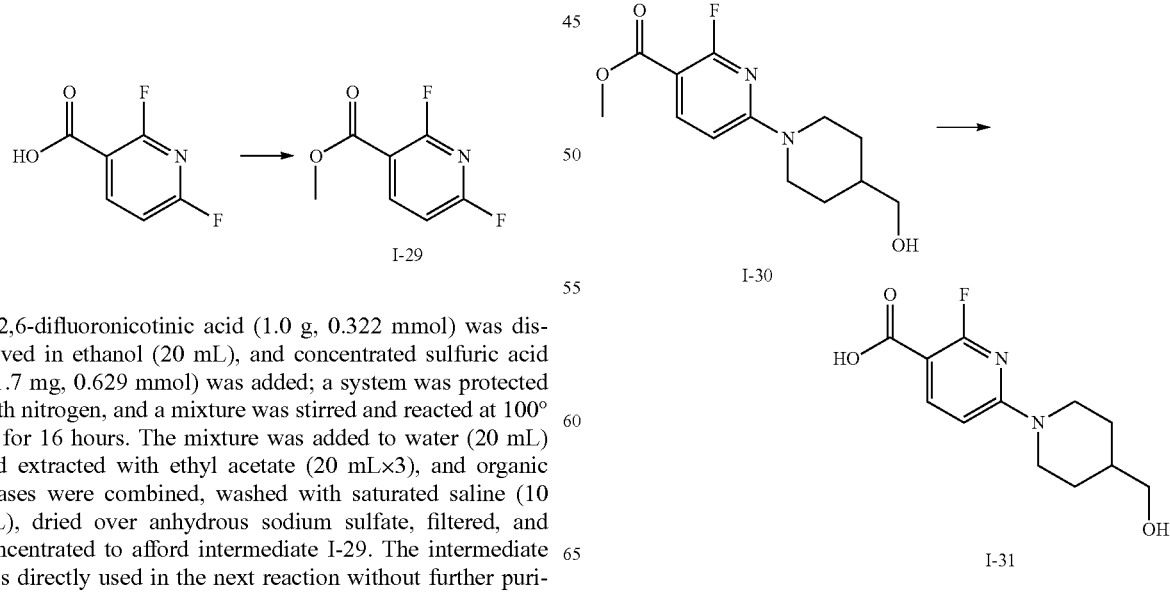

Intermediate I-29 (350 mg, 2.02 mmol) was dissolved in anhydrous N,N-dimethylformamide (15 mL), followed by successive addition of 4-hydroxymethylpiperidine (255 mg, 2.22 mmol) and potassium carbonate (558 mg, 4.04 mmol); a reaction system under nitrogen protection was warmed up to 100° C. and reacted for 16 hours; after a mixture was cooled to room temperature, the mixture was added with water (20 mL), and extracted with ethyl acetate (20 mL×3). Organic phases were combined, washed with saturated saline (10 mL), dried over anhydrous sodium sulfate and filtered, and a filtrate was concentrated to dryness. A residue was purified by silica gel chromatography to afford intermediate I-30. LC-MS (ESI) [M+H]$^+$ 269.1.

Reference Example 31: Preparation of Intermediate I-31

Intermediate I-30 (100 mg, 0.373 mmol) was dissolved in anhydrous tetrahydrofuran (5 mL); then, lithium hydroxide monohydrate (78.3 mg, 1.87 mmol) was dissolved in water (5.00 mL) and added dropwise to a reaction, and a reaction system was protected with argon and stirred at room temperature for 2 hours. A mixture was adjusted to be weakly acidic with 1 N hydrochloric acid, a solid was precipitated, and filtration was performed to afford a crude product of intermediate I-31. The intermediate was directly used in the next reaction without further purification. LC-MS (ESI) [M+H]$^+$ 255.2.

Reference Example 32: Preparation of Intermediate I-32

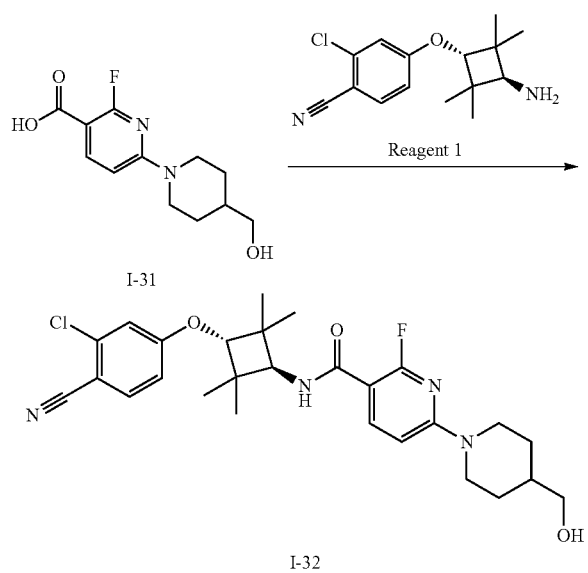

Intermediate I-31 (55 mg) was dissolved in N,N-dimethylformamide (10 mL), followed by successive addition of 1-hydroxybenzotriazole (58.6 mg, 0.434 mmol), 1-(3-dimethylaminopropyl)-3-ethylcarbodiimide hydrochloride (83.3 mg, 0.434 mmol), N,N-diisopropylethylamine (0.107 mL, 0.651 mmol) and reagent 1 (60.5 mg). A reaction mixture was stirred and reacted at room temperature for 16 hours. A reaction solution was filtered, and a filter cake was washed with ethyl acetate (5 mL×3) and dried to afford intermediate I-32. LC-MS (ESI) [M+H]$^+$ 515.2.

Reference Example 33: Preparation of Intermediate I-33

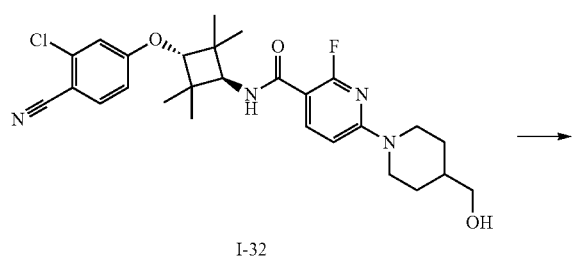

Intermediate I-32 (80 mg, 0.155 mmol) was dissolved in anhydrous dichloromethane (10 mL), and a system was cooled to 0° C. and added with Dess-Martin periodinane (98.8 mg, 0.233 mmol). A reaction system was protected with argon, and stirred and reacted at room temperature for 2 hours. Filtration was performed, and a filtrate was quenched with a saturated aqueous sodium bicarbonate solution (10 mL) and extracted with dichloromethane (10 mL×3). Organic phases were combined, washed with saturated saline (10 mL), and dried over anhydrous sodium sulfate. Filtration was performed, and a filtrate was concentrated under reduced pressure to remove an organic solvent to afford a crude product. The crude product was purified by silica gel chromatography to afford intermediate I-33.

Reference Example 34: Preparation of Intermediate I-34

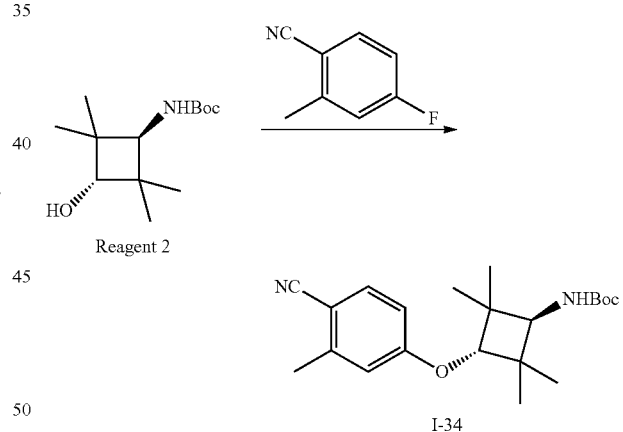

Reagent 2 (500 mg, 2.05 mmol) was dissolved in N,N-dimethylformamide (10 mL), and 4-fluoro-2-methylbenzonitrile (277 mg, 2.05 mmol) was added successively; when the temperature was reduced to 0° C., 60% sodium hydride (164 mg, 4.1 mmol) was added, and the whole system was conducted under nitrogen; after addition was completed, a system was warmed up to 70° C. and reacted for 2 hours. Water was added for quenching, and ethyl acetate (10 mL×3) was used for extraction; organic phases were combined, washed with saturated saline (10 mL), dried over anhydrous sodium sulfate, filtered, and concentrated to afford a crude product. The crude product was purified by silica gel chromatography to afford intermediate I-34. LC-MS (ESI) [M−100+H]$^+$259.2.

Reference Example 35: Preparation of Intermediate I-35

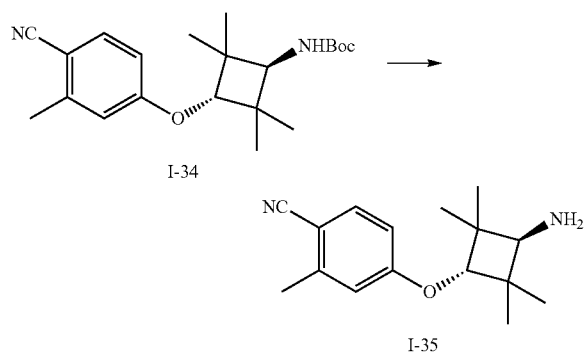

Intermediate I-34 (120 mg, 0.335 mmol) was dissolved in anhydrous dioxane (10 mL), a solution of hydrogen chloride in dioxane (15 mL, 3 M) was added, and a reaction system was protected with argon, and stirred and reacted at room temperature for 16 hours. A mixture was concentrated under reduced pressure to remove an organic solvent to afford a crude product, and the crude product was purified by beating with ethyl acetate (20 mL); suction filtration was performed, and a filter cake was purified by beating with anhydrous acetonitrile (20 mL); the suction filtration was performed, and a filter cake was dried to afford intermediate I-35. LC-MS (ESI) [M+H]$^+$ 259.1.

Reference Example 36: Preparation of Intermediate I-36

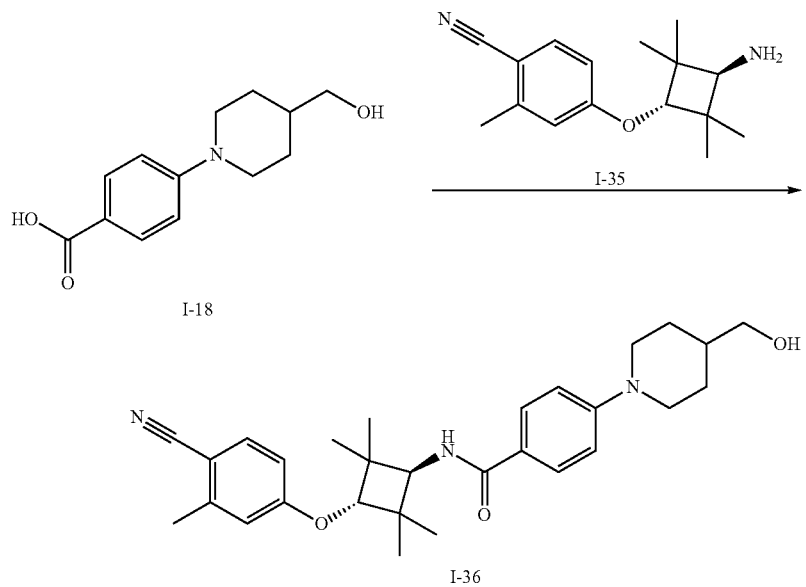

Intermediate I-18 (100 mg) was dissolved in N,N-dimethylformamide (15 mL), followed by successive addition of 1-hydroxybenzotriazole (114 mg, 0.85 mmol), 1-(3-dimethylaminopropyl)-3-ethylcarbodiimide hydrochloride (163 mg, 0.85 mmol), N,N-diisopropylethylamine (0.21 mL, 1.28 mmol) and intermediate I-35 (125 mg). A reaction mixture was stirred and reacted at room temperature for 16 hours. A reaction solution was filtered, and a filter cake was washed with ethyl acetate (5 mL×3) and dried to afford intermediate I-36. LC-MS (ESI) [M+H]$^+$ 476.2.

Reference Example 37: Preparation of Intermediate I-37

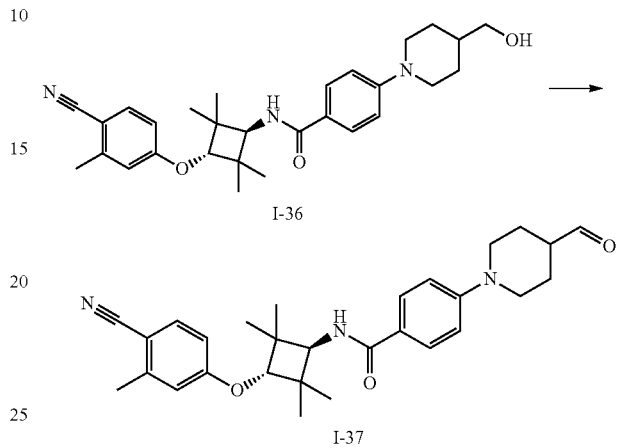

Intermediate I-36 (63 mg, 0.132 mmol) was dissolved in anhydrous dichloromethane (10 mL), and a system was cooled to 0° C. and added with Dess-Martin periodinane (83.9 mg, 0.198 mmol). A reaction system was protected with argon, and stirred and reacted at room temperature for 2 hours. Filtration was performed, and a filtrate was quenched with a saturated aqueous sodium bicarbonate solution (10 mL) and extracted with dichloromethane (10 mL×3). Organic phases were combined, washed with saturated saline (10 mL), and dried over anhydrous sodium sulfate. Filtration was performed, and a filtrate was concentrated under reduced pressure to remove an organic solvent to afford a crude product. The crude product was purified by silica gel chromatography to afford intermediate I-37.

Reference Example 38: Preparation of Intermediate I-38

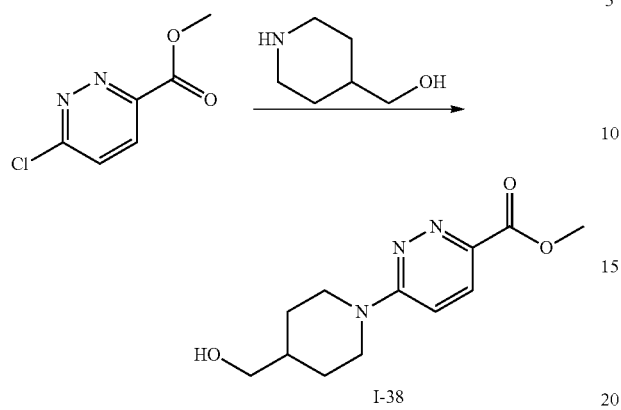

At room temperature, methyl 6-chloropyridazine-3-carboxylate (7.00 g, 40.6 mmol) and diisopropylethylamine (10.5 mL, 81.1 mmol) were dissolved in 1,4-dioxane (200 mL). 4-hydroxymethylpiperidine (9.34 g, 81.1 mmol) was added to the above-mentioned mixture. After addition was completed, a reaction mixture was stirred at 110° C. overnight under argon protection. A reaction solution was concentrated under reduced pressure to remove an organic solvent to afford a crude product of intermediate I-38, and the crude product was directly used in the next reaction without purification. LC-MS (ESI) [M+H]+ 252.2.

Reference Example 39: Preparation of Intermediate I-39

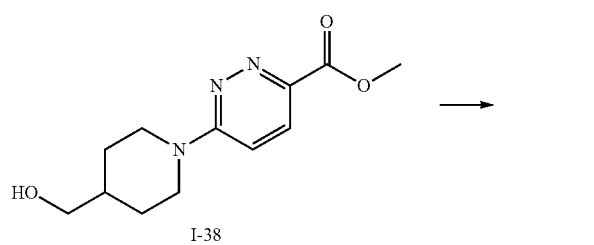

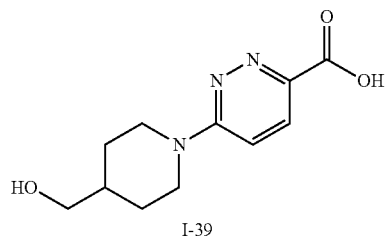

At room temperature, intermediate I-38 (10.0 g, 39.8 mmol) was dissolved in tetrahydrofuran (150 mL) and methanol (50 mL); then, a solution of lithium hydroxide monohydrate (3.34 g, 79.6 mmol) in water (30 mL) was added dropwise to the above-mentioned solution. After addition was completed, a reaction mixture was stirred at room temperature overnight. A reaction solution was concentrated under reduced pressure to remove an organic solvent, and a residue was adjusted to pH=3 with a aqueous hydrochloric acid solution (2 N). The mixture was separated and purified by chromatography to afford intermediate I-39. LC-MS (ESI) [M+H]+ 238.2. $^1$H NMR (400 MHz, DMSO-d$_6$) δ 7.79 (d, J=8.0 Hz, 1H), 7.27 (d, J=12.0 Hz, 1H), 4.52 (d, J=12.0 Hz, 2H), 3.28 (d, J=8.0 Hz, 2H), 2.99 (t, J=12.0 Hz, 2H), 1.70-1.80 (m, 3H), 1.15-1.20 (m, 2H).

Reference Example 40: Preparation of Intermediate I-40

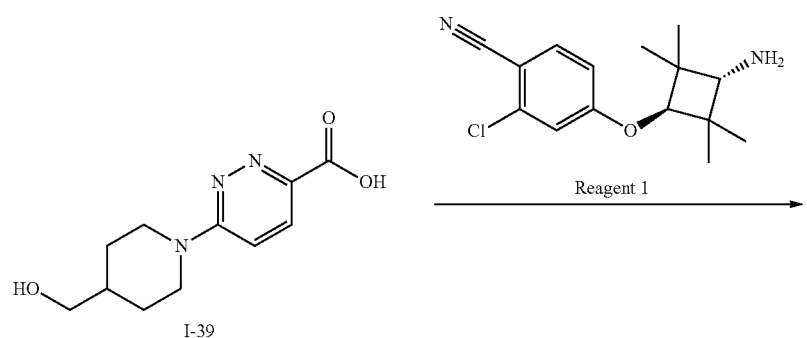

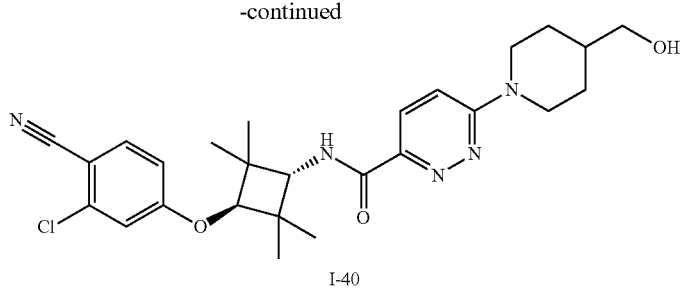

I-40

At room temperature, intermediate I-39 (200 mg, 0.843 mmol) and reagent 1 (266 mg) were dissolved in N,N-dimethylformamide (10 mL). Under the conditions of argon replacement and stirring, 1-hydroxybenzotriazole (171 mg, 1.26 mmol), 1-(3-dimethylaminopropyl)-3-ethylcarbodiimide hydrochloride (196 mg, 1.26 mmol) and N,N-diisopropylethylamine (0.418 mL, 2.53 mmol) were added to the above-mentioned mixture. After addition was completed, a reaction mixture was stirred at room temperature overnight. A reaction solution was diluted with water (20 mL) and extracted with ethyl acetate (50 mL×3), and organic phases were dried and filtered. Concentration was performed under reduced pressure to remove an organic solvent, and a residue was purified by silica gel chromatography to afford intermediate I-40. LC-MS (ESI) [M+H]$^+$ 498.2.

Reference Example 41: Preparation of Intermediate I-41

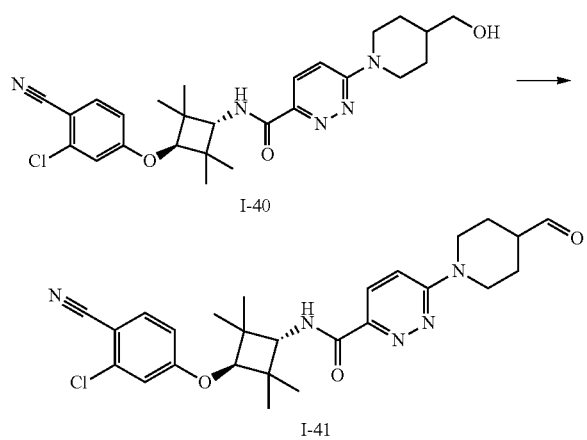

In an ice-water bath, intermediate I-40 (120 mg, 0.241 mmol) was dissolved in dichloromethane (10 mL). Under the conditions of argon replacement and stirring, Dess-Martin periodinane (204 mg, 0.482 mmol) was added. After addition was completed, a reaction mixture was stirred and reacted at room temperature for 3 hours. A reaction solution was added with a saturated sodium sulfite solution (10 mL) for quenching, and extracted with dichloromethane (10 mL×3). Organic phases were combined, washed with saturated sodium bicarbonate (50 mL), dried and filtered. A filtrate was concentrated under reduced pressure, and a residue was purified by silica gel chromatography to afford intermediate I-41.

Reference Example 42: Preparation of Intermediate I-42

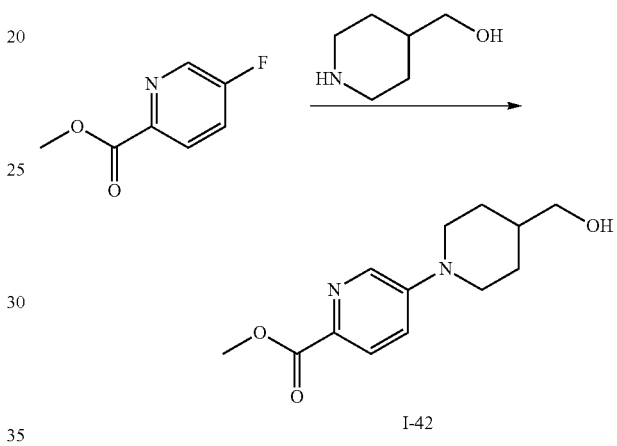

A compound of methyl 5-fluoropyridine-2-carboxylate (900 mg, 5.80 mmol) was dissolved in N,N-dimethylformamide (50 mL), followed by addition of compounds of 4-piperidinemethanol (670 mg, 5.82 mmol) and diisopropylethylamine (2.87 mL, 17.4 mmol). A reaction mixture was stirred at 100° C. for 16 hours. After concentration, water (100 mL) was added for dilution, and ethyl acetate (100 mL×3) was used for extraction. Organic phases were combined, washed with saturated saline (100 mL), and dried over anhydrous sodium sulfate. Filtration was performed, and a filtrate was concentrated under reduced pressure to remove an organic solvent to afford a residue. The residue was separated and purified by silica gel chromatography to afford intermediate I-42. LC-MS (ESI) [M+H]$^+$ 251.0.

Reference Example 43: Preparation of Intermediate I-43

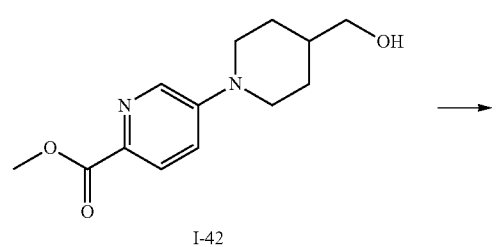

I-42

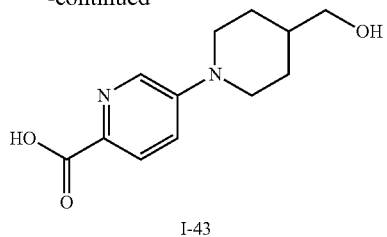

I-43

Intermediate I-42 (300 mg, 1.20 mmol) was dissolved in tetrahydrofuran and water (5 mL/5 mL), and lithium hydroxide monohydrate (403 mg, 9.60 mmol) was added. A reaction mixture was stirred and reacted at room temperature for 18 hours. Most tetrahydrofuran was removed by concentration, a solution was adjusted to have a pH value of about 5 with a 1 N aqueous hydrochloric acid solution, and then the solution was separated and purified by chromatography to afford intermediate I-43. LC-MS (ESI) [M+H]$^+$ 237.0.

Reference Example 44: Preparation of Intermediate I-44

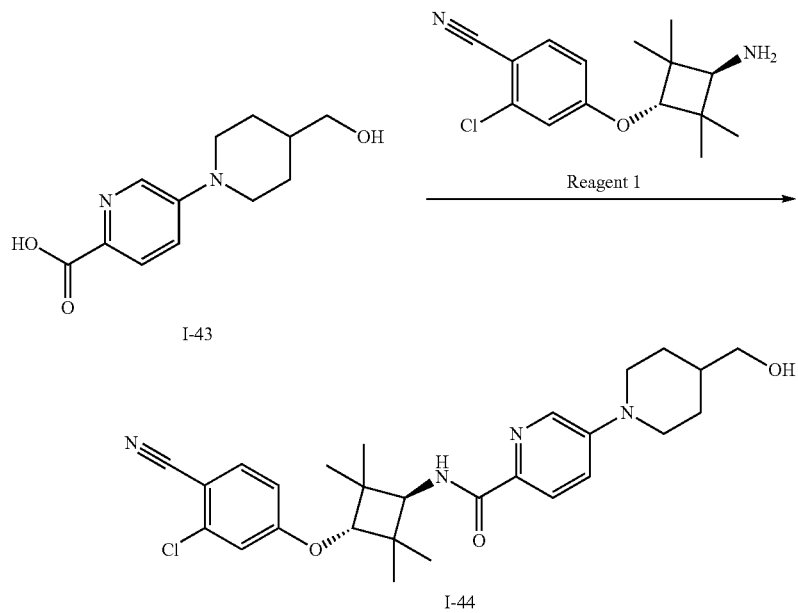

At room temperature, intermediate I-43 (260 mg) was dissolved in N,N-dimethylformamide (10 mL), followed by successive addition of reagent 1 (300 mg), 1-hydroxybenzotriazole (257 mg, 1.904 mmol), 1-(3-dimethylaminopropyl)-3-ethylcarbodiimide hydrochloride (366 mg, 1.904 mmol) and N,N-diisopropylethylamine (0.47 mL, 2.856 mmol). A reaction mixture was stirred and reacted at room temperature for 48 hours, diluted with water (50 mL) and extracted with dichloromethane (50 mL×3). Organic phases were combined, washed with saturated saline (30 mL), and dried over anhydrous sodium sulfate. Filtration was performed, and a filtrate was concentrated under reduced pressure to remove an organic solvent to afford a crude product. The crude product was separated and purified by silica gel chromatography to afford intermediate I-44. LC-MS (ESI) [M+H]$^+$ 497.1.

Reference Example 45: Preparation of Intermediate I-45

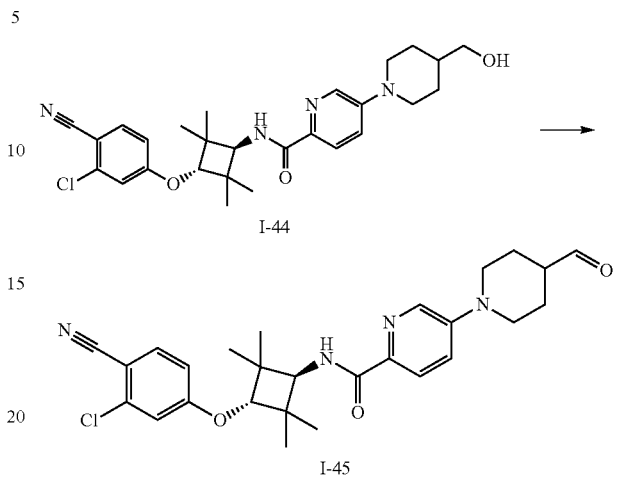

Intermediate I-44 (70 mg, 0.141 mmol) was dissolved in dichloromethane (5 mL), and Dess-Martin periodinane (120 mg, 0.282 mmol) was added slowly. A reaction mixture was stirred and reacted at room temperature for 2 hours. A reaction solution was filtered, and a filtrate was quenched with an aqueous sodium bicarbonate solution (20 mL) and extracted with dichloromethane (30 mL×3). Organic phases were combined, washed with saturated saline (20 mL), and dried over anhydrous sodium sulfate. Filtration was performed, and a filtrate was concentrated under reduced pressure to remove an organic solvent to afford a crude product. The crude product was separated and purified by silica gel chromatography to afford intermediate I-45.

Reference Example 46: Preparation of Intermediate I-46

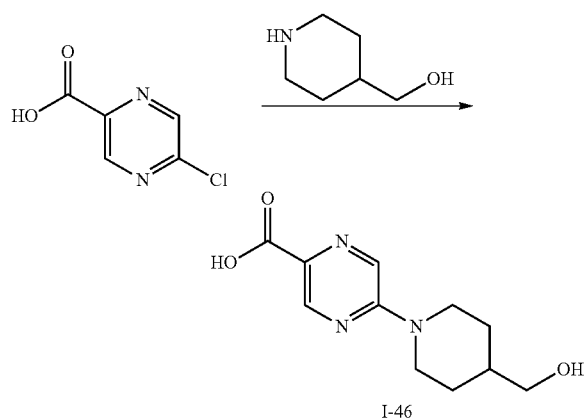

I-46

A compound of 5-chloropyrazine-2-carboxylic acid (500 mg, 3.15 mmol) was dissolved in N,N-dimethylformamide (40 mL), followed by addition of compounds of 4-piperidinemethanol (365 mg, 3.17 mmol) and N,N-diisopropylethylamine (1.56 mL, 9.45 mmol); a reaction mixture was stirred and reacted at 100° C. for 16 hours. After concentration, water (80 mL) was added for dilution, and dichloromethane (100 mL×3) was used for extraction. Organic phases were combined, washed with saturated saline (80 mL), and dried over anhydrous sodium sulfate. Filtration was performed, and a filtrate was concentrated under reduced pressure to remove an organic solvent to afford a crude product. The crude product was separated and purified by silica gel chromatography to afford intermediate I-46. LC-MS (ESI) [M+H]$^+$ 238.3.

Reference Example 47: Preparation of Intermediate I-47

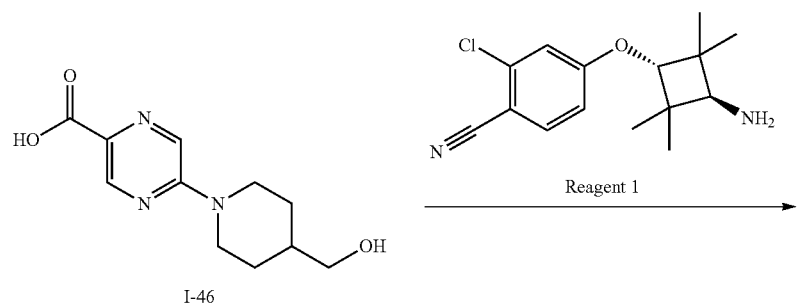

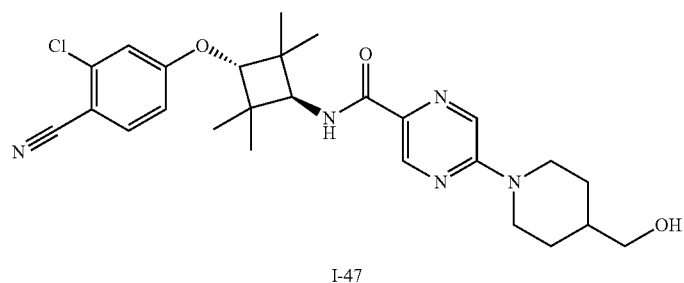

I-47

Intermediate I-46 (200 mg, 0.843 mmol) was dissolved in N,N-dimethylformamide (10 mL), followed by successive addition of reagent 1 (235 mg), 1-hydroxybenzotriazole (227 mg, 1.69 mmol), 1-(3-dimethylaminopropyl)-3-ethylcarbodiimide hydrochloride (323 mg, 1.69 mmol) and N,N-diisopropylethylamine (0.42 mL, 2.53 mmol). A reaction mixture was stirred and reacted at room temperature for 48 hours, diluted with water (50 mL) and extracted with dichloromethane (50 mL×3). Organic phases were combined, washed with saturated saline (30 mL), and dried over anhydrous sodium sulfate. Filtration was performed, and a filtrate was concentrated under reduced pressure to remove an organic solvent to afford a crude product. The crude product was separated and purified by silica gel chromatography to afford intermediate I-47. LC-MS (ESI) [M+H]$^+$ 498.2.

Reference Example 48: Preparation of Intermediate I-48

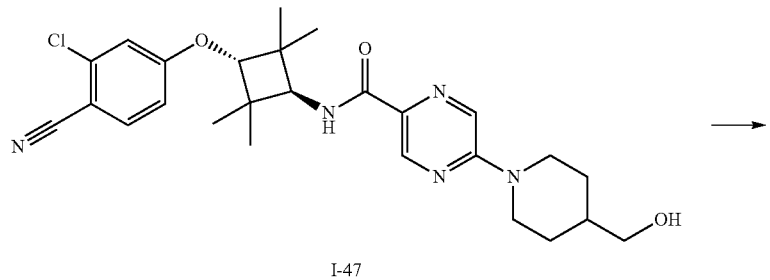

I-47

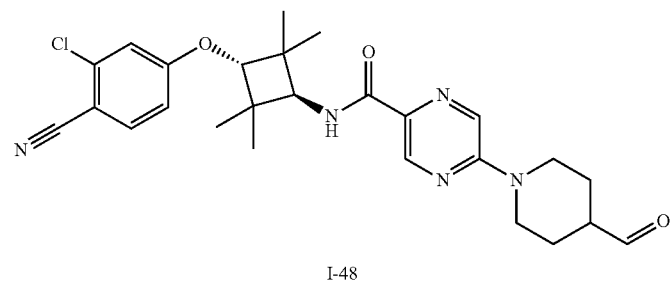

I-48

Intermediate I-47 (120 mg, 0.241 mmol) was dissolved in dichloromethane (5 mL), and Dess-Martin periodinane (204 mg, 0.482 mmol) was added slowly. A reaction mixture was stirred and reacted at room temperature for 2 hours. A reaction solution was filtered, and a filtrate was quenched with an aqueous sodium bicarbonate solution (20 mL) and extracted with dichloromethane (30 mL×3). Organic phases were combined, washed with saturated saline (30 mL), and dried over anhydrous sodium sulfate. Filtration was performed, and a filtrate was concentrated under reduced pressure to remove an organic solvent to afford a crude product of intermediate I-48. The crude product was directly used in the next reaction without further purification.

Reference Example 49: Preparation of Intermediate I-49

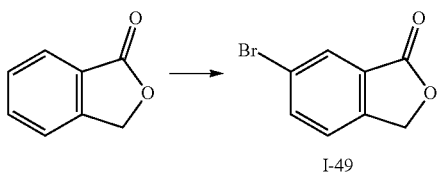

I-49

At room temperature, isobenzofuran-1(3H)-one (1.00 g, 7.46 mmol) was dissolved in a mixed solvent of chloroform (20 mL) and glacial acetic acid (10 mL); N-bromosuccinimide (1.59 g, 8.95 mmol) was added under stirring and argon protection, and nitrogen replacement was performed again. Under nitrogen protection, a mixture was stirred and reacted at 80° C. for 16 hours. A mixture was cooled to room temperature, subsequently poured into water (10 mL) and extracted with dichloromethane (10 mL×3). Organic phases were combined, washed with saturated saline (20 mL), dried over anhydrous sodium sulfate and filtered, and a filtrate was spin-dried. The residue was separated and purified by silica gel chromatography to afford intermediate I-49. $^1$H NMR (400 MHz, CDCl$_3$) δ 8.06 (d, J=1.5 Hz, 1H), 7.81 (dd, J=8.1, 1.7 Hz, 1H), 7.40 (dd, J=8.1, 0.4 Hz, 1H), 5.29 (s, 2H).

Reference Example 50: Preparation of Intermediate I-50

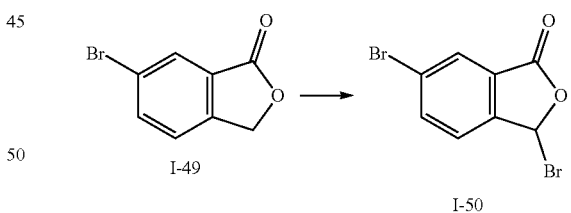

At 25° C., intermediate I-49 (700 mg, 3.29 mmol) was dissolved in carbon tetrachloride (10 mL), followed by addition of N-bromosuccinimide (702 mg, 3.95 mmol) and benzoyl peroxide (79.7 mg, 0.329 mmol). Then, a mixture was reacted at 60° C. for 3 hours, and a reaction solution was cooled to room temperature, added with a saturated sodium bicarbonate solution (10 mL) and extracted with dichloromethane (10 mL×3); organic phases were combined, washed with saturated saline (10 mL), dried over anhydrous sodium sulfate and filtered. A filtrate was concentrated under reduced pressure to remove an organic solvent, and then separated and purified by silica gel chromatography to afford intermediate I-50. $^1$H NMR (400 MHz, CDCl$_3$) δ 8.05 (d, J=1.6 Hz, 1H), 7.90 (dd, J=8.2, 1.7 Hz, 1H), 7.53 (d, J=8.2 Hz, 1H), 7.37 (s, 1H).

Reference Example 51: Preparation of Intermediate I-51

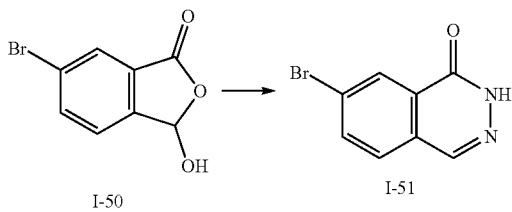

At 25° C., intermediate I-50 (700 mg, 2.40 mmol) was dissolved in ethanol (10 mL); then, the temperature was reduced to 0° C., and 85% hydrazine hydrate (600.7 mg) was added. Under nitrogen protection, a reaction mixture was stirred at reflux and reacted for 2 hours. A reaction system was poured into water (10 mL) and filtered. A filter cake was washed with water (10 mL×3) to afford intermediate I-51. $^1$H NMR (400 MHz, DMSO-$d_6$) δ 12.82 (s, 1H), 8.40 (s, 1H), 8.32 (d, J=1.9 Hz, 1H), 8.13 (dd, J=8.4, 2.0 Hz, 1H), 7.92 (d, J=8.4 Hz, 1H).

Reference Example 52: Preparation of Intermediate I-52

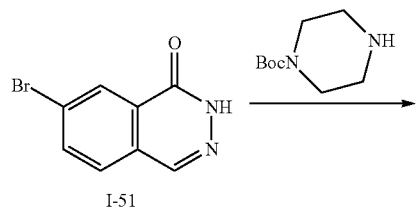

At 25° C., intermediate I-51 (400 mg, 1.77 mmol) was dissolved in 1,4-dioxane (15 mL). N—BOC piperazine (330 mg, 1.77 mmol) and sodium tert-butoxide (510 mg, 5.31 mmol) were added, and nitrogen was replaced; chloro(2-dicyclohexylphosphino-2',6'-di-isopropoxy-1,1'-biphenyl)(2-amino-1,1'-biphenyl-2-yl)palladium(II) (138 mg, 0.177 mmol) were added, and a reaction mixture was stirred at 100° C. overnight. A reaction system was filtered and subsequently concentrated under reduced pressure to remove an organic solvent to afford a crude product, and a crude product residue was separated and purified by silica gel chromatography to afford intermediate I-52. LC-MS (ESI) [M+H]$^+$ 331.1.

Reference Example 53: Preparation of Intermediate I-53

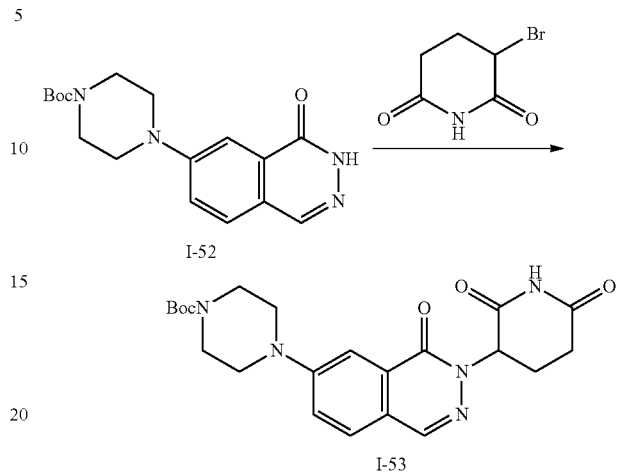

At 25° C., intermediate I-52 (400 mg, 1.21 mmol) was dissolved in tetrahydrofuran (8 mL), 60% sodium hydride (96.8 mg, 2.42 mmol) was added, and a reaction mixture was stirred at room temperature for 0.5 hours. 3-bromopiperidine-2,6-dione (464.6 mg, 2.42 mmol) was added dropwise and dissolved in tetrahydrofuran (2 mL), and the mixture was stirred and reacted at room temperature for 16 hours; water (20 mL) was poured into a reaction solution, and ethyl acetate (20 mL×2) was used for extraction; organic phases were combined, washed with saturated saline (50 mL), dried over anhydrous sodium sulfate and filtered, and a filtrate was spin-dried. The residue was separated and purified by silica gel chromatography to afford intermediate I-53. LC-MS (ESI) [M+H−56]$^+$ 386.1.

Reference Example 54: Preparation of Intermediate I-54

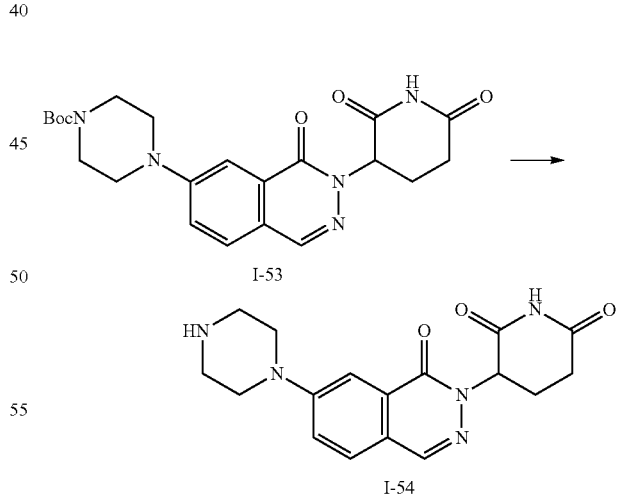

At 25° C., intermediate I-53 (240 mg, 0.544 mmol) was dissolved in dichloromethane (3 mL). A solution of hydrogen chloride in dioxane (3 mL, 4 M) was added, and a reaction mixture was stirred and reacted at room temperature for 1 hour. After a reaction was completed, a reaction solution was concentrated to afford intermediate I-54. The crude product was directly used in the next reaction without further purification. LC-MS (ESI) [M+H]$^+$ 342.2.

Reference Example 55: Preparation of Intermediate I-55

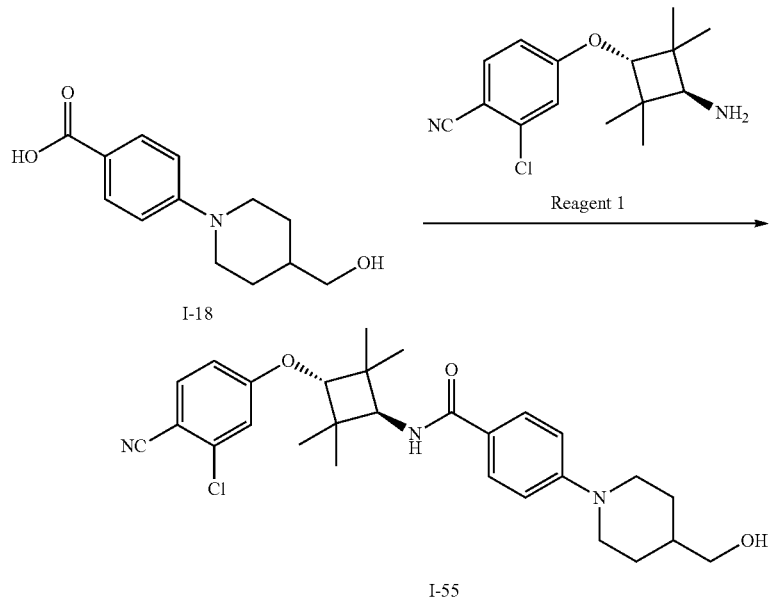

Intermediate I-18 (38.8 g) was dissolved in N,N-dimethylformamide (300 mL), followed by successive addition of 1-hydroxybenzotriazole (25.7 g, 190.4 mmol), 1-(3-dimethylaminopropyl)-3-ethylcarbodiimide hydrochloride (36.56 g, 190.4 mmol), N,N-diisopropylethylamine (42.25 mL, 285.6 mmol) and reagent 1 (30.0 g). A reaction mixture was stirred and reacted at room temperature for 16 hours. A reaction solution was filtered, and a filter cake was washed with ethyl acetate (20 mL×3) and dried to afford intermediate I-55. LC-MS (ESI) [M+H]+ 496.2.

Reference Example 56: Preparation of Intermediate I-56

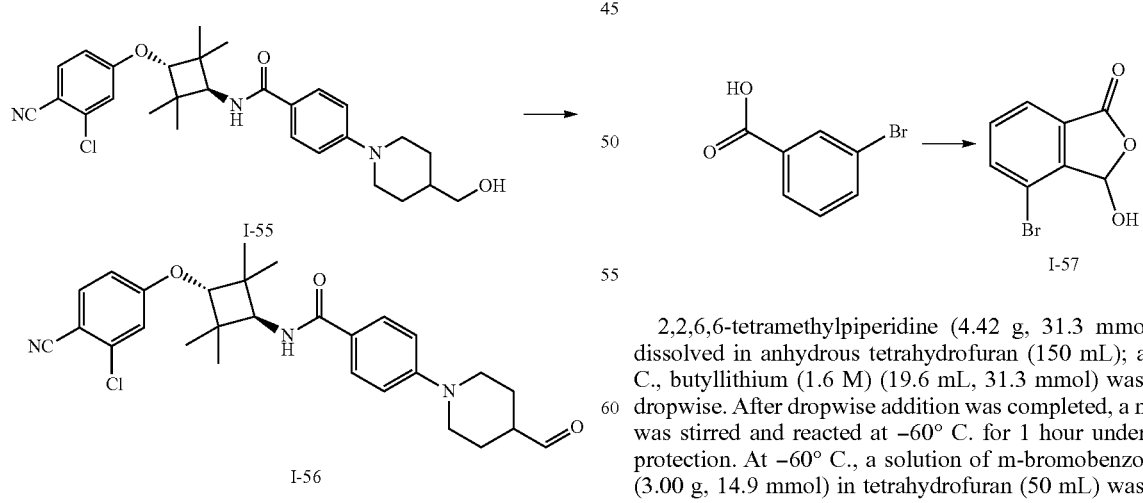

Intermediate I-55 (32 g, 64.52 mmol) was dissolved in anhydrous dichloromethane (200.0 mL), a system was cooled to 0° C., and Dess-Martin periodinane (41 g, 96.77 mmol) was added. A reaction system was protected with argon, and stirred and reacted at room temperature for 2 hours. A filtrate was quenched with a saturated aqueous sodium bicarbonate solution (200 mL) and extracted with dichloromethane (200 mL×3). Organic phases were combined, washed with saturated saline (200 mL), and dried over anhydrous sodium sulfate. Filtration was performed, and a filtrate was concentrated under reduced pressure to remove an organic solvent to afford a crude product. The crude product was separated and purified by silica gel chromatography to afford intermediate I-56.

Reference Example 57: Preparation of Intermediate I-57

2,2,6,6-tetramethylpiperidine (4.42 g, 31.3 mmol) was dissolved in anhydrous tetrahydrofuran (150 mL); at −60° C., butyllithium (1.6 M) (19.6 mL, 31.3 mmol) was added dropwise. After dropwise addition was completed, a mixture was stirred and reacted at −60° C. for 1 hour under argon protection. At −60° C., a solution of m-bromobenzoic acid (3.00 g, 14.9 mmol) in tetrahydrofuran (50 mL) was added dropwise, and a mixture was stirred and reacted at −60° C. for 1 hour under argon protection. At −60° C., N,N-dimethylformamide (4.36 g, 59.6 mmol) was added dropwise. After dropwise addition was completed, the mixture was slowly warmed up to room temperature and stirred and reacted at room temperature for 0.5 hours. At 0° C., a reaction was quenched with water (500 mL), and a product was extracted with ethyl acetate (200 mL×3); organic phases were combined, dried over anhydrous sodium sulfate and filtered, and a filtrate was concentrated under reduced pressure to remove an organic solvent to afford a crude product; the crude product was separated and purified by silica gel chromatography to afford intermediate I-57. $^1$H NMR (400 MHz, DMSO-$d_6$) δ 8.28 (s, 1H), 7.99 (dd, J=7.9, 0.7 Hz, 1H), 7.88-7.81 (m, 1H), 7.60 (t, J=7.7 Hz, 1H), 6.62 (s, 1H).

Reference Example 58: Preparation of Intermediate I-58

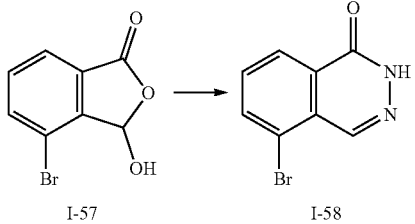

Intermediate I-57 (700 mg, 3.06 mmol) was dissolved in glacial acetic acid (10.0 mL), and a system was protected with argon and warmed up to 90° C.; 85% hydrazine hydrate (460 mg) was added dropwise, and after dropwise addition was completed, a mixture was stirred and reacted at 90° C. for 4 hours; the temperature was kept at 80° C., and 80° C. preheated hot water (20.0 mL) was slowly added dropwise. After dropwise addition was completed, the mixture was slowly cooled to room temperature, and a solid was precipitated; suction filtration was performed, and a filter cake was washed with water (10.0 mL) and dried in vacuo under reduced pressure to afford intermediate I-58. LC-MS (ESI) [M+H]$^+$ 225.0.

Reference Example 59: Preparation of Intermediate I-59

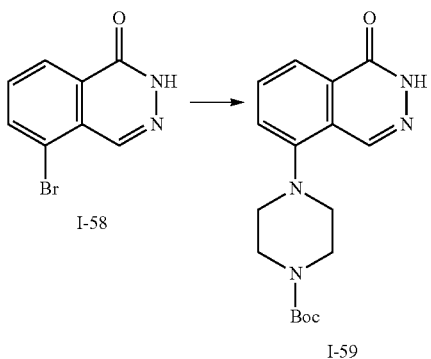

Intermediate I-58 (510 mg, 2.27 mmol) was dissolved in anhydrous dioxane (50.0 mL), followed by addition of tert-butyl piperazine-1-carboxylate (635 mg, 3.41 mmol), sodium tert-butoxide (654 mg, 6.81 mmol), chloro(2-dicyclohexylphosphino-2',6'-di-isopropoxy-1,1'-biphenyl)(2-amino-1,1'-biphenyl-2-yl)palladium(II) (87.8 mg, 0.227 mmol). A reaction system was protected with argon, and stirred and reacted at 100° C. for 16 hours. A mixture was cooled to room temperature, and concentrated under reduced pressure to remove an organic solvent to afford a crude product; the crude product was separated and purified by silica gel chromatography to afford intermediate I-59. LC-MS (ESI) [M+H]$^+$ 331.2.

Reference Example 60: Preparation of Intermediate I-60

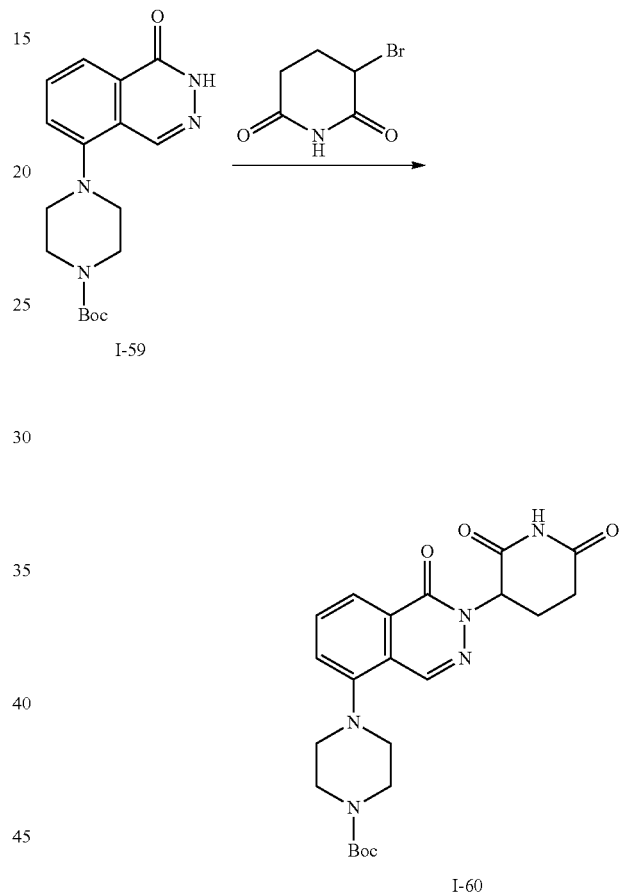

Intermediate I-59 (150 mg, 0.454 mmol) was dissolved in a mixed solvent of dimethyl sulfoxide/tetrahydrofuran (2.00 mL/2.00 mL), and sodium hydride (60%, 90.8 mg, 2.27 mmol) was added. A reaction system was protected with argon, and stirred and reacted at room temperature for 0.5 hours. A solution of 3-bromopiperidine-2,6-dione (174 mg, 0.908 mmol) in tetrahydrofuran (0.50 mL) was added dropwise. After dropwise addition was completed, a mixture was stirred and reacted at room temperature for 0.5 hours. The mixture was quenched with citric acid (100 mg). The mixture was pour into water (20.0 mL), and a product was extracted with ethyl acetate (20.0 mL×3); organic phases were combined, dried over anhydrous sodium sulfate and filtered; a filtrate was concentrated under reduced pressure to remove an organic solvent to afford a crude product, and the crude product was separated and purified by silica gel chromatography to afford intermediate I-60. LC-MS (ESI) [M+H]$^+$ 442.1.

Reference Example 61: Preparation of Intermediate I-61

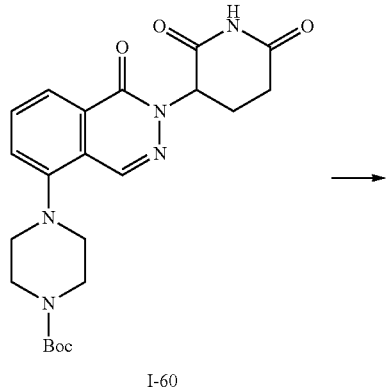

I-60

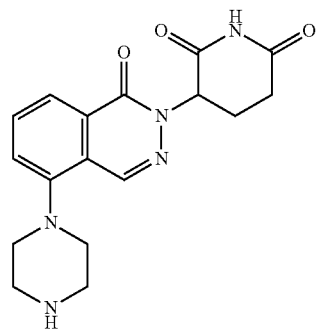

I-61

Intermediate I-60 (120 mg, 0.272 mmol) was dissolved in dichloromethane (2.00 mL), and trifluoroacetic acid (0.50 mL) was added. A reaction system was protected with argon, and stirred and reacted at room temperature for 16 hours. A mixture was concentrated to remove an organic solvent to afford a crude product, and the crude product was separated and purified by silica gel chromatography to afford intermediate I-61. LC-MS (ESI) [M+H]⁺ 342.1.

Reference Example 62: Preparation of Intermediate I-62

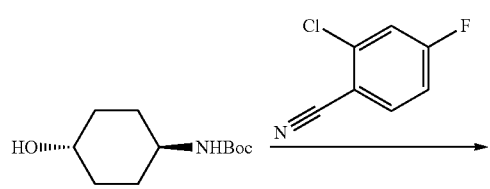

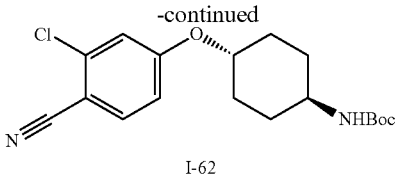

I-62

In an ice-water bath, trans-4-Boc-aminocyclohexanol (5.00 g, 23.2 mmol) was dissolved in N,N-dimethylformamide (100 mL); under nitrogen protection and stirring, sodium hydride (1.11 g, 27.9 mmol, 60% mass fraction) was added. After a reaction mixture was stirred for 1 hour in an ice-water bath, 2-chloro-4-fluorobenzonitrile (3.65 g, 23.5 mmol) was added. After addition was completed, the reaction mixture was stirred at room temperature for 3 hours. A reaction solution was diluted with water (100 mL) and extracted with ethyl acetate (50 mL×3), and organic phases were dried and filtered. A filtrate was concentrated under reduced pressure, and a residue was separated and purified by silica gel chromatography to afford a white solid of intermediate I-62. LC-MS (ESI) [M−56+H]⁺295.1.

Reference Example 63: Preparation of Intermediate I-63

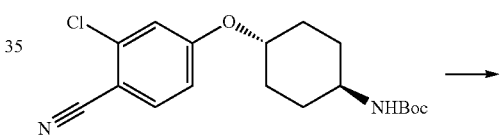

I-62

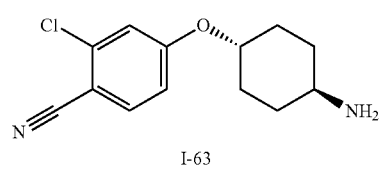

I-63

At room temperature, intermediate I-62 (6.00 g, 17.1 mmol) was dissolved in a solution of hydrogen chloride in dioxane (100 mL, 4 M). After addition was completed, a reaction mixture was stirred at room temperature overnight. A reaction solution was concentrated under reduced pressure to remove an organic solvent to afford a crude product of intermediate I-63, and the crude product was directly used in the next reaction without purification. LC-MS (ESI) [M+H]⁺ 251.2.

Reference Example 64: Preparation of Intermediate I-64

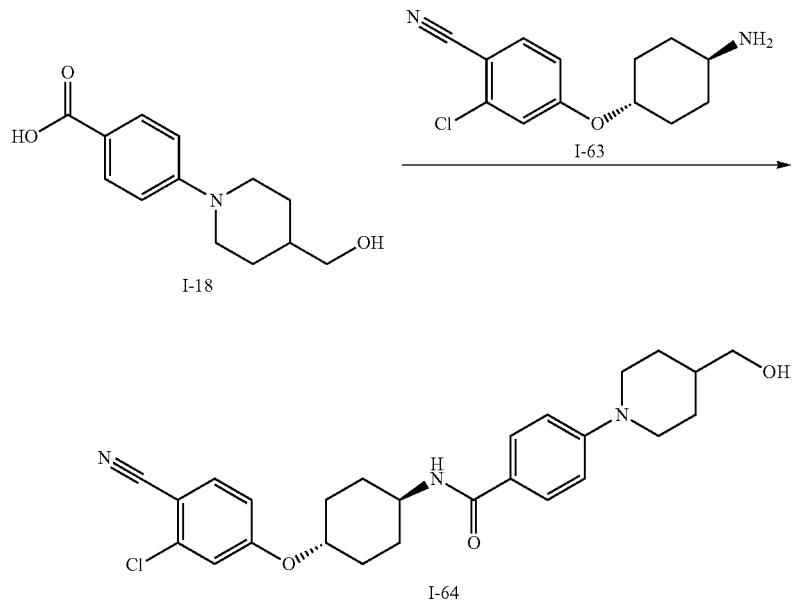

Intermediate I-18 (1.40 g, 5.95 mmol) was dissolved in N,N-dimethylformamide (20.0 mL), followed by successive addition of 1-hydroxybenzotriazole (1.21 g, 8.93 mmol), 1-(3-dimethylaminopropyl)-3-ethylcarbodiimide hydrochloride (1.71 g, 8.93 mmol), N,N-diisopropylethylamine (2.31 g, 17.9 mmol) and intermediate I-63 (1.71 g). A reaction mixture was stirred and reacted at room temperature for 16 hours. A reaction solution was filtered, and a filter cake was washed with ethyl acetate (15 mL×3) and dried to afford intermediate I-64. LC-MS (ESI) [M+H]$^+$ 468.1.

Reference Example 65: Preparation of Intermediate I-65

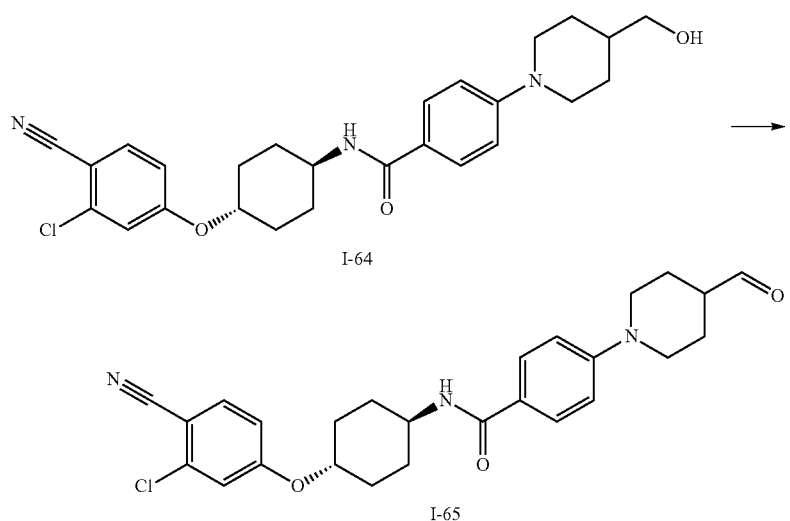

Intermediate I-64 (100 mg, 0.214 mmol) was dissolved in anhydrous dichloromethane (10.0 mL), and a system was cooled to 0° C. and added with Dess-Martin periodinane (181 mg, 0.428 mmol). A reaction system was protected with argon, and stirred and reacted at room temperature for 2 hours. Filtration was performed, and a filtrate was quenched with a saturated aqueous sodium bicarbonate solution (10.0 mL) and extracted with dichloromethane (10.0 mL×3). Organic phases were combined, washed with saturated saline (10.0 mL), and dried over anhydrous sodium sulfate. Filtration was performed, and a filtrate was concentrated under reduced pressure to remove an organic solvent to afford a crude product of intermediate I-65. The crude product was directly used in the next reaction without purification.

Reference Example 66: Preparation of Intermediate I-66

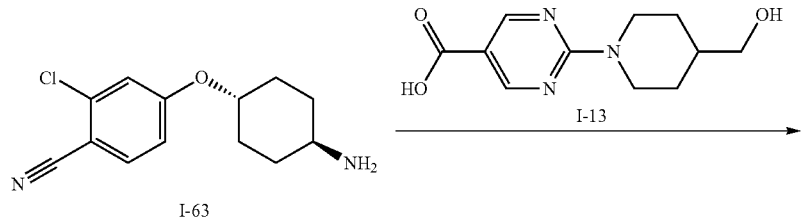

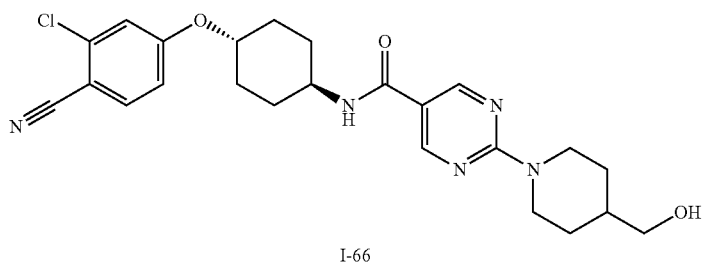

Intermediate I-63 (700 mg) was dissolved in N,N-dimethylformamide (10 mL), followed by successive addition of intermediate I-13 (578 mg), 1-hydroxybenzotriazole (660 mg, 4.89 mmol), 1-ethyl-3-(3-dimethylaminopropyl)carbodiimide hydrochloride (940 mg, 4.90 mmol) and N,N-diisopropylethylamine (1.2 mL, 7.32 mmol). A reaction mixture was stirred and reacted at room temperature for 4 hours, diluted with water (50 mL), and extracted with dichloromethane (50 mL×3). Organic phases were combined, washed with saturated saline (30 mL), and dried over anhydrous sodium sulfate. Filtration was performed, and a filtrate was concentrated under reduced pressure to remove an organic solvent to afford a crude product. The crude product was separated and purified by silica gel chromatography to afford intermediate I-66. LC-MS (ESI) $[M+H]^+$ 470.0.

Reference Example 67: Preparation of Intermediate I-67

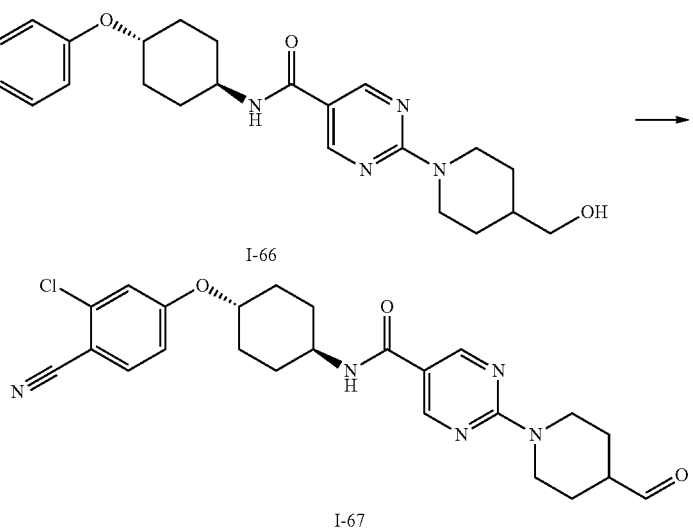

Intermediate I-66 (150 mg, 0.319 mmol) was dissolved in dimethylsulfoxide (10 mL), and then 2-iodoxybenzoic acid (270 mg, 0.964 mmol) was added slowly. A reaction mixture was stirred and reacted at room temperature for 16 hours. A reaction was quenched with an aqueous solution (30 mL), and ethyl acetate (30 mL×3) was used for extraction. Organic phases were combined, washed with saturated saline (20 mL), and dried over anhydrous sodium sulfate. Filtration was performed, and a filtrate was concentrated under reduced pressure to remove an organic solvent to afford a residue. The residue was separated and purified by silica gel chromatography to afford intermediate I-67.

Reference Example 68: Preparation of Intermediate I-68

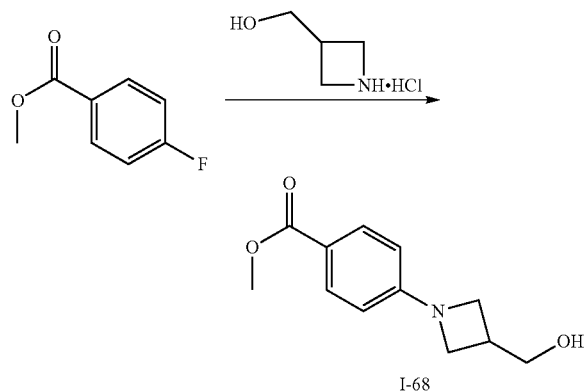

I-68

Methyl p-fluorobenzoate (5.00 g, 32.4 mmol) was dissolved in anhydrous N,N-dimethylformamide (20.0 mL), followed by successive addition of 3-azetidinemethanol hydrochloride (4.81 g, 38.9 mmol) and anhydrous potassium carbonate (11.2 g, 81.1 mmol). A reaction system was protected with argon, and stirred and reacted at 80° C. for 16 hours. A mixture was cooled to room temperature, water (20.0 mL) was added, and a product was extracted with ethyl acetate (20.0 mL×3); organic phases were combined, dried over anhydrous sodium sulfate and filtered; a filtrate was concentrated under reduced pressure to remove an organic solvent to afford a crude product, and the crude product was separated and purified by silica gel chromatography to afford intermediate I-68. LC-MS (ESI) [M+H]⁺ 222.2.

Reference Example 69: Preparation of Intermediate I-69

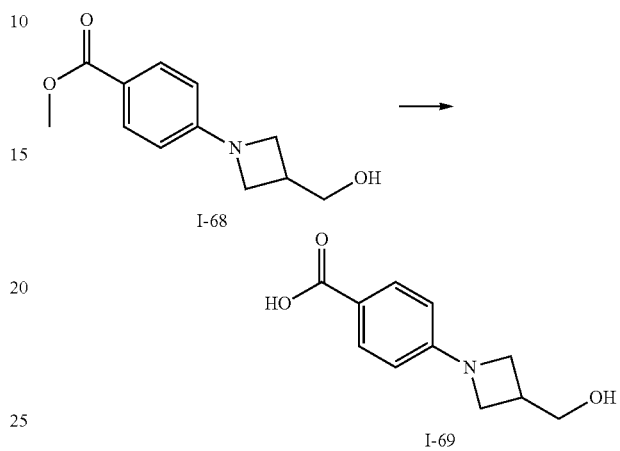

Intermediate I-68 (200 mg, 0.904 mmol) was dissolved in anhydrous tetrahydrofuran (5.00 mL); then, lithium hydroxide monohydrate (190 mg, 4.52 mmol) was dissolved in water (5.00 mL) and added dropwise to a reaction; a reaction system was protected with argon and stirred at room temperature for 2 hours. A mixture was adjusted to be weakly acidic with 1 N hydrochloric acid, a solid was precipitated, and filtration was performed to afford a crude product of intermediate I-69. The crude product was directly used in the next reaction without purification. LC-MS (ESI) [M+H]⁺ 208.0.

Reference Example 70: Preparation of Intermediate I-70

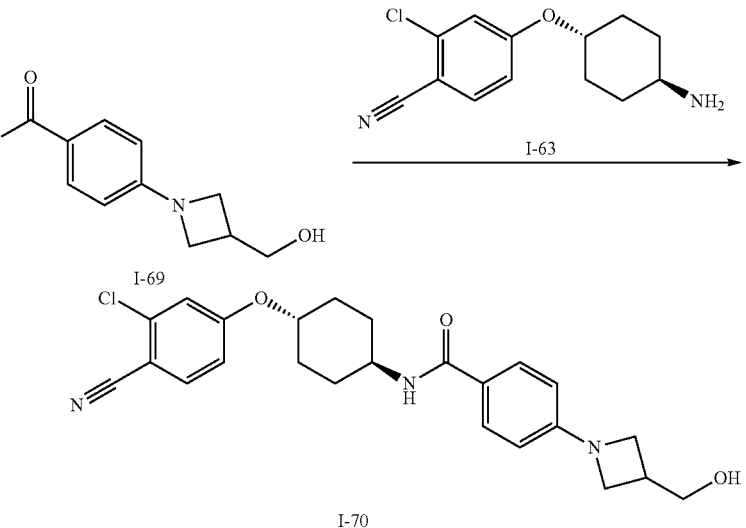

Intermediate I-69 (160 mg) was dissolved in N,N-dimethylformamide (20.0 mL), followed by successive addition of 1-hydroxybenzotriazole (209 mg, 1.546 mmol), 1-ethyl-3-(3-dimethylaminopropyl)carbodiimide hydrochloride (297 mg, 1.546 mmol), N,N-diisopropylethylamine (0.380 mL, 2.17 mmol) and intermediate I-63 (194 mg, 0.773 mmol). A reaction mixture was stirred and reacted at room temperature for 16 hours. A reaction solution was filtered, and a filter cake was washed with ethyl acetate (2 mL×3) and dried to afford intermediate I-70. LC-MS (ESI) [M+H]+ 440.0.

Reference Example 71: Preparation of Intermediate I-71

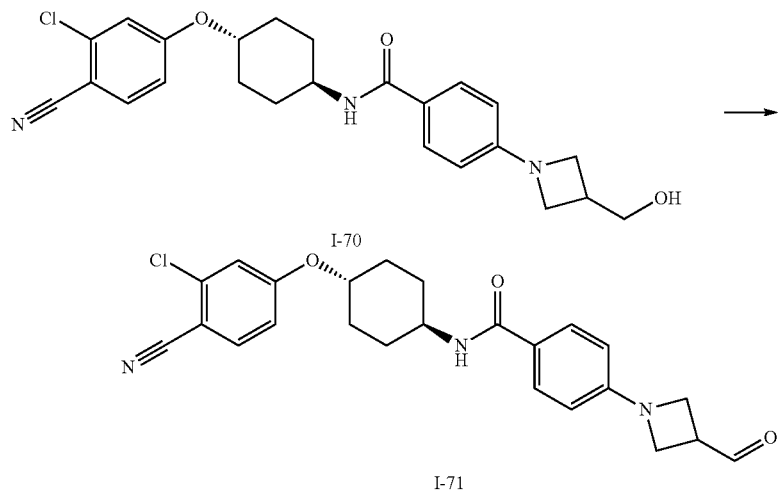

Intermediate I-70 (100 mg, 0.227 mmol) was dissolved in anhydrous dichloromethane (10.0 mL), and a system was cooled to 0° C. and added with Dess-Martin periodinane (193 mg, 0.454 mmol). A reaction system was protected with argon, and stirred and reacted at room temperature for 2 hours. Filtration was performed, and a filtrate was quenched with a saturated aqueous sodium bicarbonate solution (10.0 mL) and extracted with dichloromethane (10.0 mL×3). Organic phases were combined, washed with saturated saline (10.0 mL), and dried over anhydrous sodium sulfate. Filtration was performed, and a filtrate was concentrated under reduced pressure to remove an organic solvent to afford a crude product. The crude product was separated and purified by silica gel chromatography to afford intermediate I-71.

Reference Example 22: Preparation of Intermediate I-2

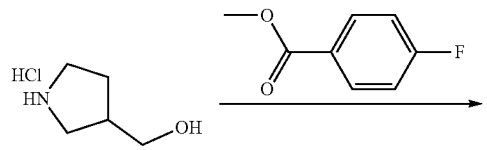

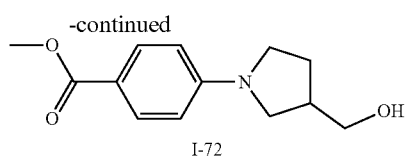

3-hydroxymethylpyrrole hydrochloride (1.20 g, 8.72 mmol) was dissolved in anhydrous N,N-dimethylformamide (20.0 mL), followed by addition of methyl p-fluorobenzoate (1.48 g, 9.59 mmol) and anhydrous potassium carbonate (3.62 g, 26.2 mmol). A reaction system was protected with argon, and stirred and reacted at 120° C. for 16 hours. A reaction solution was cooled to room temperature, water (100 mL) was added, and a product was extracted with ethyl acetate (50.0 mL×3); organic phases were combined, dried over anhydrous sodium sulfate and filtered; a filtrate was concentrated under reduced pressure to remove an organic solvent to afford a crude product, and the crude product was separated and purified by silica gel chromatography to afford intermediate I-72. LC-MS (ESI) [M+H]+ 236.2.

Reference Example 73: Preparation of Intermediate I-73

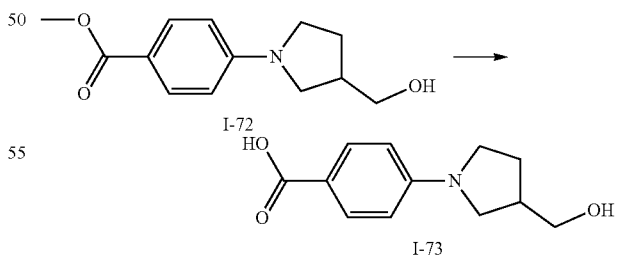

Intermediate I-72 (400 mg, 1.70 mmol) was dissolved in a mixed solvent of tetrahydrofuran/methanol (2.00 mL/2.00 mL), and a solution of sodium hydroxide (204 mg, 5.10 mmol) in water (2.00 mL) was added. A reaction system was protected with argon, and stirred and reacted at 70° C. for 4 hours. A system was adjusted to have pH=6.0 with dilute hydrochloric acid (1 N), and a large amount of solid was precipitated; suction filtration was performed, and a filter cake was dried to afford intermediate I-73. LC-MS (ESI) [M+H]⁺ 222.2.

Reference Example 74: Preparation of Intermediate I-74

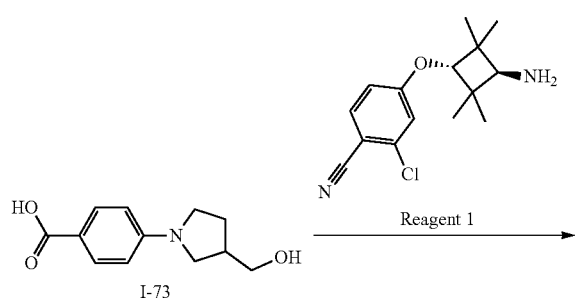

Intermediate I-73 (350 mg, 1.58 mmol) was dissolved in anhydrous N,N-dimethylformamide (20.0 mL), followed by addition of reagent 1 (599 mg), 1-(3-dimethylaminopropyl)-3-ethylcarbodiimide hydrochloride (454 mg, 2.37 mmol), 1-hydroxybenzotriazole (320 mg, 2.37 mmol) and N,N-diisopropylethylamine (613 mg, 4.74 mmol). A reaction system was protected with argon, and was stirred and reacted at room temperature for 16 hours. A mixture was poured into water (100 mL), a solid was precipitated, and suction filtration was performed; the solid was dried, and washed with ethyl acetate (25 mL) by beating, the suction filtration was performed, and a filter cake was dried to afford intermediate I-74. LC-MS (ESI) [M+H]⁺ 482.3.

Reference Example 75: Preparation of Intermediate I-75

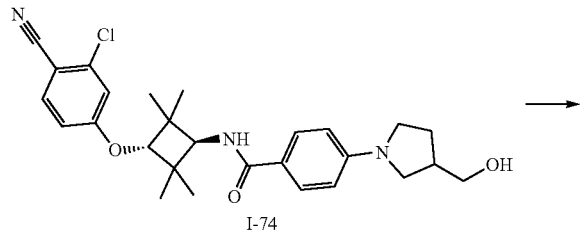

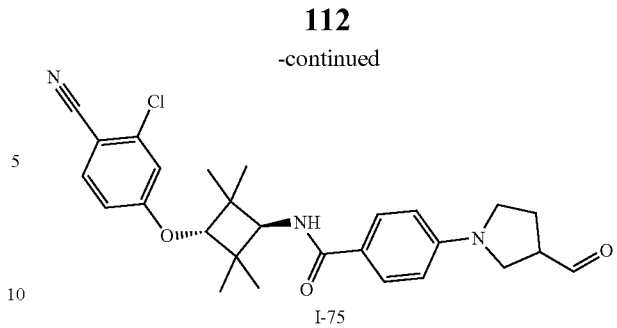

Intermediate I-74 (150 mg, 0.311 mmol) was dissolved in anhydrous dichloromethane (20.0 mL); at 0° C., Dess-Martin periodinane (198 mg, 0.467 mmol) was added. A reaction system was protected with argon, and stirred and reacted at 20° C. for 16 hours. A mixture was diluted with dichloromethane (50.0 mL), and washed with water (20.0 mL×2); organic phases were separated, dried over anhydrous sodium sulfate and filtered; a filtrate was concentrated under reduced pressure to remove an organic solvent to afford a crude product, and the crude product was separated and purified by silica gel chromatography to afford intermediate I-75. LC-MS (ESI) [M+H]⁺ 480.1.

Reference Example 76: Preparation of Intermediate I-76

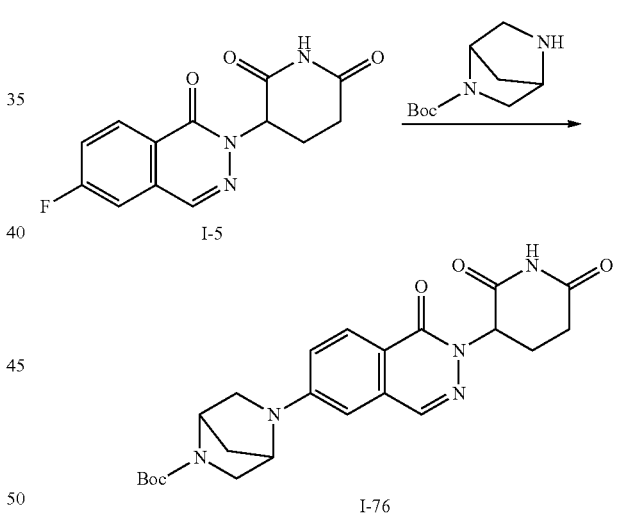

Intermediate I-5 (230 mg) was dissolved in anhydrous dimethyl sulfoxide (10.0 mL), followed by addition of tert-butyl 2,5-diazabicyclo[2.2.1]heptane-2-carboxylate (198 mg, 1.00 mmol) and N,N-diisopropylethylamine (324 mg, 2.51 mmol). A reaction system was protected with argon, and stirred and reacted at 140° C. for 24 hours. A reaction solution was cooled to room temperature and diluted with water (50.0 mL), and a product was extracted with ethyl acetate (20.0 mL×3); organic phases were combined, dried over anhydrous sodium sulfate and filtered; a filtrate was concentrated under reduced pressure to remove an organic solvent to afford a crude product, and the crude product was separated and purified by silica gel chromatography to afford intermediate I-76. LC-MS (ESI) [M+H]⁺ 454.1.

Reference Example 77: Preparation of Intermediate I-77

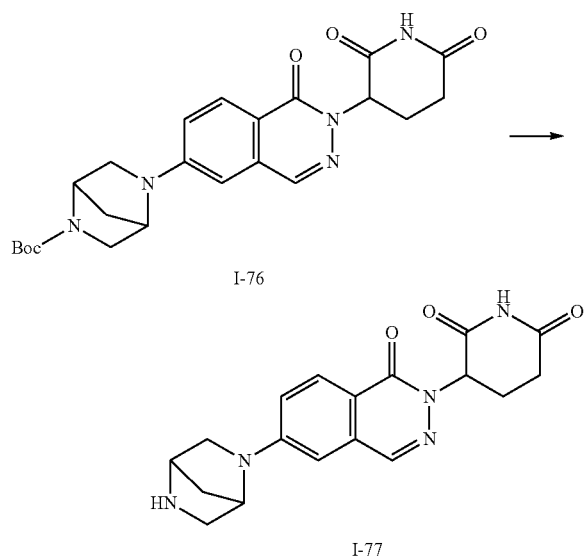

I-76

I-77

Intermediate I-76 (234 mg, 0.516 mmol) was dissolved in dichloromethane (3.00 mL), and trifluoroacetic acid (1.00 mL) was added. A reaction system was protected with argon, and stirred and reacted at room temperature for 16 hours. A mixture was loaded as a sample by a wet process, and separated and purified by silica gel chromatography to afford intermediate I-77. LC-MS (ESI) [M+H]$^+$ 354.1.

Reference Example 78: Preparation of Intermediate I-78

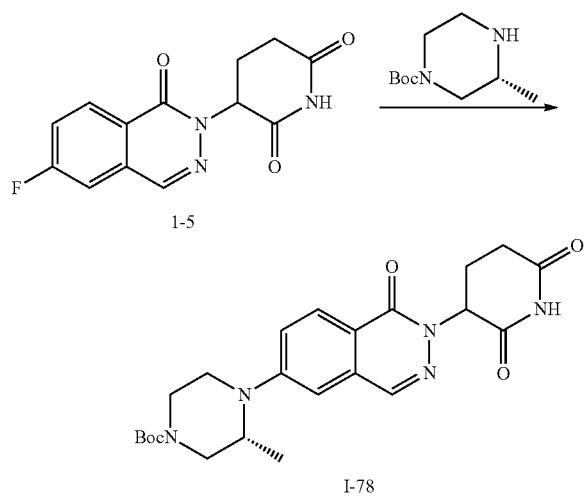

I-5

I-78

Intermediate I-5 (200 mg), (R)-1-Boc-3-methylpiperazine (729 mg, 3.64 mmol) and N,N-diisopropylethylamine (2 mL) were mixed in dimethyl sulfoxide (10 mL). A reaction mixture was stirred and reacted at 130° C. for 3 days. The mixture was cooled to room temperature, and subsequently poured into water (100 mL) and extracted with ethyl acetate (20 mL×2). Organic phases were combined, washed with a saturated aqueous sodium chloride solution (20 mL), dried over anhydrous sodium sulfate, and filtered. A filtrate was concentrated to dryness under reduced pressure. The residue was separated and purified by silica gel chromatography to afford intermediate I-78. LC-MS (ESI) [M+H]$^+$ 456.1.

Reference Example 79: Preparation of Intermediate I-79

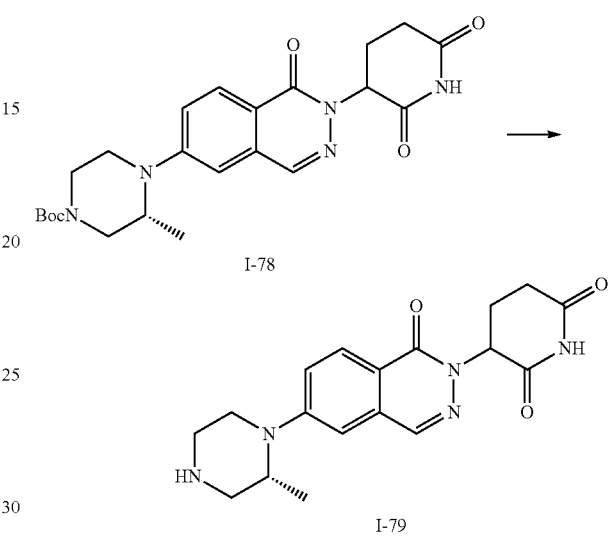

I-78

I-79

Intermediate I-78 (50.0 mg, 0.110 mmol) was mixed in dichloromethane (2 mL), and trifluoroacetic acid (1 mL) was added dropwise at room temperature under stirring. A reaction mixture was stirred and reacted at room temperature for 1 hour. A solvent was removed from the mixture under reduced pressure. The residue was separated and purified by silica gel chromatography to afford intermediate I-79. LC-MS (ESI) [M+H]$^+$ 356.1.

Reference Example 80: Preparation of Intermediate I-80

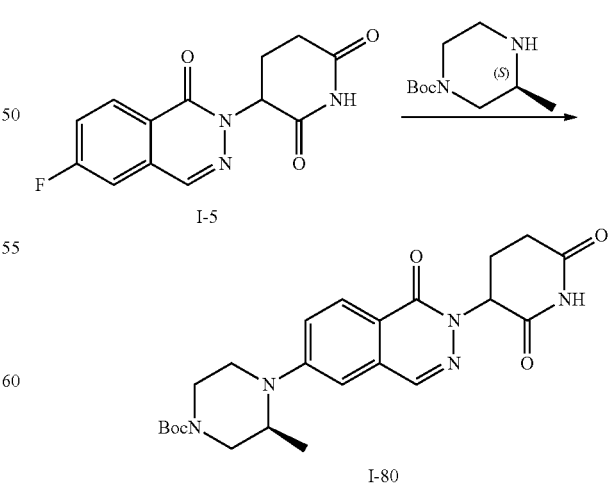

I-5

I-80

Intermediate I-5 (200 mg), (S)-1-Boc-3-methylpiperazine (729 mg, 3.64 mmol) and N,N-diisopropylethylamine (2 mL) were mixed in dimethyl sulfoxide (10 mL). A reaction mixture was stirred and reacted at 130° C. for 3 days. The mixture was cooled to room temperature, and subsequently poured into water (100 mL) and extracted with ethyl acetate (20 mL×2). Organic phases were combined, washed with a saturated aqueous sodium chloride solution (20 mL), dried over anhydrous sodium sulfate, and filtered. A filtrate was concentrated to dryness under reduced pressure. The residue was separated and purified by silica gel chromatography to afford intermediate I-80. LC-MS (ESI) [M+H]$^+$ 456.1.

Reference Example 81: Preparation of Intermediate I-81

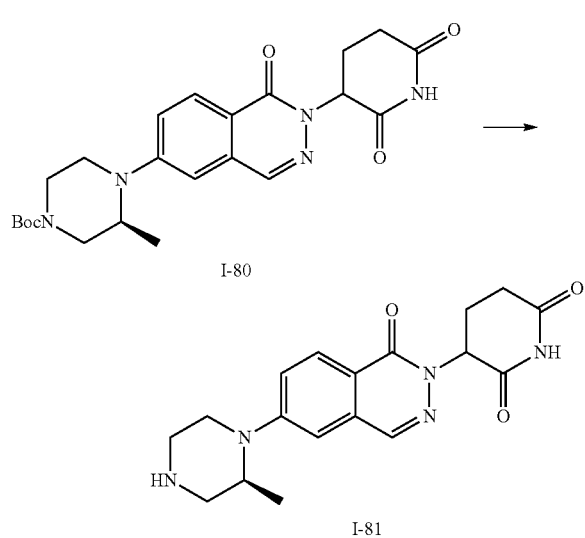

Intermediate I-80 (30.0 mg, 0.0659 mmol) was mixed in dichloromethane (2 mL), and trifluoroacetic acid (1 mL) was added dropwise at room temperature under stirring. A reaction mixture was stirred and reacted at room temperature for 1 hour. A solvent was removed from the mixture under reduced pressure to afford intermediate I-81, and a crude product was directly used in the next reaction without further purification. LC-MS (ESI) [M+H]$^+$ 356.1.

Reference Example 82: Preparation of Intermediate I-82

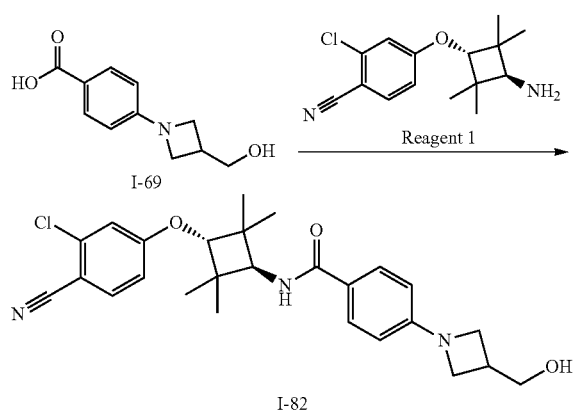

Intermediate I-69 (150 mg) was dissolved in N,N-dimethylformamide (20.0 mL), followed by successive addition of 1-hydroxybenzotriazole (147 mg, 1.09 mmol), 1-(3-dimethylaminopropyl)-3-ethylcarbodiimide hydrochloride (208 mg, 1.09 mmol), N,N-diisopropylethylamine (0.400 mL, 2.17 mmol) and reagent 1 (202 mg). A reaction mixture was stirred and reacted at room temperature for 16 hours. A reaction solution was filtered, and a filter cake was washed three times with ethyl acetate (2 mL×3) and dried to afford intermediate I-82.

Reference Example 83: Preparation of Intermediate I-83

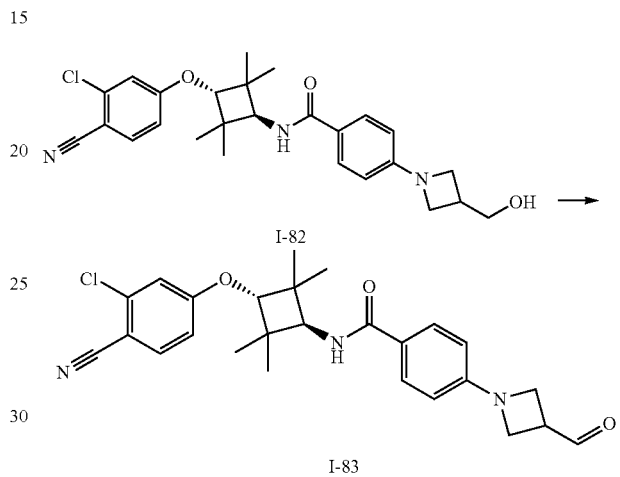

Intermediate I-82 (200 mg, 0.43 mmol) was dissolved in anhydrous dichloromethane (10.0 mL), and a system was cooled to 0° C. and added with Dess-Martin periodinane (274 mg, 0.645 mmol). A reaction system was protected with argon, and stirred and reacted at room temperature for 2 hours. A filtrate was quenched with a saturated aqueous sodium bicarbonate solution (10.0 mL) and extracted with dichloromethane (10.0 mL×3). Organic phases were combined, washed with saturated saline (10.0 mL), and dried over anhydrous sodium sulfate. Filtration was performed, and a filtrate was concentrated under reduced pressure to remove an organic solvent to afford a crude product of intermediate I-83. The crude product was directly used in the next reaction without further purification.

Reference Example 84: Preparation of Intermediate I-84

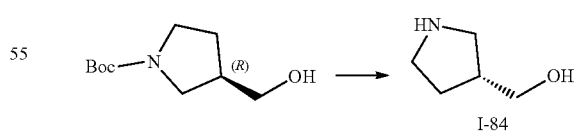

At room temperature, (R)-1-BOC-3-hydroxymethylpyrrolidine (1.60 g, 8.00 mmol) was dissolved in dioxane (2.00 mL); subsequently, a solution of hydrogen chloride in dioxane (20.0 mL, 4 M) was added and stirred at room temperature overnight. A reaction solution was concentrated to afford a crude product of intermediate I-84. The crude product was directly used in the next reaction without purification.

Reference Example 85: Preparation of Intermediate I-85

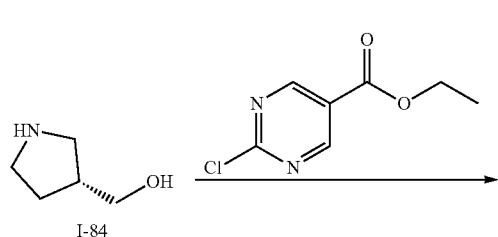

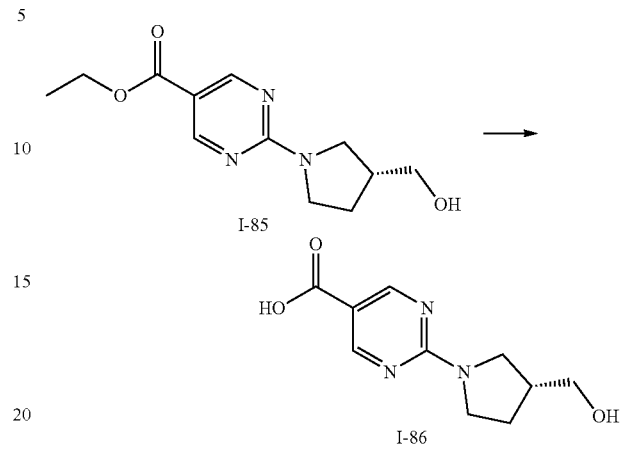

At room temperature, ethyl 2-chloropyrimidine-5-carboxylate (500 mg, 2.68 mmol) was dissolved in dimethyl sulfoxide (8.00 mL), followed by addition of intermediate I-84 (406 mg) and N,N-diisopropylethylamine (1.33 mL, 8.04 mmol); a reaction solution was stirred at 50° C. for 2 hours. Water (10.0 mL) was added, and ethyl acetate (10 mL×3) was used for extraction. Organic phases were combined, washed with saturated saline (10.0 mL), and dried over anhydrous sodium sulfate. Filtration and concentration were performed to afford a crude product, and the crude product was separated and purified by silica gel chromatography to afford intermediate I-85. LC-MS (ESI) [M+H]⁺ 252.2.

Reference Example 86: Preparation of Intermediate I-86

At room temperature, intermediate I-85 (520 mg, 2.06 mmol) was dissolved in a mixed solvent of tetrahydrofuran (8.00 mL) and water (2.00 mL); subsequently, lithium hydroxide monohydrate (433 mg, 10.3 mmol) was added and stirred at room temperature overnight. Water (6.00 mL) was added first, and then ethyl acetate (5.00 mL) was used for extraction; an aqueous phase was adjusted to have pH of 1.0 with 2 N dilute hydrochloric acid, and then ethyl acetate (10 mL×3) was used for extraction. Organic phases were combined, washed with saturated saline (10.0 mL), and dried over anhydrous sodium sulfate. Filtration was performed, and a filtrate was concentrated to dryness to afford intermediate I-86. LC-MS (ESI) [M+H]⁺ 224.1.

Reference Example 87: Preparation of Intermediate I-87

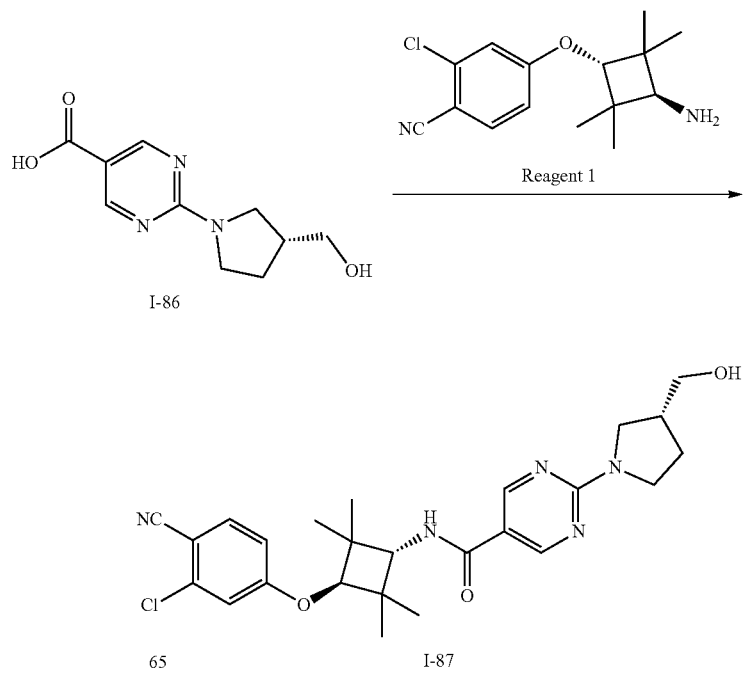

At room temperature, intermediate I-86 (200 mg, 0.897 mmol) was dissolved in N,N-dimethylformamide (5.00 mL), followed by addition of N,N-diisopropyl ethyl amine (347 mg, 2.69 mmol), reagent 1 (283 mg, 0.897 mmol), 1-hydroxybenzotriazole (242 mg, 1.79 mmol) and 1-(3-dimethylaminopropyl)-3-ethylcarbodiimide hydrochloride (344 mg, 1.79 mmol); stirring was performed at room temperature for 1 hour. Water (10.0 mL) was added first, and a large amount of solid was precipitated; filtration was performed, and a filtrate was extracted with ethyl acetate (10 mL×3). Organic phases were combined, washed with saturated saline (10.0 mL), and dried over anhydrous sodium sulfate. The filtration was performed, and a filtrate was concentrated, combined with a filter residue obtained just now, and spin-dried to afford intermediate I-87. LC-MS (ESI) [M+H]$^+$ 484.1.

Reference Example 88: Preparation of Intermediate I-88

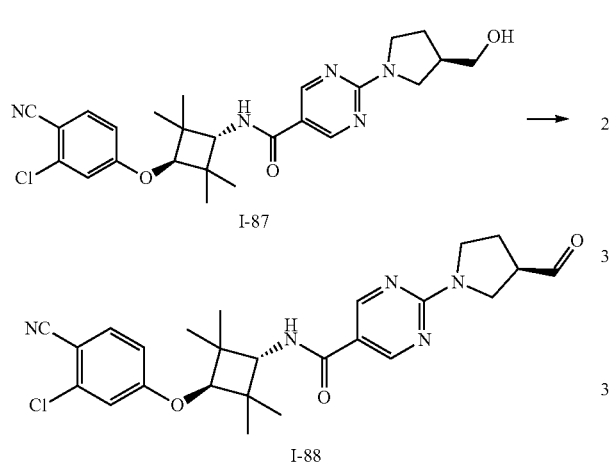

At room temperature, intermediate I-87 (150 mg, 0.310 mmol) was dissolved in dimethyl sulfoxide (5.00 mL); subsequently, 2-iodoxybenzoic acid (434 mg, 1.55 mmol) was added, argon replacement was performed three times, and stirring was performed at 80° C. for 30 minutes. A mixture was cooled to room temperature, diluted with water (10.0 mL), and extracted with ethyl acetate (10 mL×3). Organic phases were combined, washed with saturated saline (10.0 mL), and dried over anhydrous sodium sulfate. Filtration was performed, and a filtrate was concentrated under reduced pressure to afford a crude product of intermediate I-88. The crude product was directly used in the next reaction without further purification.

Reference Example 89: Preparation of Intermediate I-89

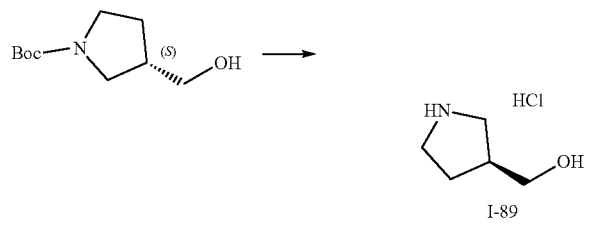

(S)-1-BOC-3-hydroxymethylpyrrolidine (1.0 g, 4.97 mmol) was dissolved in anhydrous dioxane (10 mL), and a solution of hydrogen chloride in dioxane (15 mL, 4 M) was added; a reaction system was protected with argon, and stirred and reacted at room temperature for 16 hours. A mixture was concentrated under reduced pressure to remove an organic solvent to afford a crude product, and the crude product was purified by beating with ethyl acetate (20 mL); suction filtration was performed, and a filter cake was purified by beating with anhydrous acetonitrile (20 mL); the suction filtration was performed, and the filter cake was dried to afford intermediate I-89. LC-MS (ESI) [M+H]$^+$ 102.4.

Reference Example 90: Preparation of Intermediate I-90

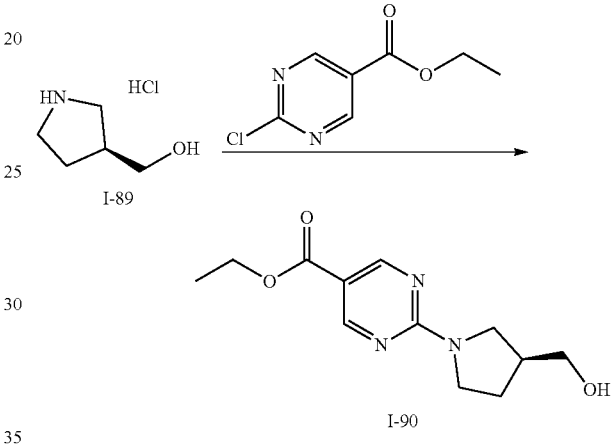

Intermediate I-89 (500 mg, 3.61 mmol) was dissolved in dimethyl sulfoxide (10 mL), followed by successive addition of ethyl 2-chloropyrimidine-5-carboxylate (670 mg, 3.61 mmol) and N,N-diisopropylethylamine (1.78 mL, 10.8 mmol); after argon replacement at room temperature for 3 times, a reaction mixture was stirred and reacted at 50° C. for 3 hours under argon protection. After the mixture was cooled to room temperature, liquid separation was performed, and organic phases were concentrated to dryness under reduced pressure. A residue was added with water (10 mL) and extracted with ethyl acetate (20 mL×3). Organic phases were combined, washed with saturated saline (10 mL), dried over anhydrous sodium sulfate and filtered, and a filtrate was concentrated to dryness. The residue was separated and purified by silica gel chromatography to afford intermediate I-90. LC-MS (ESI) [M+H]$^+$ 252.0.

Reference Example 91: Preparation of Intermediate I-91

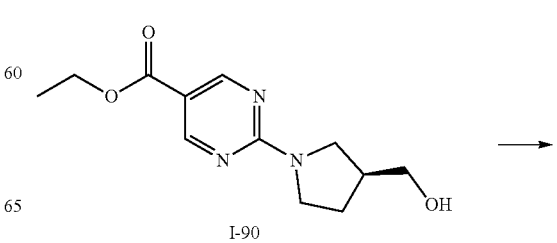

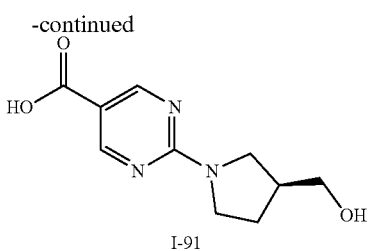

I-91

Intermediate I-90 (700 mg, 2.79 mmol) was dissolved in anhydrous tetrahydrofuran (10 mL); then, lithium hydroxide monohydrate (583 mg, 13.9 mmol) was dissolved in water (10.00 mL) and added dropwise to a reaction solution, and a reaction system was protected with argon and stirred at room temperature for 2 hours. A mixture was adjusted to be weakly acidic with 1 N hydrochloric acid, a solid was precipitated, and filtration was performed to afford a crude product of intermediate I-91. The crude product was directly used in the next reaction without further purification. LC-MS (ESI) [M+H]$^+$ 224.1.

Reference Example 92: Preparation of Intermediate I-92

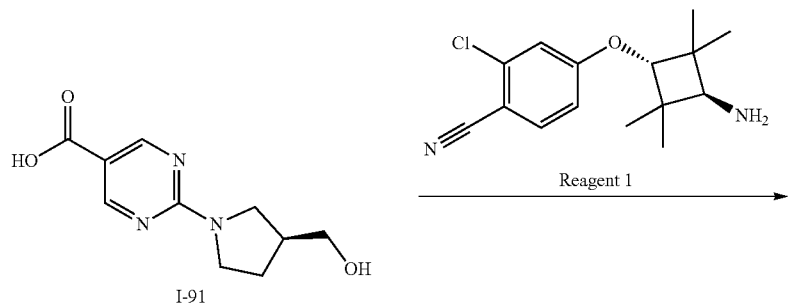

Intermediate I-91 (200 mg) was dissolved in N,N-dimethylformamide (10 mL), followed by successive addition of 1-hydroxybenzotriazole (242 mg, 1.794 mmol), 1-(3-dimethyl aminopropyl)-3-ethyl carbodiimide hydrochloride (344 mg, 1.794 mmol), N,N-diisopropylethyl amine (0.4 mL, 2.69 mmol) and reagent 1 (245 mg). A reaction mixture was stirred and reacted at room temperature for 16 hours. A reaction solution was filtered, and a filter cake was washed with ethyl acetate (5 mL×3) and dried to afford intermediate I-92. LC-MS (ESI) [M+H]$^+$ 484.0.

Reference Example 93: Preparation of Intermediate I-93

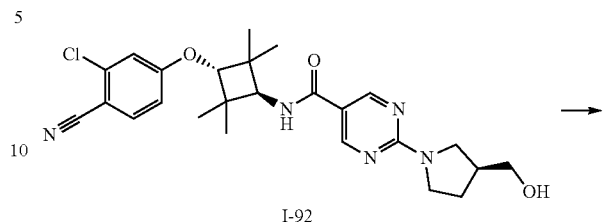

I-92

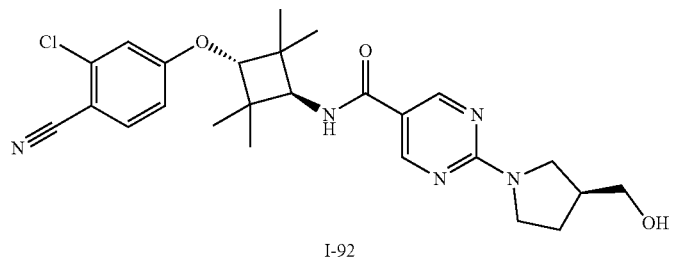

I-93

Intermediate I-92 (150 mg, 0.31 mmol) was dissolved in anhydrous dichloromethane (10 mL), and a system was cooled to 0° C. and added with Dess-Martin periodinane (197 mg, 0.465 mmol). A reaction system was protected with argon, and stirred and reacted at room temperature for 2 hours. A filtrate was quenched with a saturated aqueous sodium bicarbonate solution (10 mL) and extracted with dichloromethane (10 mL×3). Organic phases were combined, washed with saturated saline (10 mL), and dried over anhydrous sodium sulfate. Filtration was performed, and a filtrate was concentrated under reduced pressure to remove an organic solvent to afford a crude product. The crude product was separated and purified by silica gel chromatography to afford intermediate I-93.

Reference Example 94: Preparation of Intermediate I-94

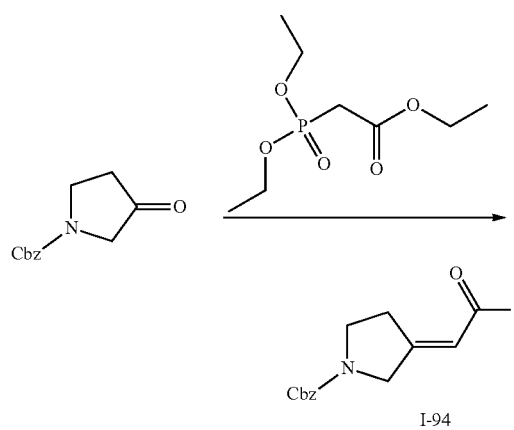

At 0° C., sodium hydride (mass fraction 60%) (438 mg, 11.0 mmol) was added to tetrahydrofuran (10 mL), and argon was replaced; after stirring at 0° C. for 5 minutes, a solution of triethyl phosphonoacetate (2.66 g, 11.9 mmol) in tetrahydrofuran (10 mL) was slowly added dropwise, and a reaction was stirred at 0° C. for 30 minutes; then, a solution of N-Cbz-3-pyrrolidone (2.00 g, 9.13 mmol) in tetrahydrofuran (10 mL) was slowly added dropwise; after addition was completed, a reaction mixture was stirred and reacted at room temperature for 2 hours. After a reaction was completed, water (30 mL) was added for dilution, concentration was performed under reduced pressure, and a residual solution was extracted with ethyl acetate (30 mL×3); organic phases were combined, washed with water (30 mL×3), dried over anhydrous sodium sulfate and filtered; a filtrate was concentrated under reduced pressure, and a residue was separated and purified by silica gel chromatography to afford intermediate I-94. LC-MS (ESI) [M+H]$^+$ 290.2.

Reference Example 95: Preparation of Intermediate I-95

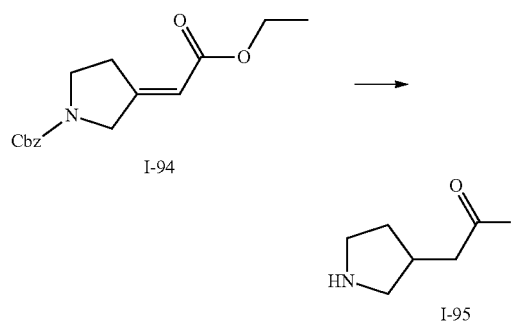

At room temperature, intermediate I-94 (1.84 g, 6.37 mmol) was dissolved in methanol (20 mL), palladium/carbon (mass fraction 10%) (1.35 g, 1.27 mmol) was added, and after addition was completed, hydrogen was replaced, and a reaction mixture was stirred and reacted at room temperature for 16 hours under a hydrogen atmosphere. After a reaction was completed, a reaction solution was filtered through diatomite, and a filtrate was concentrated under reduced pressure to afford a crude product of intermediate I-95. The crude product was directly used in the next reaction without further purification. $^1$H NMR (400 MHz, DMSO-d$_6$) δ 4.09-4.01 (m, 2H), 3.40 (d, J=8.4 Hz, 3H), 2.93-2.65 (m, 2H), 2.38-2.20 (m, 3H), 1.95-1.75 (m, 1H), 1.36-1.20 (m, 1H), 1.18 (t, J=7.1 Hz, 3H).

Reference Example 96: Preparation of Intermediate I-96

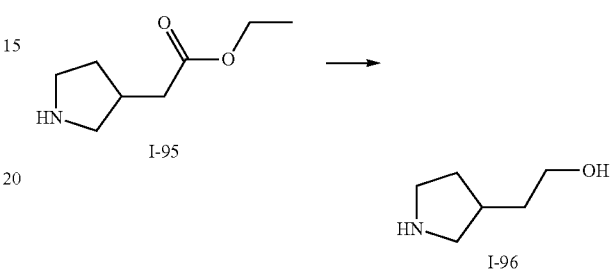

Intermediate I-95 (900 mg, 5.73 mmol) was dissolved in tetrahydrofuran (20 mL), and argon was replaced; at 0° C., lithium aluminum hydride (435 mg, 11.5 mmol) was slowly added in portions; after addition was completed, a reaction mixture was stirred and reacted at 0° C. for 2 hours. After a reaction was completed, water (0.9 mL) was added and stirred for 5 minutes; then, anhydrous sodium sulfate was added under stirring, filtration was performed with diatomite, and a filtrate was concentrated under reduced pressure to afford a crude product of intermediate I-96. The crude product was directly used in the next reaction without further purification. LC-MS (ESI) [M+H]$^+$ 116.1.

Reference Example 97: Preparation of Intermediate I-97

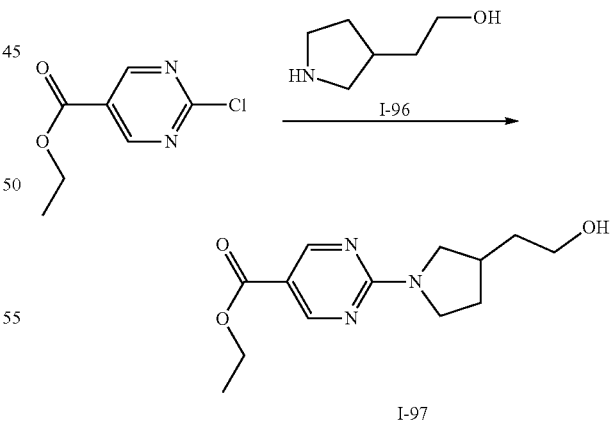

At room temperature, ethyl 2-chloropyrimidine-5-carboxylate (730 mg, 3.9 mmol) was dissolved in dimethyl sulfoxide (5 mL), followed by addition of intermediate I-96 (450 mg) and N,N-diisopropylethylamine (1.5 g, 11.7 mmol); after addition was completed, a reaction mixture was stirred and reacted at 50° C. for 2 hours. After a reaction was completed, the reaction mixture was concentrated, and separated and purified by silica gel chromatography to afford intermediate I-97. LC-MS (ESI) [M+H]+ 266.0.

Reference Example 98: Preparation of Intermediate I-98

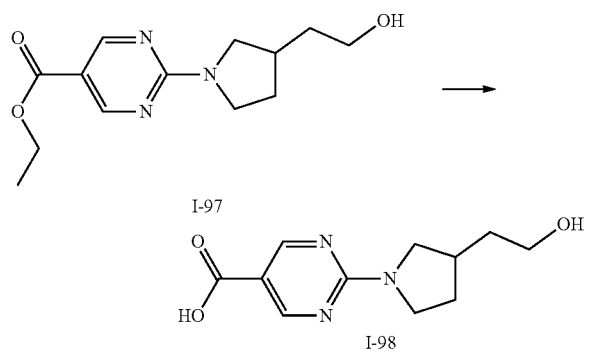

At room temperature, intermediate I-97 (170 mg, 0.64 mmol) was dissolved in tetrahydrofuran (3 mL), and a solution of lithium hydroxide monohydrate (134 mg, 3.2 mmol) in water (1 mL) was added; after addition was completed, a reaction mixture was stirred and reacted at room temperature overnight. After a reaction was completed, a reaction solution was adjusted to have pH=5-6 with a 1 N hydrochloric acid solution, subsequently diluted with saturated saline (10 mL), and extracted with ethyl acetate (10 mL×5); organic phases were combined, dried over anhydrous sodium sulfate and filtered, and a filtrate was concentrated under reduced pressure to afford a crude product of intermediate I-98. The crude product was directly used in the next reaction without further purification. LC-MS (ESI) [M+H]+ 238.1.

Reference Example 99: Preparation of Intermediate I-99

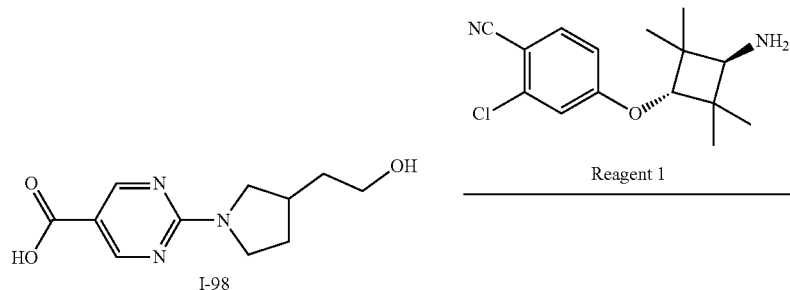

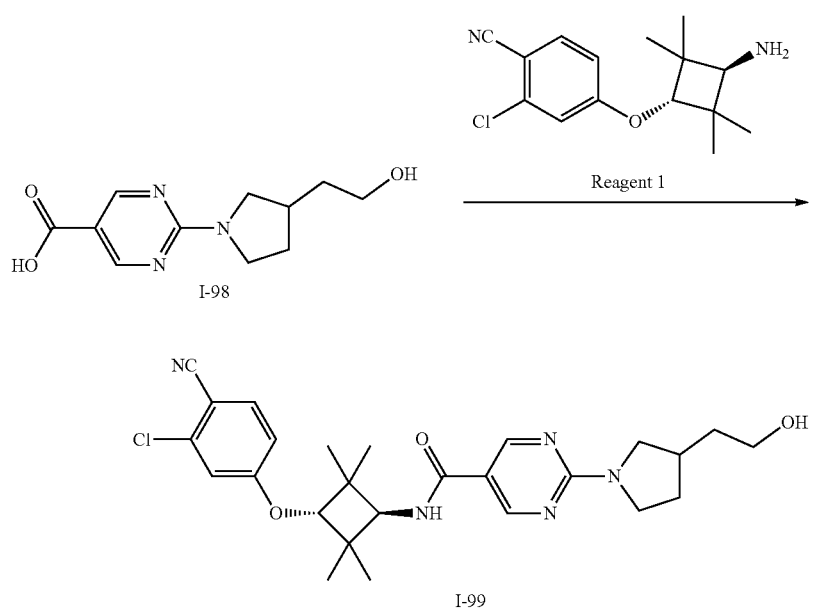

At room temperature, intermediate I-98 (120 mg, 0.51 mmol) was dissolved in a N,N-dimethylformamide (5 mL) solution, followed by successive addition of reagent 1 (142 mg), 1-hydroxybenzotriazole (138 mg, 1.02 mmol), 1-(3-dimethylaminopropyl)-3-ethylcarbodiimide hydrochloride (196 mg, 1.02 mmol) and N,N-diisopropylethylamine (197 mg, 1.53 mmol); after addition was completed, a reaction mixture was stirred and reacted at room temperature for 4 hours. After a reaction was completed, water (20 mL) was added for dilution, and ethyl acetate (20 mL×3) was used for extraction; organic phases were combined, washed with water (20 mL×3), dried over anhydrous sodium sulfate and filtered; a filtrate was concentrated under reduced pressure, and a residue was separated and purified by silica gel chromatography to afford intermediate I-99. LC-MS (ESI) [M+H]+ 498.1.

Reference Example 100: Preparation of Intermediate I-100

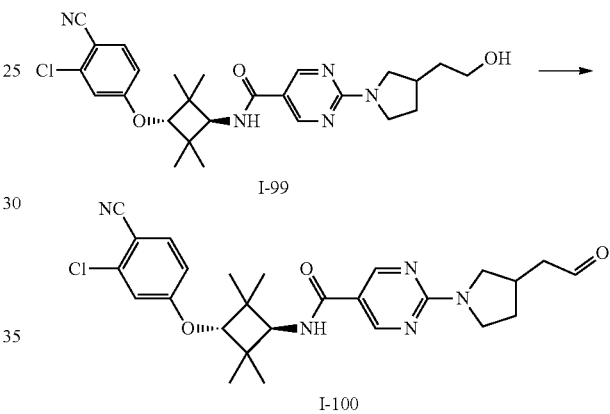

At room temperature, intermediate I-99 (80 mg, 0.16 mmol) was dissolved in dimethyl sulfoxide (5 mL), and 2-iodoxybenzoic acid (224 mg, 0.80 mmol) was added; after addition was completed, a reaction mixture was stirred and reacted at 80° C. for 30 minutes. After a reaction was completed, water (10 mL) was added for dilution, and ethyl acetate (20 mL×3) was used for extraction; organic phases were combined, washed with water (20 mL×3), dried over anhydrous sodium sulfate and filtered, and a filtrate was concentrated under reduced pressure to afford a crude product of intermediate I-100. The crude product was directly used in the next reaction without further purification.

Reference Example 101: Preparation of Intermediate I-101

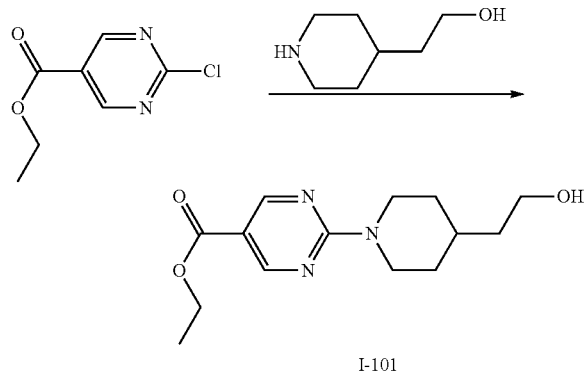

At room temperature, ethyl 2-chloropyrimidine-5-carboxylate (200 mg, 1.07 mmol) was dissolved in dimethyl sulfoxide (5 mL), followed by addition of 4-piperidineethanol (165 mg, 1.28 mmol) and N, N-diisopropylethylamine (414 g, 3.21 mmol); a reaction mixture was stirred and reacted at 50° C. for 2 hours. After a reaction was completed, water (20 mL) was added for dilution, and ethyl acetate (20 mL×3) was used for extraction; organic phases were combined, washed with water (20 mL×3), dried over anhydrous sodium sulfate and filtered; a filtrate was concentrated under reduced pressure, and a residue was separated and purified by silica gel chromatography to afford intermediate I-101. LC-MS (ESI) [M+H]$^+$ 280.1.

Reference Example 102: Preparation of Intermediate I-102

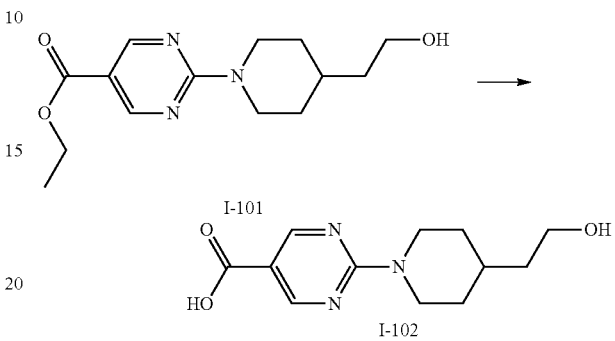

At room temperature, intermediate I-101 (240 mg, 0.86 mmol) was dissolved in tetrahydrofuran (3 mL), and a solution of lithium hydroxide monohydrate (181 mg, 4.3 mmol) in water (1 mL) was added; after addition was completed, a reaction mixture was stirred and reacted at room temperature overnight. After a reaction was completed, a reaction solution was adjusted to have pH=5-6 with a 1 N hydrochloric acid solution and filtered, and a filter cake was dried to afford intermediate I-102. LC-MS (ESI) [M+H]$^+$ 252.1.

Reference Example 103: Preparation of Intermediate I-103

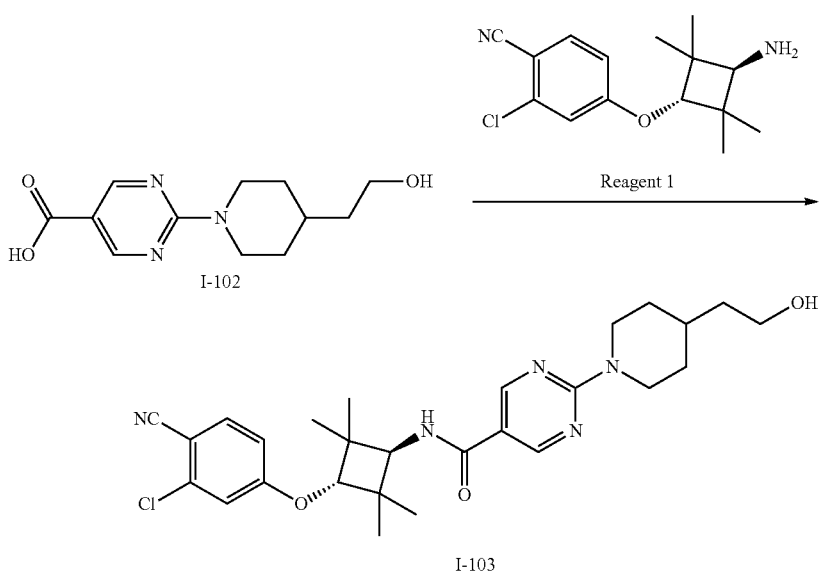

At room temperature, intermediate I-102 (140 mg, 0.56 mmol) was dissolved in a N,N-dimethylformamide (5 mL)

solution, followed by successive addition of reagent 1 (156 mg), 1-hydroxybenzotriazole (157 mg, 1.12 mmol), 1-(3-dimethylaminopropyl)-3-ethylcarbodiimide hydrochloride (215 mg, 1.12 mmol) and N,N-diisopropylethylamine (217 mg, 1.68 mmol); after addition was completed, a reaction mixture was stirred and reacted at room temperature for 4 hours. After a reaction was completed, water (20 mL) was added for dilution, and ethyl acetate (20 mL×3) was used for extraction; organic phases were combined, washed with water (20 mL×3), dried over anhydrous sodium sulfate and filtered; a filtrate was concentrated under reduced pressure, and a residue was separated and purified by silica gel chromatography to afford intermediate I-103. LC-MS (ESI) [M+H]$^+$ 512.3.

Reference Example 104: Preparation of Intermediate I-104

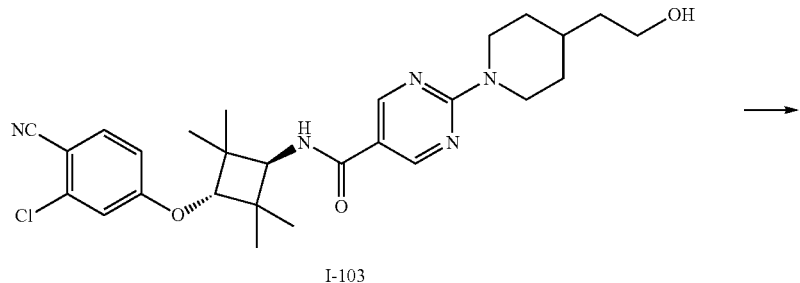

I-103

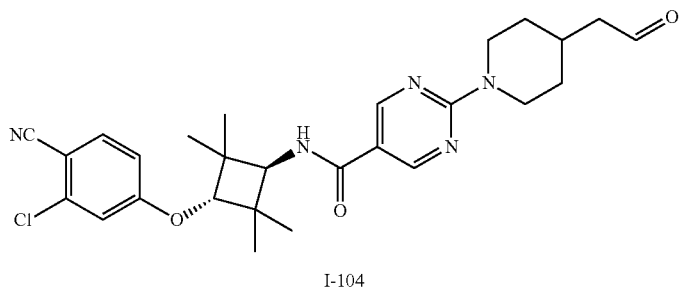

I-104

At 0° C., intermediate I-103 (60 mg, 0.12 mmol) was dissolved in dichloromethane (10 mL), and Dess-Martin periodinane (102 mg, 0.24 mmol) was added; a reaction mixture was stirred and reacted at room temperature for 2 hours. After a reaction was completed, a saturated sodium sulfite solution (10 mL) was added for dilution, standing for layering was performed, and an aqueous phase was extracted with dichloromethane (10 mL×2); organic phases were combined, and washed successively with a saturated sodium sulfite solution (10 mL×2), a saturated sodium bicarbonate solution (10 mL×3) and water (10 mL×3), dried over anhydrous sodium sulfate and filtered; a filtrate was concentrated under reduced pressure to afford a crude product of intermediate I-104. The crude product was directly used in the next reaction without further purification.

Reference Example 105: Preparation of Intermediate I-105

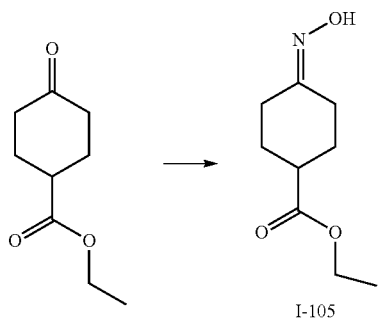

I-105

At room temperature, hydroxylamine hydrochloride (8.69 g, 125 mmol) was dissolved in water (130 mL), and anhydrous sodium acetate (13.6 g, 166 mmol) was added; a mixture was stirred at room temperature for 10 minutes, and ethyl p-cyclohexanone formate was added dropwise (13.0 g, 83.2 mmol). A reaction system was protected with argon, and stirred and reacted at 45° C. for 16 hours. A reaction solution was cooled to room temperature, and a product was extracted with ethyl acetate (100 mL×2); organic phases were combined, dried over anhydrous sodium sulfate and filtered; a filtrate was concentrated under reduced pressure to remove an organic solvent to afford a crude product; the crude product was separated and purified by silica gel chromatography to afford intermediate I-105. LC-MS (ESI) [M+H]$^+$ 186.1.

Reference Example 106: Preparation of Intermediate I-106

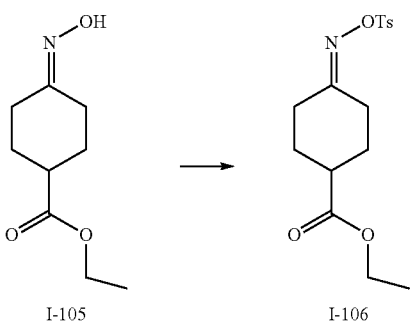 [SMILES: CCOC(=O)C1CCC(=NO)CC1 ; CCOC(=O)C1CCC(=NOS(=O)(=O)c2ccc(C)cc2)CC1]

At room temperature, intermediate I-105 (11.2 g, 60.5 mmol) was dissolved in anhydrous pyridine (50.0 mL), a reaction system was protected with argon and cooled to −15° C., and 4-toluenesulfonyl chloride (17.3 g, 90.8 mmol) was added. A reaction mixture was stirred and reacted at −15° C. for 2 hours. The mixture was poured into ice water, and a solid was precipitated; after stirring at 5° C. for 20 minutes, suction filtration was performed, and a filter cake was dried to afford intermediate I-106. LC-MS (ESI) [M+H]$^+$ 340.2.

Reference Example 107: Preparation of Intermediate I-107

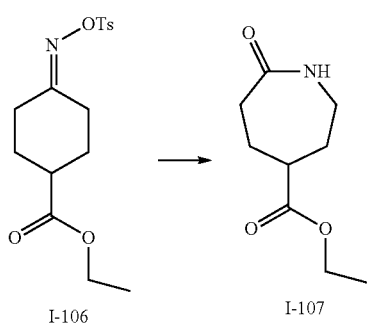 [SMILES: CCOC(=O)C1CCC(=NOS(=O)(=O)c2ccc(C)cc2)CC1 ; CCOC(=O)C1CCNC(=O)CC1]

At room temperature, intermediate I-106 (12.5 g, 36.8 mmol) was dissolved in glacial acetic acid (30.0 mL), and a reaction system was protected with argon and stirred and reacted at room temperature for 16 hours. Concentration was performed under reduced pressure to remove glacial acetic acid, a residue was added with a saturated aqueous sodium bicarbonate solution (40.0 mL) and stirred for 15 minutes, and a product was extracted with ethyl acetate (30.0 mL×3). Organic phases were combined and dried over anhydrous sodium sulfate, suction filtration was performed, and a filtrate was concentrated under reduced pressure to remove an organic solvent to afford a crude product; the crude product was separated and purified by silica gel chromatography to afford intermediate I-107. LC-MS (ESI) [M+H]$^+$ 186.2.

Reference Example 108: Preparation of Intermediate I-108

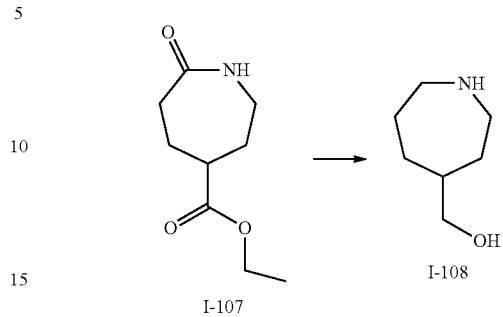

Lithium aluminum hydride (2.56 g, 67.5 mmol) was dissolved in anhydrous tetrahydrofuran (100 mL); at 0° C., a solution of intermediate I-107 (2.50 g, 13.5 mmol) in anhydrous tetrahydrofuran (20.0 mL) was added dropwise. A reaction system was protected with argon, and stirred and reacted at room temperature for 2 hours. Then, the temperature was raised to 60° C., and a reaction was stirred for 4 hours. A mixture was cooled to room temperature; at 0° C., sodium sulfate decahydrate (10.0 g) was added, and a reaction was stirred for 0.5 hour. Suction filtration was performed, and a filtrate was concentrated under reduced pressure to remove an organic solvent to afford intermediate I-108. LC-MS (ESI) [M+H]$^+$ 130.1.

Reference Example 109: Preparation of Intermediate I-109

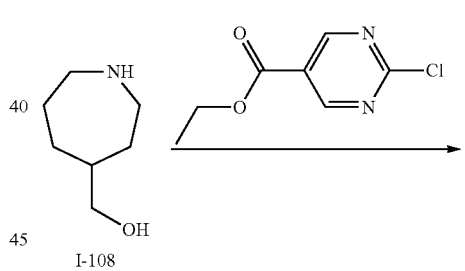

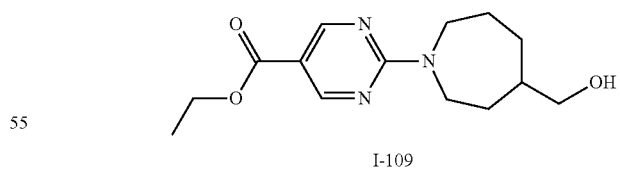

At room temperature, intermediate I-108 (560 mg, 4.33 mmol) was dissolved in anhydrous dichloromethane (50.0 mL), followed by addition of ethyl 2-chloropyrimidine-5-carboxylate (970 mg, 5.20 mmol) and N,N-diisopropylethylamine (1.68 g, 13.0 mmol). A reaction system was protected with argon, and stirred and reacted at room temperature for 16 hours. A mixture was separated and purified by silica gel chromatography to afford intermediate I-109. LC-MS (ESI) [M+H]$^+$ 280.2.

Reference Example 110: Preparation of Intermediate I-110

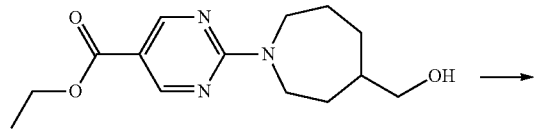

At room temperature, intermediate I-109 (240 mg, 0.860 mmol) was dissolved in a mixed solvent of tetrahydrofuran/methanol (3.00 mL/3.00 mL), and a solution of lithium hydroxide monohydrate (114 mg, 2.72 mmol) in water (3.00 mL) was added. A reaction system was protected with argon, and stirred and reacted at room temperature for 16 hours. A mixture was adjusted to have system pH of 6.0 with 1 N hydrochloric acid, and a solid was precipitated; suction filtration was performed, and a filter cake was dried to afford intermediate I-110. LC-MS (ESI) [M+H]$^+$ 252.2.

Reference Example 111: Preparation of Intermediate I-111

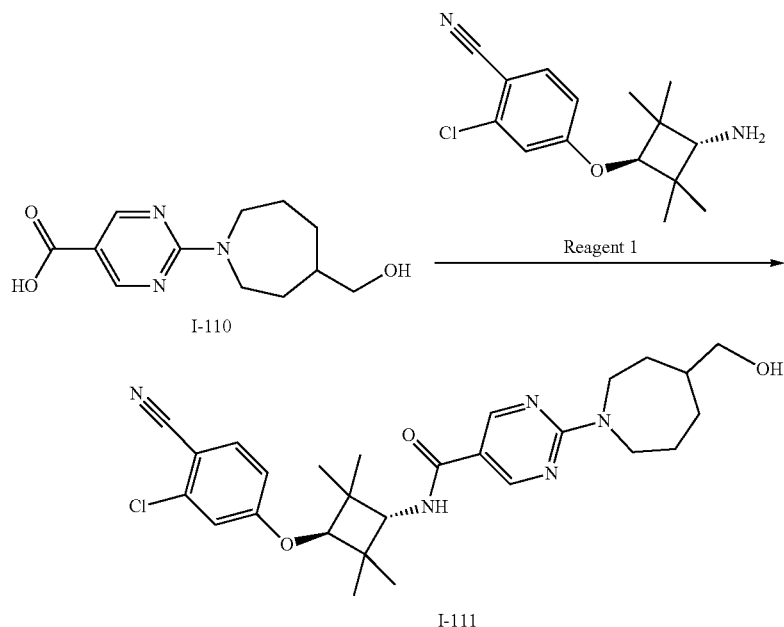

At room temperature, intermediate I-110 (180 mg, 0.716 mmol) was dissolved in anhydrous N,N-dimethylformamide (20.0 mL), followed by addition of reagent 1 (293 mg), 1-(3-dimethylaminopropyl)-3-ethylcarbodiimide hydrochloride (274 mg, 1.43 mmol), 1-hydroxybenzotriazole (193 mg, 1.43 mmol) and N,N-diisopropylethylamine (370 mg, 2.86 mmol). A reaction system was protected with argon, and stirred and reacted at room temperature for 16 hours. A mixture was separated and purified by column chromatography (C18, acetonitrile/water=0-70%) to afford intermediate I-111. LC-MS (ESI) [M+H]$^+$ 512.2.

Reference Example 112: Preparation of Intermediate I-112

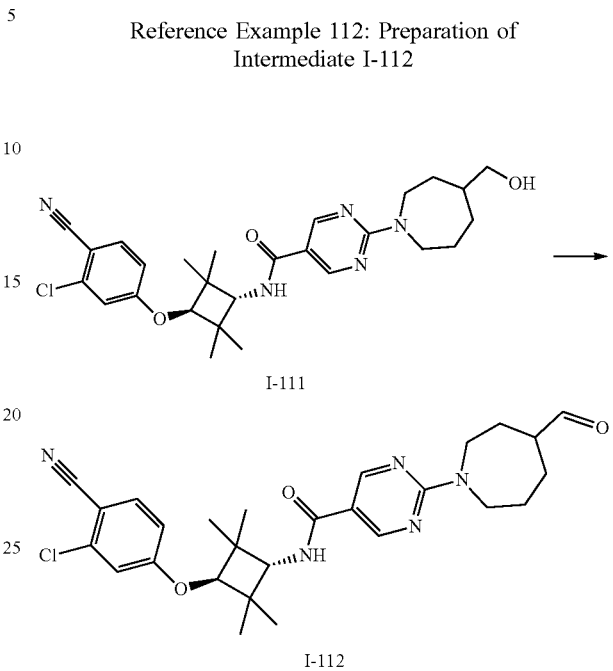

Intermediate I-111 (200 mg, 0.391 mmol) was dissolved in anhydrous dichloromethane (20.0 mL); at 0° C., Dess-Martin periodinane (249 mg, 0.587 mmol) was added. A reaction system was protected with argon, and stirred and reacted at room temperature for 2 hours. A mixture was separated and purified by silica gel chromatography to afford intermediate I-112. LC-MS (ESI) [M+H]$^+$ 510.1.

Reference Example 113: Preparation of Intermediate I-113

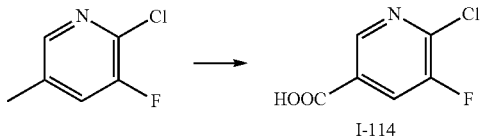

At room temperature, 2-chloro-3-fluoro-5-methylpyridine (1.00 g, 6.87 mmol) was added to water (5.00 mL), followed by addition of potassium permanganate (2.17 g, 13.7 mmol) and pyridine (5.52 mL, 68.7 mmol). After stirring at 100° C. for 1 hour, potassium permanganate (4.34 g, 27.4 mmol) was added, followed by stirring at 100° C. overnight. Water (10.0 mL) was added, and ethyl acetate (20.0 mL×2) was used for extraction; an aqueous phase was adjusted to have pH of about 2.0 with 2 N dilute hydrochloric acid, and extracted with ethyl acetate (20.0 mL×2); the combined organic phases were washed with saturated saline (20 mL) and concentrated to afford a crude product of intermediate I-113. The crude product was directly used in the next reaction without purification. LC-MS (ESI) [2M−H]⁻ 349.0.

Reference Example 114: Preparation of Intermediate I-114

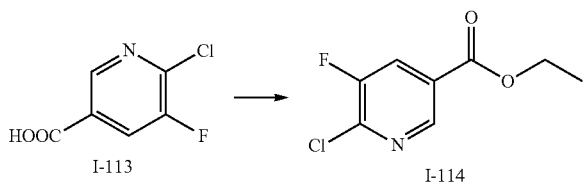

At room temperature, intermediate I-113 (650 mg) was dissolved in ethanol (10.0 mL) and cooled to 0° C. in an ice-water bath; thionyl chloride (0.676 mL, 9.26 mmol) was slowly added by an injector, the temperature was slowly raised to room temperature, and then heating at reflux was performed and reacted for 4 hours. Concentration was performed, and a residual solution was added with a saturated sodium bicarbonate solution (10.0 mL) and extracted with ethyl acetate (30.0 mL×2); organic phases were combined, washed with saturated saline (30 mL), dried over anhydrous sodium sulfate and filtered, and concentration was performed to afford a crude product; the crude product was separated and purified by silica gel chromatography to afford intermediate I-114. LC-MS (ESI) [M+H]⁺ 204.1.

Reference Example 115: Preparation of Intermediate I-115

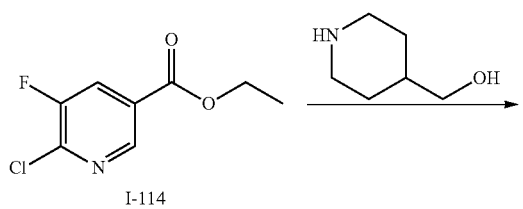

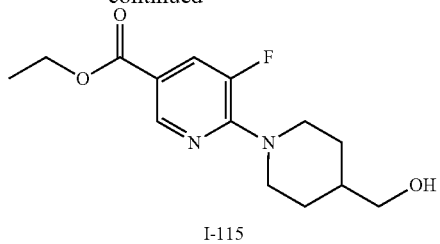

At room temperature, intermediate I-114 (340 mg, 1.67 mmol) was dissolved in dimethyl sulfoxide (10.0 mL), followed by addition of 4-hydroxymethylpiperidine (192 mg, 1.67 mmol) and N,N-diisopropylethylamine (646 mg, 5.01 mmol); stirring was performed at 50° C. overnight. A reaction solution was cooled to room temperature, first added with water (10.0 mL) and then extracted with ethyl acetate (20 mL×2); organic phases were combined, washed with saturated saline (20 mL), dried over anhydrous sodium sulfate, filtered and concentrated to afford a crude product; the crude product was separated and purified by silica gel chromatography to afford intermediate I-115. LC-MS (ESI) [M+H]⁺ 283.1.

Reference Example 116: Preparation of Intermediate I-116

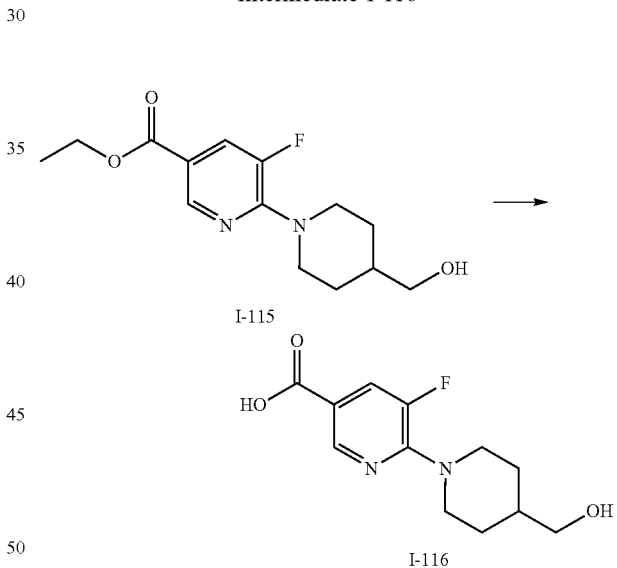

At room temperature, intermediate I-115 (340 mg, 1.20 mmol) was dissolved in a mixed solvent of tetrahydrofuran (5.00 mL) and water (1.00 mL), followed by addition of lithium hydroxide monohydrate (252 mg, 6.00 mmol); stirring was performed at room temperature overnight. Water (5.00 mL) was added first, and then ethyl acetate (3.00 mL) was used for washing; an aqueous phase was adjusted to have pH of 2.0 with 2 N dilute hydrochloric acid, and then extracted with ethyl acetate (8 mL×2); extract liquors were combined, washed with saturated saline (5.00 mL), dried over anhydrous sodium sulfate, filtered and concentrated to afford a crude product of intermediate I-116. The crude product was directly used in the next reaction without purification. LC-MS (ESI) [M+H]⁺ 255.1.

Reference Example 117: Preparation of Intermediate I-117

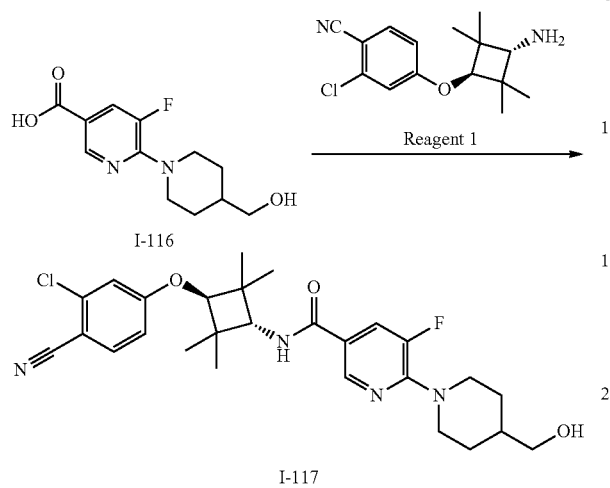

Intermediate I-116 (130 mg) was dissolved in N,N-dimethylformamide (10 mL), followed by successive addition of 1-hydroxybenzotriazole (138 mg, 1.02 mmol), 1-(3-dimethylaminopropyl)-3-ethylcarbodiimide hydrochloride (196 mg, 1.02 mmol), N,N-diisopropylethylamine (0.3 mL, 1.53 mmol) and reagent 1 (142 mg). A reaction mixture was stirred and reacted at room temperature for 16 hours. A reaction solution was filtered, and a filter cake was washed with ethyl acetate (2 mL×3) and dried to afford intermediate I-117. LC-MS (ESI) [M+H]+ 515.0.

Reference Example 118: Preparation of Intermediate I-118

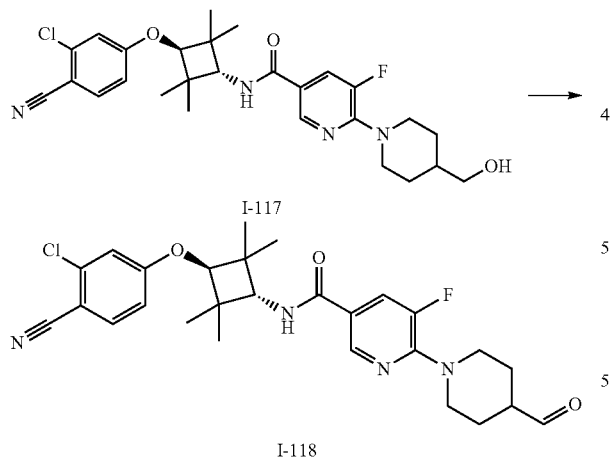

Intermediate I-117 (100 mg, 0.194 mmol) was dissolved in anhydrous dichloromethane (15.0 mL), and a system was cooled to 0° C. and added with Dess-Martin periodinane (123 mg, 0.291 mmol). A reaction system was protected with argon, and stirred and reacted at room temperature for 2 hours. Filtration was performed, and a filtrate was quenched with a saturated aqueous sodium bicarbonate solution (20.0 mL) and extracted with dichloromethane (15.0 mL×3). Organic phases were combined, washed with saturated saline (10.0 mL), dried over anhydrous sodium sulfate and filtered; a filtrate was concentrated under reduced pressure to remove an organic solvent to afford a crude product of intermediate I-118. The crude product was directly used in the next reaction without purification.

Reference Example 119: Preparation of Intermediate I-119

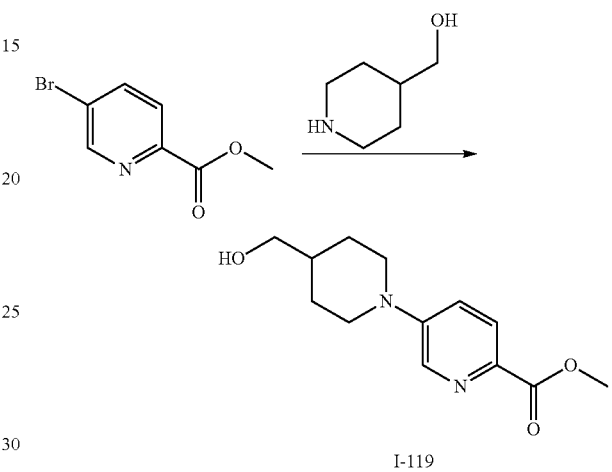

Methyl 5-bromopyridine-2-carboxylate (10.0 g, 46.3 mmol) was dissolved in anhydrous toluene (200 mL), followed by successive addition of 4-piperidinemethanol (10.7 g, 92.6 mmol), anhydrous potassium carbonate (19.2 g, 139 mmol), tris(dibenzylideneacetone)dipalladium (848 mg, 0.926 mmol) and 2-dicyclohexylphosphino-2',6'-diisopropoxy-1,1'-biphenyl (864 mg, 1.85 mmol); a mixture under argon protection was stirred and reacted at 100° C. for 16 hours. A mixture was cooled, and suction filtration was performed; a filter cake was washed with dichloromethane (100 mL), and a filtrate was dried over anhydrous sodium sulfate and concentrated to dryness to afford a crude product; the crude product was separated and purified by silica gel chromatography to afford intermediate I-119. LC-MS (ESI) [M+H]+ 251.2.

Reference Example 120: Preparation of Intermediate I-120

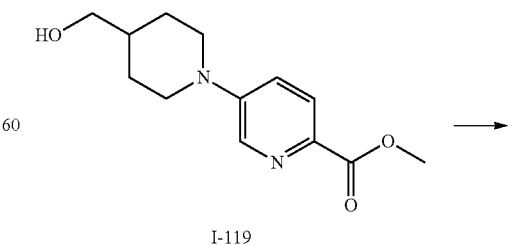

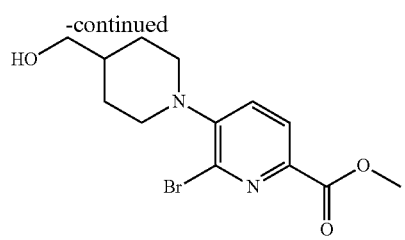

I-120

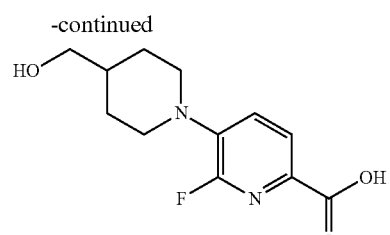

I-121

Intermediate I-119 (300 mg, 1.20 mmol) was dissolved in anhydrous tetrahydrofuran (30.0 mL), N-bromosuccinimide (214 mg, 1.20 mmol) was added, and a system under nitrogen protection was stirred and reacted at room temperature for 16 hours. A reaction solution was concentrated, and separated and purified by silica gel chromatography to afford intermediate I-120.

Reference Example 121: Preparation of Intermediate I-121

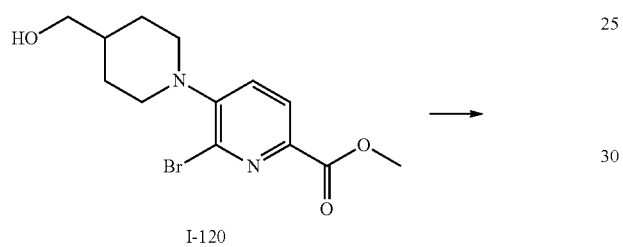

I-120

Intermediate I-120 (220 mg, 0.668 mmol) was dissolved in anhydrous dimethyl sulfoxide (10.0 mL) and potassium fluoride (116 mg, 2.00 mmol) was added. A reaction system was protected with argon and stirred and reacted at 150° C. for 3 days. A mixture was cooled to room temperature, filtered, and separated and purified by a preparative high performance liquid phase (a formic acid condition) to afford intermediate I-121. LC-MS (ESI) [M+H]$^+$ 255.2.

Reference Example 122: Preparation of Intermediate I-122

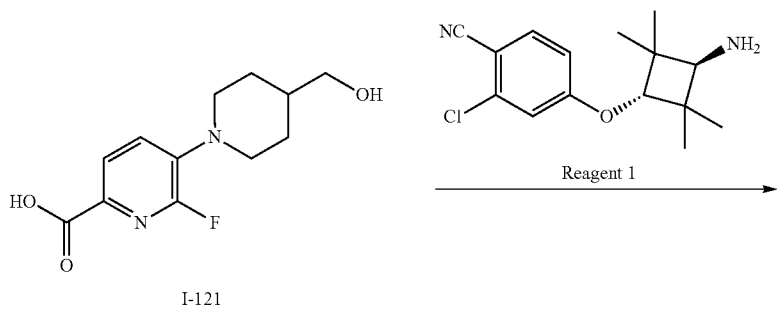

I-121

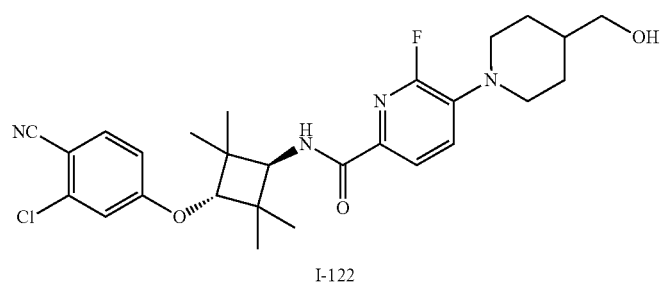

I-122

At room temperature, intermediate I-121 (35 mg, 0.14 mmol) was dissolved in a N,N-dimethylformamide (5 mL) solution, followed by successive addition of reagent 1 (39 mg), 1-hydroxybenzotriazole (38 mg, 0.28 mmol), 1-(3-dimethylaminopropyl)-3-ethylcarbodiimide hydrochloride (54 mg, 0.28 mmol) and N,N-diisopropylethylamine (54 mg, 0.42 mmol); a reaction mixture was stirred and reacted at room temperature for 16 hours. Water (20 mL) was added for dilution, and ethyl acetate (20 mL×3) was used for extraction; organic phases were combined, washed with water (20 mL×3), dried over anhydrous sodium sulfate and filtered; a filtrate was concentrated under reduced pressure, and a residue was separated and purified by silica gel chromatography to afford intermediate I-122. LC-MS (ESI) [M+H]$^+$ 515.0.

Reference Example 123: Preparation of Intermediate I-123

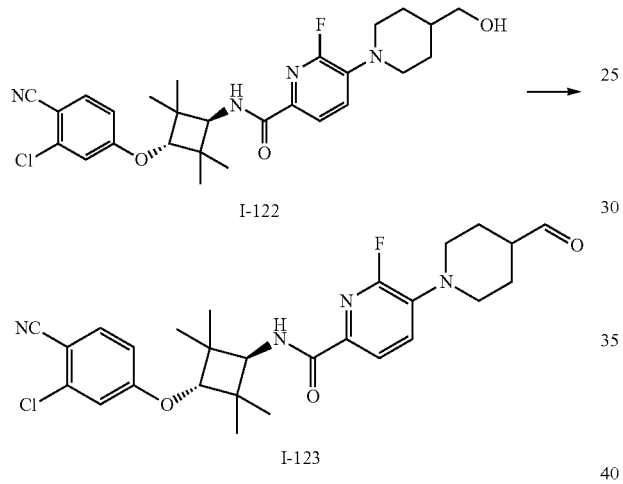

I-122

I-123

At room temperature, intermediate I-122 (30 mg, 0.058 mmol) was dissolved in dimethyl sulfoxide (5 mL), and 2-iodoxybenzoic acid (81 mg, 0.29 mmol) was added; after addition was completed, a reaction mixture was stirred and reacted at 80° C. for 1 hour. Water (10 mL) was added for dilution, and ethyl acetate (20 mL×3) was used for extraction; organic phases were combined, washed with water (20 mL×3), dried over anhydrous sodium sulfate and filtered; a filtrate was concentrated under reduced pressure to afford a crude product of intermediate I-123. The crude product was directly used in the next reaction without further purification.

Reference Example 124: Preparation of Intermediate I-124

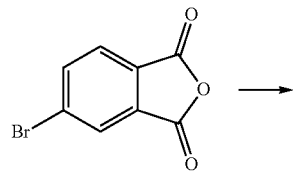

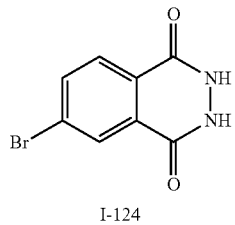

I-124

At 25° C., 4-bromophthalic anhydride (20.0 g, 88.1 mmol) was dissolved in glacial acetic acid (200 mL); the temperature was raised to 120° C., and stirring was performed for 1 hour. After cooling to room temperature, hydrazine hydrate (4.85 g, 96.9 mmol) was added dropwise to generate a large amount of white solids; the temperature was raised to 120° C. to react for 1 hour. The temperature was reduced to room temperature by cooling; filtration was performed, and a filter cake was rinsed with water (200 mL) and ethyl acetate (200 mL) respectively. A filter cake was collected and dried to afford intermediate I-124. LC-MS (ESI) [M+H]$^+$ 243.0.

Reference Example 125: Preparation of Intermediate I-125

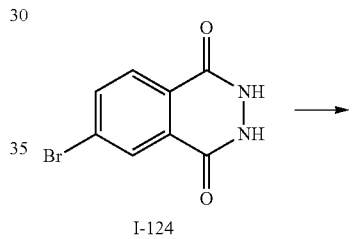

I-124

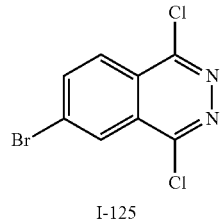

I-125

At 25° C., I-124 (16.2 g, 67.2 mmol) was dissolved in phosphorus oxychloride (100 mL); the temperature was raised to 100° C. to react for 3 hours. After cooling, spin-drying was performed to afford a crude product, the crude product was dissolved in ethyl acetate (200 mL) and added to water (200 mL), and a white solid was precipitated. A filter cake was obtained by filtering, rinsed with ethyl acetate (200 mL), and dried. Organic phases were separated from a filtrate, washed with water (100 mL) and saturated saline (100 mL) respectively, dried over anhydrous sodium sulfate, filtered, and concentrated under reduced pressure. The filter cake and the organic phases were combined, and the resulting residue was concentrated to afford intermediate I-125. LC-MS (ESI) [M+H]$^+$ 277.0.

Reference Example 126: Preparation of Intermediate I-126

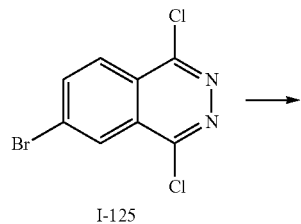

At 25° C., I-125 (8.00 g, 28.8 mmol) was dissolved in N,N-dimethylacetamide (100 mL), followed by addition of potassium fluoride (8.36 g, 143.9 mmol) and 18-crown-6 (3.04 g, 11.5 mmol); the temperature was raised to 120° C. to react for 16 hours. Water (200 mL) was added after cooling. The above-mentioned reaction solution was extracted with ethyl acetate (100 mL×3). Organic phases were combined, washed with saturated saline (50 mL), dried over anhydrous sodium sulfate, filtered, and concentrated under reduced pressure. The resulting crude product was purified by column chromatography to afford intermediate I-126. LC-MS (ESI) [M+H]+ 247.0.

Reference Example 127: Preparation of Intermediate I-127

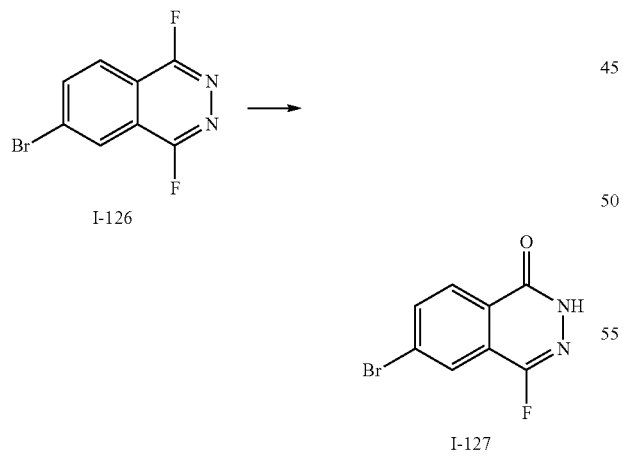

At 25° C., I-126 (1.50 g, 6.12 mmol) was dissolved in dimethyl sulfoxide (25 mL) and water (5 mL), and the temperature was raised to 100° C. to react for 5 hours. After cooling, a reaction solution was added with water (200 mL) and extracted with ethyl acetate (200 mL×3). Organic phases were combined, washed with saturated saline (50 mL), dried over anhydrous sodium sulfate, filtered, and concentrated under reduced pressure to afford intermediate I-127. LC-MS (ESI) [M+H]+ 245.0.

Reference Example 128: Preparation of Intermediate I-128

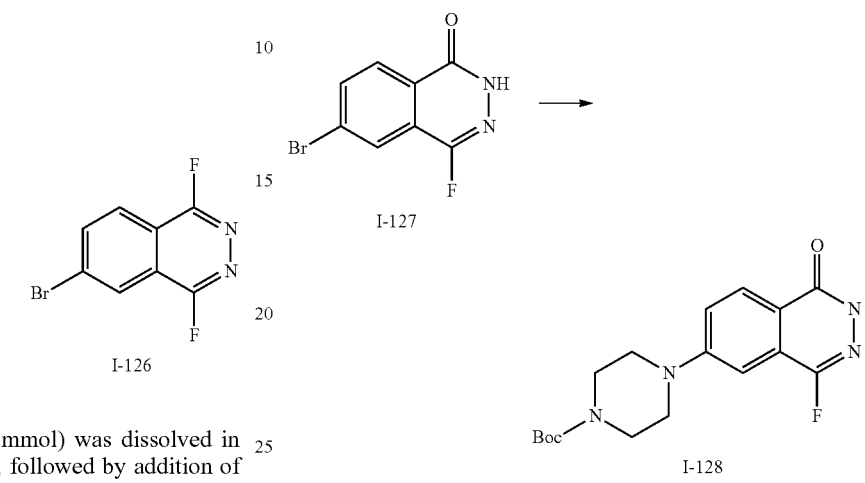

At 25° C., to a solution of I-127 (1.30 g, 5.35 mmol) in N,N-dimethylacetamide (20 mL) was successively added N-tert-butoxycarbonylpiperazine (1.50 g, 8.03 mmol), tris(dibenzylideneacetone)dipalladium (494.49 mg, 0.54 mmol), 1,1'-binaphthyl-2,2'-diphenyl phosphine (666.28 mg, 1.07 mmol) and sodium tert-butoxide (1.29 g, 13.38 mmol). The temperature was raised to 85° C. to react for 2 hours. After cooling, the above-mentioned reaction solution was added with water (50 mL) and extracted with ethyl acetate (50 mL×3). Organic phases were combined, washed with saturated saline (50 mL), dried over anhydrous sodium sulfate, filtered, and concentrated under reduced pressure to afford intermediate I-128. LC-MS (ESI) [M+H]+ 349.2.

Reference Example 129: Preparation of Intermediate I-129

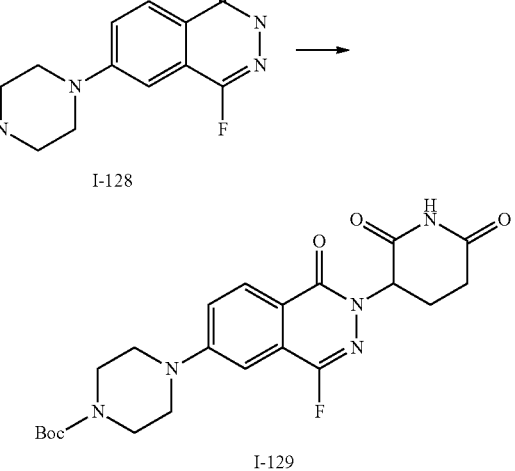

At 25° C., I-128 (330 mg, 0.95 mmol) was dissolved in tetrahydrofuran (10 mL); the above-mentioned solution was successively added with 3-bromo-2,6-piperidinedione (364 mg, 1.89 mmol), sodium hydride (75.8 mg, 1.89 mmol, 60%) and potassium iodide (314 mg, 1.89 mmol), and warmed up to 60° C. and reacted for 3 hours. After cooling, the above-mentioned reaction solution was added with a saturated aqueous ammonium chloride solution (20 mL) and extracted with ethyl acetate (20 mL×3). Organic phases were combined, washed with saturated saline (20 mL), dried over anhydrous sodium sulfate, filtered, and concentrated under reduced pressure to afford intermediate I-129. LC-MS (ESI) [M+H]$^+$ 460.2.

Reference Example 130 Preparation of Intermediate I-130

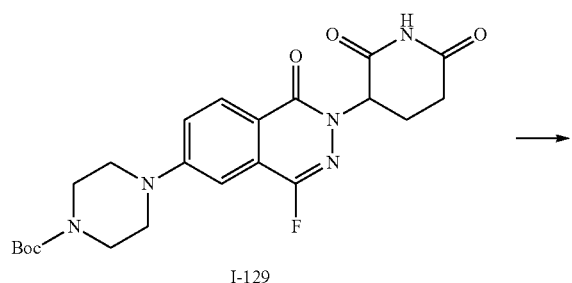

At 25° C., to a solution of I-129 (220 mg, 0.48 mmol) in dichloromethane (10 mL) was added trifluoroacetic acid (5 mL), followed by stirring for 1 hour. A reaction solution was concentrated under reduced pressure to afford intermediate I-130. LC-MS (ESI) [M+H]$^+$ 360.2.

Reference Example 131: Preparation of Intermediate I-131

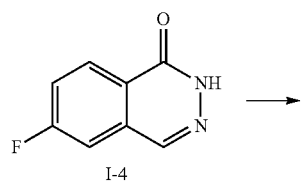

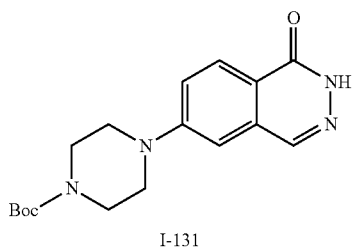

Intermediate I-4 (22.0 g, 134 mmol) was dissolved in anhydrous DMSO (500 mL), followed by successive addition of 1-tert-butoxycarbonylpiperazine (37.4 g, 201 mmol) and diisopropylethylamine (52.0 g, 402 mmol); a reaction system under argon protection was warmed up to 140° C. and stirred for 24 hours. A mixture was cooled to room temperature and subsequently poured into water (1000 mL), and a large amount of solids was precipitated; suction filtration was performed, and a filter cake was collected and purified by beating with ethyl acetate (300 mL) for 16 hours. The suction filtration was performed, and the filter cake was dried to afford intermediate compound I-131. LC-MS (ESI) [M+H]$^+$ 331.1.

Reference Example 132: Preparation of Intermediate I-132

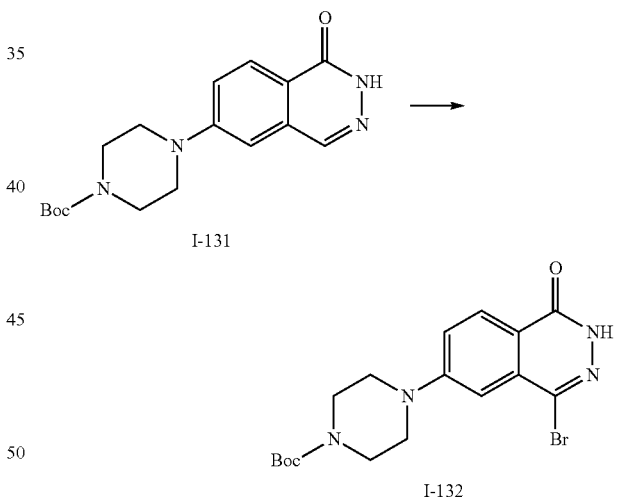

I-131 (5.00 g, 15.15 mmol) and potassium carbonate (4.18 g, 30.30 mmol) were dissolved in N,N-dimethylformamide (300 mL); benzyltrimethylammonium tribromide (11.78 g, 30.30 mmol) was added at room temperature, and a reaction was stirred at 40° C. for 48 hours. After cooling to room temperature, water (10 mL) was added for dilution, and ethyl acetate (30 mL×2) was used for extraction. Organic phases were combined, washed with saturated saline (30 mL×2), dried over anhydrous sodium sulfate, and filtered. A filtrate was concentrated under reduced pressure to remove an organic solvent. A residue was separated and purified by silica gel chromatography to afford intermediate I-132. LCMS (ESI) [M+H]$^+$ 409.2.

Reference Example 133: Preparation of Intermediate I-133

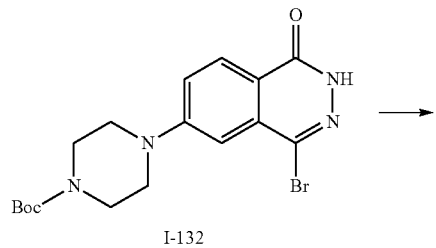

I-132

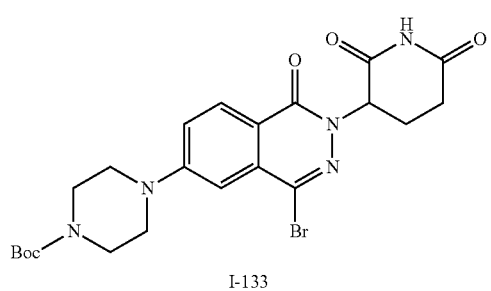

I-133

At 0° C., I-132 (600 mg, 1.47 mmol) was dissolved in N,N-dimethylformamide (50 mL), and sodium hydride (294 mg, 7.35 mmol, 60%) was added; after stirring at 0° C. for 30 minutes, 3-bromo-2,6-piperidinedione (422 mg, 2.20 mmol) and potassium iodide (200 mg) were added, and a reaction was stirred at room temperature for 16 hours. A reaction solution was diluted with water (10 mL) and extracted with ethyl acetate (30 mL×2). Organic phases were combined, washed with saturated saline (30 mL×2), dried over anhydrous sodium sulfate, and filtered. A filtrate was concentrated under reduced pressure to remove an organic solvent. A residue was separated and purified by silica gel chromatography to afford intermediate I-133. LCMS (ESI) [M+H]$^+$ 520.2.

Reference Example 134: Preparation of Intermediate I-134

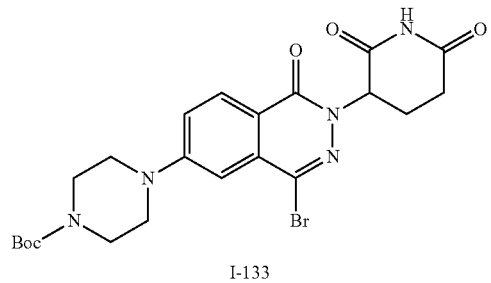

I-133

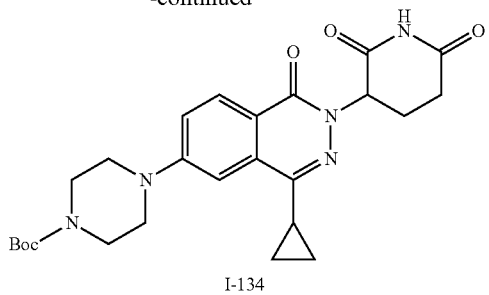

I-134

I-134 (134 mg, 0.26 mmol), potassium cyclopropylfluoroborate (114 mg, 0.78 mmol), 1,1'-bisdiphenylphosphinoferrocene palladium dichloride (19.0 mg, 0.026 mmol) and potassium carbonate (106.6 mg, 0.78 mmol) were dissolved in 1,4-dioxane/water (10 mL/1 mL), and a reaction solution had a microwave reaction at 100° C. for 2 hours. The reaction solution was diluted with water (10 mL) and extracted with ethyl acetate (30 mL×2). Organic phases were combined, washed with saturated saline (30 mL×2), dried over anhydrous sodium sulfate, and filtered. A filtrate was concentrated under reduced pressure to remove an organic solvent. A residue was separated and purified by silica gel chromatography to afford intermediate I-134. LCMS (ESI) [M+H]$^+$ 482.2.

Reference Example 135: Preparation of Intermediate I-135

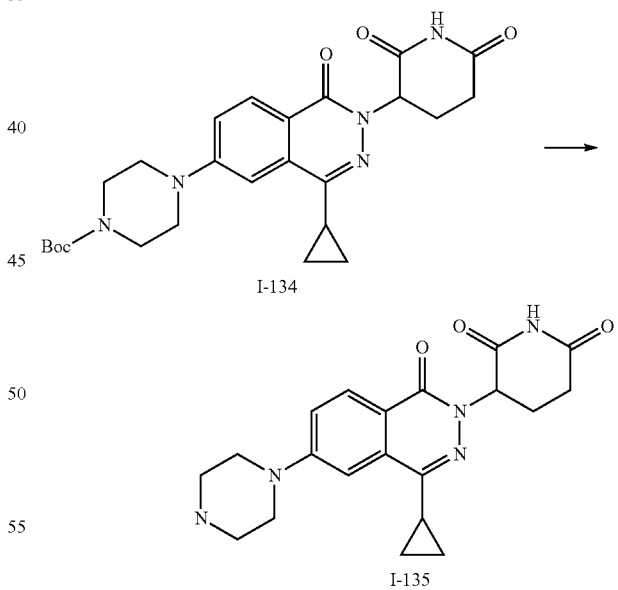

At room temperature, I-134 (80.00 mg, 0.17 mmol) was dissolved in dichloromethane (5 mL), trifluoroacetic acid (5 mL) was added, and a reaction was stirred at room temperature for 3 hours. Concentration was performed under reduced pressure to remove an organic solvent to afford intermediate compound I-135, and the compound was directly used in the next reaction without purification. LCMS (ESI) [M+H]$^+$ 382.2.

Reference Example 136: Preparation of Intermediate I-136

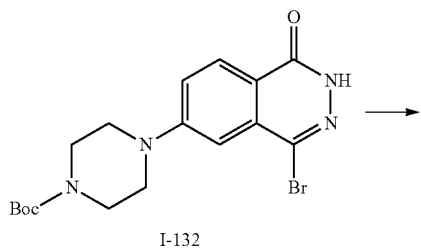
I-132

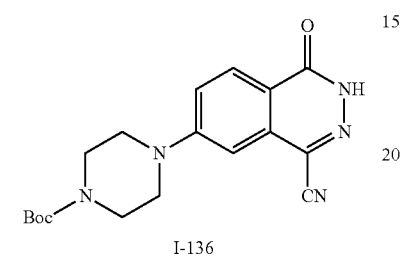
I-136

At room temperature, I-132 (1.00 g, 2.44 mmol) was dissolved in N,N-dimethylacetamide (15 mL), cuprous cyanide (656 mg, 7.33 mmol) was added, and a microwave reaction was performed at 140° C. for 16 hours. A reaction solution was filtered, a filter cake was rinsed with ethyl acetate (100 mL), and a filtrate was collected. The filtrate was washed with water (100 mL) and saturated saline (100 mL) respectively, dried over anhydrous sodium sulfate, and filtered. The filtrate was concentrated under reduced pressure, and the resulting residue was purified by silica gel column chromatography to afford intermediate I-136. LC-MS (ESI) [M+H]$^+$ 356.2.

Reference Example 137: Preparation of Intermediate I-137

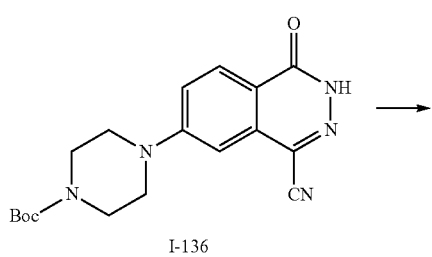
I-136

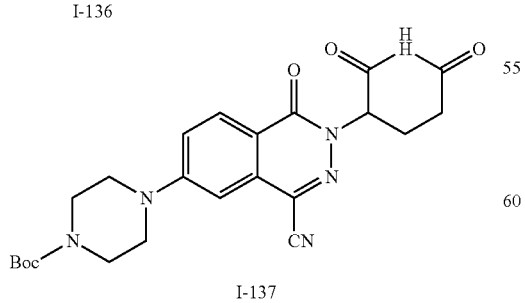
I-137

At room temperature, I-136 (550 mg, 1.55 mmol) was dissolved in tetrahydrofuran (20 mL), followed by successive addition of sodium hydride (124 mg, 3.10 mmol, 60%), potassium iodide (514 mg, 3.10 mmol), 3-bromo-2,6-piperidinedione (594 mg, 3.10 mmol); stirring was performed at 60° C. for 3 hours. A reaction solution was added with a saturated aqueous ammonium chloride solution (50 mL) and extracted with ethyl acetate (100 mL×3). Organic phases were combined, washed with saturated saline (50 mL), dried over anhydrous sodium sulfate, filtered, and concentrated under reduced pressure. The resulting residue was purified by silica gel column chromatography to afford intermediate I-137. LC-MS (ESI) [M+H]$^+$ 467.2.

Reference Example 138: Preparation of Intermediate I-138

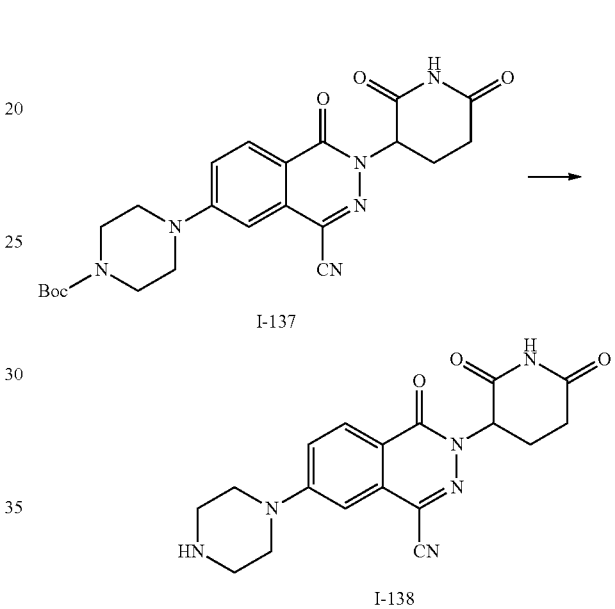
I-137

I-138

At room temperature, I-137 (200 mg, 0.43 mmol) was dissolved in dichloromethane (10 mL), and trifluoroacetic acid (5 mL) was added, followed by stirring for 1 hour. Concentration was performed directly under reduced pressure to afford intermediate I-138, and the intermediate was directly used in the next reaction without purification. LC-MS (ESI) [M+H]$^+$ 367.2.

Reference Example 139: Preparation of Intermediate I-139

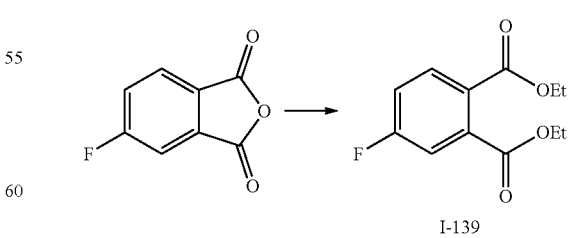
I-139

At room temperature, 4-fluorophthalic anhydride (4.00 g, 24.1 mmol) was dissolved in ethanol (10 mL), and then sulfuric acid (2 mL) was added; a reaction was stirred at 100° C. for 16 hours. A reaction solution was diluted with water (10 mL), adjusted to have PH greater than 7 with a saturated sodium bicarbonate solution, and extracted with ethyl acetate (20 mL×3). Organic phases were combined, washed with saturated saline (20 mL×2), dried over anhydrous sodium sulfate, and filtered. A filtrate was concentrated under reduced pressure to remove an organic solvent to afford a crude product; the crude product was separated and purified by silica gel chromatography to afford intermediate I-139. LCMS (ESI) [M+H]$^+$ 241.2.

Reference Example 140: Preparation of Intermediate I-140

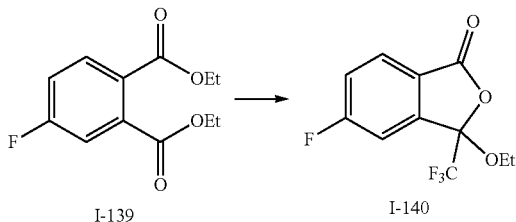 [SMILES: CCOC(=O)c1ccc(F)cc1C(=O)OCC ; CCOC1(C(F)(F)F)OC(=O)c2ccc(F)cc21]

At 0° C., I-139 (3.50 g, 14.6 mmol) and cesium fluoride (110.65 mg, 0.73 mmol) were added to ethylene glycol dimethyl ether (50 mL); at 0° C., (trifluoromethyl)trimethylsilane (2.48 g, 17.5 mmol) was added; a reaction was stirred at room temperature for 3 hours. A reaction solution was diluted with water (10 mL) and extracted with ethyl acetate (50 mL×2); organic phases were combined, washed with saturated saline (20 mL×3), dried over anhydrous sodium sulfate, and filtered. A filtrate was concentrated under reduced pressure to remove an organic solvent to afford a crude product, and the crude product was separated and purified by silica gel chromatography to afford intermediate I-140. LCMS (ESI) [M+H]$^+$ 265.0.

Reference Example 141: Preparation of Intermediate I-141

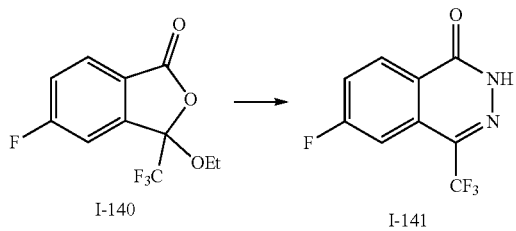 [SMILES: CCOC1(C(F)(F)F)OC(=O)c2ccc(F)cc21 ; O=c1[nH]nc(C(F)(F)F)c2cc(F)ccc12 ; "I-140"]

At room temperature, I-140 (2.00 g, 7.57 mmol) was dissolved in ethanol (20 mL), hydrazine hydrate (758 mg, 15.1 mmol) was added, and a reaction was stirred at 80° C. for 5 hours. A reaction solution was diluted with water (10 mL) and extracted with ethyl acetate (20 mL×3); organic phases were combined, washed with saturated saline (20 mL×3), dried over anhydrous sodium sulfate, and filtered. A filtrate was concentrated under reduced pressure to remove an organic solvent to afford a crude product, and the crude product was separated and purified by silica gel chromatography to afford intermediate I-140. LCMS (ESI) [M+H]$^+$ 233.0.

Reference Example 142: Preparation of Intermediate I-142

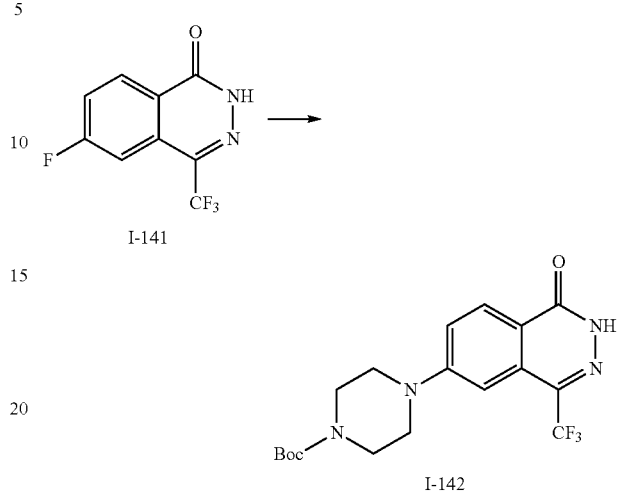

At room temperature, I-141 (410 mg, 1.77 mmol), 1-tert-butoxycarbonylpiperazine (493 mg, 2.64 mmol) and N,N-diisopropylethylamine (460 mg, 3.54 mmol) were dissolved in dimethyl sulfoxide (10 mL); a reaction was stirred at 140° C. for 16 hours. A reaction solution was diluted with water (10 mL) and extracted with ethyl acetate (20 mL×3); organic phases were combined, washed with saturated saline (20 mL×3), dried over anhydrous sodium sulfate, and filtered. A filtrate was concentrated under reduced pressure to remove an organic solvent to afford a crude product, and the crude product was separated and purified by silica gel chromatography to afford intermediate I-142. LCMS (ESI) [M+H]$^+$ 399.2.

Reference Example 143: Preparation of Intermediate I-143

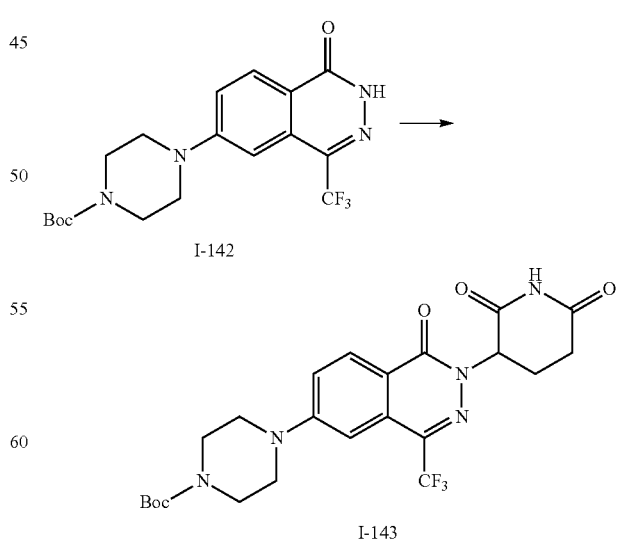

At 0° C., I-142 (444 mg, 1.11 mmol) was dissolved in N,N-dimethylformamide (30 mL), and sodium hydride (222 mg, 5.55 mmol, 60%) was added; after stirring at 0° C. for 30 minutes, 3-bromo-2,6-piperidinedione (320 mg, 1.66 mmol) and potassium iodide (100 mg) were added, and a reaction was stirred at 70° C. for 24 hours. A reaction solution was diluted with water (10 mL) and extracted with ethyl acetate (30 mL×2); organic phases were combined, washed with saturated saline (30 mL×2), dried over anhydrous sodium sulfate, and filtered. A filtrate was concentrated under reduced pressure to remove an organic solvent to afford a crude product, and the crude product was separated and purified by silica gel chromatography to afford intermediate I-143. LCMS (ESI) [M+H]⁺ 510.2.

Reference Example 144: Preparation of Intermediate I-144

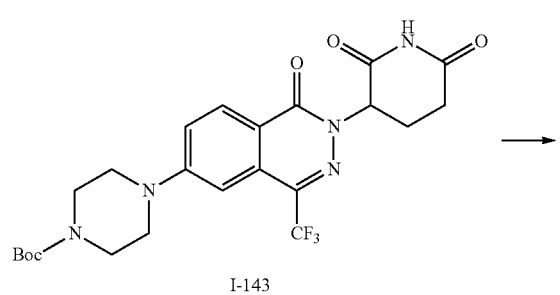

I-143

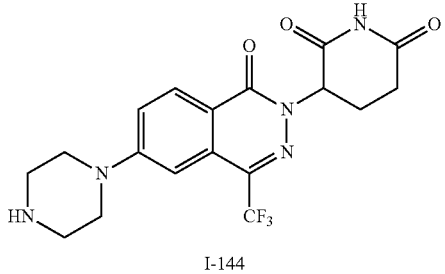

I-144

At room temperature, I-143 (234 mg, 0.46 mmol) was dissolved in dichloromethane (5 mL), trifluoroacetic acid (5 mL) was added, and a reaction was stirred at room temperature for 2 hours. A reaction solution was concentrated under reduced pressure to remove an organic solvent to afford crude product I-144. The crude product directly was used in the next reaction without purification. LCMS (ESI) [M+H]⁺ 410.2.

Preparation of Embodiments

Embodiment 1: Preparation of Compound 1

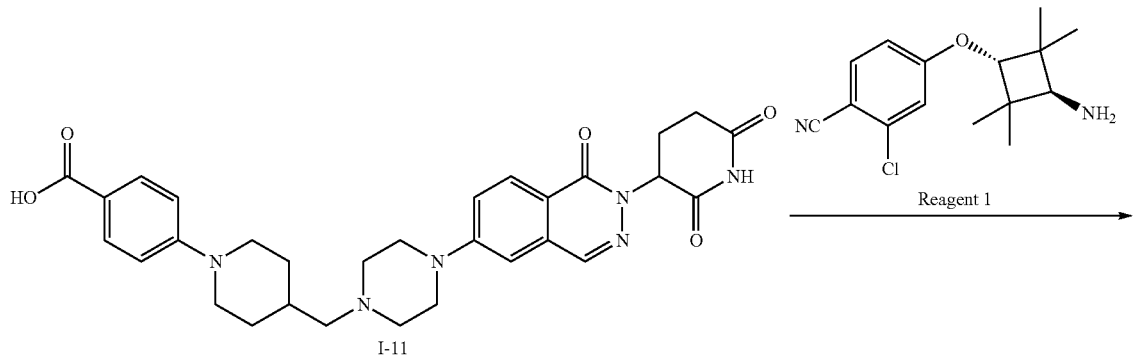

I-11      Reagent 1

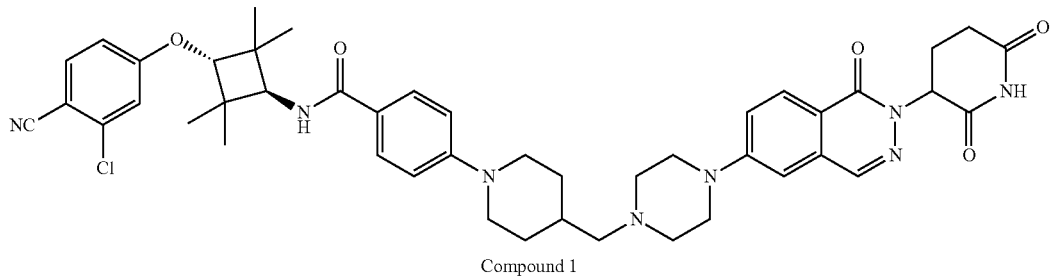

Compound 1

Intermediate I-11 (19 mg), reagent 1 (19 mg) and N,N-diisopropylethylamine (22.0 mg, 0.17 mmol) were dissolved in dichloromethane (4.00 mL), and 2-(7-azabenzotriazol-1-yl)-N,N,N',N'-tetramethyluronium hexafluorophosphate (19 mg, 0.051 mmol) was added. A reaction solution was stirred at room temperature overnight under nitrogen protection. The reaction solution was concentrated under reduced pressure to afford a residue, and the residue was separated and purified by preparative HPLC (containing formic acid) to afford compound 1. LC-MS (ESI) [M+H]$^+$ m/z=819.4. $^1$H NMR (400 MHz, DMSO-d6) δ 10.99 (s, 1H), 8.24 (s, 1H), 8.04 (d, J=9.0 Hz, 1H), 7.90 (d, J=8.7 Hz, 1H), 7.74 (d, J=8.6 Hz, 2H), 7.54-7.43 (m, 2H), 7.30-7.20 (m, 2H), 7.04-6.90 (m, 3H), 5.75 (dd, J=12.1, 5.4 Hz, 1H), 4.32 (s, 1H), 4.05 (d, J=9.2 Hz, 1H), 3.86 (d, J=12.5 Hz, 2H), 3.42 (t, J=5.0 Hz, 4H), 2.99-2.86 (m, 1H), 2.80 (t, J=12.0 Hz, 2H), 2.65-2.52 (m, 6H), 2.22 (d, J=6.7 Hz, 2H), 2.13-2.03 (m, 1H), 1.84-1.75 (m, 3H), 1.25-1.20 (m, 8H), 1.13 (s, 6H).

Embodiment 2: Preparation of Compound 2

At room temperature, intermediate I-15 (100 mg, 0.201 mmol) was dissolved in a mixed solvent of dichloromethane (4.00 mL) and methanol (1.00 mL), followed by addition of intermediate I-7 (50.0 mg), sodium acetate (60.0 mg, 0.735 mmol) and sodium triacetoxyborohydride (93.0 mg, 0.441 mmol). After addition was completed, a reaction solution was stirred at room temperature overnight. Dichloromethane (10.0 mL) was added for dilution, and then a saturated sodium bicarbonate solution (10.0 mL) was added; organic phases were separated, and an aqueous phase was extracted with dichloromethane (20 mL×2); the organic phases were combined, washed with saturated saline (10.0 mL), dried over anhydrous sodium sulfate, filtered and concentrated under reduced pressure to afford a residue, and the residue was separated and purified by preparative HPLC (containing formic acid) to afford compound 2. LC-MS (ESI) [M+H]$^+$ 821.4. $^1$H NMR (400 MHz, CDCl$_3$) δ 8.70 (s, 2H), 8.25 (d, J=9.0 Hz, 1H), 8.04 (s, 1H), 7.97 (s, 1H), 7.57 (d, J=8.7 Hz, 1H), 7.38-7.28 (m, 2H), 6.96 (d, J=2.3 Hz, 1H), 6.89 (s, 1H), 6.80 (dd, J=8.8, 2.4 Hz, 1H), 5.92 (d, J=8.1 Hz, 1H), 5.82 (s, 1H), 4.87 (d, J=11.9 Hz, 2H), 4.13 (d, J=7.9 Hz, 1H), 4.04 (s, 1H), 3.51-3.34 (m, 4H), 2.95 (dd, J=27.0, 16.0 Hz, 3H), 2.78 (d, J=13.2 Hz, 2H), 2.61 (s, 4H), 2.29 (d, J=6.9 Hz, 3H), 1.92 (d, J=11.3 Hz, 4H), 1.25 (s, 6H), 1.21 (s, 6H).

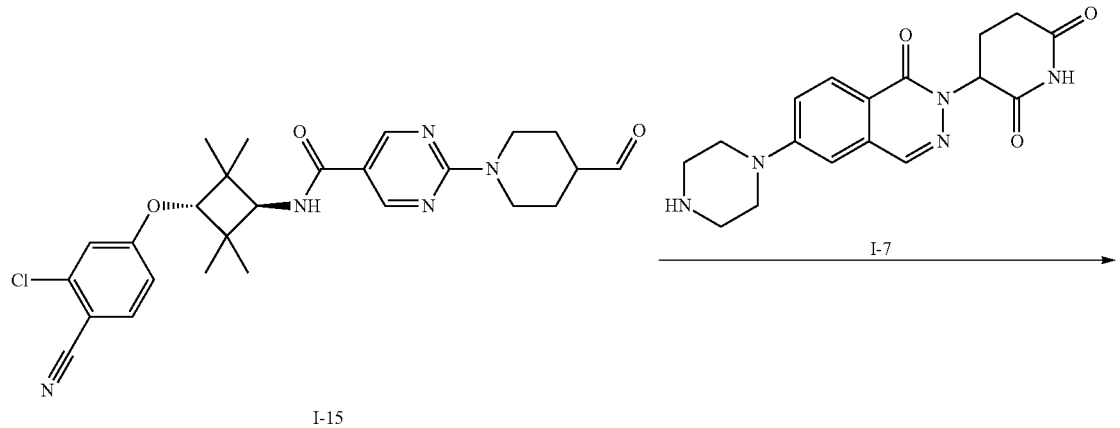

I-15

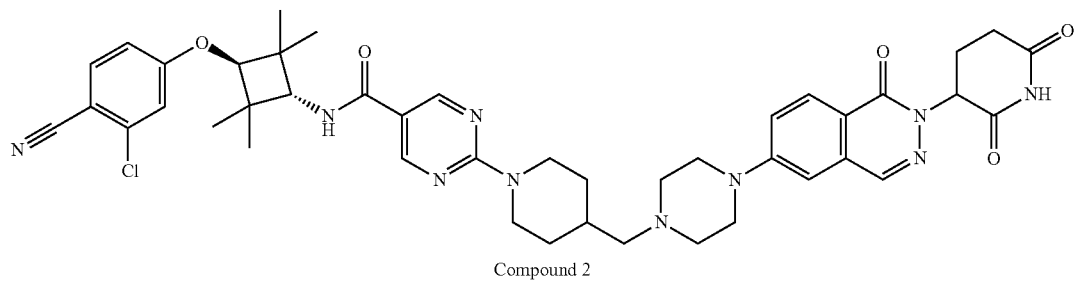

Compound 2

Embodiment 3: Preparation of Compound 3

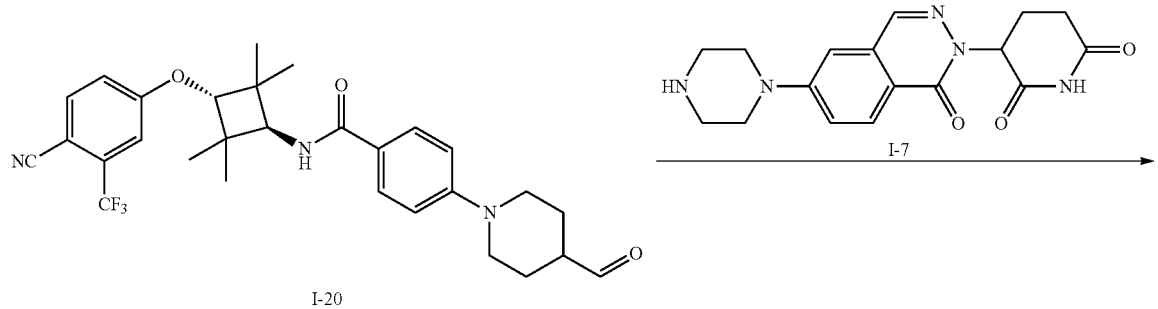

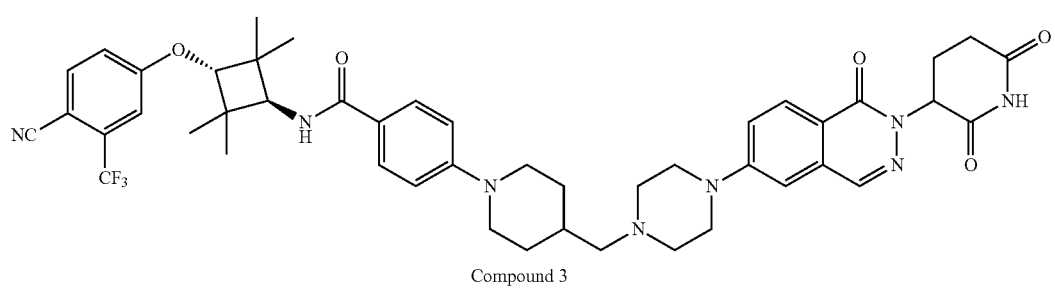

Compound 3

Intermediate I-20 (90 mg, 0.170 mmol) was dissolved in a mixed solvent of anhydrous dichloromethane and methanol (10 mL/10 mL), and intermediate I-7 (58 mg, 0.170 mmol) was added; a system was protected with argon, and stirred and reacted at room temperature for 0.5 hours. Sodium triacetoxyborohydride (108 mg, 0.510 mmol) was added in portions, and a system was protected with argon, and stirred and reacted at room temperature for 3 hours. After concentration, water (20 mL) was added for dilution, and dichloromethane (20 mL×3) was used for extraction. Organic phases were combined, washed with saturated saline (30 mL), and dried over anhydrous sodium sulfate. Filtration was performed, and a filtrate was concentrated under reduced pressure to remove an organic solvent to afford a crude product. The crude product was separated and purified by preparative HPLC (containing formic acid) to afford compound 3. LC-MS (ESI) [M+H]$^+$ 853.3. $^1$H NMR (400 MHz, DMSO-d$_6$) δ 11.00 (s, 1H), 8.25 (s, 1H), 8.11 (d, J=8.7 Hz, 1H), 8.05 (d, J=9.0 Hz, 1H), 7.75 (d, J=8.8 Hz, 2H), 7.54-7.47 (m, 2H), 7.40 (d, J=2.4 Hz, 1H), 7.32-7.23 (m, 2H), 6.96 (d, J=9.0 Hz, 2H), 5.75 (dd, J=12.0, 5.3 Hz, 1H), 4.40 (s, 1H), 4.08 (d, J=9.1 Hz, 1H), 3.87 (d, J=12.5 Hz, 2H), 3.42 (d, J=4.4 Hz, 6H), 2.97-2.86 (m, 1H), 2.80 (t, J=11.8 Hz, 2H), 2.64-2.58 (m, 1H), 2.53 (d, J=4.7 Hz, 3H), 2.22 (d, J=6.5 Hz, 2H), 2.14-2.04 (m, 1H), 1.82 (d, J=10.3 Hz, 3H), 1.23 (s, 6H), 1.19 (s, 2H), 1.14 (s, 6H).

Embodiment 4: Preparation of Compound 4

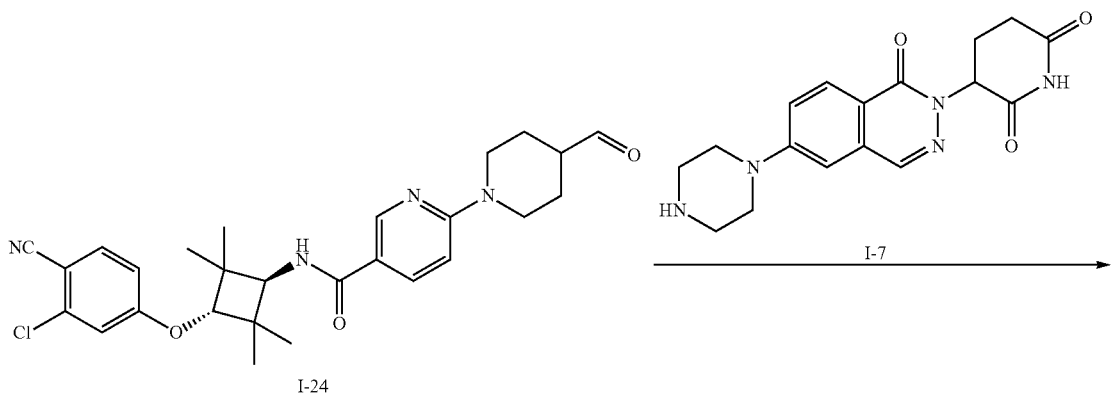

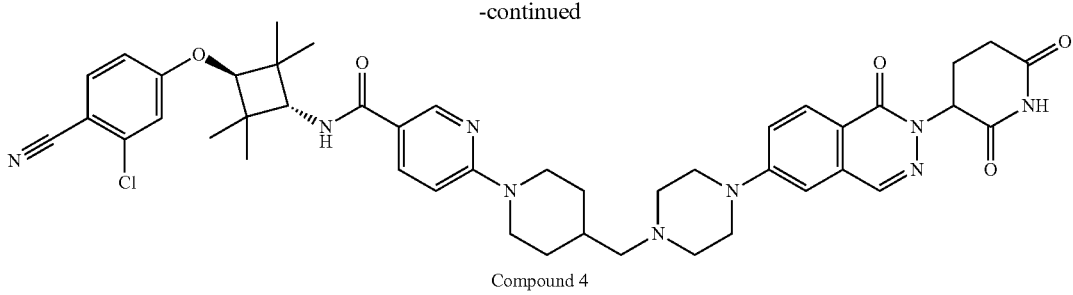

Compound 4

Intermediate I-24 (100 mg) was dissolved in dichloromethane and methanol (5 mL/1 mL), followed by successive addition of intermediate I-7 (68 mg) and sodium acetate (49 mg, 0.60 mmol); a reaction mixture was stirred and reacted at room temperature for 30 minutes, and then sodium triacetoxyborohydride (127 mg, 0.60 mmol) was added; after addition was completed, the reaction mixture was stirred and reacted at room temperature overnight. Water (10 mL) was added for dilution, standing for layering was performed, and organic phases were extracted with dichloromethane (10 mL×2); the organic phases were combined, washed with water (10 mL×3), dried over anhydrous sodium sulfate and filtered, and a filtrate was concentrated under reduced pressure; a residue was separated and purified by preparative HPLC (containing formic acid) to afford compound 4. LC-MS (ESI) [M+H]$^+$ 820.2. $^1$H NMR (400 MHz, DMSO-d$_6$) δ 11.00 (s, 1H), 8.62 (d, J=2.4 Hz, 1H), 8.24 (s, 1H), 8.04 (d, J=9.0 Hz, 1H), 7.96-7.88 (m, 2H), 7.58 (d, J=9.3 Hz, 1H), 7.50 (dd, J=9.1, 2.2 Hz, 1H), 7.25 (d, J=2.2 Hz, 1H), 7.21 (d, J=2.4 Hz, 1H), 7.01 (dd, J=8.8, 2.4 Hz, 1H), 6.86 (d, J=9.2 Hz, 1H), 5.75 (dd, J=11.9, 5.3 Hz, 1H), 4.42 (d, J=13.1 Hz, 2H), 4.30 (s, 1H), 4.05 (d, J=9.2 Hz, 1H), 3.42 (s, 4H), 2.92 (t, J=12.5 Hz, 3H), 2.65-2.51 (m, 6H), 2.21 (d, J=7.0 Hz, 2H), 2.13-2.04 (m, 1H), 1.95-1.77 (m, 3H), 1.22 (s, 6H), 1.12 (s, 6H), 1.08 (s, 2H).

Embodiment 5: Preparation of Compound 5

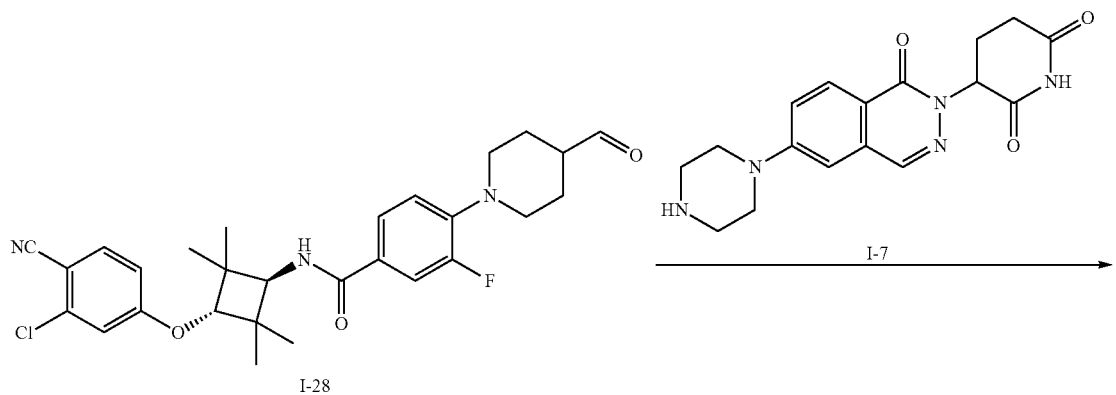

I-28     I-7

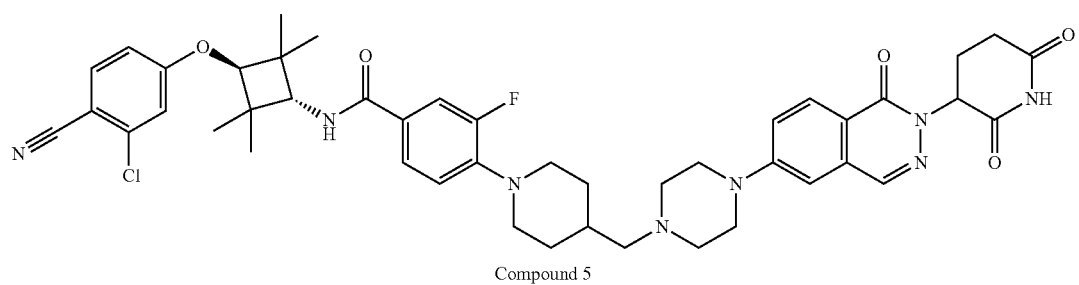

Compound 5

Intermediate I-28 (110 mg) was dissolved in dichloromethane and methanol (5 mL/1 mL), followed by successive addition of intermediate I-7 (74 mg) and sodium acetate (53 mg, 0.65 mmol); a reaction mixture was stirred and reacted at room temperature for 30 minutes, and then sodium triacetoxyborohydride (137 mg, 0.65 mmol) was added; after addition was completed, the reaction mixture was stirred and reacted at room temperature overnight. Water (10 mL) was added for dilution, standing for layering was performed, and organic phases were extracted with dichloromethane (10 mL×2); the organic phases were combined, washed with water (10 mL×3), dried over anhydrous sodium sulfate and filtered, and a filtrate was concentrated under reduced pressure; a residue was separated and purified by preparative HPLC (containing formic acid) to afford compound 5. LC-MS (ESI) [M+H]$^+$ 837.2. $^1$H NMR (400 MHz, DMSO-$d_6$) δ 11.00 (s, 1H), 8.25 (s, 1H), 8.04 (d, J=9.0 Hz, 1H), 7.91 (d, J=8.7 Hz, 1H), 7.71-7.59 (m, 3H), 7.50 (d, J=9.7 Hz, 1H), 7.28-7.18 (m, 2H), 7.09 (t, J=8.9 Hz, 1H), 7.01 (dd, J=8.8, 2.3 Hz, 1H), 5.75 (dd, J=12.0, 5.2 Hz, 1H), 4.32 (s, 1H), 4.06 (d, J=9.3 Hz, 1H), 3.58-3.43 (m, 8H), 3.00-2.85 (m, 2H), 2.76 (t, J=11.1 Hz, 2H), 2.69-2.58 (m, 2H), 2.26 (d, J=6.7 Hz, 2H), 2.08 (d, J=4.8 Hz, 1H), 1.90-1.71 (m, 4H), 1.30 (d, J=10.3 Hz, 2H), 1.22 (s, 6H), 1.13 (s, 6H).

Embodiment 6: Preparation of Compound 6

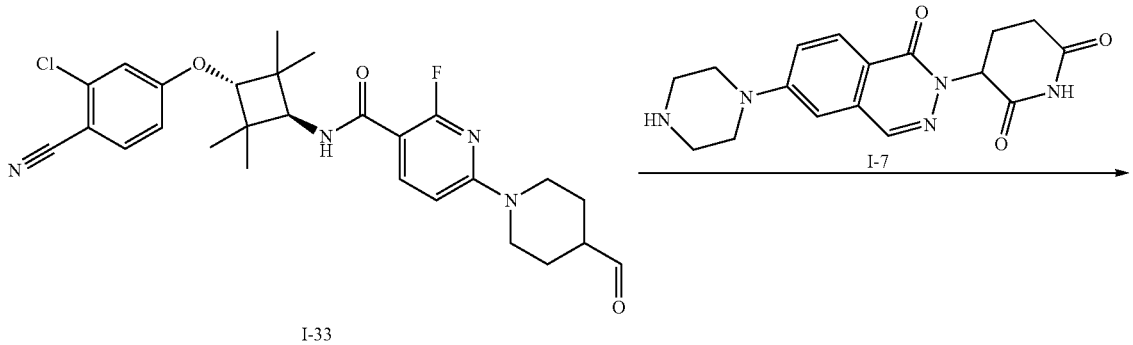

I-33

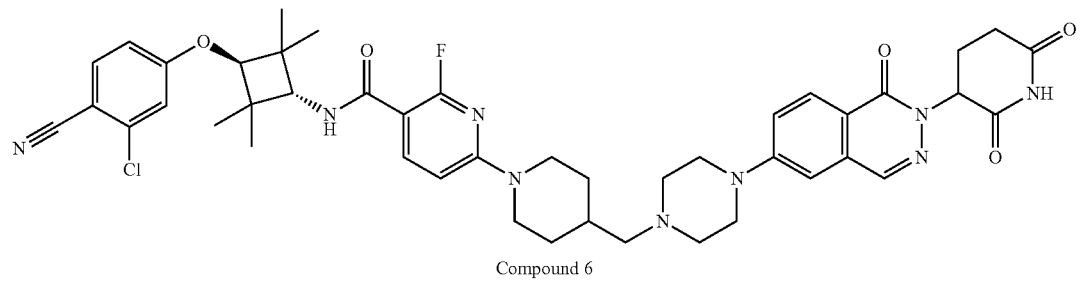

Compound 6

Intermediate I-33 (50 mg, 0.097 mmol) was dissolved in a mixed solvent of anhydrous dichloromethane and methanol (5 mL/5 mL), and intermediate I-7 (33.1 mg, 0.097 mmol) was added; a system was protected with argon, and stirred and reacted at room temperature for 0.5 hours. Sodium triacetoxyborohydride (61.7 mg, 0.291 mmol) was added in portions, and a system was protected with argon, and stirred and reacted at room temperature for 3 hours. A mixture was washed with water (10 mL×3), dried over anhydrous sodium sulfate and filtered; a filtrate was concentrated under reduced pressure to remove an organic solvent to afford a crude product, and the crude product was purified by silica gel chromatography to afford compound 6. LC-MS (ESI) [M+H]$^+$ 838.2. $^1$H NMR (400 MHz, DMSO-$d_6$) δ 11.01 (s, 1H), 8.25 (s, 1H), 8.05 (d, J=9.0 Hz, 1H), 7.97-7.86 (m, 2H), 7.50 (dd, J=9.1, 2.1 Hz, 1H), 7.33 (t, J=7.7 Hz, 1H), 7.24 (dd, J=10.6, 2.2 Hz, 2H), 7.02 (dd, J=8.8, 2.4 Hz, 1H), 6.78 (dd, J=8.7, 2.3 Hz, 1H), 5.75 (dd, J=12.0, 5.4 Hz, 1H), 4.31 (d, J=12.7 Hz, 3H), 3.94 (d, J=8.4 Hz, 1H), 3.46 (s, 5H), 2.93 (ddd, J=18.3, 16.4, 8.7 Hz, 3H), 2.68-2.54 (m, 3H), 2.21 (d, J=7.0 Hz, 2H), 2.13-2.06 (m, 1H), 1.94-1.76 (m, 3H), 1.24 (t, J=13.1 Hz, 2H), 1.19 (s, 6H), 1.12 (s, 6H), 1.10-1.02 (m, 2H).

Embodiment 7: Preparation of Compound 7

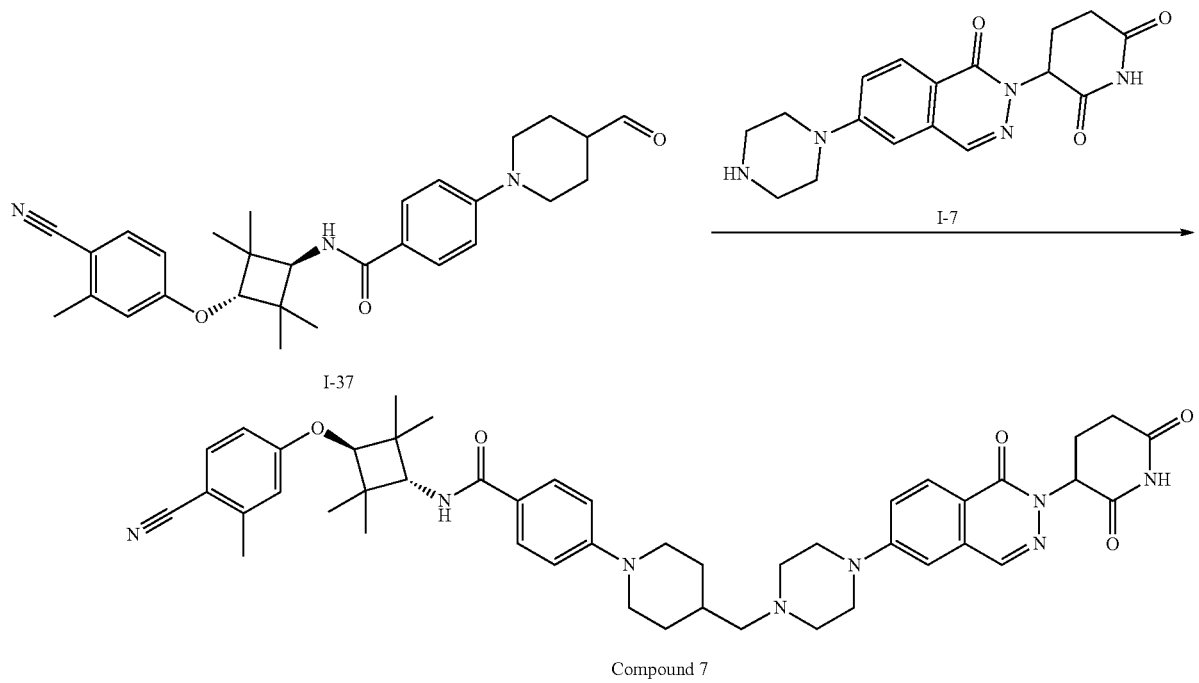

Intermediate I-37 (60 mg, 0.127 mmol) was dissolved in a mixed solvent of anhydrous dichloromethane and methanol (5 mL/5 mL), and intermediate I-7 (43.3 mg) was added successively; a system was protected with argon, and stirred and reacted at room temperature for 0.5 hours. Sodium triacetoxyborohydride (80.7 mg, 0.381 mmol) was added in portions, and a system was protected with argon, and stirred and reacted at room temperature for 3 hours. A mixture was washed with water (10 mL×3), dried over anhydrous sodium sulfate and filtered; a filtrate was concentrated under reduced pressure to remove an organic solvent to afford a crude product, and the crude product was purified by silica gel chromatography to afford target compound 7. LC-MS (ESI) [M+H]$^+$ 799.2. $^1$H NMR (400 MHz, DMSO-d$_6$) δ 11.01 (s, 1H), 8.25 (s, 1H), 8.05 (d, J=9.0 Hz, 1H), 7.72 (dd, J=16.6, 8.7 Hz, 3H), 7.53-7.46 (m, 2H), 7.25 (d, J=1.9 Hz, 1H), 6.95 (dd, J=11.3, 5.5 Hz, 3H), 6.82 (dd, J=8.6, 2.4 Hz, 1H), 5.75 (dd, J=12.0, 5.3 Hz, 1H), 4.24 (s, 1H), 4.04 (d, J=9.1 Hz, 1H), 3.86 (d, J=12.5 Hz, 2H), 3.49 (d, J=31.4 Hz, 4H), 2.96-2.75 (m, 3H), 2.66-2.53 (m, 4H), 2.45 (s, 3H), 2.22 (d, J=6.5 Hz, 2H), 2.12-1.96 (m, 2H), 1.82 (d, J=10.5 Hz, 3H), 1.27 (d, J=29.8 Hz, 3H), 1.22 (s, 6H), 1.13 (s, 6H).

Embodiment 8: Preparation of Compound 8

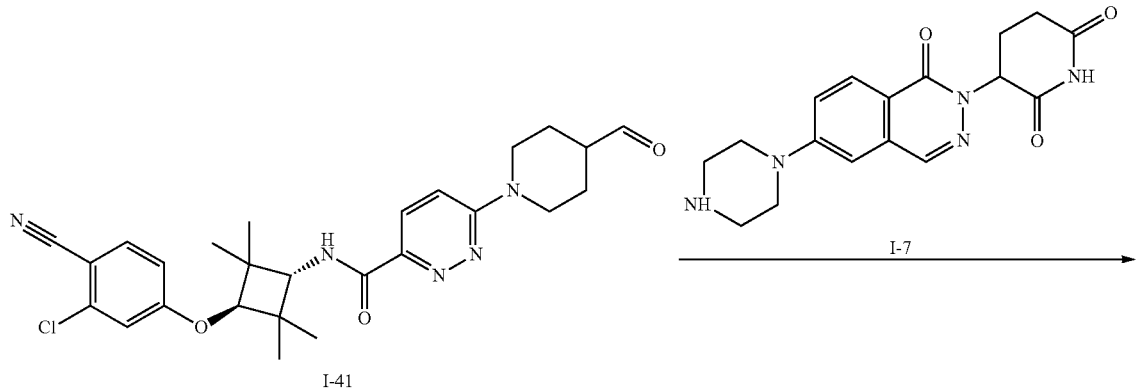

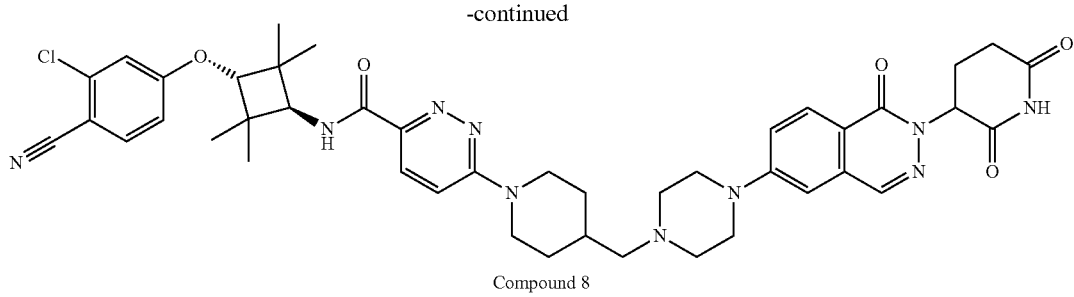

Compound 8

At room temperature, intermediate I-41 (100 mg, 0.202 mmol), intermediate I-7 (68.6 mg, 0.202 mmol) and sodium acetate (82.7 mg, 1.01 mmol) were dissolved in dichloromethane (5 mL) and methanol (1 mL). Under the conditions of argon protection and stirring, sodium triacetoxyborohydride (128 mg, 0.605 mmol) was added. After addition was completed, a reaction mixture was stirred at room temperature overnight. A reaction solution was concentrated under reduced pressure, a residue was diluted with water (20 mL) and extracted with dichloromethane (20 mL×3). Organic phases were combined and concentrated under reduced pressure, and a residue was separated and purified by preparative HPLC (containing formic acid) to afford compound 8 (containing monomolecular formate). LC-MS (ESI) [M+H]$^+$ 821.2. $^1$H NMR (400 MHz, DMSO-d$_6$) δ 11.00 (s, 1H), 8.46 (s, 1H), 8.27-8.20 (m, 2H), 8.04 (d, J=9.0 Hz, 1H), 7.91 (d, J=8.8 Hz, 1H), 7.82 (d, J=9.6 Hz, 1H), 7.50 (d, J=7.2 Hz, 1H), 7.37 (d, J=9.7 Hz, 1H), 7.25 (d, J=2.2 Hz, 2H), 7.04 (dd, J=8.8, 2.3 Hz, 1H), 5.75 (dd, J=12.0, 5.2 Hz, 1H), 4.57-4.43 (m, 3H), 4.01 (d, J=9.1 Hz, 1H), 3.43 (s, 4H), 3.05 (t, J=12.0 Hz, 3H), 2.97-2.86 (m, 1H), 2.69-2.52 (m, 6H), 2.23 (d, J=7.0 Hz, 2H), 2.13-1.92 (m, 3H), 1.86 (d, J=12.1 Hz, 2H), 1.22 (s, 6H), 1.14 (s, 6H).

Embodiment 9: Preparation of Compound 9

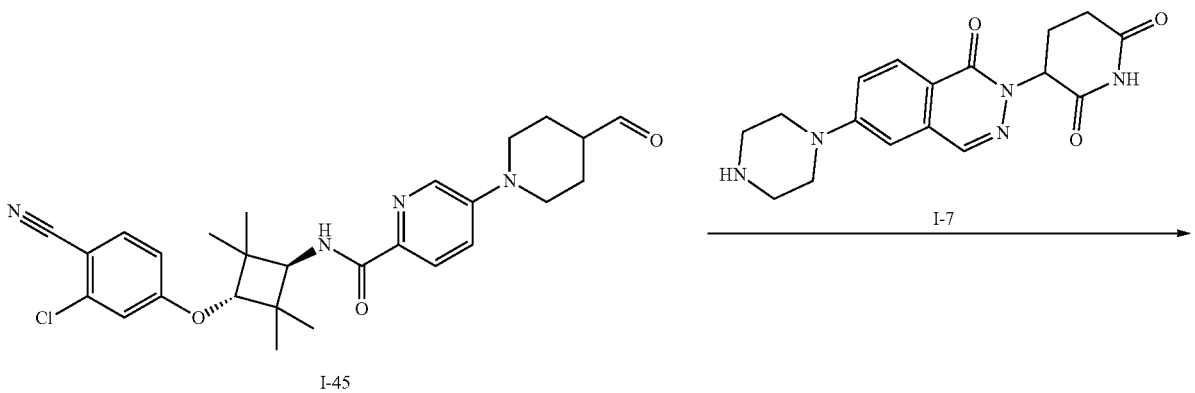

I-45

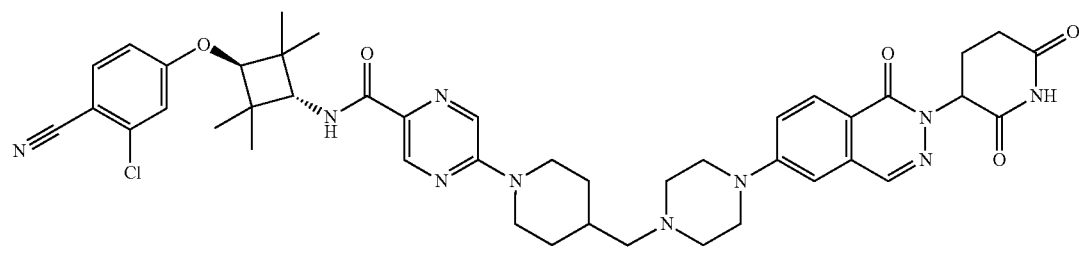

Compound 9

Intermediate I-45 (50 mg, 0.101 mmol) was dissolved in a mixed solvent of anhydrous dichloromethane and methanol (5 mL/5 mL), and intermediate I-7 (34.5 mg) was added; a system was protected with argon, and stirred and reacted at room temperature for 0.5 hours. Sodium triacetoxyborohydride (64 mg, 0.303 mmol) was added in portions, and a system was protected with argon, and stirred and reacted at room temperature for 3 hours. After concentration, water (20 mL) was added for dilution, and dichloromethane (20 mL×3) was used for extraction. Organic phases were combined, washed with saturated saline (30 mL), and dried over anhydrous sodium sulfate. Filtration was performed, and a filtrate was concentrated under reduced pressure to remove an organic solvent to afford a crude product. The crude product was separated and purified by preparative HPLC (containing formic acid) to afford compound 9. LC-MS (ESI) [M+H]$^+$ 820.3. $^1$H NMR (400 MHz, DMSO-d$_6$) δ 11.01 (s, 1H), 8.34 (d, J=2.4 Hz, 1H), 8.25 (s, 1H), 8.07 (dd, J=17.5, 9.0 Hz, 2H), 7.90 (d, J=8.7 Hz, 1H), 7.84 (d, J=8.8 Hz, 1H), 7.54-7.48 (m, 1H), 7.42 (dd, J=8.9, 2.6 Hz, 1H), 7.25 (d, J=2.2 Hz, 2H), 7.04 (dd, J=8.8, 2.3 Hz, 1H), 5.76 (dd, J=11.9, 5.3 Hz, 1H), 4.43 (s, 1H), 3.95 (d, J=9.1 Hz, 3H), 3.44 (s, 6H), 2.97-2.83 (m, 3H), 2.67-2.53 (m, 4H), 2.22 (d, J=6.4 Hz, 2H), 2.13-2.04 (m, 1H), 1.83 (d, J=10.2 Hz, 3H), 1.22 (d, J=6.5 Hz, 2H), 1.20 (s, 6H), 1.13 (s, 6H).

Embodiment 10: Preparation of Compound 10

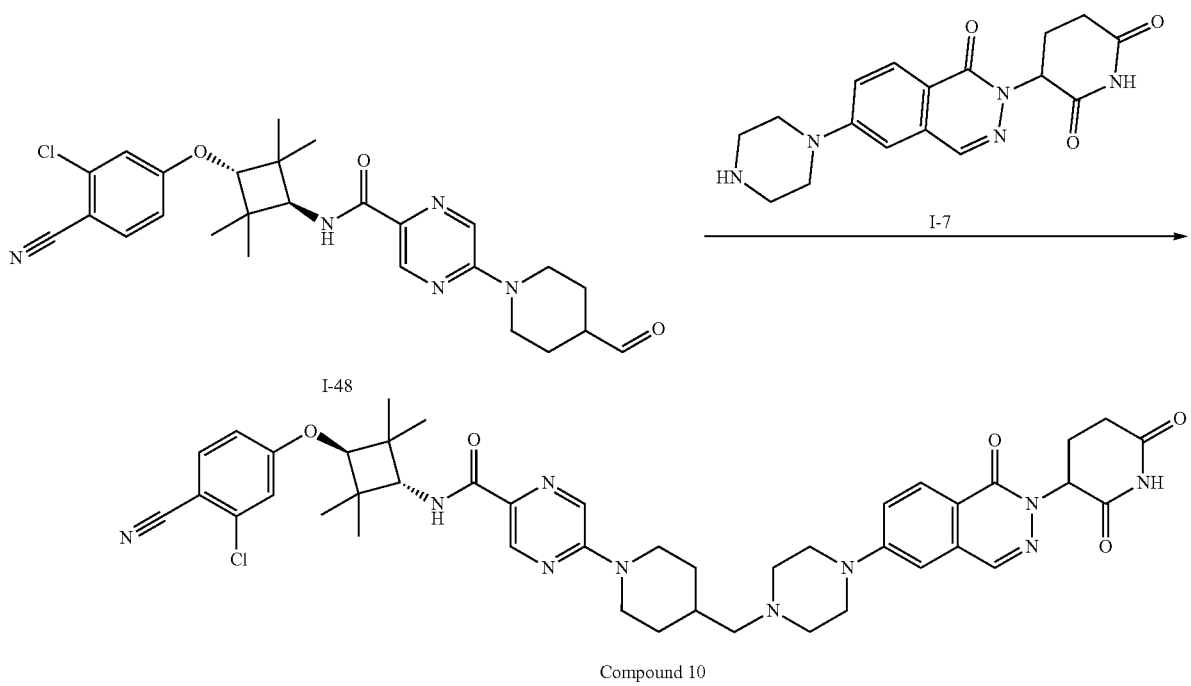

Intermediate I-48 (120 mg) was dissolved in dichloromethane and methanol (5 mL/5 mL), and intermediate I-7 (82 mg) was added; a reaction mixture was stirred at room temperature for 30 minutes, and subsequently, sodium triacetoxyborohydride (102 mg, 0.481 mmol) was added; then, the mixture was stirred and reacted at room temperature for 16 hours. After concentration, water (20 mL) was added for dilution, and dichloromethane (20 mL×3) was used for extraction. Organic phases were combined, washed with saturated saline (30 mL), and dried over anhydrous sodium sulfate. Filtration was performed, and a filtrate was concentrated under reduced pressure to remove an organic solvent to afford a crude product. The crude product was separated and purified by preparative HPLC (containing formic acid) to afford compound 10. LC-MS (ESI) [M+H]$^+$ 821.1. $^1$H NMR (400 MHz, DMSO-d$_6$) δ 11.00 (s, 1H), 8.61 (d, J=0.9 Hz, 1H), 8.34 (s, 1H), 8.25 (s, 1H), 8.04 (d, J=9.0 Hz, 1H), 7.90 (d, J=8.7 Hz, 1H), 7.81 (d, J=9.0 Hz, 1H), 7.53-7.46 (m, 1H), 7.25 (d, J=2.5 Hz, 2H), 7.03 (dd, J=8.8, 2.4 Hz, 1H), 5.75 (dd, J=12.0, 5.3 Hz, 1H), 4.49 (d, J=13.0 Hz, 2H), 4.43 (s, 1H), 3.96 (d, J=9.0 Hz, 1H), 3.43 (s, 6H), 3.09-2.87 (m, 4H), 2.65-2.52 (m, 5H), 2.22 (d, J=7.0 Hz, 2H), 2.14-2.04 (m, 1H), 1.98-1.79 (m, 3H), 1.19 (s, 6H), 1.13 (s, 6H).

Embodiment 11: Preparation of Compound 11

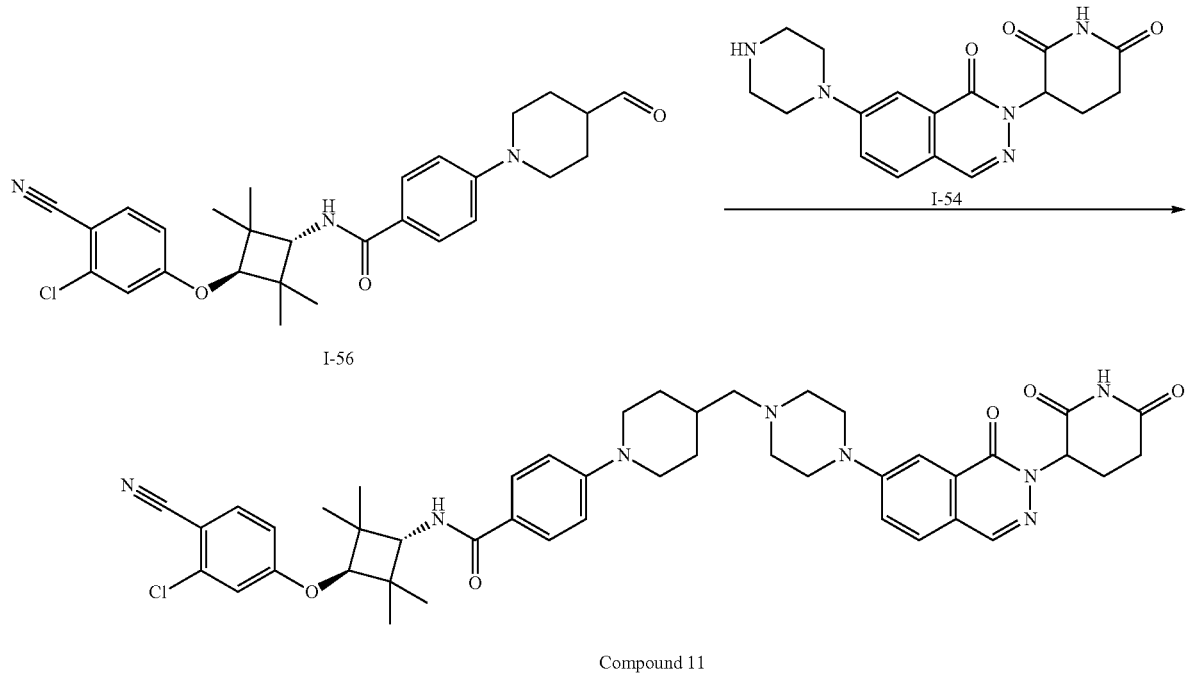

Compound 11

At 25° C., intermediate I-56 (80 mg, 0.162 mmol) was dissolved in dichloromethane (10 mL). Intermediate I-54 (61.2 mg), sodium acetate (13.3 mg, 0.162 mmol) and sodium triacetoxyborohydride (34.3 mg, 0.162 mmol) were added, and a reaction mixture was stirred and reacted at room temperature for 3 hours. A reaction system was concentrated, a residue was dissolved in N,N-dimethylformamide (3 mL) and filtered; a filtrate was separated and purified by preparative HPLC (containing formic acid) to afford compound 11. LC-MS (ESI) [M+H]+ 819.5. $^1$H NMR (400 MHz, DMSO-d$_6$) δ 11.01 (s, 1H), 8.26 (s, 1H), 7.91 (d, J=8.8 Hz, 1H), 7.79 (d, J=8.9 Hz, 1H), 7.74 (d, J=8.9 Hz, 2H), 7.62 (dd, J=9.0, 2.5 Hz, 1H), 7.49 (t, J=6.1 Hz, 2H), 7.21 (d, J=2.4 Hz, 1H), 7.00 (dd, J=8.8, 2.4 Hz, 1H), 6.96 (d, J=9.0 Hz, 2H), 5.76 (dd, J=12.0, 5.2 Hz, 1H), 4.32 (s, 1H), 4.05 (d, J=9.2 Hz, 1H), 3.86 (d, J=12.9 Hz, 2H), 3.41 (s, 4H), 2.98-2.86 (m, 1H), 2.80 (t, J=11.7 Hz, 2H), 2.69-2.52 (m, 6H), 2.23 (d, J=6.4 Hz, 2H), 2.14-2.04 (m, 1H), 1.92-1.78 (m, 3H), 1.28-1.18 (m, 8H), 1.13 (s, 6H).

Embodiment 12: Preparation of Compound 12

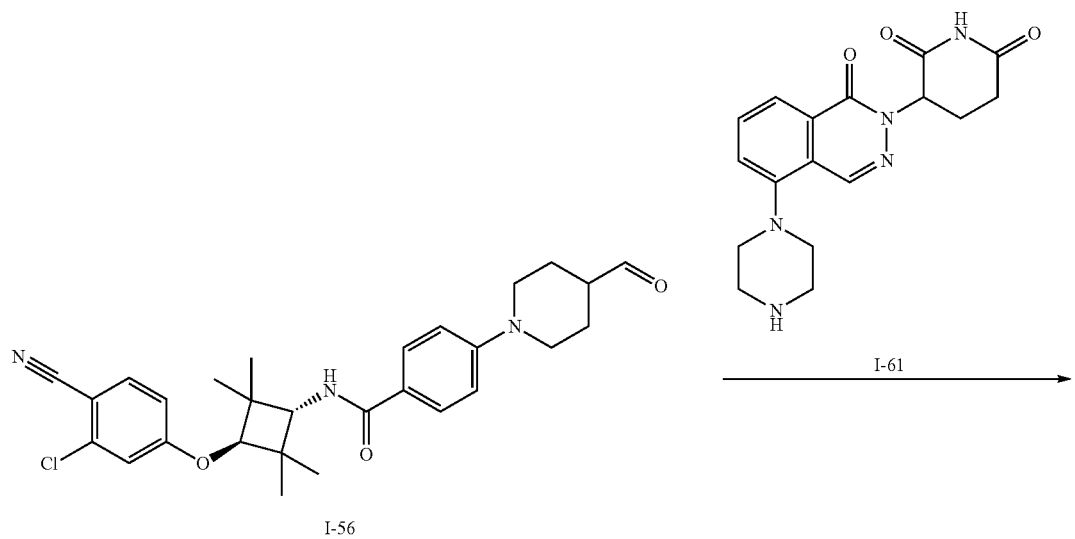

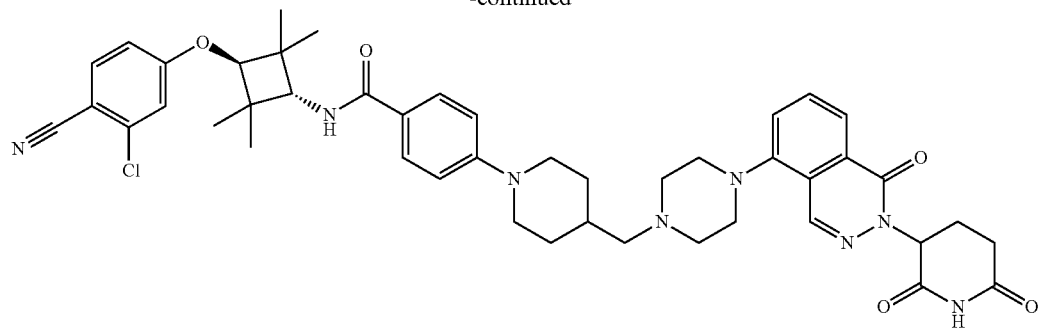

Compound 12

Intermediate I-56 (89.4 mg, 0.181 mmol) was dissolved in a mixed solvent of dichloromethane/methanol (10.0 mL/2.00 mL), followed by addition of intermediate I-61 (80.0 mg), anhydrous sodium acetate (74.2 mg, 0.905 mmol) and sodium triacetoxyborohydride (76.7 mg, 0.362 mmol). A reaction system was protected with argon, and was stirred and reacted at room temperature for 2 hours. Dichloromethane (50.0 mL) was used for dilution, and water (20.0 mL×2) was used for washing; organic phases were separated, dried over anhydrous sodium sulfate and filtered; a filtrate was concentrated under reduced pressure to remove an organic solvent to afford a crude product, and the crude product was separated and purified by preparative HPLC (containing formic acid) to afford compound 12. LC-MS (ESI) [M+H]$^+$ 819.4. $^1$H NMR (400 MHz, DMSO-$d_6$) δ 11.05 (s, 1H), 8.43 (s, 1H), 7.91 (dd, J=8.2, 6.3 Hz, 2H), 7.80 (t, J=7.9 Hz, 1H), 7.74 (d, J=8.8 Hz, 2H), 7.57 (d, J=7.6 Hz, 1H), 7.48 (d, J=9.2 Hz, 1H), 7.21 (d, J=2.4 Hz, 1H), 7.02-6.94 (m, 3H), 5.80 (dd, J=11.9, 5.2 Hz, 1H), 4.32 (s, 1H), 4.05 (d, J=9.1 Hz, 1H), 3.86 (d, J=12.3 Hz, 2H), 3.08 (s, 4H), 3.01-2.86 (m, 2H), 2.79 (t, J=11.7 Hz, 3H), 2.69-2.54 (m, 6H), 2.27 (d, J=6.4 Hz, 2H), 2.17-2.09 (m, 1H), 1.82 (d, J=12.3 Hz, 3H), 1.22 (s, 6H), 1.13 (s, 6H).

Embodiment 13: Preparation of Compound 13

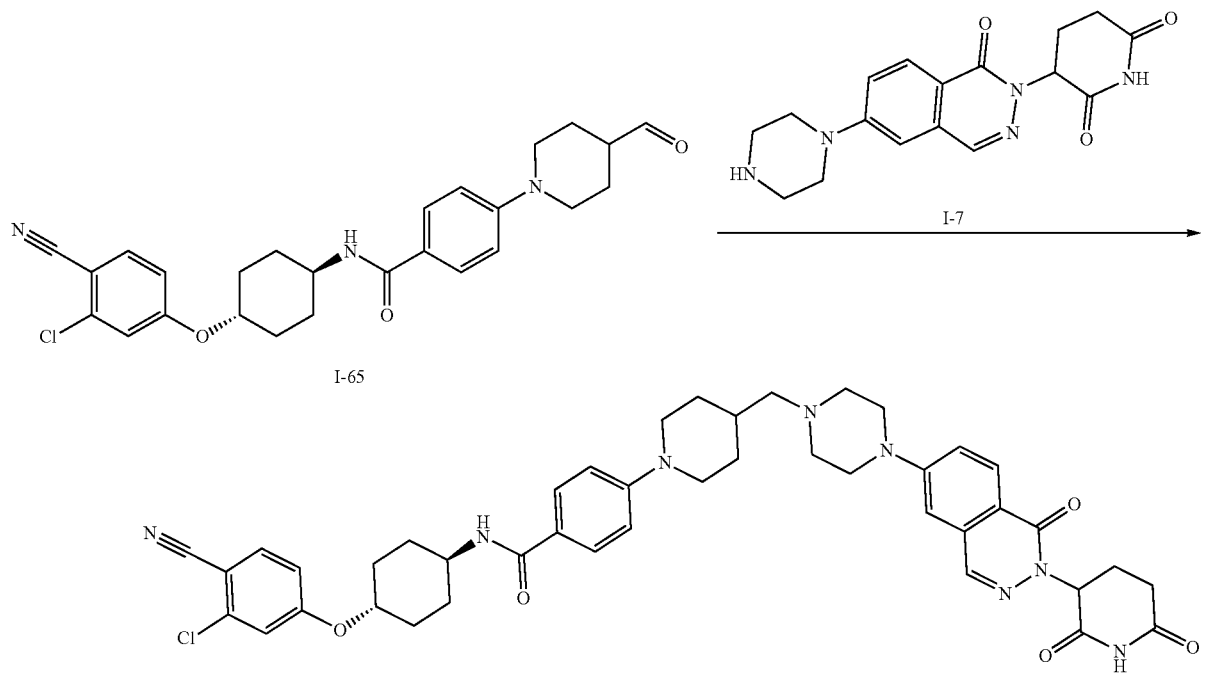

Compound 13

Intermediate I-65 (80.0 mg) was dissolved in a mixed solvent of anhydrous dichloromethane/methanol (5.00 mL/5.00 mL), and intermediate I-7 (58.8 mg) was added; a system was protected with argon, and stirred and reacted at room temperature for 0.5 hours. Sodium triacetoxyborohydride (109 mg, 0.516 mmol) was added in portions, and a system was protected with argon, and stirred and reacted at room temperature for 3 hours. A mixture was washed with water (15.0 mL×3), dried over anhydrous sodium sulfate and filtered; a filtrate was concentrated under reduced pressure to remove an organic solvent to afford a crude product, and the crude product was separated and purified by preparative HPLC (containing formic acid) to afford compound 13. LC-MS (ESI) [M+H]+ 791.4. ¹H NMR (400 MHz, DMSO-d₆) δ 11.01 (s, 1H), 8.25 (s, 1H), 8.01 (dd, J=28.8, 8.2 Hz, 2H), 7.85 (d, J=8.8 Hz, 1H), 7.73 (d, J=8.6 Hz, 2H), 7.50 (d, J=8.2 Hz, 1H), 7.37 (d, J=1.9 Hz, 1H), 7.25 (s, 1H), 7.16-7.11 (m, 1H), 6.93 (d, J=8.7 Hz, 2H), 5.75 (dd, J=11.7, 5.1 Hz, 1H), 4.53 (s, 1H), 3.89-3.60 (m, 7H), 2.97-2.86 (m, 1H), 2.77 (t, J=11.7 Hz, 2H), 2.66-2.52 (m, 5H), 2.16 (dd, J=45.6, 7.3 Hz, 5H), 1.93-1.74 (m, 5H), 1.51 (dd, J=19.8, 10.1 Hz, 4H), 1.27-1.10 (m, 3H).

Embodiment 14: Preparation of Compound 14

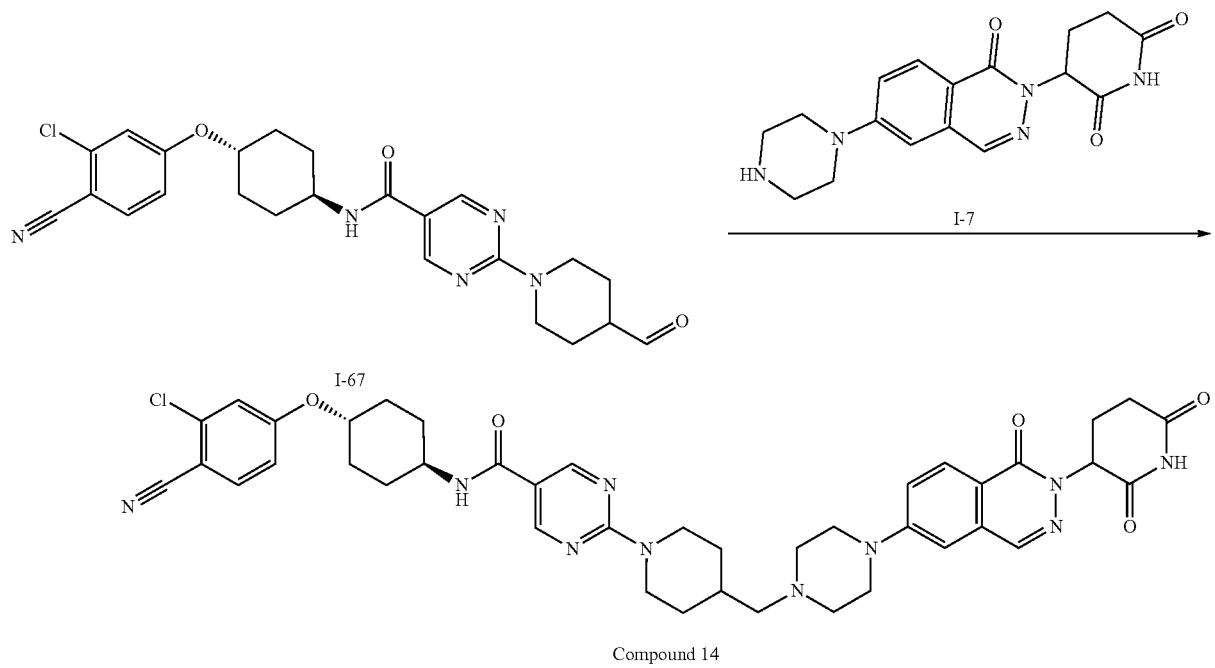

At room temperature, intermediate I-67 (90.0 mg), intermediate I-7 (65.7 mg) and sodium acetate (78.9 mg, 0.962 mmol) were dissolved in dichloromethane (5 mL) and methanol (1 mL). Under the conditions of argon protection and stirring, sodium triacetoxyborohydride (122 mg, 0.577 mmol) was added. After addition was completed, a reaction mixture was stirred at room temperature overnight. A reaction solution was concentrated under reduced pressure, a residue was diluted with water (20 mL) and extracted with dichloromethane (20 mL×3). Organic phases were combined and concentrated under reduced pressure, and the residue was separated and purified by preparative HPLC (containing formic acid) to afford compound 14. LC-MS (ESI) [M+H]+ 793.1. ¹H NMR (400 MHz, CD₃OD) δ 8.72 (s, 2H), 8.22 (s, 1H), 8.15 (d, J=9.1 Hz, 1H), 7.69 (d, J=8.8 Hz, 1H), 7.49 (dd, J=9.1, 2.4 Hz, 1H), 7.19 (d, J=2.4 Hz, 2H), 7.03 (dd, J=8.8, 2.4 Hz, 1H), 5.79 (dd, J=11.8, 5.4 Hz, 1H), 4.50-4.40 (m, 1H), 3.98-3.85 (m, 1H), 3.53-3.46 (m, 4H), 3.00 (t, J=11.6 Hz, 2H), 2.96-2.67 (m, 4H), 2.67-2.57 (m, 4H), 2.32 (d, J=6.9 Hz, 2H), 2.28-2.14 (m, 4H), 2.10-1.88 (m, 6H), 1.71-1.47 (m, 5H).

Embodiment 15: Preparation of Compound 15

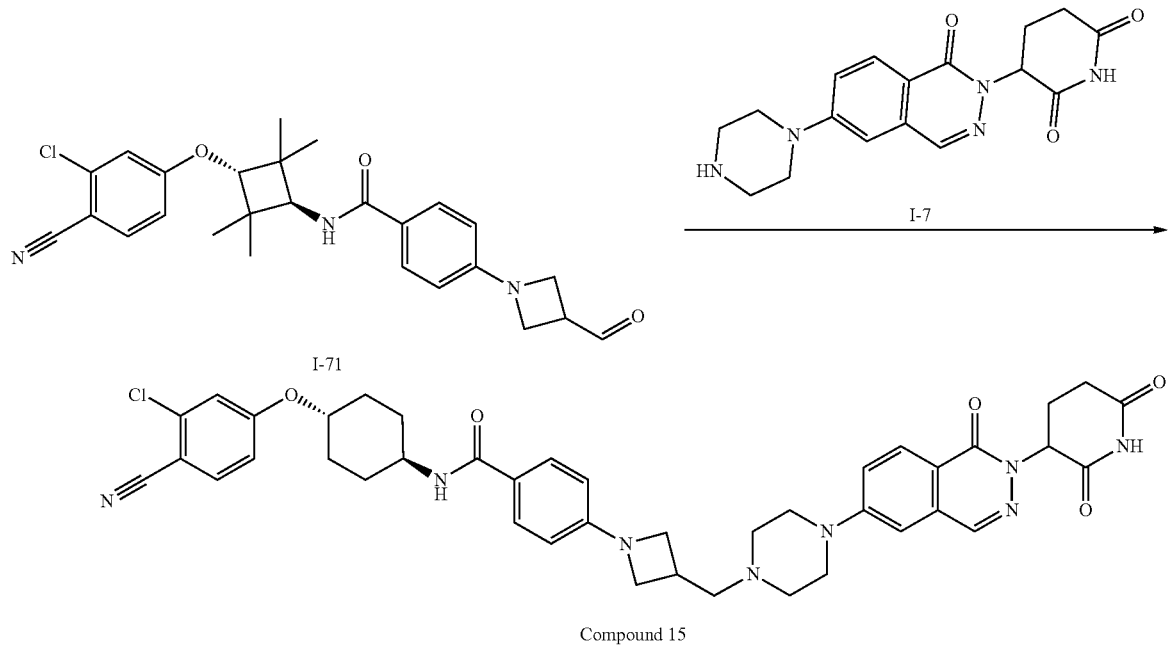

Intermediate I-71 (40 mg, 0.091 mmol) was dissolved in a mixed solvent of anhydrous dichloromethane/methanol (5.00 mL/5.00 mL), and intermediate I-7 (31 mg) was added; a system was protected with argon, and stirred and reacted at room temperature for 0.5 hours. Sodium triacetoxyborohydride (58 mg, 0.273 mmol) was added in portions, and a system was protected with argon, and stirred and reacted at room temperature for 3 hours. After concentration, water (20 mL) was added for dilution and dichloromethane (20 mL×3) was used for extraction. Organic phases were combined, washed with saturated saline (30 mL), and dried over anhydrous sodium sulfate. Filtration was performed, and a filtrate was concentrated under reduced pressure to remove an organic solvent to afford a crude product. The crude product was separated and purified by preparative HPLC (containing formic acid) to afford compound 15. LC-MS (ESI) [M+H]+ 763.2. $^1$H NMR (400 MHz, DMSO-$d_6$) δ 11.00 (s, 1H), 8.24 (s, 1H), 8.04 (d, J=9.0 Hz, 1H), 7.91 (d, J=7.6 Hz, 1H), 7.86 (d, J=8.8 Hz, 1H), 7.72 (d, J=8.6 Hz, 2H), 7.50 (dd, J=9.1, 2.1 Hz, 1H), 7.38 (d, J=2.4 Hz, 1H), 7.26 (d, J=2.1 Hz, 1H), 7.14 (dd, J=8.8, 2.4 Hz, 1H), 6.40 (d, J=8.7 Hz, 2H), 5.75 (dd, J=12.0, 5.3 Hz, 1H), 4.53 (s, 1H), 4.01 (t, J=7.6 Hz, 2H), 3.80 (s, 1H), 3.61-3.53 (m, 3H), 3.46 (s, 2H), 3.06-2.83 (m, 3H), 2.64 (dd, J=12.9, 5.4 Hz, 3H), 2.55 (d, J=7.7 Hz, 5H), 2.15-2.04 (m, 3H), 1.89 (d, J=9.1 Hz, 2H), 1.59-1.43 (m, 4H).

Embodiment 16: Preparation of Compound 16

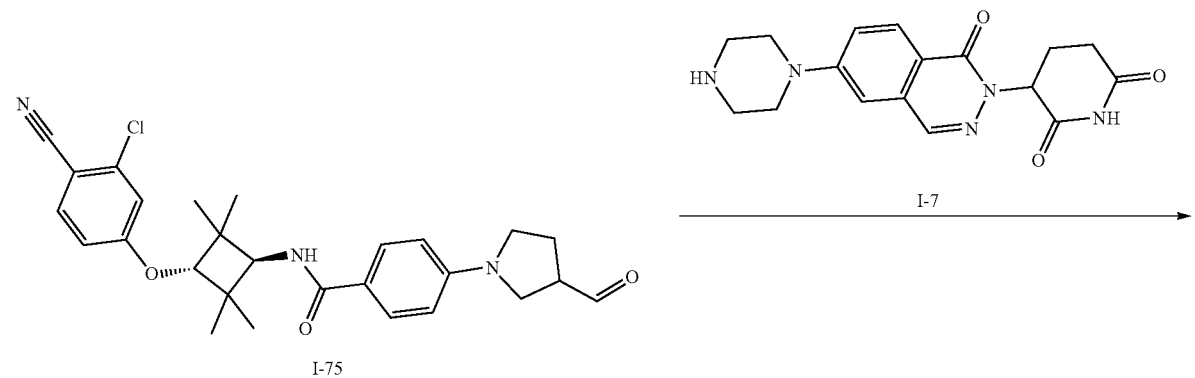

-continued

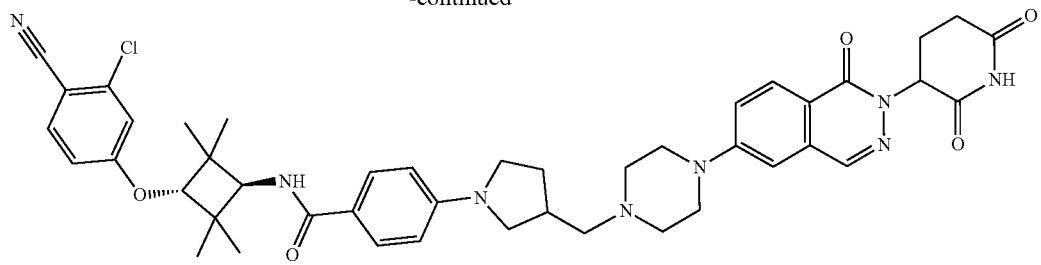

Compound 16

Intermediate I-75 (80.0 mg, 0.167 mmol) was dissolved in a mixed solvent of dichloromethane/methanol (6.00 mL/2.00 mL), followed by addition of intermediate I-7 (91.1 mg) and anhydrous sodium acetate (68.5 mg, 0.835 mmol). A reaction system was protected with argon, and was stirred and reacted at room temperature for 0.5 hours. Sodium triacetoxyborohydride (70.8 mg, 0.334 mmol) was added. A reaction system was protected with argon, and was stirred and reacted at room temperature for 2 hours. Dichloromethane (50.0 mL) was used for dilution, and water (10.0 mL×2) was used for washing; organic phases were separated, dried over anhydrous sodium sulfate and filtered; a filtrate was concentrated under reduced pressure to remove an organic solvent to afford a crude product, and the crude product was separated and purified by preparative HPLC (containing formic acid) to afford compound 16. LC-MS (ESI) [M+H]+ 805.1. $^1$H NMR (400 MHz, DMSO-$d_6$) δ 11.01 (s, 1H), 8.25 (s, 1H), 8.04 (d, J=9.0 Hz, 1H), 7.90 (d, J=8.8 Hz, 1H), 7.74 (d, J=8.8 Hz, 2H), 7.51 (dd, J=9.2, 2.2 Hz, 1H), 7.39 (d, J=9.2 Hz, 1H), 7.26 (d, J=2.2 Hz, 1H), 7.21 (d, J=2.4 Hz, 1H), 7.00 (dd, J=8.8, 2.4 Hz, 1H), 6.55 (d, J=8.9 Hz, 2H), 5.75 (dd, J=12.1, 5.5 Hz, 1H), 4.32 (s, 1H), 4.05 (d, J=9.1 Hz, 1H), 3.47-3.43 (m, 4H), 3.06 (dd, J=9.6, 7.0 Hz, 2H), 2.99-2.83 (m, 2H), 2.67-2.54 (m, 6H), 2.42 (d, J=5.0 Hz, 2H), 2.18-2.00 (m, 3H), 1.75 (dd, J=12.1, 8.0 Hz, 2H), 1.22 (s, 6H), 1.13 (s, 6H).

Embodiment 17: Preparation of Compound 17

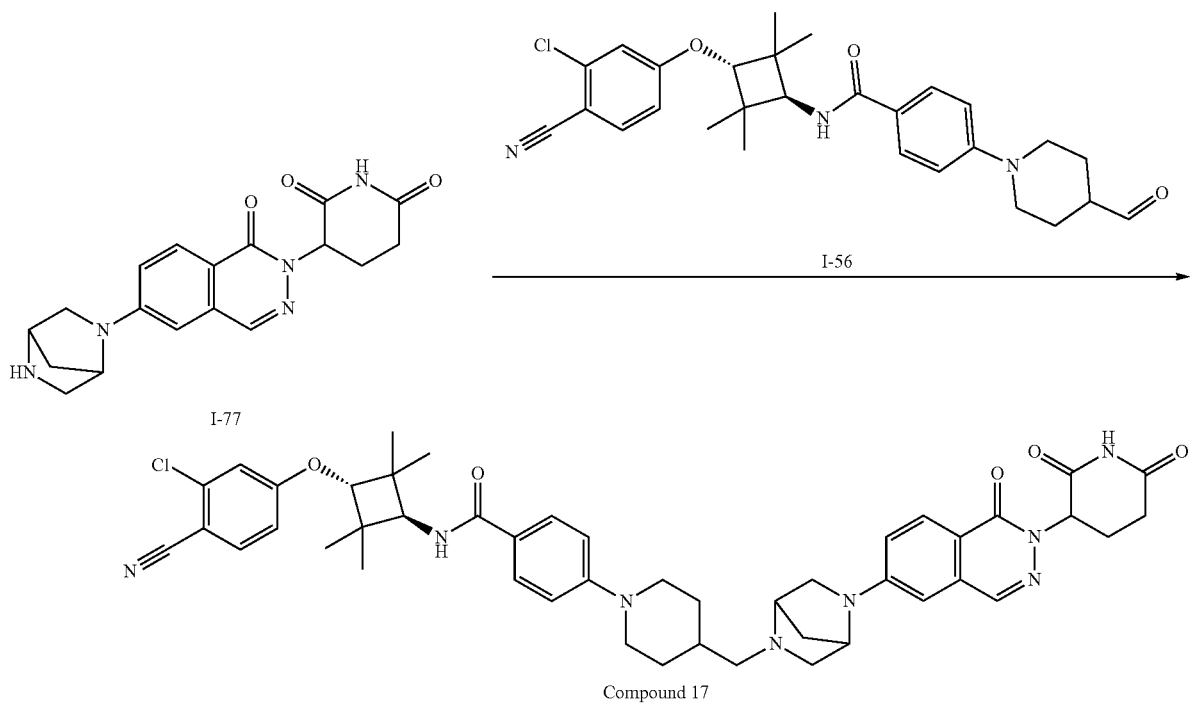

Intermediate I-77 (190 mg) was dissolved in a mixed solvent of dichloromethane/methanol (10.0 mL/3.00 mL), followed by addition of intermediate I-56 (241 mg, 0.487 mmol) and anhydrous sodium acetate (167 mg, 2.03 mmol). A reaction system was protected with argon, and was stirred and reacted at room temperature for 2 hours. Dichloromethane (50.0 mL) was used for dilution, and water (10.0 mL×2) was used for washing; organic phases were separated, dried over anhydrous sodium sulfate and filtered; a filtrate was concentrated under reduced pressure to remove an organic solvent to afford a crude product, and the crude product was separated and purified by preparative HPLC (containing formic acid) to afford compound 17. LC-MS (ESI) [M+H]+

831.2. $^1$H NMR (400 MHz, DMSO-d$_6$) δ 11.00 (s, 1H), 8.19 (s, 1H), 8.00 (d, J=8.9 Hz, 1H), 7.90 (d, J=8.8 Hz, 1H), 7.71 (d, J=8.9 Hz, 2H), 7.48 (d, J=9.3 Hz, 1H), 7.20 (d, J=2.4 Hz, 1H), 7.13 (d, J=7.5 Hz, 1H), 7.00 (dd, J=8.8, 2.4 Hz, 1H), 6.93 (d, J=9.0 Hz, 2H), 6.88 (s, 1H), 5.74 (dd, J=11.9, 5.2 Hz, 1H), 4.55 (s, 1H), 4.31 (s, 1H), 4.04 (d, J=9.2 Hz, 1H), 3.81 (s, 2H), 3.60 (s, 1H), 3.45-3.41 (m, 1H), 3.05-2.82 (m, 3H), 2.81-2.52 (m, 5H), 2.35 (dd, J=10.4, 4.4 Hz, 2H), 2.13-2.03 (m, 1H), 1.99-1.69 (m, 5H), 1.65-1.38 (m, 2H), 1.21 (s, 6H), 1.12 (s, 6H).

Embodiment 18. Preparation of Compound 18

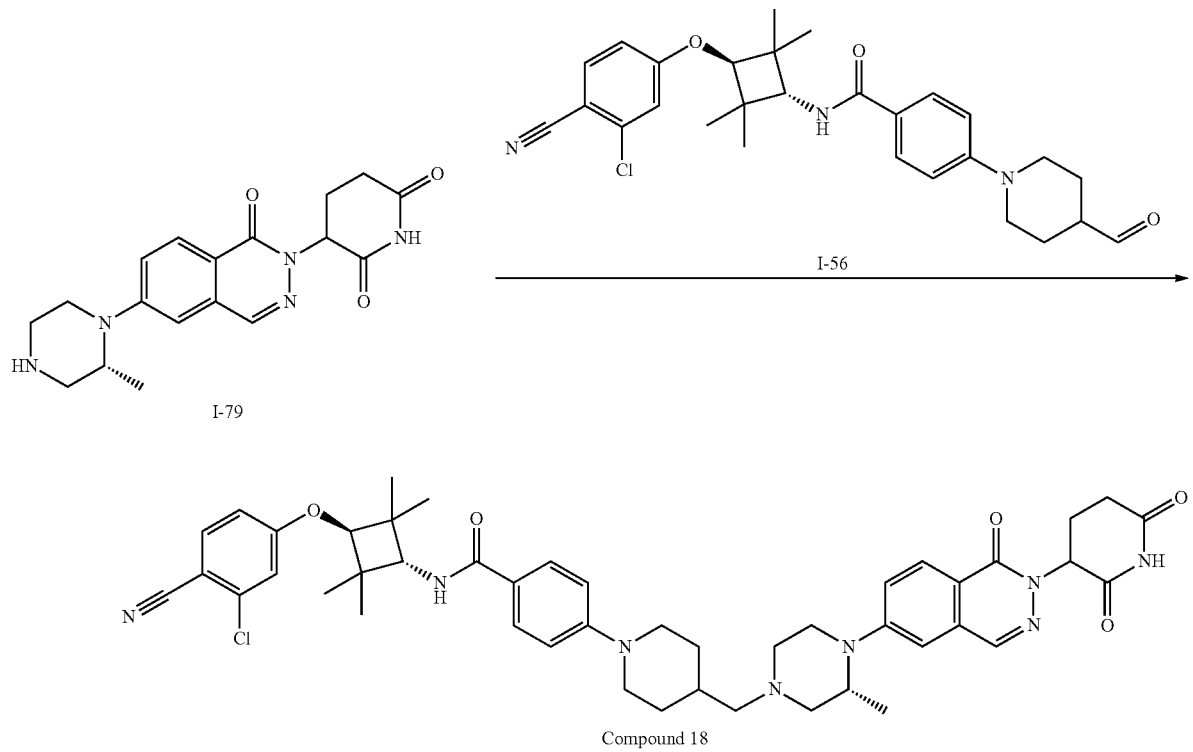

Intermediate I-79 (40.0 mg), intermediate I-56 (42.1 mg, 0.0852 mmol) and sodium acetate (34.9 mg, 0.426 mmol) were mixed in dichloromethane (0.5 mL) and methanol (1.5 mL). After a reaction mixture was stirred and reacted at room temperature for half an hour, sodium triacetoxyborohydride (54.3 mg, 0.256 mmol) was added. The reaction mixture was continuously stirred and reacted at room temperature for two hours. A solvent was removed from the mixture under reduced pressure. A residue was dissolved in N,N-dimethylformamide (1.5 mL), and filtered; a filtrate was separated and purified by preparative HPLC (containing formic acid) to afford compound 18. LC-MS (ESI) [M+H]$^+$ 833.2. $^1$H NMR (400 MHz, CDCl$_3$) δ 8.24 (d, J=9.0 Hz, 1H), 8.03 (s, 1H), 8.01 (s, 1H), 7.68 (d, J=8.8 Hz, 2H), 7.56 (d, J 8.7 Hz, 1H), 6.96 (d, J=2.4 Hz, 1H), 6.92 (d, J=8.9 Hz, 2H), 6.84 (s, 1H), 6.81 (dd, J=8.7, 2.4 Hz, 1H), 6.11 (d, J=8.1 Hz, 1H), 5.83 (dd, J=11.1, 5.3 Hz, 1H), 4.25-4.18 (m, 1H), 4.15 (d, J=8.1 Hz, 1H), 4.04 (s, 1H), 3.86 (d, J=12.6 Hz, 2H), 3.55 (d, J=11.8 Hz, 1H), 3.25 (t, J=11.8 Hz, 1H), 2.97-2.75 (m, 6H), 2.39-2.18 (m, 5H), 1.97-1.88 (m, 2H), 1.86-1.51 (m, 5H), 1.34 (d, J=12.2 Hz, 3H), 1.26 (s, 6H), 1.22 (s, 6H).

Embodiment 19: Preparation of Compound 19

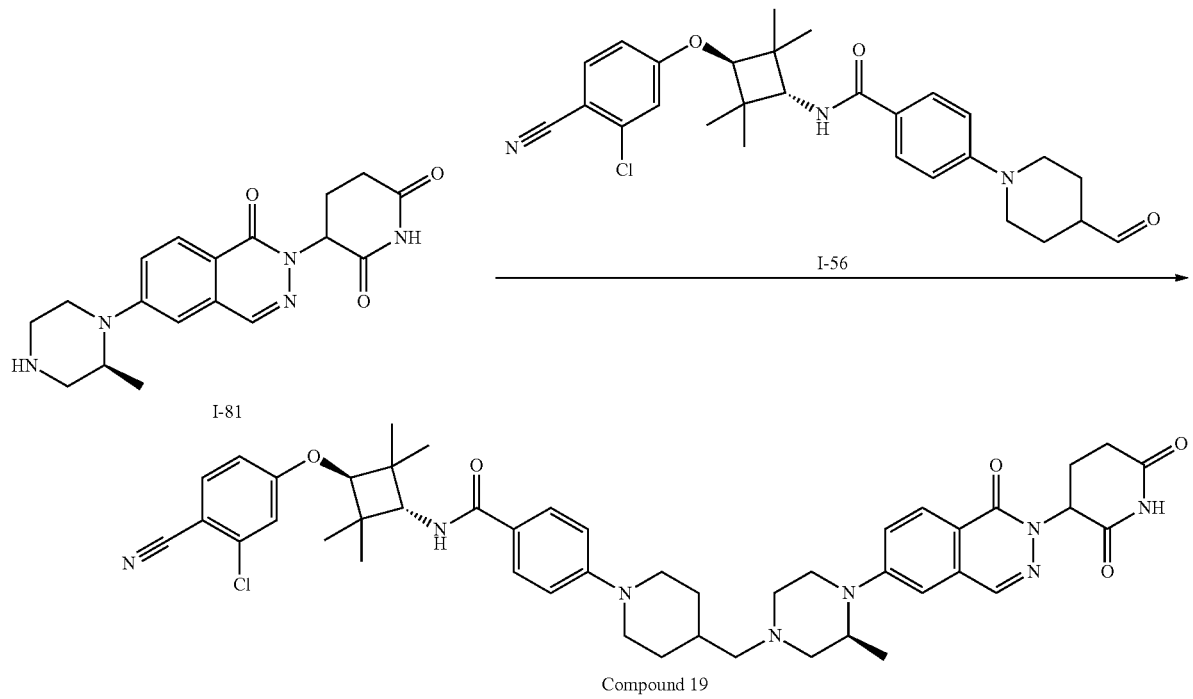

Intermediate I-81 (30.0 mg), intermediate I-56 (31.6 mg, 0.0639 mmol) and sodium acetate (26.2 mg, 0.320 mmol) were mixed in dichloromethane (0.5 mL) and methanol (1 mL). After a reaction mixture was stirred and reacted at room temperature for half an hour, sodium triacetoxyborohydride (40.7 mg, 0.192 mmol) was added. The reaction mixture was continuously stirred and reacted at room temperature for two hours. A solvent was removed from the mixture under reduced pressure. A residue was dissolved in N,N-dimethylformamide (1 mL), and filtered; a filtrate was separated and purified by preparative HPLC (containing formic acid) to afford compound 19. LC-MS (ESI) [M+H]$^+$ 833.2. $^1$H NMR (400 MHz, CDCl$_3$) δ 8.24 (d, J=9.0 Hz, 1H), 8.03 (s, 1H), 7.99 (s, 1H), 7.68 (d, J=8.6 Hz, 2H), 7.56 (d, J=8.8 Hz, 1H), 6.96 (d, J=2.4 Hz, 1H), 6.92 (d, J=8.7 Hz, 2H), 6.84 (s, 1H), 6.81 (dd, J=8.7, 2.4 Hz, 1H), 6.11 (d, J=8.1 Hz, 1H), 5.83 (dd, J=11.1, 5.3 Hz, 1H), 4.25-4.17 (m, 1H), 4.15 (d, J=8.1 Hz, 1H), 4.04 (s, 1H), 3.86 (d, J=12.5 Hz, 2H), 3.55 (d, J=11.9 Hz, 1H), 3.25 (t, J=11.9 Hz, 1H), 2.97-2.75 (m, 6H), 2.39-2.19 (m, 5H), 1.96-1.88 (m, 2H), 1.79-1.59 (m, 5H), 1.34 (d, J=12.4 Hz, 3H), 1.26 (s, 6H), 1.22 (s, 6H).

Embodiment 20: Preparation of Compound 20

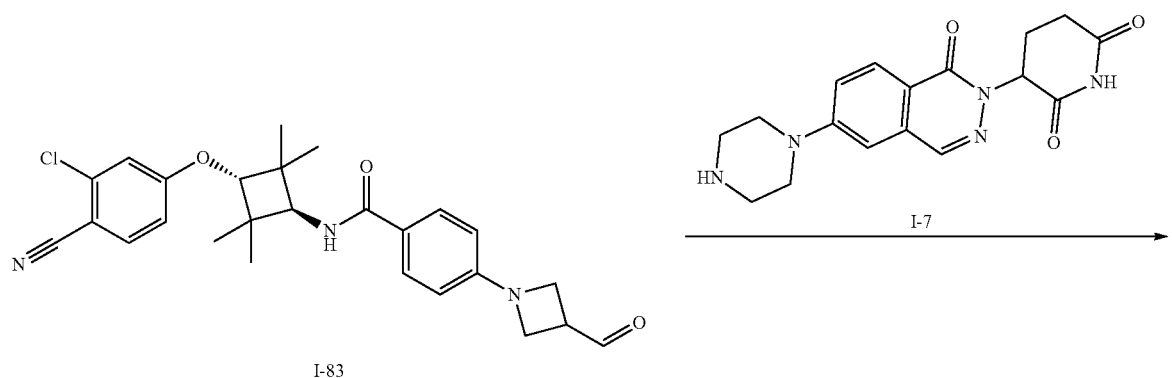

-continued

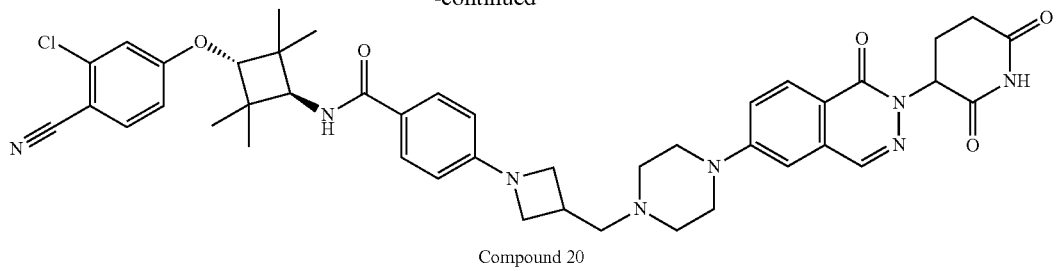

Compound 20

Intermediate I-83 (150 mg) was dissolved in a mixed solvent of anhydrous dichloromethane/methanol (5.00 mL/5.00 mL), and intermediate I-7 (110 mg) was added; a system was protected with argon, and stirred and reacted at room temperature for 0.5 hours. Sodium triacetoxyborohydride (205 mg, 0.966 mmol) was added in portions, and a system was protected with argon, and stirred and reacted at room temperature for 3 hours. A mixture was washed with water (10.0 mL×3), dried over anhydrous sodium sulfate and filtered; a filtrate was concentrated under reduced pressure to remove an organic solvent to afford a crude product; the crude product was first separated and purified by silica gel chromatography, and then purified by beating with anhydrous acetonitrile (15.0 mL); suction filtration was performed, and a filter cake was dried; finally, the dried filter cake was separated and purified by preparative HPLC (containing formic acid) to afford compound 20. LC-MS (ESI) [M+H]⁺ 791.2. ¹H NMR (400 MHz, DMSO-d₆) δ 11.01 (s, 1H), 8.25 (s, 1H), 8.05 (d, J=8.9 Hz, 1H), 7.90 (d, J=8.7 Hz, 1H), 7.74 (d, J=8.4 Hz, 2H), 7.48 (dd, J=24.3, 8.9 Hz, 2H), 7.28-7.18 (m, 2H), 7.01 (dd, J=8.7, 1.9 Hz, 1H), 6.44 (d, J=8.4 Hz, 2H), 5.75 (dd, J=12.0, 5.2 Hz, 1H), 4.32 (s, 1H), 4.03 (dd, J=16.4, 8.4 Hz, 3H), 3.61-3.55 (m, 4H), 3.01 (s, 1H), 2.93 (dd, J=21.7, 9.0 Hz, 1H), 2.69-2.62 (m, 3H), 2.57 (s, 5H), 2.14-2.05 (m, 1H), 1.23 (s, 2H), 1.21 (s, 6H), 1.13 (s, 6H).

Embodiment 21: Preparation of Compound 21

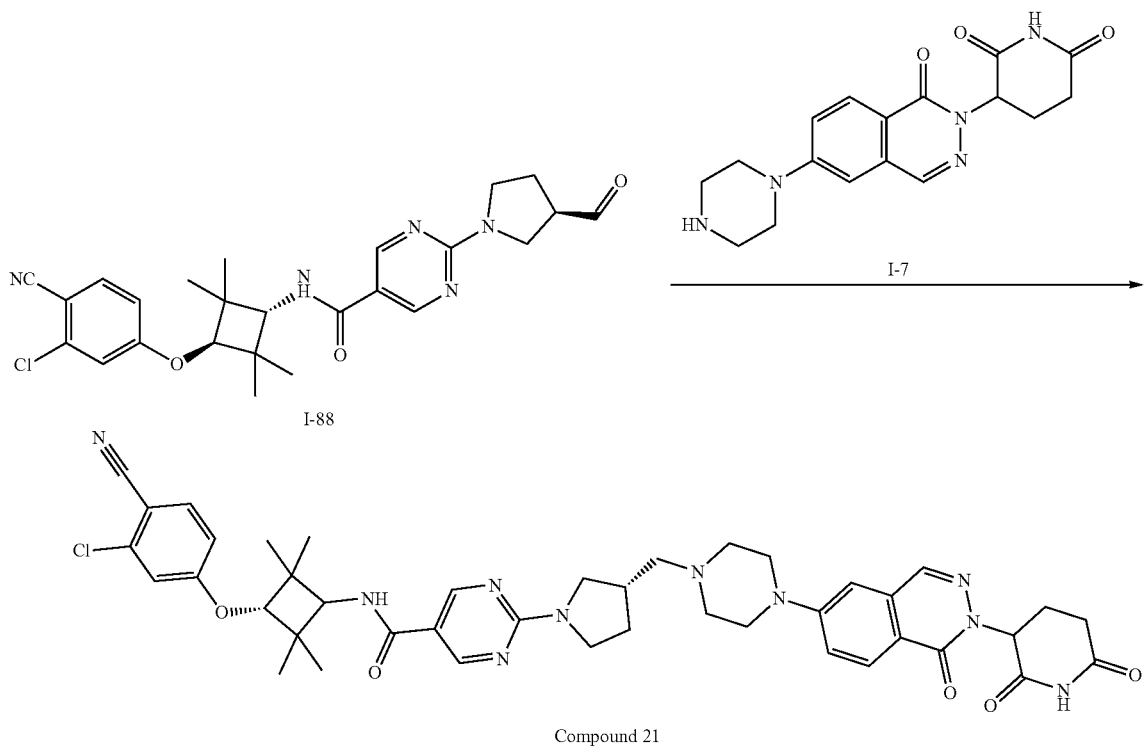

Compound 21

At room temperature, intermediate I-88 (100 mg) was dissolved in a mixed solvent of dichloromethane (8.00 mL) and methanol (2.00 mL), followed by addition of intermediate I-7 (94.0 mg), sodium acetate (68.0 mg, 0.828 mmol) and sodium triacetoxyborohydride (132 mg, 0.621 mmol); stirring was performed at room temperature overnight. A saturated sodium bicarbonate solution (10 mL) was added for dilution, and dichloromethane (10 mL×3) was used for extraction; organic phases were combined, washed with saturated saline (10 mL), dried over anhydrous sodium sulfate, filtered, and concentrated under reduced pressure; a residue was separated and purified by preparative HPLC (containing formic acid) to afford compound 21. LC-MS (ESI) m/z[M+H]⁺ 807.1. ¹H NMR (400 MHz, DMSO-d₆) δ 11.00 (s, 1H), 8.76 (s, 2H), 8.25 (s, 1H), 8.04 (d, J=8.7 Hz, 1H), 7.90 (d, J=8.6 Hz, 1H), 7.71 (d, J=9.2 Hz, 1H), 7.51 (d, J=8.8 Hz, 1H), 7.24 (d, J=19.5 Hz, 2H), 7.01 (d, J=8.6 Hz, 1H), 5.75 (d, J=6.7 Hz, 1H), 4.29 (s, 1H), 4.04 (d, J=9.4 Hz, 1H), 3.75 (dd, J=23.7, 16.7 Hz, 3H), 3.53-3.41 (m, 7H), 2.90 (d, J=10.9 Hz, 1H), 2.65-2.55 (m, 6H), 2.43 (s, 2H), 2.11 (s, 2H), 1.22 (s, 6H), 1.11 (s, 6H).

Embodiment 22: Preparation of Compound 22

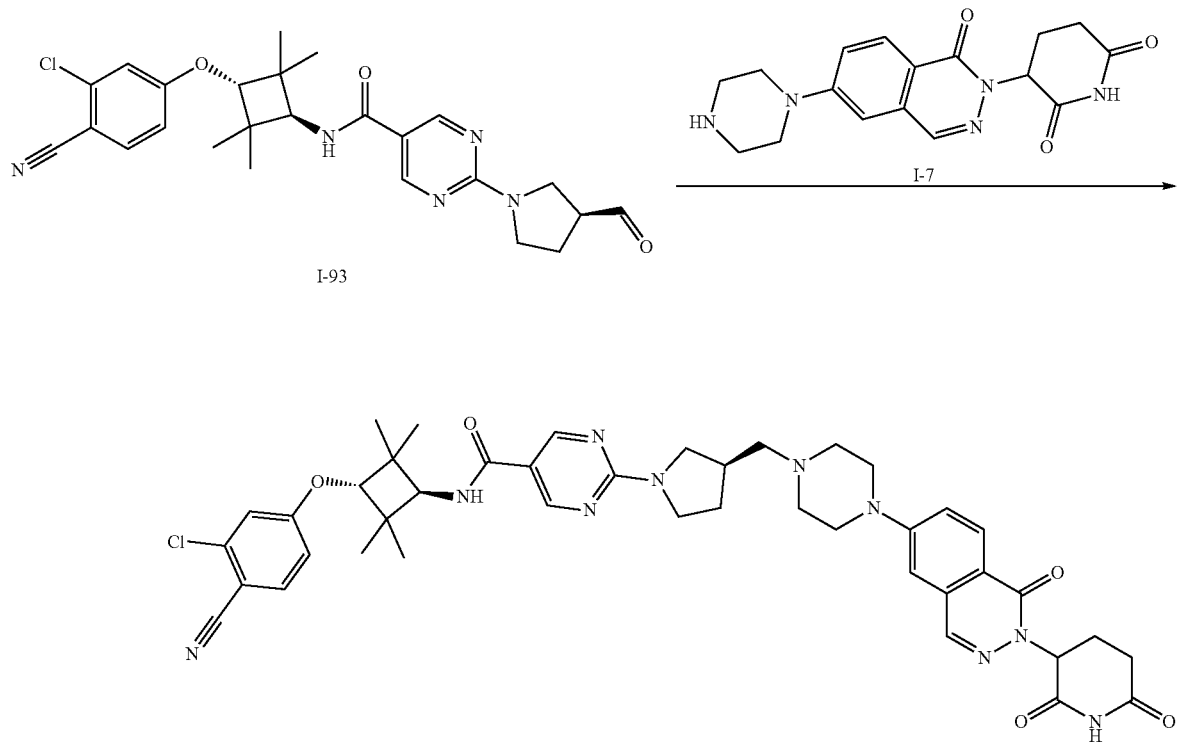

Compound 22

Intermediate I-93 (100 mg, 0.207 mmol) was dissolved in a mixed solvent of anhydrous dichloromethane/methanol (5 mL/5 mL), and intermediate I-7 (70.6 mg) was added; a system was protected with argon, and stirred and reacted at room temperature for 0.5 hours. Sodium triacetoxyborohydride (131.6 mg, 0.621 mmol) was added in portions, a system was protected with argon, and stirred and reacted at room temperature for 3 hours. A mixture was washed with water (10 mL×3), dried over anhydrous sodium sulfate and filtered; a filtrate was concentrated under reduced pressure to remove an organic solvent to afford a crude product, and the crude product was separated and purified by silica gel chromatography to afford compound 22. LC-MS (ESI) [M+H]⁺ 807.4. ¹H NMR (400 MHz, DMSO-d₆) δ 10.92 (s, 1H), 8.68 (s, 2H), 8.17 (s, 1H), 7.97 (d, J=9.0 Hz, 1H), 7.81 (d, J=8.7 Hz, 1H), 7.64 (d, J=9.2 Hz, 1H), 7.43 (d, J=7.3 Hz, 1H), 7.20-7.11 (m, 2H), 6.92 (dd, J=8.8, 2.4 Hz, 1H), 5.66 (dd, J=11.9, 5.3 Hz, 1H), 4.21 (s, 1H), 3.96 (d, J=9.2 Hz, 1H), 3.73-3.56 (m, 3H), 3.47-3.39 (m, 5H), 3.20 (dd, J=11.6, 7.4 Hz, 3H), 2.88-2.78 (m, 1H), 2.52 (dd, J=24.8, 8.2 Hz, 5H), 2.11-1.85 (m, 3H), 1.65 (dq, J=15.9, 7.9 Hz, 1H), 1.13 (s, 6H), 1.03 (s, 6H).

Embodiment 23: Preparation of Compound 23

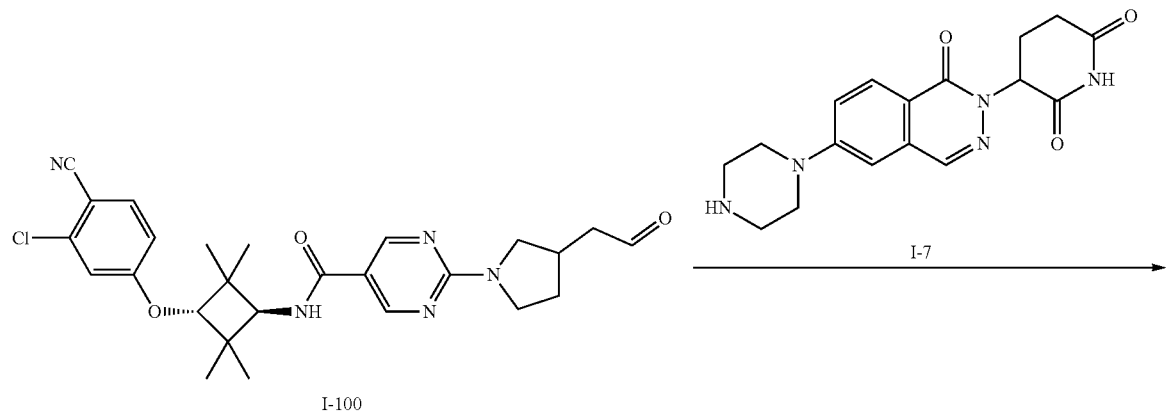

Intermediate I-100 (70 mg) was dissolved in dichloromethane/methanol (5 mL/1 mL), followed by successive addition of intermediate I-7 (50 mg) and sodium acetate (35 mg, 0.42 mmol); a reaction mixture was stirred and reacted at room temperature for 30 minutes, and then sodium triacetoxyborohydride (89 mg, 0.42 mmol) was added; after addition was completed, the reaction mixture was stirred and reacted at room temperature overnight. After a reaction was completed, water (10 mL) was added for dilution, standing for layering was performed, organic phases were separated, and an aqueous phase was extracted with dichloromethane (10 mL×2); the organic phases were combined, washed with water (10 mL×3), dried over anhydrous sodium sulfate and filtered, and a filtrate was concentrated under reduced pressure; a residue was separated and purified by preparative HPLC (containing formic acid) to afford compound 23. LC-MS (ESI) [M+H]$^+$ 821.5. $^1$H NMR (400 MHz, DMSO-$d_6$) δ 11.00 (s, 1H), 8.76 (s, 2H), 8.24 (s, 1H), 8.04 (d, J=9.1 Hz, 1H), 7.90 (d, J=8.7 Hz, 1H), 7.69 (d, J=9.3 Hz, 1H), 7.50 (d, J=9.1 Hz, 1H), 7.26 (s, 1H), 7.21 (d, J=2.4 Hz, 1H), 7.01 (dd, J=8.8, 2.4 Hz, 1H), 5.75 (dd, J=12.1, 5.0 Hz, 1H), 4.29 (s, 1H), 4.04 (d, J=9.1 Hz, 1H), 3.83 (dd, J=11.2, 7.4 Hz, 1H), 3.71 (t, J=8.5 Hz, 1H), 3.42 (s, 6H), 3.17-3.09 (m, 1H), 2.90 (dd, J=21.4, 9.1 Hz, 1H), 2.55 (s, 5H), 2.42 (s, 2H), 2.32 (d, J=9.4 Hz, 1H), 2.10 (dd, J=18.7, 14.0 Hz, 2H), 1.71-1.60 (m, 3H), 1.21 (s, 6H), 1.11 (s, 6H).

Embodiment 24: Preparation of Compound 24

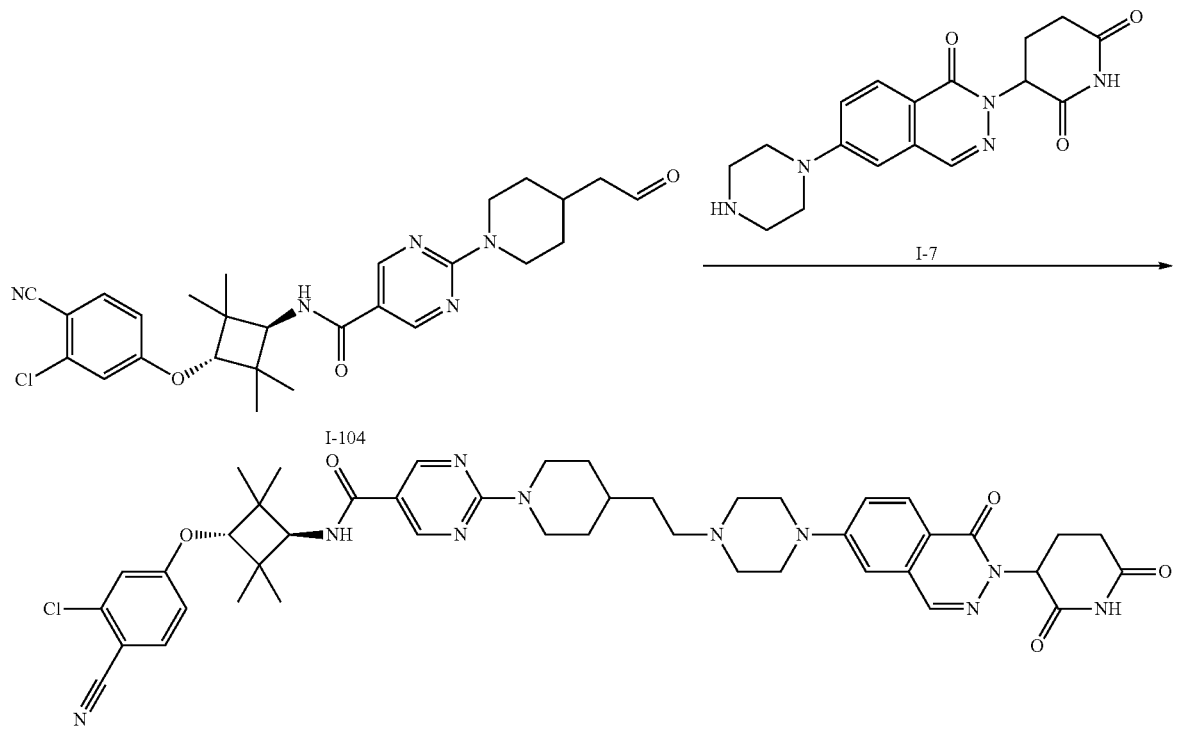

Embodiment 24

Intermediate I-104 (55 mg) was dissolved in dichloromethane/methanol (5 mL/1 mL), followed by successive addition of intermediate I-7 (34 mg) and sodium acetate (24 mg, 0.29 mmol); a reaction mixture was stirred and reacted at room temperature for 30 minutes, and then sodium triacetoxyborohydride (61 mg, 0.29 mmol) was added; after addition was completed, the reaction mixture was stirred and reacted at room temperature overnight. After a reaction was completed, water (10 mL) was added for dilution, standing for layering was performed, and organic phases were extracted with dichloromethane (10 mL×2); the organic phases were combined, washed with water (10 mL×3), dried over anhydrous sodium sulfate and filtered, and a filtrate was concentrated under reduced pressure; a residue was separated and purified by preparative HPLC (containing formic acid) to afford compound 24. LC-MS (ESI) [M+H]$^+$ 835.1. $^1$H NMR (400 MHz, DMSO-d$_6$) δ 11.00 (s, 1H), 8.75 (s, 2H), 8.24 (s, 1H), 8.04 (d, J=9.0 Hz, 1H), 7.90 (d, J=8.8 Hz, 1H), 7.70 (d, J=9.2 Hz, 1H), 7.50 (dd, J=9.2, 2.3 Hz, 1H), 7.25 (d, J=2.2 Hz, 1H), 7.22 (d, J=2.4 Hz, 1H), 7.01 (dd, J=8.8, 2.4 Hz, 1H), 5.75 (dd, J=11.9, 5.4 Hz, 1H), 4.73 (d, J=13.2 Hz, 2H), 4.29 (s, 1H), 4.03 (d, J=9.1 Hz, 1H), 3.40 (d, J=4.4 Hz, 6H), 2.95 (dd, J=21.7, 8.3 Hz, 3H), 2.64-2.52 (m, 4H), 2.42-2.36 (m, 2H), 2.13-2.04 (m, 1H), 1.79 (d, J=12.5 Hz, 2H), 1.67 (s, 1H), 1.50-1.39 (m, 2H), 1.21 (s, 6H), 1.11 (s, 6H), 1.07 (d, J=10.8 Hz, 2H).

Embodiment 25: Preparation of Compound 25

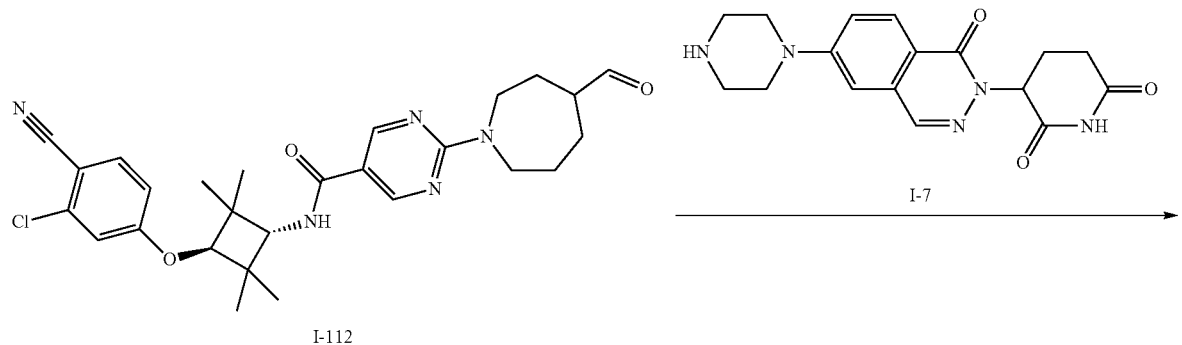

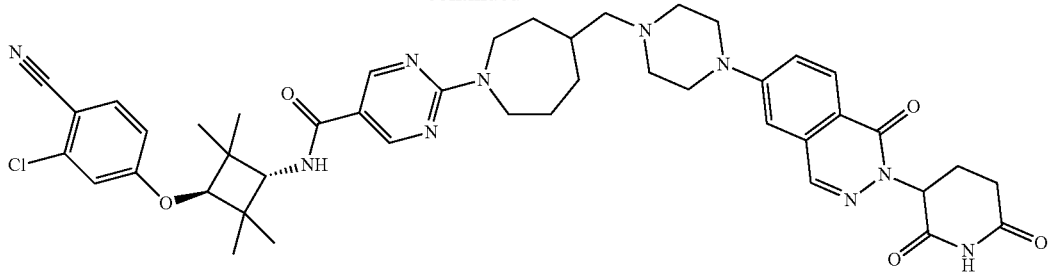

Compound 25

Intermediate I-112 (90.0 mg, 0.176 mmol) was dissolved in a mixed solvent of dichloromethane/methanol (10.0 mL/3.00 mL), followed by addition of intermediate I-7 (96.1 mg) and anhydrous sodium acetate (72.2 mg, 0.880 mmol). A reaction system was protected with argon, and was stirred and reacted at room temperature for 0.5 hours. Sodium triacetoxyborohydride (74.6 mg, 0.352 mmol) was added. A reaction system was protected with argon, and was stirred and reacted at room temperature for 16 hours. Dichloromethane (50.0 mL) was used for dilution, and water (20.0 mL×2) was used for washing; organic phases were separated, dried over anhydrous sodium sulfate and filtered; a filtrate was concentrated under reduced pressure to remove an organic solvent to afford a crude product, and the crude product was separated and purified by preparative HPLC (containing formic acid) to afford compound 25. LC-MS (ESI) [M+H]$^+$ 835.2. $^1$H NMR (400 MHz, DMSO-$d_6$) δ 11.00 (s, 1H), 8.76 (s, 2H), 8.23 (s, 1H), 8.03 (d, J=9.0 Hz, 1H), 7.90 (d, J=8.8 Hz, 1H), 7.72 (d, J=9.2 Hz, 1H), 7.48 (dd, J=9.1, 2.3 Hz, 1H), 7.23 (dd, J=7.6, 2.3 Hz, 2H), 7.01 (dd, J=8.8, 2.4 Hz, 1H), 5.74 (dd, J=12.0, 5.5 Hz, 1H), 4.29 (s, 1H), 4.07-3.96 (m, 2H), 3.90-3.73 (m, 2H), 3.67-3.58 (m, 1H), 3.40 (s, 4H), 2.97-2.85 (m, 1H), 2.75-2.52 (m, 2H), 2.49-2.42 (m, 5H), 2.25-1.90 (m, 6H), 1.84 (d, J=13.7 Hz, 1H), 1.73-1.57 (m, 2H), 1.22 (s, 6H), 1.11 (s, 6H).

Embodiment 26: Preparation of Compound 26

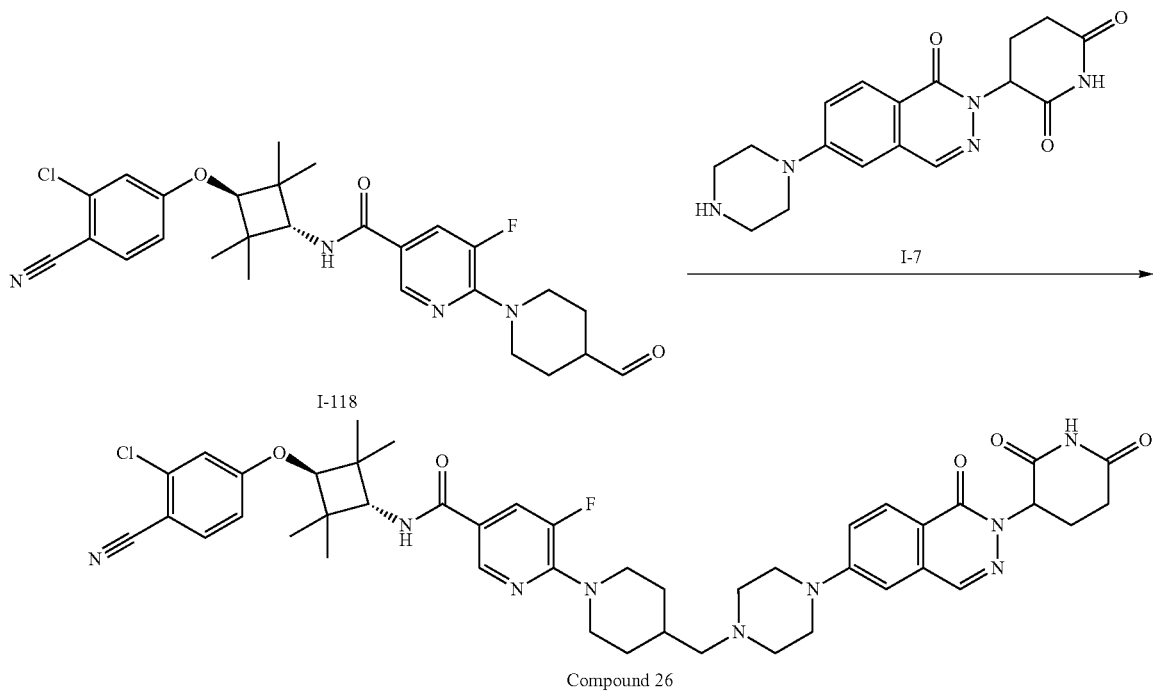

Compound 26

At room temperature, intermediate I-118 (80.0 mg) was dissolved in a mixed solvent of dichloromethane (8.00 mL) and methanol (2.00 mL), followed by addition of intermediate I-7 (53.2 mg) and sodium triacetoxyborohydride (99.2 mg, 0.468 mmol); stirring was performed at room temperature overnight. A saturated sodium bicarbonate solution (10.0 mL) was added, and dichloromethane (15 mL×2) was used for extraction; organic phases were combined, washed with saturated saline (10 mL), dried over anhydrous sodium sulfate, filtered, and concentrated under reduced pressure; a residue was separated and purified by preparative HPLC (containing formic acid) to afford compound 26. LC-MS (ESI) [M+H]$^+$ 838.1. $^1$H NMR (400 MHz, DMSO-$d_6$) δ 11.00 (s, 1H), 8.50 (s, 1H), 8.24 (s, 1H), 8.04 (d, J=9.0 Hz, 1H), 7.88 (dd, J=19.9, 5.3 Hz, 2H), 7.73 (d, J=9.2 Hz, 1H), 7.53-7.47 (m, 1H), 7.23 (dd, J=15.2, 2.3 Hz, 2H), 7.01 (dd, J=8.8, 2.4 Hz, 1H), 5.75 (dd, J=12.1, 5.4 Hz, 1H), 4.31 (s, 1H), 4.21 (d, J=13.1 Hz, 2H), 4.06 (d, J=9.1 Hz, 1H), 3.42 (s, 6H), 3.03-2.86 (m, 3H), 2.64-2.57 (m, 1H), 2.52 (d, J=3.6 Hz, 3H), 2.22 (d, J=6.9 Hz, 2H), 2.12-2.04 (m, 1H), 1.84 (d, J=13.1 Hz, 3H), 1.22 (s, 6H), 1.17 (d, J=15.4 Hz, 2H), 1.12 (s, 6H).

Embodiment 27: Preparation of Compound 27 were combined, washed with water (10 mL×3), dried over anhydrous sodium sulfate and filtered, and a filtrate was concentrated under reduced pressure; a residue was separated and purified by preparative HPLC (containing formic acid) to afford compound 27. LC-MS (ESI) [M+H]$^+$ 838.2. $^1$H NMR (400 MHz, DMSO-d$_6$) δ 11.00 (s, 1H), 8.24 (s, 1H), 8.04 (d, J=9.5 Hz, 1H), 7.90 (d, J=8.8 Hz, 1H), 7.86 (d, J=8.9 Hz, 1H), 7.78 (d, J=8.8 Hz, 1H), 7.60 (s, 1H), 7.53-7.48 (m, 1H), 7.25 (s, 2H), 7.03 (d, J=8.7 Hz, 1H),

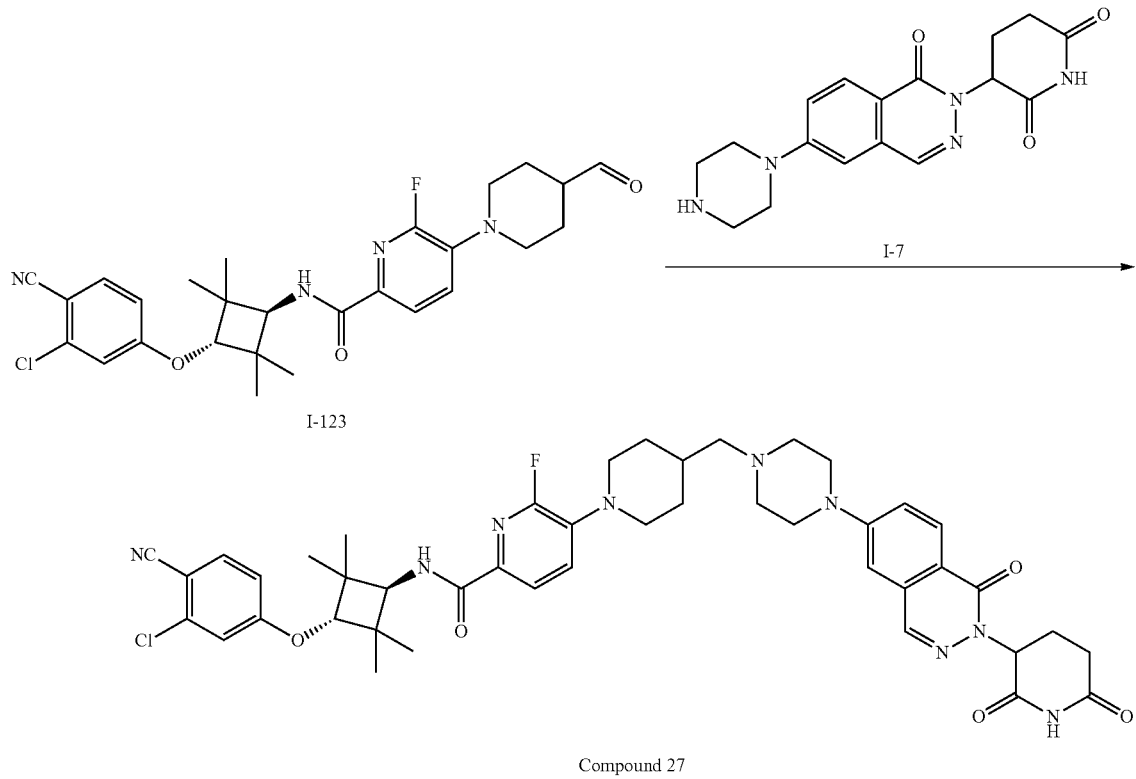

Intermediate I-123 (25 mg) was dissolved in dichloromethane/methanol (5 mL/1 mL), followed by successive addition of intermediate I-7 (17 mg) and sodium acetate (12 mg, 0.15 mmol); a reaction mixture was stirred and reacted at room temperature for 30 minutes, and then sodium triacetoxyborohydride (32 mg, 0.15 mmol) was added; the reaction mixture was stirred and reacted at room temperature overnight. Water (10 mL) was added for dilution, standing for layering was performed, and an aqueous phase was extracted with dichloromethane (10 mL×2); organic phases 5.80-5.69 (m, 1H), 4.47 (s, 1H), 3.93 (d, J=9.0 Hz, 1H), 3.57 (s, 3H), 3.42 (s, 6H), 2.83 (s, 3H), 2.58 (s, 2H), 2.54 (s, 2H), 2.25 (s, 2H), 2.12-2.05 (m, 1H), 1.84 (s, 2H), 1.28 (s, 2H), 1.20 (s, 6H), 1.14 (s, 6H).

Embodiment 28: Preparation of Compound 28A and Compound 28B

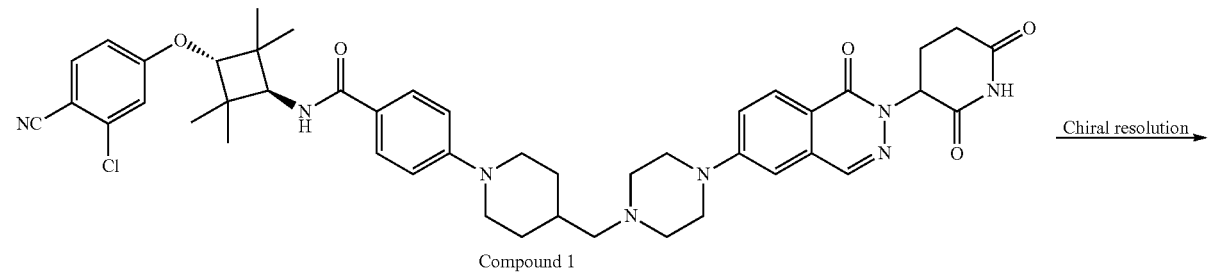

-continued

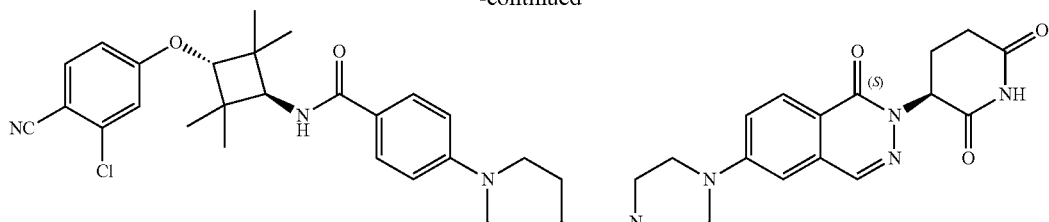

Compound 28A (Rt = 10.206 min)

+

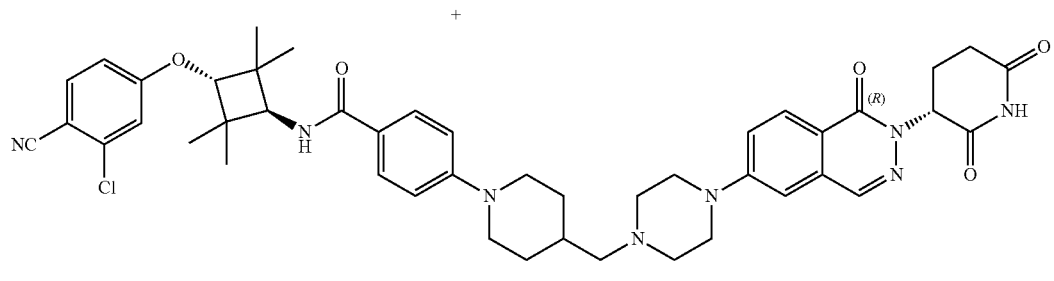

Compound 28B (Rt = 13.352 min)

Compound 1 (5 g) was chirally resolved to afford compound 28A (Rt=10.206 min) and compound 28B (Rt=13.352 min). Chiral resolution method: Instrument: Shimadzu LC-20AP HPLC Column: ChiralPak IC, 300×50 mm I.D., 10 μm; Mobile phase: A: Methanol (0.1% ammonia water) B: Dichloromethane; Elution gradient: 70% B; Flow rate: 80 mL/min; Column temperature: room temperature; Detection wavelength: 220 nm; Cycle time: ~6 min; Chiral analysis method: Instrument: Waters UPC2 analytical SFC (SFC—H), Column: ChiralCel OJ, 150×4.6 mm I.D., 3 μm; Mobile phase: A: Carbon dioxide B: Ethanol (0.05% diethylamine); Elution gradient: 50% B; Flow rate: 2.0 mL/min; Back pressure: 1500 psi; Column temperature: 35° C.; Detection wavelength: 220 nm; Compound 28A: Rt=10.206 min. LC-MS (ESI) [M+H]$^+$ m/z=819.6. $^1$H NMR (400 MHz, DMSO-d$_6$) δ 10.96 (s, 1H), 8.24 (s, 1H), 8.04 (d, J=9.00 Hz, 1H), 7.90 (d, J=8.63 Hz, 1H), 7.74 (d, J=8.76 Hz, 2H), 7.44-7.55 (m, 2H), 7.24 (d, J=1.75 Hz, 1H), 7.19 (d, J=2.38 Hz, 1H), 6.90-7.03 (m, 3H), 5.76 (dd, J=5.19, 12.07 Hz, 1H), 4.31 (s, 1H), 4.06 (d, J=9.13 Hz, 1H), 3.85 (d, J=12.26 Hz, 2H), 3.37-3.47 (m, 4H), 2.85-2.99 (m, 1H), 2.78 (t, J=11.69 Hz, 2H), 2.50-2.65 (m, 8H), 2.20 (d, J=6.38 Hz, 2H), 2.04-2.13 (m, 1H), 1.72-1.85 (m, 3H), 1.22 (s, 6H), 1.12 (s, 6H).

Compound 28B: Rt=13.352 min. LC-MS (ESI) [M+H]$^+$ m/z=819.6. $^1$H NMR (400 MHz, DMSO-d$_6$) δ 10.91 (s, 1H), 8.24 (s, 1H), 8.04 (d, J=9.01 Hz, 1H), 7.90 (d, J=8.75 Hz, 1H), 7.74 (d, J=8.63 Hz, 2H), 7.43-7.56 (m, 2H), 7.14-7.28 (m, 2H), 6.89-7.04 (m, 3H), 5.70-5.81 (m, 1H), 4.31 (s, 1H), 4.05 (d, J=9.13 Hz, 1H), 3.86 (d, J=12.01 Hz, 2H), 3.37-3.52 (m, 4H), 2.86-2.99 (m, 1H), 2.78 (t, J=11.76 Hz, 2H), 2.50-2.67 (m, 8H), 2.21 (d, J=6.00 Hz, 2H), 2.03-2.13 (m, 1H), 1.72-1.87 (m, 3H), 1.22 (s, 6H), 1.12 (s, 6H).

Embodiment 29: Preparation of Compound 29

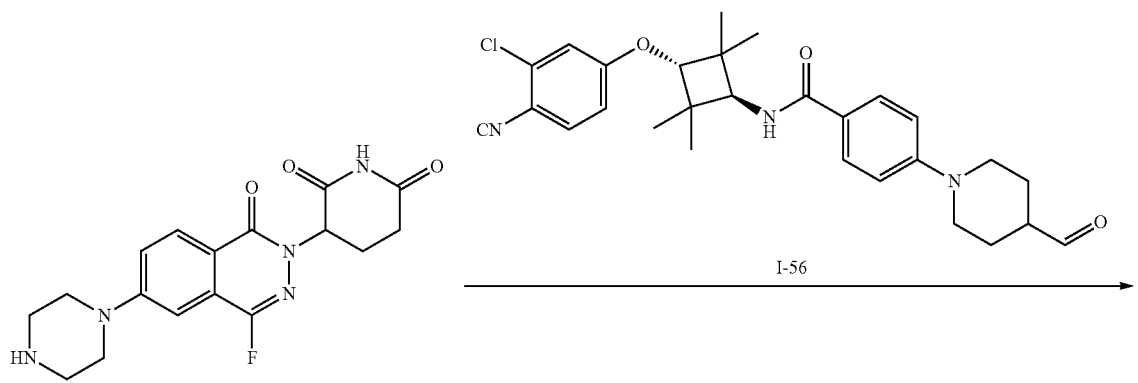

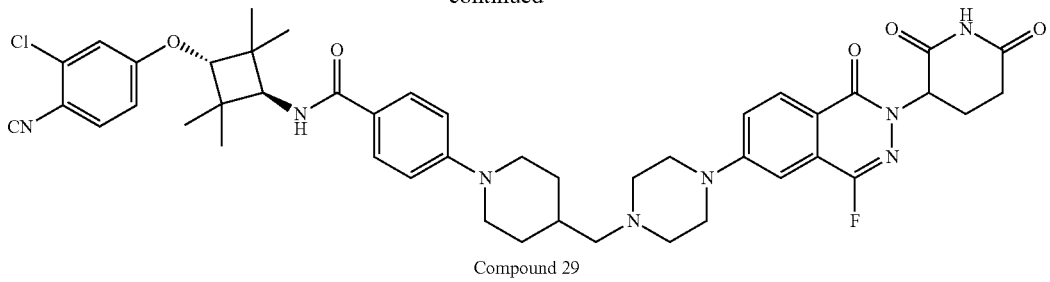

Compound 29

At 25° C., to a solution of I-130 (260 mg, 0.48 mmol) in N,N-dimethylacetamide (1 mL) and dichloromethane (10 mL) was successively added I-56 (262 mg, 0.53 mmol), sodium triacetoxyborohydride (203 mg, 0.96 mmol) and glacial acetic acid (2.88 mg, 0.048 mmol); stirring was performed at 25° C. for 2 hours. The above-mentioned reaction solution was added with water (20 mL) and extracted with dichloromethane (20 mL×3). Organic phases were combined, washed with saturated saline (50 mL), dried over anhydrous sodium sulfate, filtered, concentrated under reduced pressure, and separated and purified by HPLC to afford compound 29. LC-MS (ESI) [M+H]+ 837.5. $^1$H NMR (400 MHz, DMSO-$d_6$) δ 11.06 (s, 1H), 8.09 (d, J=9.0 Hz, 1H), 7.91 (d, J=8.7 Hz, 1H), 7.74 (d, J=8.7 Hz, 2H), 7.62 (d, J=9.0 Hz, 1H), 7.51 (d, J=9.2 Hz, 1H), 7.21 (d, J=2.5 Hz, 1H), 7.14 (s, 1H), 7.05-6.88 (m, 3H), 5.75 (dd, J=12.5, 5.5 Hz, 1H), 4.32 (s, 1H), 4.05 (d, J=9.1 Hz, 1H), 3.87 (d, J=12.4 Hz, 2H), 3.57-3.40 (m, 4H), 3.34-3.32 (m, 8H), 2.99-2.87 (m, 1H), 2.80 (t, J=12.2 Hz, 2H), 2.66-2.57 (m, 1H), 2.29-2.03 (m, 2H), 1.88-1.73 (m, 3H), 1.22 (s, 6H), 1.13 (s, 6H).

Embodiment 30: Preparation of Compound 30

At room temperature, I-135 (60.0 mg, 0.16 mmol) and I-56 (93.0 mg, 0.19 mmol) were dissolved in dichloromethane/methanol (3 mL/1 mL), and 2 drops of acetic acid were added dropwise; a reaction was stirred at room temperature for 0.5 hours; then, sodium triacetoxyborohydride (66.0 mg, 0.32 mmol) was added, and the reaction was stirred at room temperature for 1.5 hours. A reaction solution was diluted with water (10 mL), and extracted with dichloromethane (20 mL×2); organic phases were combined, washed with saturated saline (20 mL×2), dried over anhydrous sodium sulfate, and filtered. A filtrate was concentrated under reduced pressure to remove an organic solvent. The resulting residue was purified by C18 reverse-phase column to afford compound 30. LCMS (ESI) [M+H]+ 859.6. $^1$H NMR (400 MHz, DMSO-$d_6$) δ 10.98 (s, 1H), 8.08-8.06 (d, J=8.8 Hz, 1H), 7.92-7.90 (d, J=8.8 Hz, 1H), 7.75-7.72 (d, J=8.8 Hz, 2H), 7.52-7.44 (m, 3H), 7.21-7.20 (d, J=2.4 Hz, 1H), 7.02-6.95 (m, 3H), 5.57-5.66 (d, J=9.6 Hz, 1H), 4.32 (s, 1H), 4.06-4.04 (d, J=8.8 Hz, 1H), 3.88-3.85 (d, J=12.4 Hz, 2H), 3.46-3.35 (m, 4H), 2.87-2.76 (m, 3H), 2.60-2.52 ((m, 6H), 2.47-2.44 (m, 1H), 2.24-2.22 (m, 2H), 2.05-2.05 (m, 1H), 1.83-1.81 (m, 3H), 1.21 (s, 8H), 1.12 (s, 6H), 0.96-0.92 (m, 2H), 0.82-0.80 (m, 2H).

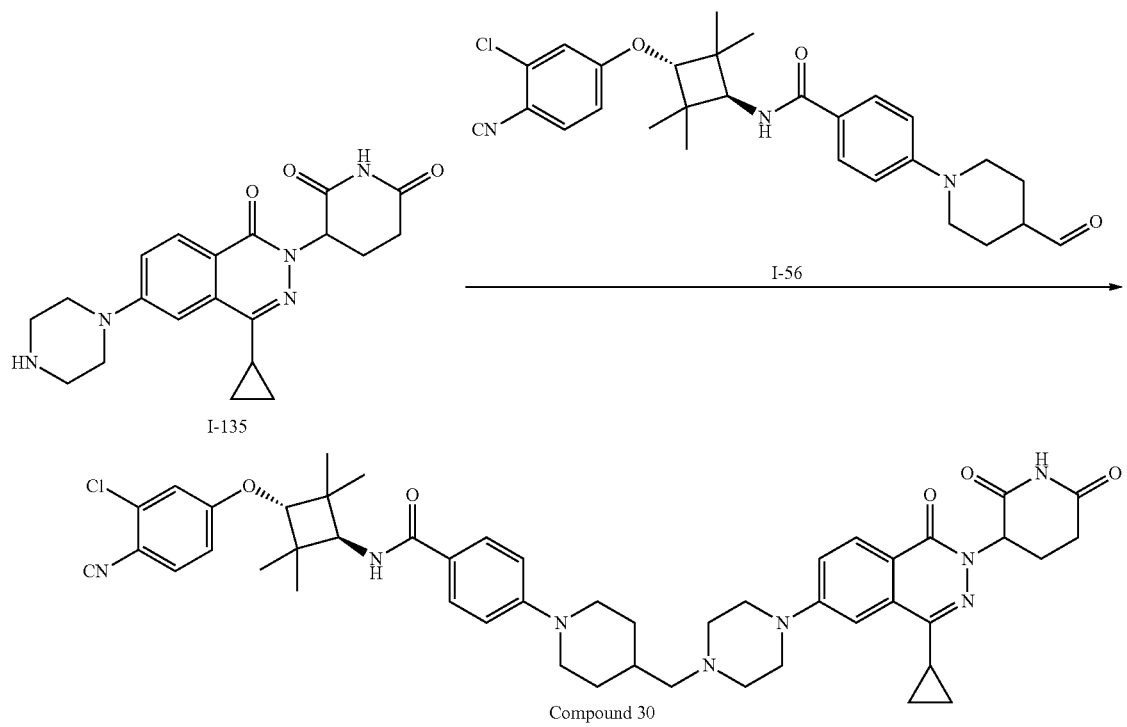

Embodiment 31: Preparation of Compound 31

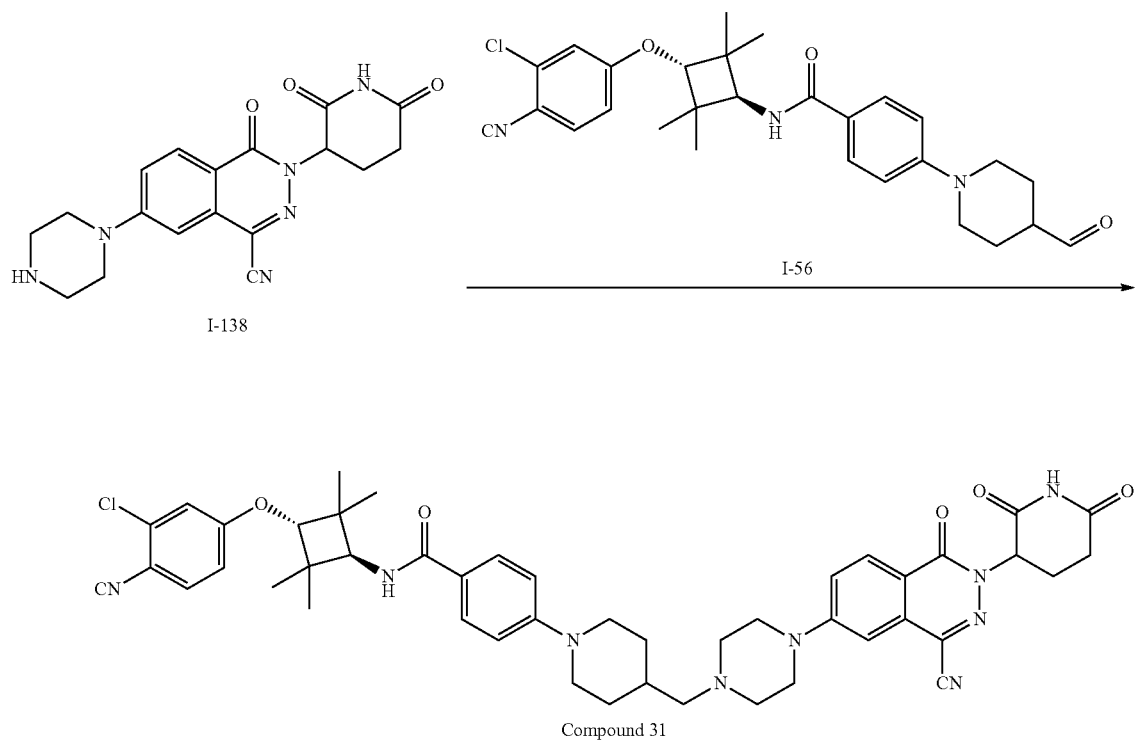

At room temperature, I-138 (a TFA salt, 200 mg, 0.43 mmol) was dissolved in N,N-dimethylacetamide (1 mL) and dichloromethane (10 mL), followed by successive addition of I-56 (234 mg, 0.47 mmol), sodium triacetoxyborohydride (182 mg, 0.86 mmol) and glacial acetic acid (2.58 mg, 0.043 mmol); stirring was performed at room temperature for 2 hours. A reaction solution was added with water (20 mL) and extracted with dichloromethane (20 mL×3). Organic phases were combined, washed with saturated saline (50 mL), dried over anhydrous sodium sulfate, filtered, and concentrated under reduced pressure. The resulting residue was purified by C18 reverse-phase column chromatography to afford compound 31. LC-MS (ESI) [M+H]$^+$ 844.6. $^1$H NMR (400 MHz, DMSO-$d_6$) δ 11.14 (s, 1H), 8.12 (d, J=9.0 Hz, 1H), 7.91 (d, J=8.7 Hz, 1H), 7.74 (d, J=8.6 Hz, 2H), 7.66 (d, J=9.2 Hz, 1H), 7.51 (d, J=9.3 Hz, 1H), 7.21 (d, J=2.4 Hz, 1H), 7.13-6.89 (m, 4H), 5.87 (dd, J=12.7, 5.3 Hz, 1H), 4.32 (s, 1H), 4.06 (d, J=9.0 Hz, 1H), 3.88 (d, J=12.4 Hz, 2H), 3.50 (s, 4H), 2.92 (ddd, J=17.0, 13.5, 5.4 Hz, 1H), 2.80 (t, J=12.1 Hz, 2H), 2.70-2.59 (m, 1H), 2.55 (s, 8H), 2.32-2.11 (m, 2H), 1.83 (d, J=12.5 Hz, 3H), 1.22 (s, 6H), 1.13 (s, 6H).

Embodiment 32: Preparation of Compound 32

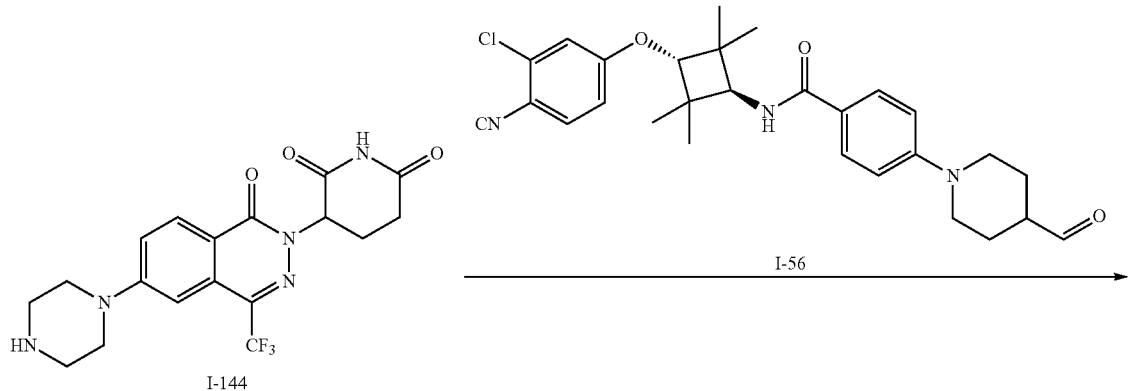

-continued

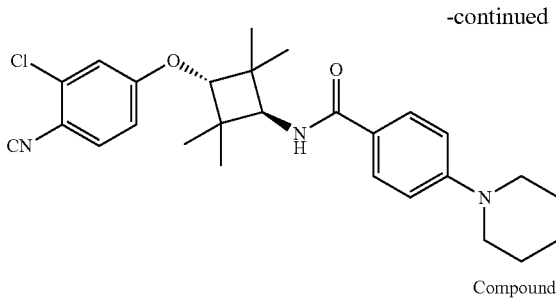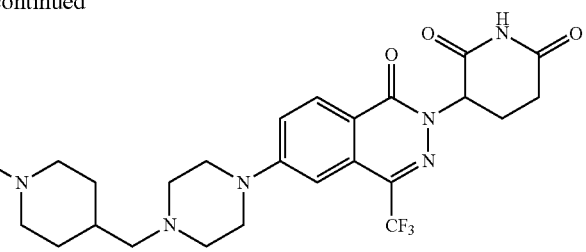

Compound 32

At room temperature, I-144 (180 mg, 0.44 mmol) and I-56 (217 mg, 0.44 mmol) were dissolved in dichloromethane/methanol (10 mL/5 mL); a reaction was stirred at room temperature for 0.5 hours, and 2 drops of acetic acid were added dropwise; then, sodium triacetoxyborohydride (187 mg, 0.88 mmol) was added, and a reaction was stirred at room temperature for 1.5 hours. A reaction solution was diluted with water (10 mL), and extracted with dichloromethane (30 mL×2); organic phases were combined, washed with saturated saline (30 mL×2), dried over anhydrous sodium sulfate, and filtered. A filtrate was concentrated under reduced pressure to remove an organic solvent. The resulting residue was purified by C18 reverse-phase column chromatography to afford compound 32. LCMS (ESI) [M+H]$^+$ 887.6. $^1$H NMR (400 MHz, DMSO-d$_6$) δ 11.11 (s, 1H), 8.19-8.17 (d, J=8.8 Hz, 1H), 7.92-7.90 (d, J=8.8 Hz, 1H), 7.75-7.66 (m, 3H), 7.52-7.49 (d, J=9.2 Hz, 1H), 7.21-7.20 (d, J=2.4 Hz, 1H), 7.02-6.96 (m, 4H), 5.84-5.80 (dd, J=12.0, 5.2 Hz, 1H), 4.32 (s, 1H), 4.06-4.04 (d, J=9.2 Hz, 1H), 3.89-3.86 (d, J=12.0 Hz, 2H), 3.45-3.45 (m, 4H), 2.93-2.89 (m, 1H), 2.82-2.76 (t, J=12.4 Hz, 2H), 2.67-2.52 (m, 6H), 2.19-2.17 (m, 3H), 1.84-1.81 (m, 3H), 1.21 (s, 8H), 1.12 (s, 6H).

Experimental Example 1: Androgen Receptor In-Cell-Western Assay

This assay evaluated compound performance in VCap cells. An intracellular androgen receptor was assayed by In-Cell-Western according to the assay procedure described below.

In a 96-well cell culture plate (Corning 3599) pretreated by poly-D-Lysin, Vcap cells were seeded to a Vcap cell assay medium [phenol red containing DMEM (Gibco Cat. No.: 11995065); fetal bovine serum FBS (Gibco Cat. No.: 10099141C)] at a volume of 100 μL/well and a cell density of 50,000 cells/well. Cells were cultured for at least two days.

1. First, cells were treated with a compound. The compound was subjected to a gradient dilution by using DMSO and a cell culture medium, so that DMSO contained in the cell culture plate was diluted to 0.5%: a polypropylene plate was used according to the following protocol:
(1) (i) A 200× stock solution plate was prepared in DMSO; (ii) a 10 mM stock solution was diluted at 1:4 (10 μL stock solution+40 μL DMSO=2000 uM) with DMSO to enter row 2; (iii) a 1:4 (10 μL protac+40 μL DMSO) gradient dilution was performed from row 2 to row 9, row 1 was reserved for a 2000 uM reference compound and row 10 was reserved for DMSO. (iv) There were 8 concentrations (the final concentrations on the 200× plate was 2000 uM, 400 uM, 80 uM, etc.) in total. (2) (i) A 3× stock solution was prepared in the medium; (ii) 3 μL of the 200× stock solution was transferred to 197 μL of the medium (by a 12-channel pipette, from row 1 to row 10), i.e. a 3× stock solution plate. (iii) Uniform mixing was performed for the stock solution plate. (3) (i) The medium of Vcap cells was replaced with a fresh medium, with the medium volume of 100 μL. (ii) The uniformly-mixed 3× stock solution was transferred to the cell culture plate (by the 12-channel pipette, 50 μL of the stock solution was transferred from row 1 to row 10). (iii) The cells were cultured for 24 hours.
2. The expression level of the intracellular androgen receptor after compound treatment was detected, and assay was performed according to the following method.
(1) (i) An equal volume of 8% paraformaldehyde was added to the cell culture plate for cell fixation. A fixative solution in the cell plate was discarded, and the cell plate was washed three times with PBS. (ii) A Triton solution was prepared (the stock solution was diluted at 1:1000). The solution in the cell plate was discarded, and a volume of 200 μL of a Triton diluent was added to each well. (iii) A 2× blocking solution was prepared (a 10× blocking stock solution was diluted at 1:4). The solution in the cell plate was discarded, and a volume of 100 μL of the 2× blocking solution was added to each well. (iv) A primary antibody solution (Androgen receptor Rabbit mAb, Cell Signaling Technology Cat. No.: 5153; 1:1000 dilution) was prepared. The solution in the cell plate was discarded, a volume of 100 μL of a primary antibody diluent was added to each well, and incubation was performed at 4 degrees overnight. (v) The primary antibody solution was discarded, and the cell plate was washed with 1× Wash buffer (Wash buffer in the present application means a washing buffer solution). (vi) A secondary antibody solution (Goat anti Rabbit IgG (H+L) Secondary Antibody, HRP, Thermo Cat. No.: 31460; 1:5000 dilution) was prepared, and a volume of 100 μL of a secondary antibody diluent was added to each well for incubation. (vii) The secondary antibody solution in the cell plate was discarded, and the cell plate was washed with 1× Wash buffer. (viii) A TMB chromogenic solution (BD Cat. No.: 550534) was prepared, and a volume of 100 μL of the chromogenic solution was added to each well. (ix) A volume of 50 μL of a stop solution (BD Cat. No.: 550534) was added to each well. (x) Absorption values at OD 450 nm and 570 nm were read by EnVision. (2) (i) Normalized analysis was performed for the number of cells in each well. The solution in the cell plate was discarded, and the cell plate was washed three times with wash buffer. (ii) A Janus diluent (1:3 dilution) was prepared. (iii) A volume of 50 μL of the diluent was added to each well for incubation. (iv) The solution in the plate was discarded, and the cell plate was washed with deionized water. (v) 1 M hydrochloric acid was prepared (concentrated hydrochloric acid was diluted at 1:24), and a volume of 200 μL of a hydrochloric acid diluent was added to each well to treat the cells. (vi) An absorption value at OD 595 nm was read with Flex Station. (vii) According to the readings obtained, the effect of the tested compound on androgen receptor expression was calculated.

The experimental results are as shown in Table 1.

TABLE 1

Evaluation of Compound for Androgen Receptor Degradation Activity in VCaP Cells

| Embodiment number | $DC_{50}$ (nM) | $D_{max}$ (%) | Embodiment number | $DC_{50}$ (nM) | $D_{max}$ (%) |
|---|---|---|---|---|---|
| 1 | 10 | 97 | 2 | 5.3 | 114 |
| 3 | 12 | 104 | 4 | 6.8 | 98 |
| 5 | 8.4 | 105 | 7 | 15 | 92 |
| 8 | 8.9 | 75 | 10 | 35 | 87 |
| 11 | 38 | 80 | 13 | 9.6 | 94 |
| 14 | 11 | 91 | 15 | 16 | 84 |
| 16 | 5.7 | 92 | 17 | 6.9 | 88 |
| 23 | 6.9 | 98 | 24 | 6.8 | 106 |
| 25 | 10 | 116 | 26 | 32 | 109 |
| 28A | 2.7 | 126 | 28B | 7.2 | 101 |
| 29 | 8.9 | 169 | 32 | 5.2 | 145 |

$D_{max}$: a maximum degradation degree of AR in VCaP cells. $DC_{50}$: a compound concentration required to achieve half the maximum degradation degree of AR in VCaP cells.

Experimental Example 2: Inhibitory Effect of Tested Compound on VCap Cell Proliferation A tumor cell line Vcap (ATCC Cat. No. CRL-2876) was respectively cultured with DMEM (Gibco Cat. No. 11965-092) medium containing 10% FBS (Gibco Cat. No. 10099-141C). During testing, Vcap cells were replaced with a DMEM culture fluid containing 5% FBS and 0.1 nM R1881 (Sigma Cat. No. R0908). The assay method was as follows:

Vcap cells were seeded to a 384-well plate (Perkin Elmer Cat. No. 6007460) at a cell density of 1200 cells/well and a volume of 20 μL/well; after the cells were incubated overnight in a carbon dioxide incubator (Thermo), the prepared compound solutions with different concentrations were added at a volume of 5 μL/well; meanwhile, a corresponding solvent was provided as a control; after the cells were continuously incubated in the incubator for 6 days, the cell plate and the contents thereof were equilibrated to room temperature; 25 μL of a Cell Titer Glor (Promega Cat. No. G7573) reagent was added to each well; after vibration and uniform mixing, incubation in the dark was performed for 10-30 minutes, and a signal value was detected with Envision microplate reader (PerkinElmer).

Experimental Data Processing Method

A percentage inhibition rate of compound-treated wells was calculated through solvent control wells on the plate, GraphPad prism was used to fit the percentage inhibition rate data corresponding to different concentrations, and $IC_{50}$ value was calculated by a 4-parameter nonlinear logistic formula. The experimental results are shown in Table 2.

TABLE 2

Evaluation of Compound for VCaP Cell Proliferation Inhibitory Activity

| Embodiment number | $IC_{50}$ (nM) | $E_{max}$ (%) | Embodiment number | $IC_{50}$ (nM) | $E_{max}$ (%) |
|---|---|---|---|---|---|
| 2 | 11 | 60 | 4 | 33 | 69 |
| 5 | 37 | 62 | 14 | 20 | 61 |
| 20 | 42 | 60 | 23 | 20 | 56 |
| 24 | 18 | 53 | 25 | 27 | 62 |
| 26 | 45 | 60 | 28A | 9.7 | 74 |
| 28B | 33 | 71 | 29 | 56 | 66 |

$E_{max}$: a maximum degree of VCaP cell proliferation inhibition. $IC_{50}$: a compound concentration required to achieve half the maximum degree of VCaP cell proliferation inhibition.

Experimental Example 3: In-Vivo Pharmacokinetic Experiments of Compounds of the Present Invention In this experimental example, the in-vivo pharmacokinetic evaluation was made for mice by intravenous injection and oral administration.

Experimental methods and conditions: male CD1 mice, 6 to 8 weeks old; all animals had free access to food and water; 5 min, 15 min, 30 min, 1 hr, 2 hr, 4 hr, 8 hr and 24 hr after the mice were subjected to a single intravenous injection of 1 mg/Kg of a compound to be tested (solvent 5% DMSO/ 15% Solutol/80% Saline) (saline in the present application all means a saline solution), or 15 min, 30 min, 1 hr, 2 hr, 4 hr, 6 hr, 8 hr and 24 hr after the mice were subjected to oral intragastric administration of 10 mg/kg (solvent 5% DMSO/ 10% Solutol/85% Saline), blood was collected from orbits, not less than 50 μL of each sample was collected, and heparin sodium was used for anticoagulation; the collected samples were placed on ice, and the plasma was centrifugally separated within 1 hour for testing. The drug concentration in the plasma was detected by liquid chromatography tandem mass spectrometry (LC/MS/MS), and the pharmacokinetic parameters were calculated by Phoenix WinNonlin software. Embodiment 82 in CN110612294 A was taken as a control sample 1. The experimental results are as shown in Table 3.

TABLE 3

Pharmacokinetics of Oral Administration (10 mg/kg)

| Compound | $T_{1/2}$ (hr) | $C_{max}$ (ng/mL) | $AUC_{0-inf}$ (ng*hr/mL) | F (%) |
|---|---|---|---|---|
| Compound 1 | 6.22 | 1260 | 18896 | 68.8 |
| Compound 29 | 7.91 | 677 | 13404 | 24.1 |
| Control sample 1 | 4.58 | 660 | 7696 | 16.5 |

The experimental data show that the in-vivo pharmacokinetic results of oral administration of the compound of the present invention in mice represent longer $T_{1/2}$, higher in-vivo exposure amount $AUC_{0-inf}$ and oral bioavailability F.

Experimental Example 4: In-Vivo Pharmacokinetic Experiments of Compounds of the Present Invention In this experimental example, the in-vivo pharmacokinetic evaluation was made for rats by intravenous injection and oral administration.

Experimental methods and conditions: male SD rats, 6 to 8 weeks old; all animals had free access to food and water; 5 min, 15 min, 30 min, 1 hr, 2 hr, 4 hr, 8 hr, 24 hr and 48 hr after the rats were subjected to a single intravenous injection of 1 mg/Kg of a compound to be tested (solvent 5% DMSO/15% Solutol/80% Saline), or 15 min, 30 min, 1 hr, 2 hr, 4 hr, 6 hr, 8 hr, 24 hr and 48 hr after the rats were subjected to oral intragastric administration of 10 mg/kg (solvent 5% DMSO/10% Solutol/85% Saline), blood was collected from orbits, not less than 50 μL of each sample was collected, and heparin sodium was used for anticoagulation; the collected samples were placed on ice, and the plasma was centrifugally separated within 1 hour for testing. The drug concentration in the plasma was detected by liquid chromatography tandem mass spectrometry (LC/MS/MS), and the pharmacokinetic parameters were calculated by Phoenix WinNonlin software. Embodiment 82 in CN110612294 A was taken as a control sample 1. The experimental results are as shown in Table 4.

TABLE 4

Pharmacokinetics of Oral Administration (10 mg/kg)

| Compound | $T_{1/2}$ (hr) | $C_{max}$ (ng/mL) | $AUC_{0\text{-}inf}$ (ng*hr/mL) | F (%) |
|---|---|---|---|---|
| Compound 1 | 7.62 | 147 | 2646 | 11.9 |
| Compound 28A | 8.28 | 173 | 3212 | 5.13 |
| Compound 29 | 13.4 | 253 | 6197 | 11.9 |
| Control sample 1 | 5.87 | 43.6 | 603 | 0.82 |

The experimental data show that the in-vivo pharmacokinetic results of oral administration of the compound of the present invention in rats represent longer $T_{1/2}$, higher in-vivo exposure amount $AUC_{0\text{-}inf}$ and oral bioavailability F.

Experimental Example 5: In-Vivo Pharmacokinetic Experiments of Compounds of the Present Invention In this experimental example, the in-vivo pharmacokinetic evaluation was made for dogs by intravenous injection and oral administration.

Experimental methods and conditions: male Beijing Marshall beagles, 12 to 18 months old; the beagles were subjected to administration half an hour after feeding; 5 min, 15 min, 30 min, 1 hr, 2 hr, 4 hr, 8 hr, 24 hr, 48 hr and 72 hr after the beagles were subjected to a single intravenous injection of 1 mg/Kg of a compound to be tested (solvent 5% DMSO/10% Solutol/85% Saline), or 15 min, 30 min, 1 hr, 2 hr, 4 hr, 6 hr, 8 hr, 24 hr, 48 hr and 72 hr after the beagles were subjected to oral intragastric administration of 10 mg/kg (solvent 5% DMSO/10% Solutol/85% Saline), blood was collected from orbits, not less than 50 μL of each sample was collected, and heparin sodium was used for anticoagulation; the collected samples were placed on ice, and the plasma was centrifugally separated within 1 hour for testing. The drug concentration in the plasma was detected by liquid chromatography tandem mass spectrometry (LC/MS/MS), and the pharmacokinetic parameters were calculated by Phoenix WinNonlin software. Embodiment 82 in CN110612294 A was taken as a control sample 1. The experimental results are as shown in Table 5.

TABLE 5

Pharmacokinetics of Oral Administration (10 mg/kg)

| Compound | $T_{1/2}$ (hr) | $C_{max}$ (ng/mL) | $AUC_{0\text{-}inf}$ (ng*hr/mL) | F (%) |
|---|---|---|---|---|
| Compound 1 | 19.9 | 482 | 14074 | 44.1 |
| Compound 28A | 34.3 | 868 | 15420 | 33.9 |
| Control sample 1 | 14.9 | 303 | 7841 | 12.0 |

The experimental data show that the in-vivo pharmacokinetic results of oral administration of the compound of the present invention in dogs represent longer $T_{1/2}$, higher in-vivo exposure amount $AUC_{0\text{-}inf}$ and oral bioavailability F.

What is claimed is:

1. A compound selected from the group consisting of:

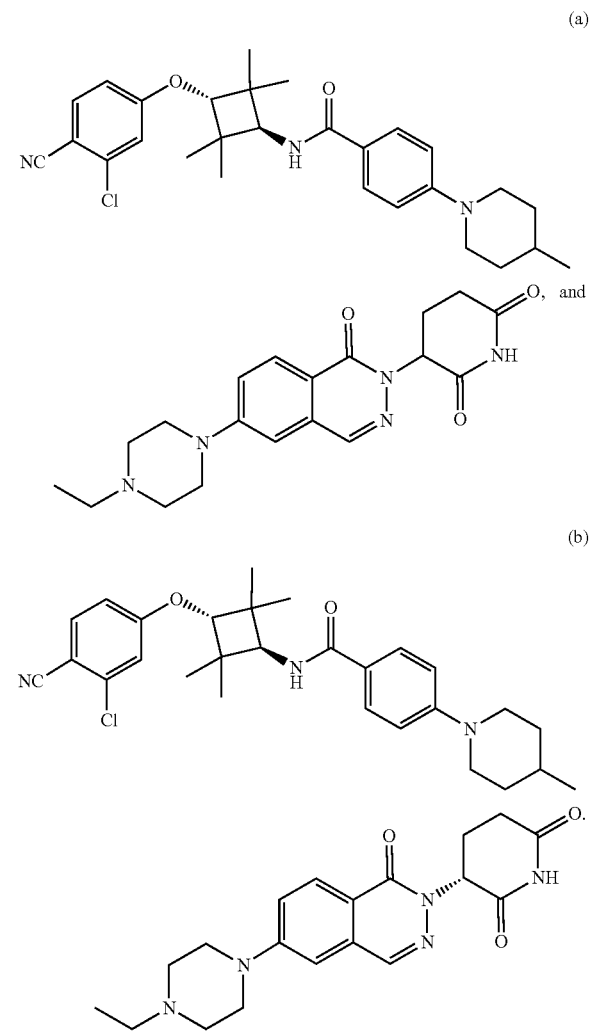

2. The compound of claim 1, wherein the compound is:
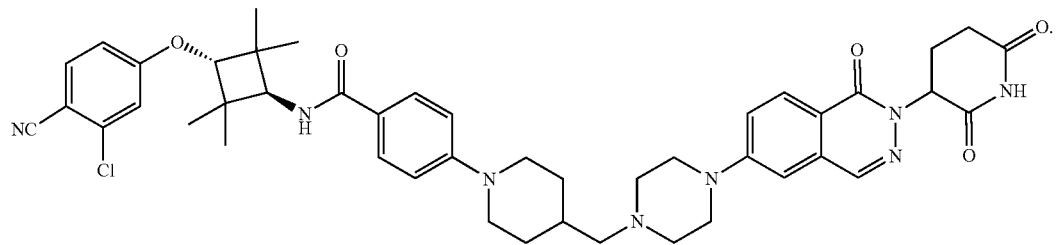 [SMILES: CC1(C)[C@H](NC(=O)c2ccc(N3CCC(CN4CCN(c5ccc6c(=O)n(C7CCC(=O)NC7=O)ncc6c5)CC4)CC3)cc2)C(C)(C)[C@H]1Oc1ccc(C#N)c(Cl)c1]
3. The compound of claim 1, wherein the compound is:
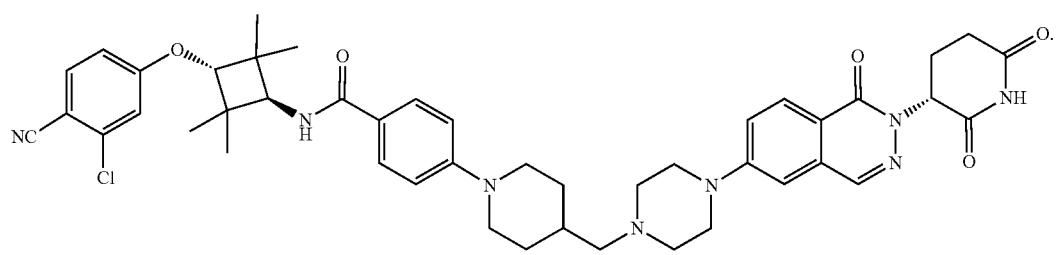 [SMILES: CC1(C)[C@H](NC(=O)c2ccc(N3CCC(CN4CCN(c5ccc6c(=O)n([C@@H]7CCC(=O)NC7=O)ncc6c5)CC4)CC3)cc2)C(C)(C)[C@H]1Oc1ccc(C#N)c(Cl)c1]
4. A compound of the formula:
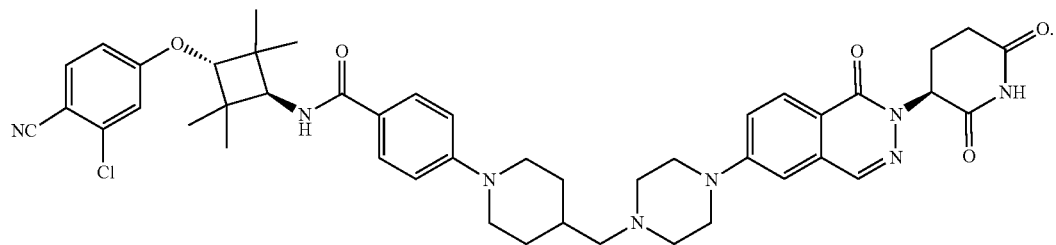 [SMILES: CC1(C)[C@H](NC(=O)c2ccc(N3CCC(CN4CCN(c5ccc6c(=O)n([C@H]7CCC(=O)NC7=O)ncc6c5)CC4)CC3)cc2)C(C)(C)[C@H]1Oc1ccc(C#N)c(Cl)c1]
5. A compound selected from the group consisting of:
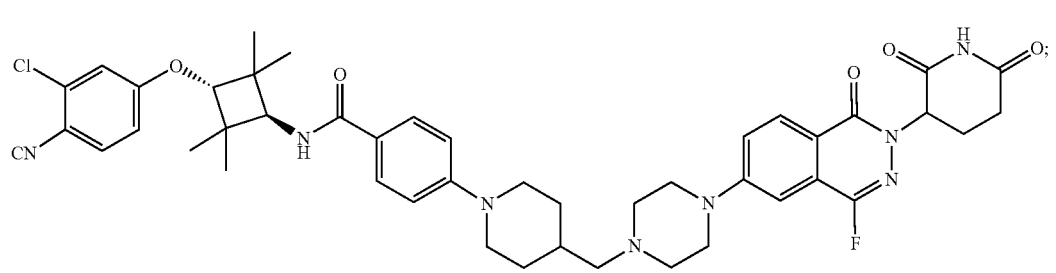
(i)
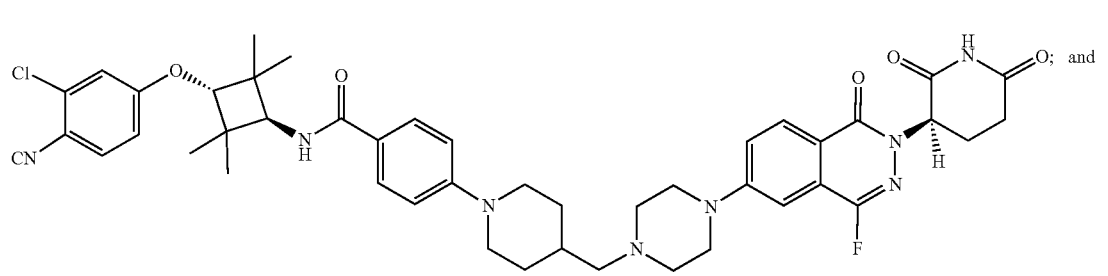
(ii)
; and

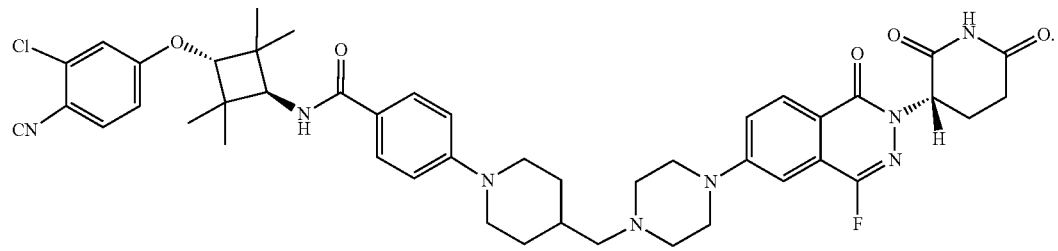

6. The compound of claim 5, wherein the compound is:

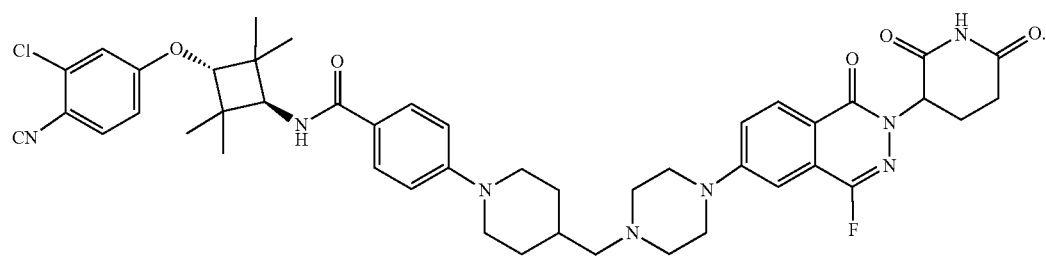

7. The compound of claim 5, wherein the compound is:

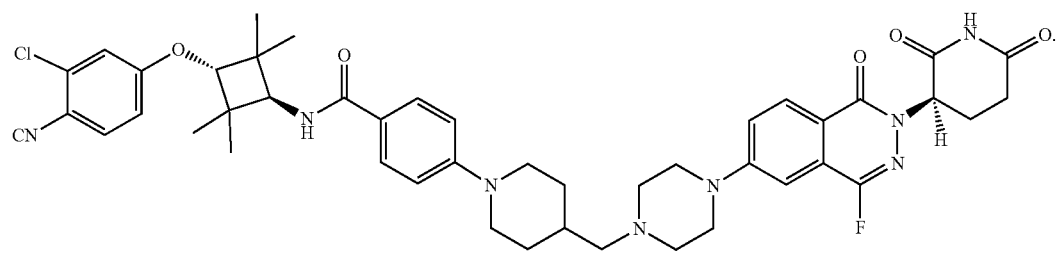

8. The compound of claim 5, wherein the compound is:

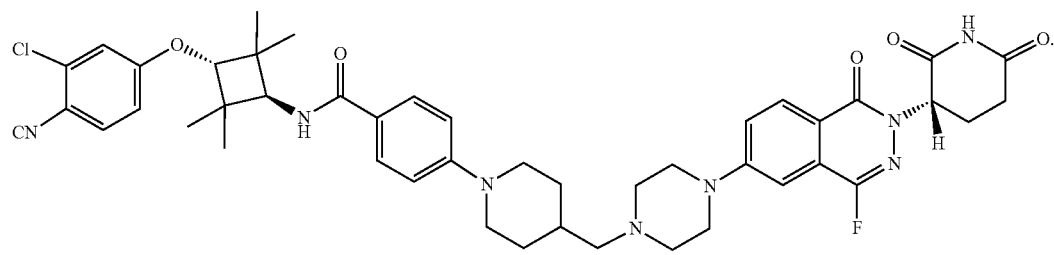

9. A method for treating prostate cancer in a subject in need thereof, the method comprising administering to the subject an effective amount of the compound of claim 2.

10. The method of claim 9, wherein administering is orally administering.

11. A method for treating prostate cancer in a subject in need thereof, the method comprising administering to the subject an effective amount of the compound of claim 3.

12. The method of claim 11, wherein administering is orally administering.

13. A method for treating prostate cancer in a subject in need thereof, the method comprising administering to the subject an effective amount of the compound of claim 4.

14. The method of claim 13, wherein administering is orally administering.

15. A method for treating prostate cancer in a subject in need thereof, the method comprising administering to the subject an effective amount of the compound of claim 6.

16. The method of claim 15, wherein administering is orally administering.

17. A method for treating prostate cancer in a subject in need thereof, the method comprising administering to the subject an effective amount of the compound of claim 7.

18. The method of claim 17, wherein administering is orally administering.

19. A method for treating prostate cancer in a subject in need thereof, the method comprising administering to the subject an effective amount of the compound of claim 8.

20. The method of claim 19, wherein administering is orally administering.

21. A composition comprising a compound selected from the group consisting of:

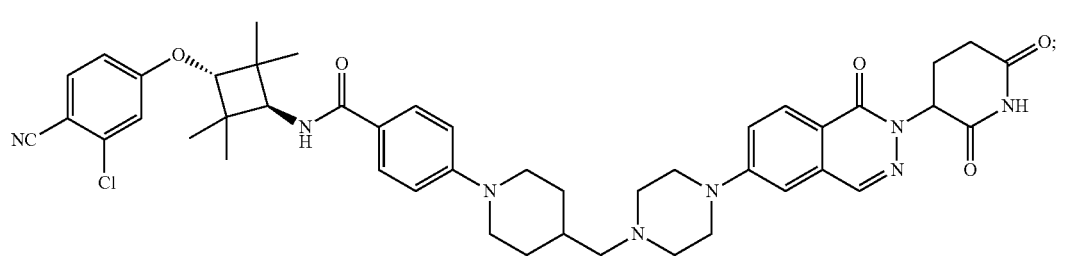

(a)

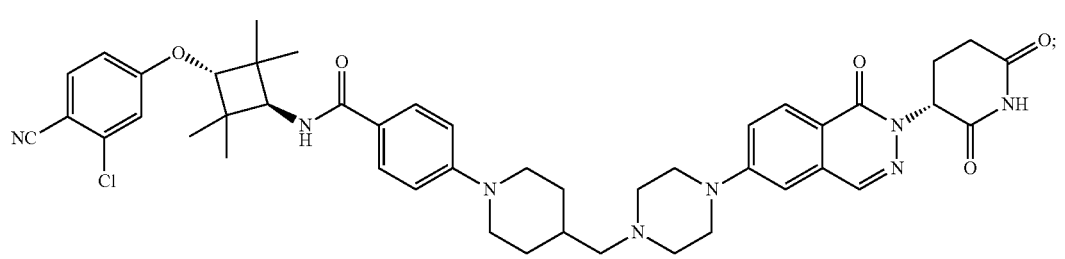

(b)

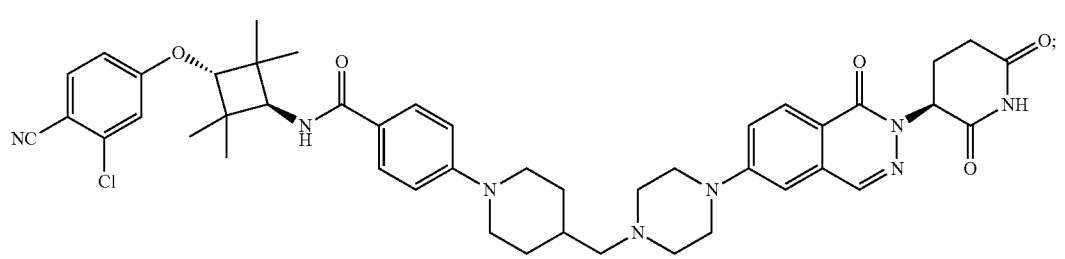

(c)

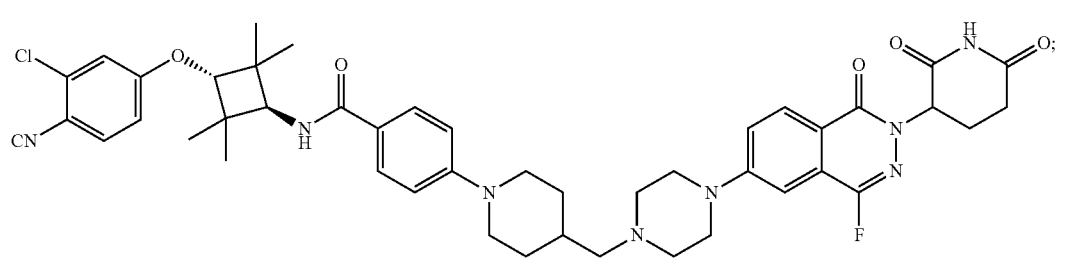

(d)

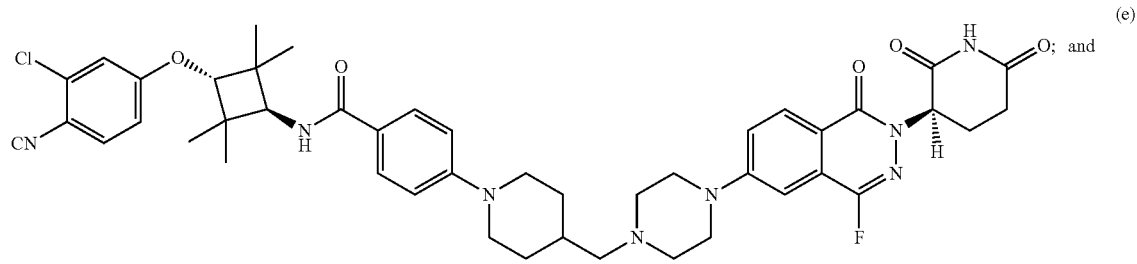

(e); and

-continued
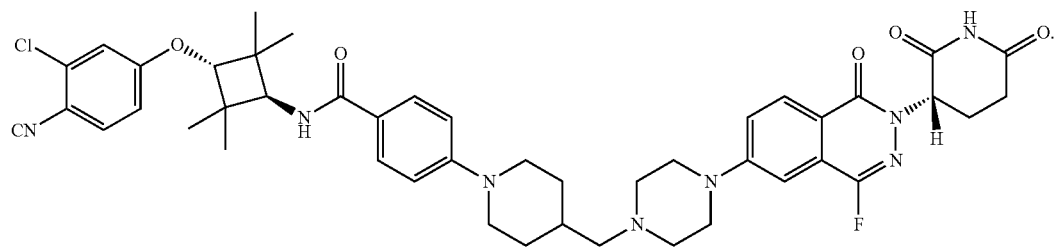
(f)
22. The composition of claim 21, wherein the compound is
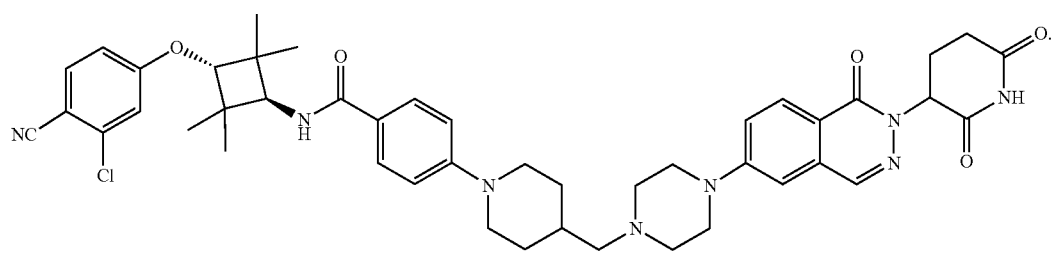 [SMILES: CC1(C)[C@H](NC(=O)c2ccc(N3CCC(CN4CCN(c5ccc6c(=O)n(C7CCC(=O)NC7=O)ncc6c5)CC4)CC3)cc2)C(C)(C)[C@H]1Oc1ccc(C#N)c(Cl)c1]
23. The composition of claim 21, wherein the compound is
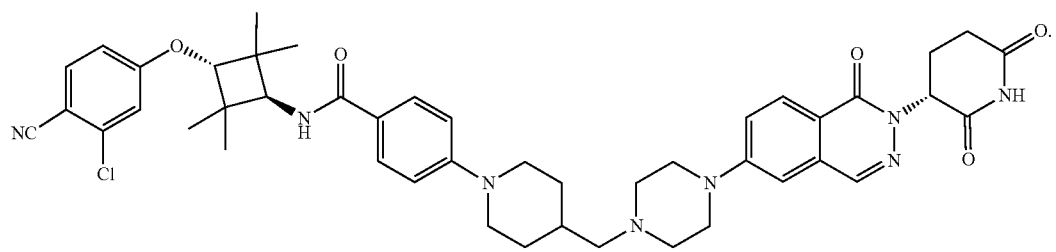 [SMILES: CC1(C)[C@H](NC(=O)c2ccc(N3CCC(CN4CCN(c5ccc6c(=O)n([C@@H]7CCC(=O)NC7=O)ncc6c5)CC4)CC3)cc2)C(C)(C)[C@H]1Oc1ccc(C#N)c(Cl)c1]
24. The composition of claim 21, wherein the compound is
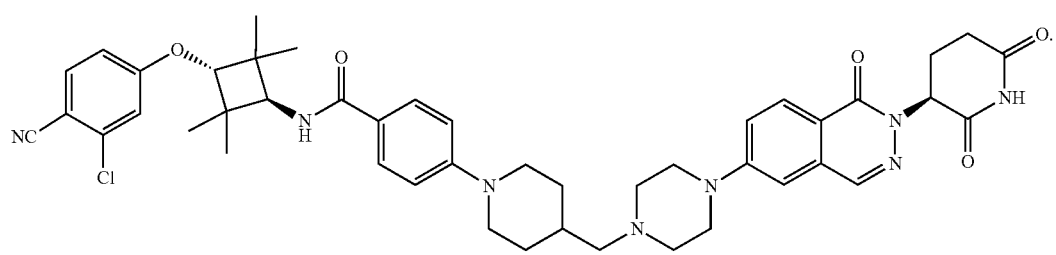 [SMILES: CC1(C)[C@H](NC(=O)c2ccc(N3CCC(CN4CCN(c5ccc6c(=O)n([C@H]7CCC(=O)NC7=O)ncc6c5)CC4)CC3)cc2)C(C)(C)[C@H]1Oc1ccc(C#N)c(Cl)c1]
25. The composition of claim 21, wherein the compound is

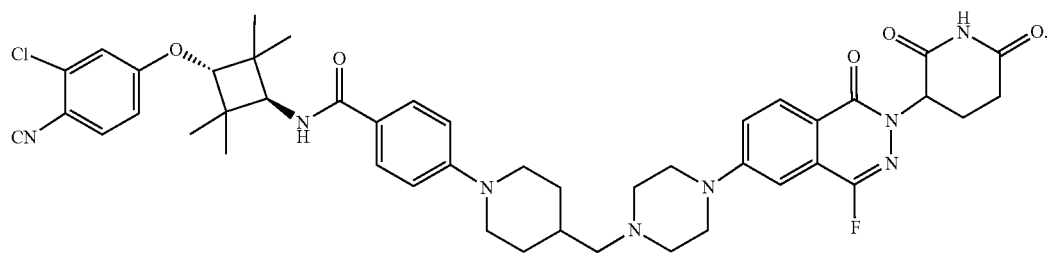

26. The composition of claim 21, wherein the compound is

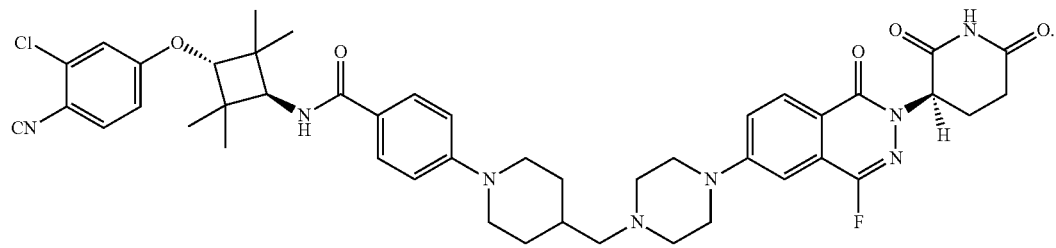

27. The composition of claim 21, wherein the compound is:

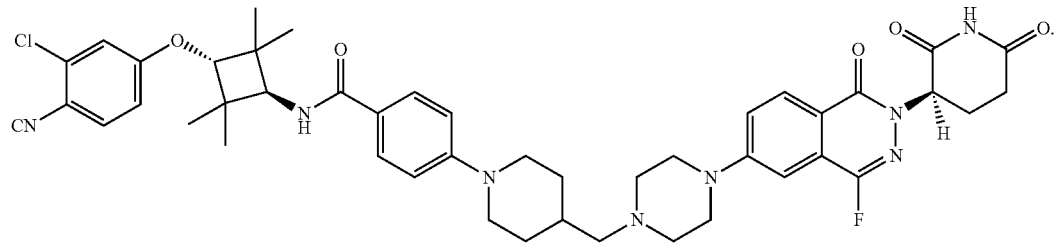

28. A method for treating prostate cancer in a subject in need thereof, the method comprising administering to the subject an effective amount of the composition of claim 23.

29. A method for treating prostate cancer in a subject in need thereof, the method comprising administering to the subject an effective amount of the composition of claim 24.

30. A method for treating prostate cancer in a subject in need thereof, the method comprising administering to the subject an effective amount of the composition of claim 25.

* * * * *

UNITED STATES PATENT AND TRADEMARK OFFICE
CERTIFICATE OF CORRECTION

PATENT NO. : 12,234,223 B2
APPLICATION NO. : 18/804443
DATED : February 25, 2025
INVENTOR(S) : Hongfu Lu et al.

Page 1 of 4

It is certified that error appears in the above-identified patent and that said Letters Patent is hereby corrected as shown below:

In the Specification

At Column 4, Line 39, delete:
"or heteroatom groups independently selected from 0, NH, S,"
And replace it with the following:
"or heteroatom groups independently selected from O, NH, S,"

At Column 9, Lines 41-52, should read:

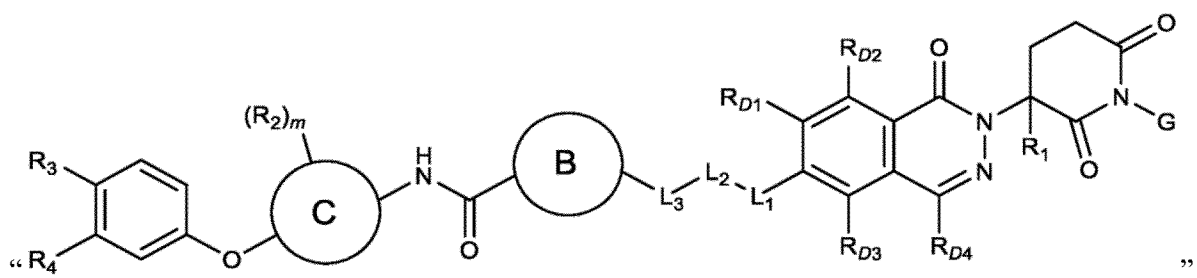

At Column 12, Lines 16-43, should read:

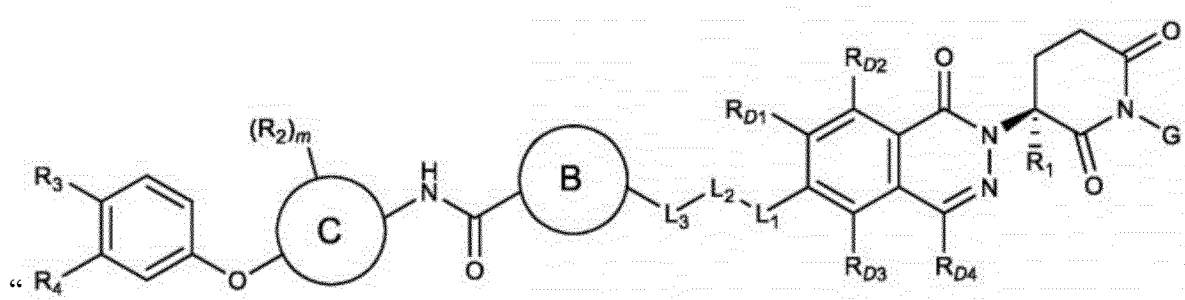

Signed and Sealed this
Seventeenth Day of June, 2025

Coke Morgan Stewart
*Acting Director of the United States Patent and Trademark Office*

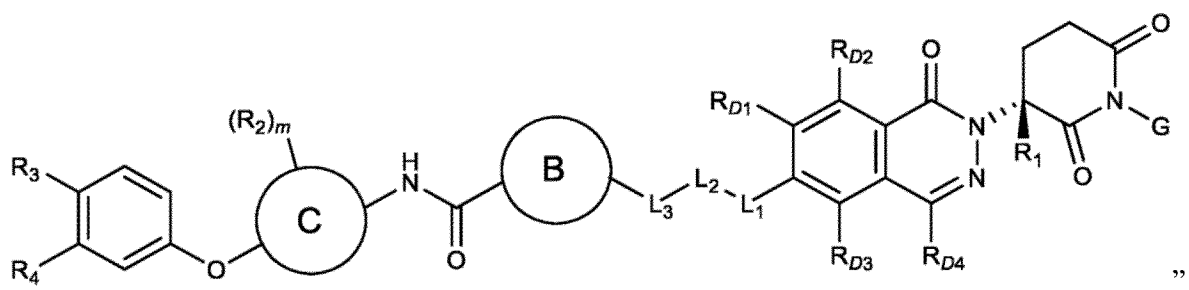
At Column 16, Line 40, delete the following chemical structure:
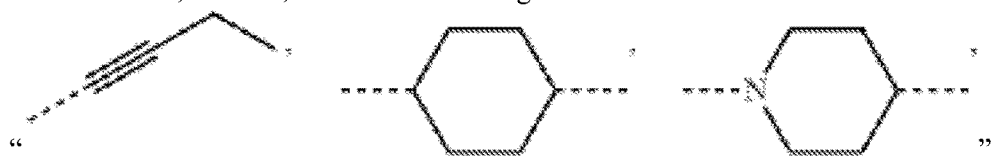
And replace them with the following three corrected chemical structures:
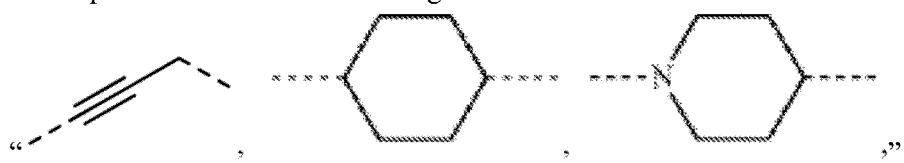
At Column 17, Line 25, should read:
At Column 18, Line 1, should read:
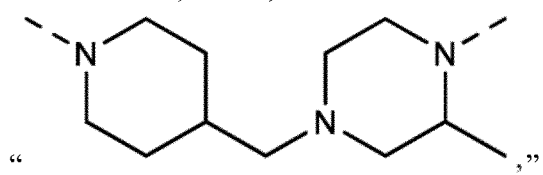
At Column 19, Line 55, should read:
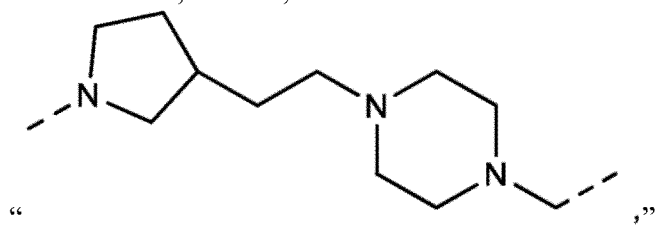

CERTIFICATE OF CORRECTION (continued)
U.S. Pat. No. 12,234,223 B2

At Column 27, last line, should read:

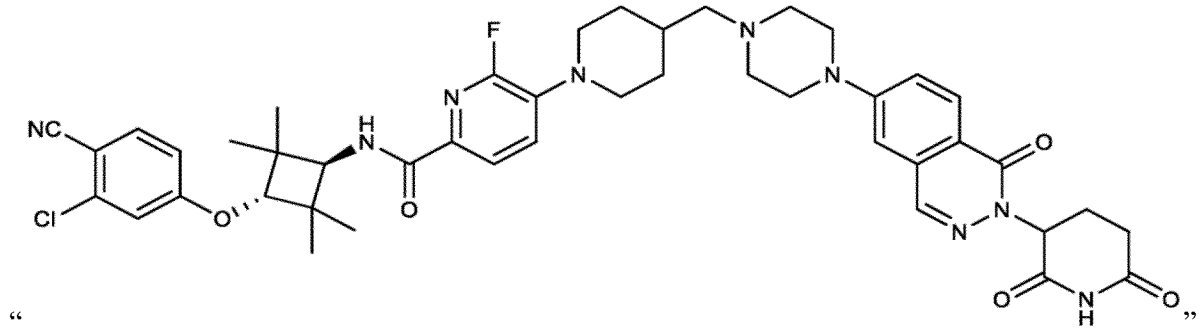

"                    "

At Column 47, the 6th chemical structure should read:

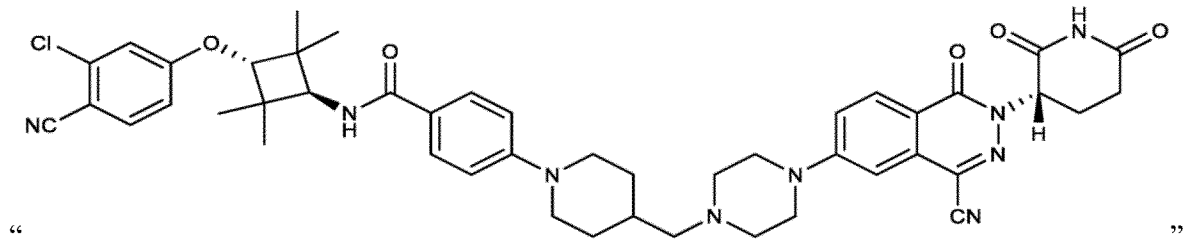

"                    "

At Column 54, Line 25, delete "hypo" and insert --hypo- --

At Column 54, Lines 28-32, insert --.-- after the chemical structure

At Column 54, Line 53, delete "sec" and insert --sec- --

At Column 54, Lines 55-58, insert --.-- after the chemical structure

At Column 55, Line 11, delete "monovalent bivalent" and insert --monovalent, bivalent--

At Column 58, Line 13, delete "R-electron" and insert --π-electron--

At Column 69, Line 58, delete "0-(7-" and insert --O-(7- --

At Column 109, Lines 56-57, delete "Reference Example 22: Preparation of Intermediate I-2" and insert the correction of --Reference Example 72: Preparation of Intermediate I-72--

At Column 119, Line 3, delete "N,N-diisopropyl ethyl amine" and insert --N,N-diisopropylethylamine--

At Column 121, Lines 57-58, delete "1-(3-dimethyl aminopropyl)-3-ethyl carbodiimide" and insert --1-(3-dimethylaminopropyl)-3-ethylcarbodiimide--

At Column 121, Line 60, delete "N,N-diisopropylethyl amine" and insert --N,N-diisopropylethylamine--

CERTIFICATE OF CORRECTION (continued)
U.S. Pat. No. 12,234,223 B2

Page 4 of 4

At Column 145, Line 16, delete "Example 130" and insert --Example 130:--

At Column 154, Line 25, delete "Preparation of Embodiments" and insert --Preparation of Embodiments:--

At Column 175, Lines 5-10, delete the chemical structure:

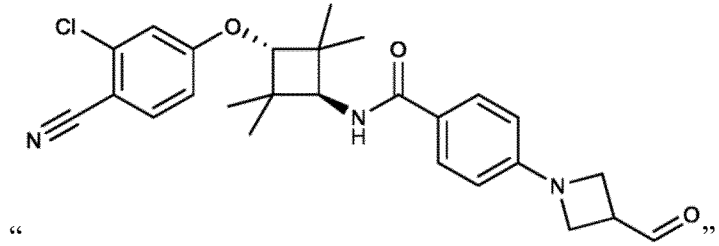

"

And replace it with the corrected chemical structure:

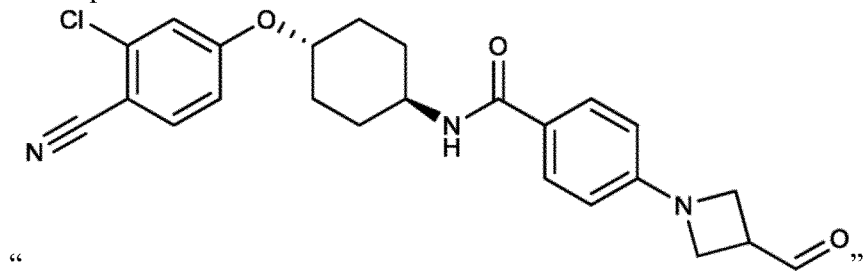

"

At Column 179, Line 12, delete "Embodiment 18." and insert --Embodiment 18:--

At Column 203, Line 60, delete "Method" and insert --Method:--